US011440914B2

(12) United States Patent
Ye et al.

(10) Patent No.: US 11,440,914 B2
(45) Date of Patent: Sep. 13, 2022

(54) TRICYCLIC AMINE COMPOUNDS AS CDK2 INHIBITORS

(71) Applicant: Incyte Corporation, Wilmington, DE (US)

(72) Inventors: Qinda Ye, Claymont, DE (US); Neil Lajkiewicz, Bedford, MA (US); Ken Mukai, Wilmington, DE (US); Liangxing Wu, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/863,770

(22) Filed: Apr. 30, 2020

(65) Prior Publication Data

US 2020/0347067 A1  Nov. 5, 2020

Related U.S. Application Data

(60) Provisional application No. 62/841,669, filed on May 1, 2019.

(51) Int. Cl.
| | | |
|---|---|---|
| *C07D 471/04* | (2006.01) | |
| *C07D 487/04* | (2006.01) | |
| *A61K 31/437* | (2006.01) | |
| *A61K 31/5025* | (2006.01) | |
| *A61K 31/519* | (2006.01) | |
| *A61P 35/00* | (2006.01) | |
| *C07D 491/147* | (2006.01) | |

(52) U.S. Cl.
CPC ............ *C07D 487/04* (2013.01); *A61P 35/00* (2018.01); *C07D 491/147* (2013.01)

(58) Field of Classification Search
CPC .. C07D 471/04; C07D 487/04; A61K 31/437; A61K 31/5025; A61K 31/519; A61P 35/00
See application file for complete search history.

(56) References Cited

U.S. PATENT DOCUMENTS

| | | |
|---|---|---|
| 4,569,933 A | 2/1986 | Cornu et al. |
| 5,304,555 A | 4/1994 | Awaya et al. |
| 5,466,692 A | 11/1995 | Ellingboe |
| 5,521,184 A | 5/1996 | Zimmermann |
| 6,812,341 B1 | 11/2004 | Conrad |
| 7,101,663 B2 | 9/2006 | Godfrey et al. |
| 7,488,802 B2 | 2/2009 | Collins et al. |
| 7,820,665 B2 | 10/2010 | Booker et al. |
| 7,897,572 B1 | 3/2011 | Davis et al. |
| 7,943,743 B2 | 5/2011 | Korman et al. |
| 8,008,449 B2 | 8/2011 | Korman et al. |
| 8,168,757 B2 | 5/2012 | Finnefrock et al. |
| 8,183,242 B2 | 5/2012 | Sun et al. |
| 8,217,149 B2 | 7/2012 | Irving et al. |
| 8,431,596 B2 | 4/2013 | Pave et al. |
| 9,850,244 B2 | 12/2017 | Xu |
| 10,308,644 B2 | 6/2019 | Wu et al. |
| 11,066,404 B2 | 7/2021 | Sokolsky et al. |
| 2003/0144309 A1 | 7/2003 | Choon-Moon |
| 2004/0086915 A1 | 5/2004 | Lin et al. |
| 2004/0204426 A1 | 10/2004 | Kubo et al. |
| 2006/0142312 A1 | 6/2006 | Flamme et al. |
| 2007/0099938 A1 | 5/2007 | Ohmoto et al. |
| 2007/0225286 A1 | 9/2007 | Ren et al. |
| 2008/0187978 A1 | 8/2008 | Flynn et al. |
| 2009/0143302 A1 | 6/2009 | Yen et al. |
| 2009/0163489 A1 | 6/2009 | Booker et al. |
| 2010/0105655 A1 | 1/2010 | Lichtenstein et al. |
| 2010/0173889 A1 | 7/2010 | Schunk et al. |
| 2011/0201605 A1 | 8/2011 | Baumann et al. |
| 2012/0220572 A1 | 8/2012 | Tong et al. |
| 2013/0190305 A1 | 7/2013 | Treu et al. |
| 2013/0210818 A1 | 8/2013 | Huang et al. |
| 2015/0045370 A1 | 2/2015 | Cohen et al. |
| 2016/0009666 A1 | 1/2016 | Ding et al. |
| 2016/0096835 A1 | 4/2016 | Cole et al. |
| 2016/0222014 A1 | 8/2016 | Venkatesan et al. |
| 2016/0264548 A1 | 9/2016 | Qui et al. |
| 2017/0121326 A1 | 5/2017 | Schiltz et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0210739 A1 | 7/2017 | Luo et al. |
| 2017/0260183 A1 | 9/2017 | Jeschke et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |

(Continued)

FOREIGN PATENT DOCUMENTS

| | | |
|---|---|---|
| AU | 2017248456 | 11/2017 |
| CA | 1231950 | 1/1988 |

(Continued)

OTHER PUBLICATIONS

International Search Report and Written Opinion in International Application No. PCT/US2020/046078, dated Oct. 20, 2020, 12 pages.

Alam et al., "Synthesis and SAR of aminopyrimidines as novel c-Jun N-terminal kinase (JNK) inhibitors," Bioorganic & Medicinal Chemistry Letters, Jun. 15, 2007, 17(12):3463-3467.

Anderson et al., "Imidazoles: SAR and development of a potent class of cyclin-dependent kinase inhibitors," Bio Med Chem Lett., Oct. 15, 2008, 18(20):5487-5492.

(Continued)

*Primary Examiner* — Bruck Kifle

(74) *Attorney, Agent, or Firm* — Fish & Richardson P.C.

(57) ABSTRACT

The present application provides tricyclic amine compounds, which are inhibitors of cyclin-dependent kinase 2 (CDK2), as well as pharmaceutical compositions thereof, and methods of treating cancer using the same.

37 Claims, 17 Drawing Sheets

Specification includes a Sequence Listing.

(56) References Cited

U.S. PATENT DOCUMENTS

| | | | |
|---|---|---|---|
| 2018/0044344 A1 | 2/2018 | Behenna et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0243245 A1 | 8/2018 | England et al. |
| 2018/0244654 A1 | 8/2018 | Schiltz et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0092784 A1 | 3/2019 | Wu et al. |
| 2019/0127467 A1 | 5/2019 | Shah et al. |
| 2019/0144439 A1 | 5/2019 | Wu et al. |
| 2019/0202824 A1 | 7/2019 | Wu et al. |
| 2019/0216782 A1 | 7/2019 | Liu et al. |
| 2019/0225601 A1 | 7/2019 | Wu et al. |
| 2019/0300524 A1 | 10/2019 | Wu et al. |
| 2019/0345170 A1 | 11/2019 | Wu et al. |
| 2020/0115378 A1 | 4/2020 | Sokolsky et al. |
| 2020/0165224 A1 | 5/2020 | Li et al. |
| 2020/0316064 A1 | 10/2020 | Yen et al. |
| 2020/0347066 A1 | 11/2020 | Ye et al. |
| 2020/0392139 A1 | 12/2020 | Sokolsky et al. |
| 2020/0399273 A1 | 12/2020 | Sokolsky et al. |
| 2021/0017156 A1 | 1/2021 | Hummel et al. |
| 2021/0047294 A1 | 2/2021 | Ye et al. |
| 2021/0107901 A1 | 4/2021 | Ye et al. |
| 2022/0009923 A1 | 1/2022 | Sokolsky et al. |

FOREIGN PATENT DOCUMENTS

| | | |
|---|---|---|
| CN | 103864770 | 6/2014 |
| CN | 104003988 | 8/2014 |
| CN | 104418860 | 3/2015 |
| CN | 104761544 | 7/2015 |
| CN | 106699785 | 5/2017 |
| CN | 107759587 | 3/2018 |
| CN | 107793413 | 3/2018 |
| EP | 0543942 | 6/1993 |
| EP | 2277881 | 1/2011 |
| EP | 2356101 | 8/2011 |
| EP | 3060550 | 8/2016 |
| EP | 3204007 | 8/2017 |
| EP | 3428162 | 1/2019 |
| EP | 3429591 | 1/2019 |
| JP | 2006188504 | 7/2006 |
| JP | 2007217322 | 8/2007 |
| RU | 2012102424 | 7/2013 |
| RU | 2509770 | 3/2014 |
| WO | WO 84/00546 | 2/1984 |
| WO | WO 2000/009495 | 2/2000 |
| WO | WO 2000/025780 | 5/2000 |
| WO | WO 2000/026197 | 5/2000 |
| WO | WO 2000/053595 | 9/2000 |
| WO | WO 00/64900 | 11/2000 |
| WO | WO 2000/078731 | 12/2000 |
| WO | WO 2001/012621 | 2/2001 |
| WO | WO 2001/014402 | 3/2001 |
| WO | WO 2001/017995 | 3/2001 |
| WO | WO 2001/047921 | 7/2001 |
| WO | WO 2001/060816 | 8/2001 |
| WO | WO 2001/064655 | 9/2001 |
| WO | WO 2001/072745 | 10/2001 |
| WO | WO 2002/000196 | 1/2002 |
| WO | WO 2002/016348 | 2/2002 |
| WO | WO 2002/020512 | 3/2002 |
| WO | WO 2002/022608 | 3/2002 |
| WO | WO 2002/042303 | 5/2002 |
| WO | WO 2002/046171 | 6/2002 |
| WO | WO 2002/046184 | 6/2002 |
| WO | WO 2002/064586 | 8/2002 |
| WO | WO 2002/066481 | 8/2002 |
| WO | WO 2002/067654 | 9/2002 |
| WO | WO 2002/078700 | 10/2002 |
| WO | WO 2002/078701 | 10/2002 |
| WO | WO 2002/092573 | 11/2002 |
| WO | WO 2002/096905 | 12/2002 |
| WO | WO 2002/102313 | 12/2002 |
| WO | WO 2003/011836 | 2/2003 |
| WO | WO 2003/011837 | 2/2003 |
| WO | WO 2003/011838 | 2/2003 |
| WO | WO 2003/024967 | 3/2003 |
| WO | WO 2003/030909 | 4/2003 |
| WO | WO 2003/037347 | 5/2003 |
| WO | WO 2003/042402 | 5/2003 |
| WO | WO 2003/047512 | 6/2003 |
| WO | WO 2003/048158 | 6/2003 |
| WO | WO 2003/051886 | 6/2003 |
| WO | WO 2003/062236 | 7/2003 |
| WO | WO 2003/066634 | 8/2003 |
| WO | WO 2003/075917 | 9/2003 |
| WO | WO 2003/076437 | 9/2003 |
| WO | WO 2003/076441 | 9/2003 |
| WO | WO 2003/082871 | 10/2003 |
| WO | WO 2003/093273 | 11/2003 |
| WO | WO 2003/099771 | 12/2003 |
| WO | WO 2004/005281 | 1/2004 |
| WO | WO 2004/035588 | 4/2004 |
| WO | WO 2004/043367 | 5/2004 |
| WO | WO 2004/046120 | 6/2004 |
| WO | WO 2004/056786 | 7/2004 |
| WO | WO 2004/056822 | 7/2004 |
| WO | WO 2004/074290 | 9/2004 |
| WO | WO 2004/080980 | 9/2004 |
| WO | WO 2004/084901 | 10/2004 |
| WO | WO 2004/087698 | 10/2004 |
| WO | WO 2004/087699 | 10/2004 |
| WO | WO 2004/089286 | 10/2004 |
| WO | WO 2004/089913 | 10/2004 |
| WO | WO 2004/091480 | 10/2004 |
| WO | WO 2004/094404 | 11/2004 |
| WO | WO 2004/110452 | 12/2004 |
| WO | WO 2004/111037 | 12/2004 |
| WO | WO 2005/005438 | 1/2005 |
| WO | WO 2005/012262 | 2/2005 |
| WO | WO 2005/019215 | 3/2005 |
| WO | WO 2005/020921 | 3/2005 |
| WO | WO 2005/028444 | 3/2005 |
| WO | WO 2005/037843 | 4/2005 |
| WO | WO 2005/040154 | 5/2005 |
| WO | WO 2005/065074 | 7/2005 |
| WO | WO 2005/068437 | 7/2005 |
| WO | WO 2005/080393 | 9/2005 |
| WO | WO 2005/085253 | 9/2005 |
| WO | WO 2005/090333 | 9/2005 |
| WO | WO 2005/097052 | 10/2005 |
| WO | WO 2005/103022 | 11/2005 |
| WO | WO 2005/107760 | 11/2005 |
| WO | WO 2005/121107 | 12/2005 |
| WO | WO 2006/021547 | 3/2006 |
| WO | WO 2006/025567 | 3/2006 |
| WO | WO 2006/037117 | 4/2006 |
| WO | WO 2006/038001 | 4/2006 |
| WO | WO 2006/051311 | 5/2006 |
| WO | WO 2006/056399 | 6/2006 |
| WO | WO 2006/065820 | 6/2006 |
| WO | WO 2006/068826 | 6/2006 |
| WO | WO 2006/068904 | 6/2006 |
| WO | WO 2006/069525 | 7/2006 |
| WO | WO 2006/070208 | 7/2006 |
| WO | WO 2006/074057 | 7/2006 |
| WO | WO 2006/074985 | 7/2006 |
| WO | WO 2006/134378 | 12/2006 |
| WO | WO 2007/002325 | 1/2007 |
| WO | WO 2007/005708 | 1/2007 |
| WO | WO 2007/008664 | 1/2007 |
| WO | WO 2007/024944 | 3/2007 |
| WO | WO 2007/030362 | 3/2007 |
| WO | WO 2007/030680 | 3/2007 |
| WO | WO 2007/060110 | 5/2007 |

(56) References Cited

FOREIGN PATENT DOCUMENTS

| | | |
|---|---|---|
| WO | WO 2007/067506 | 6/2007 |
| WO | WO 2007/076473 | 7/2007 |
| WO | WO 2007/084314 | 7/2007 |
| WO | WO 2007/091948 | 8/2007 |
| WO | WO 2007/105058 | 9/2007 |
| WO | WO 2007/129195 | 11/2007 |
| WO | WO 2007/136465 | 11/2007 |
| WO | WO 2007/138268 | 12/2007 |
| WO | WO 2007/140222 | 12/2007 |
| WO | WO 2008/002245 | 1/2008 |
| WO | WO 2008/005538 | 1/2008 |
| WO | WO 2008/009435 | 1/2008 |
| WO | WO 2008/039359 | 4/2008 |
| WO | WO 2008/064866 | 6/2008 |
| WO | WO 2008/074788 | 6/2008 |
| WO | WO 2008/100457 | 8/2008 |
| WO | WO 2008/124849 | 10/2008 |
| WO | WO 2008/156712 | 12/2008 |
| WO | WO 2009/016460 | 2/2009 |
| WO | WO 2009/017954 | 2/2009 |
| WO | WO 2009/034390 | 3/2009 |
| WO | WO 2009/044788 | 4/2009 |
| WO | WO 2009/061345 | 5/2009 |
| WO | WO 2009/064835 | 5/2009 |
| WO | WO 2009/071701 | 6/2009 |
| WO | WO 2009/076440 | 6/2009 |
| WO | WO 2009/085185 | 7/2009 |
| WO | WO 2009/085230 | 7/2009 |
| WO | WO 2009/089508 | 7/2009 |
| WO | WO 2009/103652 | 8/2009 |
| WO | WO 2009/115572 | 9/2009 |
| WO | WO 2009/124692 | 10/2009 |
| WO | WO 2009/128520 | 10/2009 |
| WO | WO 2009/152027 | 12/2009 |
| WO | WO 2009/158571 | 12/2009 |
| WO | WO 2010/009139 | 1/2010 |
| WO | WO 2010/010154 | 1/2010 |
| WO | WO 2010/072166 | 1/2010 |
| WO | WO 2010/027746 | 3/2010 |
| WO | WO 2010/033495 | 3/2010 |
| WO | WO 2010/036959 | 4/2010 |
| WO | WO 2010/043676 | 4/2010 |
| WO | WO 2010/046780 | 4/2010 |
| WO | WO 2010/075074 | 7/2010 |
| WO | WO 2010/077680 | 7/2010 |
| WO | WO 2010/083207 | 7/2010 |
| WO | WO 2010/087515 | 8/2010 |
| WO | WO 2010/089411 | 8/2010 |
| WO | WO 2010/116270 | 10/2010 |
| WO | WO 2010/129053 | 11/2010 |
| WO | WO 2010/144416 | 12/2010 |
| WO | WO 2011/042389 | 4/2011 |
| WO | WO 2011/043359 | 4/2011 |
| WO | WO 2011/050245 | 4/2011 |
| WO | WO 2011/066342 | 6/2011 |
| WO | WO 2011/075699 | 6/2011 |
| WO | WO 2011/076725 | 6/2011 |
| WO | WO 2011/082400 | 7/2011 |
| WO | WO 2011/090760 | 7/2011 |
| WO | WO 2011/092293 | 8/2011 |
| WO | WO 2011/101409 | 8/2011 |
| WO | WO 2011/130232 | 10/2011 |
| WO | WO 2011/133728 | 10/2011 |
| WO | WO 2011/136247 | 11/2011 |
| WO | WO 2011/141848 | 11/2011 |
| WO | WO 2011/143495 | 11/2011 |
| WO | WO 2011/159877 | 12/2011 |
| WO | WO 2011/161699 | 12/2011 |
| WO | WO 2012/010704 | 1/2012 |
| WO | WO 2012/016993 | 2/2012 |
| WO | WO 2012/061156 | 5/2012 |
| WO | WO 2012/062704 | 5/2012 |
| WO | WO 2012/082580 | 6/2012 |
| WO | WO 2012/107850 | 8/2012 |
| WO | WO 2012/129344 | 9/2012 |
| WO | WO 2012/134943 | 10/2012 |
| WO | WO 2012/175513 | 12/2012 |
| WO | WO 2013/071201 | 5/2013 |
| WO | WO 2013/071232 | 5/2013 |
| WO | WO 2013/103931 | 7/2013 |
| WO | WO 2013/110585 | 8/2013 |
| WO | WO 2013/123215 | 8/2013 |
| WO | WO 2013/130890 | 9/2013 |
| WO | WO 2013/136070 | 9/2013 |
| WO | WO 2013/156608 | 10/2013 |
| WO | WO 2013/169889 | 11/2013 |
| WO | WO 2013/173506 | 11/2013 |
| WO | WO 2014/020043 | 2/2014 |
| WO | WO 2014/028669 | 2/2014 |
| WO | WO 2014/031928 | 2/2014 |
| WO | WO 2014/040555 | 3/2014 |
| WO | WO 2014/060411 | 4/2014 |
| WO | WO 2014/089913 | 6/2014 |
| WO | WO 2014/109858 | 7/2014 |
| WO | WO 2014/130241 | 8/2014 |
| WO | WO 2014/130856 | 8/2014 |
| WO | WO 2014/135422 | 9/2014 |
| WO | WO 2014/155300 | 10/2014 |
| WO | WO 2014/195402 | 11/2014 |
| WO | WO 2014/202493 | 12/2014 |
| WO | WO 2015/006875 | 1/2015 |
| WO | WO 2015/030847 | 3/2015 |
| WO | WO 2015/038417 | 3/2015 |
| WO | WO 2015/047124 | 4/2015 |
| WO | WO 2015/058126 | 4/2015 |
| WO | WO 2015/058140 | 4/2015 |
| WO | WO 2015/058163 | 4/2015 |
| WO | WO 2015/061247 | 4/2015 |
| WO | WO 2015/086503 | 6/2015 |
| WO | WO 2015/095840 | 6/2015 |
| WO | WO 2015/106025 | 7/2015 |
| WO | WO 2015/086506 | 8/2015 |
| WO | WO 2015/154039 | 10/2015 |
| WO | WO 2015/157556 | 10/2015 |
| WO | WO 2015/164614 | 10/2015 |
| WO | WO 2015/172123 | 11/2015 |
| WO | WO 2016/044446 | 3/2016 |
| WO | WO 2016/058544 | 4/2016 |
| WO | WO 2016/134320 | 8/2016 |
| WO | WO 2016/159577 | 10/2016 |
| WO | WO 2016/177340 | 11/2016 |
| WO | WO 2016/180843 | 11/2016 |
| WO | WO 2016/198400 | 12/2016 |
| WO | WO 2017/007658 | 1/2017 |
| WO | WO 2017/021969 | 2/2017 |
| WO | WO 2017/029202 | 2/2017 |
| WO | WO 2017/044889 | 3/2017 |
| WO | WO 2017/075367 | 5/2017 |
| WO | WO 2017/087905 | 5/2017 |
| WO | WO 2017/110863 | 6/2017 |
| WO | WO 2017/137334 | 8/2017 |
| WO | WO 2017/163076 | 9/2017 |
| WO | WO 2017/178510 | 10/2017 |
| WO | WO 2017/178515 | 10/2017 |
| WO | WO 2017/181177 | 10/2017 |
| WO | WO 2017/198685 | 11/2017 |
| WO | WO 2018/005860 | 1/2018 |
| WO | WO 2018/013867 | 1/2018 |
| WO | WO 2018/033815 | 2/2018 |
| WO | WO 2018/050052 | 3/2018 |
| WO | WO 2018/183923 | 4/2018 |
| WO | WO 2018/082587 | 5/2018 |
| WO | WO 2018/086591 | 5/2018 |
| WO | WO 2018/119395 | 6/2018 |
| WO | WO 2018/124001 | 7/2018 |
| WO | WO 2018/141002 | 8/2018 |
| WO | WO 2018/160774 | 9/2018 |
| WO | WO 2018/177403 | 10/2018 |
| WO | WO 2018/195450 | 10/2018 |
| WO | WO 2018/226976 | 12/2018 |
| WO | WO 2019/079596 | 4/2019 |
| WO | WO 2019/079607 | 4/2019 |
| WO | WO 2019/200214 | 10/2019 |
| WO | WO 2019/207463 | 10/2019 |

(56) References Cited

FOREIGN PATENT DOCUMENTS

| WO | WO 2019/246110 | 12/2019 |
|---|---|---|
| WO | WO 2020/006497 | 1/2020 |
| WO | WO 2020/051207 | 3/2020 |
| WO | WO 2020/168178 | 8/2020 |
| WO | WO 2020/223558 | 11/2020 |

OTHER PUBLICATIONS

Atzrodt et al., "The Renaissance of H/D Exchange," Angew Chem Int Ed., 2007, 46(41):7744-7765.

Au-Yeung et al., "Selective Targeting of Cyclin E1-Amplified High-Grade Serous Ovarian Cancer by Cyclin-Dependent Kinase 2 and AKT Inhibition," Clin Cancer Res, Apr. 1, 2017, 23(7):1862-1874.

Barretina et al., "The Cancer Cell Line Encyclopedia enables predictive modelling of anticancer drug sensitivity," Nature, Mar. 28, 2012, 483(7391):603-607.

Barrière et al., "Mice thrive without Cdk4 and Cdk2," Mol Oncol., 2007, 1(1):72-83.

Berge et al., "Pharmaceutical Salts," Journal of Pharmaceutical Science, 1977, 66:1-19.

Binni et al., "Novel and recurrent p14 mutations in Italian familial melanoma," Clin Genet., 2010, 77(6):581-586.

Blank et al., "Synthesis of DL-β-(5-Cytosinyl)alanine," Journal of Organic Chemistry, Aug. 1, 1959, 24(8):1137-1138.

Blom et al., "Preparative LC-MS Purification: Improved Compound Specific Method Optimization," J Combi Chem., 2004, 6(6):874-883.

Blom et al., "Optimizing Preparative LC-MS Configurations and Methods for Parallel Synthesis Purification," J Combi Chem., 2003, 5(5):670-683.

Blom, "Two-pump at-column-dilution configuration for preparative liquid chromatography-mass spectrometry," J Combi Chem., 2002, 4(4):295-301.

Borg et al., "Novel Germline p16 Mutation in Familial Malignant Melanoma in Southern Sweden," Cancer Res., 1996, 56(11):2497-2500.

Bradley et al., "OOMMPPAA: A Tool To Aid Directed Synthesis by the Combined Analysis of Activity and Structural Data," Journal of Chemical Information and Modeling, Oct. 27, 2014, 54(10):2636-2646.

Brasca et al., "Optimization of 6,6-dimethyl pyrrolo[3,4-c]pyrazoles: Identification of PHA-793887, a potent CDK inhibitor suitable for intravenous dosing," BMC, 2010, 18(5):1844-1853.

Brendel et al., "Amyloid-PET predicts inhibition of de novo plaque formation upon chronic γ-secretase modulator treatment," Molecular Psychiatry, Oct. 2015, 20(10):1179-1187.

Brendel et al., "Monitoring of chronic γ-secretase modulator treatment by serial amyloid-PET," Molecular Psychiatry, 2015, 20(10):1141.

Byth et al., "AZD5438, a potent oral inhibitor of cyclin-dependent kinases 1, 2, and 9, leads to pharmacodynamic changes and potent antitumor effects in human tumor xenografts," Mol Can Ther., 2009, 8(7):1856-1866.

Cairns et al., "Frequency of homozygous deletion at p16/CDKN2 in primary human tumours," Nature Genetics, Oct. 1995, 11(2):210-212.

Caldon et al., "Cyclin E2 Overexpression Is Associated with Endocrine Resistance but not Insensitivity to CDK2 Inhibition in Human Breast Cancer Cells," Molec Cancer Therap., 2012, 11(7):1488-1499.

Chen et al., "Selective killing of transformed cells by cyclin/cyclin-dependent kinase 2 antagonists," Proc Natl Acad Sci USA., 1999, 96(8): 4325-4329.

Cho et al., "4-(Pyrazol-4-yl)-pyrimidines as Selective Inhibitors of Cyclin-Dependent Kinase 4/6," Journal of Medicinal Chemistry, Nov. 25, 2010, 53(22):7938-7957.

Cho et al., "Chemo- and regioselective halogenation of 4-(pyrazol-4-yl)-pyrimidines," Tetrahedron Letters, Oct. 14, 2009, 50(41):5762-5764.

Choi et al., "Design and synthesis of 7H-pyrrolo[2,3-d]pyrimidines as focal adhesion kinase inhibitors. Part 1," Bioorganic & Medicinal Chemistry Letters, Apr. 15, 2009, 16(8):2173-2176.

Cicenas et al., "Highlights of the Latest Advances in Research on CDK Inhibitors," Cancers (Basel), 2014, 6(4):2224-2242.

Ciotti et al., "A single genetic origin for the G101W CDKN2A mutation in 20 melanoma-prone families," Am J Hum Genet., 2000, 67:311-319.

Cirstea et al., "Small-molecule multi-targeted kinase inhibitor RGB-286638 triggers P53-dependent and -independent anti-multiple myeloma activity through inhibition of transcriptional CDKs," Leukemia, 2013, 27(12):2366-2375.

ClinVar Accession No. RCV000010017.2, "CDKN2A, 6-BP Del, NT363 AND Cutaneous malignant melanoma 2," Jul. 20, 1995, 1 page.

ClinVar Accession No. RCV000010020.3, "NM_001363763.2(CDKN2A):c.-4+673AGA[3] AND Cutaneous malignant melanoma 2," Jun. 1, 2001, 2 page.

ClinVar Accession No. RCV000010024.5, "CDKN2A, -34G-T AND Cutaneous malignant melanoma 2," Jan. 1, 1999, 1 page.

ClinVar Accession No. RCV000010026.2, "CDKN2A, EXON 1-BETA DEL AND Melanoma and neural system tumor syndrome," Jan. 1, 2001, 1 page.

ClinVar Accession No. RCV000010028.3, "CDKN2A, IVS2, A-G, -105 AND Cutaneous malignant melanoma 2," dated Nov. 1, 2001, 1 page.

ClinVar Accession No. RCV000022943.3, "CDKN2A, IVS1BDS, A-G, +1 AND Cutaneous malignant melanoma 2," dated Jun. 1, 2010, 1 page.

ClinVar Accession No. RCV000030680.6, "CDKN2A, 5-BP DUP, NT19 AND Melanoma-pancreatic cancer syndrome," dated Jun. 1, 2012, 1 page.

Coxon et al., "Cyclin-Dependent Kinase (CDK) Inhibitors: Structure-Activity Relationships and Insights into the CDK-2 Selectivity of 6-Substituted 2-Arylaminopurines," J Med Chem., Mar. 9, 2017, 60(5):1746-1767.

Darling et al., "Inhibition of SIK2 and SIK3 during differentiation enhances the anti-inflammatory phenotype of macrophages," Biochemical Journal, Feb. 15, 2017, 474(4):521-537.

Degorce et al., "Discovery of a Potent, Selective, Orally Bioavailable, and Efficacious Novel 2-(Pyrazol-4-ylamino)-pyrimidine Inhibitor of the Insulin-like Growth Factor-1 Receptor (IGF-1R)," Journal of Medicinal Chemistry, 2016, 59(10):4859-4866.

DePinto et al., "In vitro and in vivo activity of R547: a potent and selective cyclin-dependent kinase inhibitor currently in phase I clinical trials," Mol Can Ther., 2006, 5(11):2644-2658.

Ekholm and Reed., "Regulation of G(1) cyclin-dependent kinases in the mammalian cell cycle," Curr Opin Cell Biol., Dec. 1, 2000, 12(6):676-684.

Ellingboe et al., "Pyrido[2,3-d]pyrimidine Angiotensin II Antagonists," Journal of Medicinal Chemistry, Feb. 1, 1994, 37(4):542-550.

Erb et al., "Transcription control by the ENL YEATS domain in acute leukaemia," Nature, Mar. 1, 2017, 543(7644):270-274.

Etemadmoghadam et al., "Resistance to CDK2 inhibitors is associated with selection of polyploid cells in CCNE1-amplified ovarian cancer," Clin Cancer Res 2013; 19(21):5960-5971.

Etemadmoghadam et al., "Synthetic lethality between CCNE1 amplification and loss of BRCA1," Proc Natl Acad Sci USA., 2013, 110:19489-19494.

Genbank Accession No. GCA_000001405.27, "Genome Reference Consortium Human Build 38 patch release 12 (GRCh38.p12)," dated Dec. 21, 2017, 3 pages.

GenBank Accession No. NM_000077.5, "*Homo sapiens* cyclin dependent kinase inhibitor 2A (CDKN2A), transcript variant 1, mRNA," dated Aug. 10, 2020, 5 pages.

GenBank Accession No. NM_000321, "*Homo sapiens* RB transcriptional corepressor 1 (RB1), mRNA," dated Aug. 10, 2020, 9 pages.

GenBank Accession No. NM_001238, "*Homo sapiens* cyclin E1 (CCNE1), transcript variant 1, mRNA," dated Aug. 2, 2020, 5 pages.

GenBank Accession No. NP_000066.1, "cyclin-dependent kinase 4 [*Homo sapiens*]," dated Aug. 2, 2020, 3 pages.

(56) References Cited

OTHER PUBLICATIONS

GenBank Accession No. NP_000068, "cyclin-dependent kinase inhibitor 2A isoform p16INK4a [*Homo sapiens*]," Aug. 10, 2020, 4 pages.
GenBank Accession No. NP_000312, "retinoblastoma-associated protein [*Homo sapiens*]," dated Aug. 10, 2020, 5 pages.
GenBank Accession No. NP_001229, "G1/S-specific cyclin-E1 isoform 1 [*Homo sapiens*]," dated Aug. 2, 2020, 3 pages.
GenBank Accession No. NP_001231.2, "cyclin-T1 isoform a [*Homo sapiens*]," dated Aug. 2, 2020, 3 pages.
GenBank Accession No. NP_001250.1, "cyclin-dependent kinase 6 [*Homo sapiens*]," dated Jul. 25, 2020, 3 pages.
GenBank Accession No. NP_001777.1, "cyclin-dependent kinase 1 isoform 1 [*Homo sapiens*]," dated Aug. 2, 2020, 4 pages.
GenBank Accession No. NP_114172.1, "G2/mitotic-specific cyclin-B1 isoform 1 [*Homo sapiens*]," dated Jul. 4, 2020, 3 pages.
GenBank Accession No. NP_444284.1, "G1/S-specific cyclin-D1 [*Homo sapiens*]," dated Jul. 25, 2020, 3 pages.
GenBank Accession No. NP_444284.1, "G1/S-specific cyclin-D1 [*Homo sapiens*]," dated Jul. 26, 2020, 3 pages.
Gennaro, "Preformulation," Remington's Pharmaceutical Sciences, 17th ed., Mack Publishing Company, Easton, Pa., 1985, Chapter 76, p. 1418.
Gibson et al., "A novel method for real time quantitative RT-PCR," Genome Res., 1999, 6(10):995-1001.
Goldstein et al., "A common founder for the V126D CDKN2A mutation in seven North American melanoma-prone families," Brit J Cancer., Aug. 17, 2001, 85(4):527-530.
Goldstein et al., "CDKN2A mutations and melanoma risk in the Icelandic population," J Med Genet., 2008, 45(5):284-289.
Gruis et al., "Homozygotes for CDKN2 (p16) germline mutation in Dutch familial melanoma kindreds," Nature Genet., 1995, 10(3):351-353.
Haidle et al., "MARK inhibitors: Declaring a No-Go decision on a chemical series based on extensive DMPK experimentation," Bioorganic & Medicinal Chemistry Letters, 2017, 27(1):109-113.
Harinck et al., "Indication for CDKN2A-mutation analysis in familial pancreatic cancer families without melanomas," J Med Genet., 2012, 49:362-365.
Harland et al., "A deep intronic mutation in CDKN2A is associated with disease in a subset of melanoma pedigrees," Hum Molec Genet., 2001, 10:2679-2686.
Harland et al., "Germline mutations of the CDKN2 gene in UK melanoma families," Hum Molec Genet., 1997, 6(12):2061-2067.
Henley and Dick, "The retinoblastoma family of proteins and their regulatory functions in the mammalian cell division cycle," Cell Div., 2012, 7(1):10.
Herrera-Abreu et al., "Early Adaptation and Acquired Resistance to CDK4/6 Inhibition in Estrogen Receptor-Positive Breast Cancer," Cancer Res., 2016, 76(8):2301-2313.
Hewitt et al., "Germline mutation of ARF in a melanoma kindred," Hum Molec Genet., May 15, 2002, 11(11):1273-1279.
Holderfield et al., "RAF Inhibitors Activate the MAPK Pathway by Relieving Inhibitory Autophosphorylation," Cancer Cell, 2013, 23(5)594-602.
Honda et al., "The structure of cyclin E1/CDK2: implications for CDK2 activation and CDK2-independent roles," Embo J., 2005, 24(3):452-463.
Hsu et al., "Integrated genomic analyses in PDX model reveal a cyclin-dependent kinase inhibitor Palbociclib as a novel candidate drug for nasopharyngeal carcinoma," J Exp Clin Cancer Res., 2018, 37(1):233.
Hu et al., "Specific CP110 Phosphorylation Sites Mediate Anaphase Catastrophe after CDK2 Inhibition: Evidence for Cooperation with USP33 Knockdown," Mol Cancer Ther., 2015, 14(11):2576-2585.
International Search Report in International Application No. PCT/US2020/018271, dated Jul. 21, 2020, 21 pages.
International Search Report in International Application No. PCT/US2020/018299, dated May 13, 2020, 17 pages.
International Search Report in International Application No. PCT/US2020/020946, dated May 18, 2020, 18 pages.
International Search Report in International Application No. PCT/US2020/025335, dated Jun. 16, 2020, 15 pages.
International Search Report in International Application No. PCT/US2020/030689, dated Jun. 23, 2020, 15 pages.
International Search Report in International Application No. PCT/US2020/030851, dated Jul. 9, 2020, 19 pages.
Invitation to Pay Fees in International Application No. PCT/US2020/018271, dated May 20, 2020, 13 pages.
Jiang et al., "Requirement of Cyclin E-Cdk2 Inhibition in p16INK4a-Mediated Growth Suppression," Mol Cell Bio., Sep. 1998, 18(9):5284-5290.
Johns et al., "Pyrazolopyridine antiherpetics: SAR of C2' and C7 amine substituents," Bioorganic & Medicinal Chemistry, Apr. 1, 2005, 13(7):2397-2411.
Kamb et al., "A cell cycle regulator potentially involved in genesis of many tumor types," Science, 1994, 264:436-440.
Kannengiesser et al., "New founder germline mutations of CDKN2A in melanoma-prone families and multiple primary melanoma development in a patient receiving levodopa treatment," Genes Chromosomes Cancer, 2007, 46(8):751-760.
Katritzky et al., "QSAR modeling of the inhibition of Glycogen Synthase Kinase-3," Bioorganic & Medicinal Chemistry, Jul. 15, 2006, 14(14):4987-5002.
Katz et al., "Structure guided design of a series of selective pyrrolopyrimidinone MARK inhibitors," Bioorganic & Medicinal Chemistry Letters, Jan. 1, 2017, 27(1):114-120.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Keyomarsi et al., "Cyclin E and survival in patients with breast cancer," N Engl J Med., 2002, 347(20):1566-1575.
Kukurba et al., "RNA Sequencing and Analysis," Cold Spring Harbor Protocols., 2015, (11):951-969.
Liggett and Sidransky, "Role of the p16 tumor suppressor gene in cancer," Biology of Neoplasia, Journal of Oncology, 1998, 16(3):1197-1206.
Liu et al., "Germline p16INK4A mutation and protein dysfunction in a family with inherited melanoma," Oncogene, 1995, 11(2):405-412.
Liu et al., "Mutation of the CDKN2A 5' UTR creates an aberrant initiation codon and predisposes to melanoma," Nature Genet., 1999, 21:128-132.
Liu et al., "Construction of the pharmacophore model of glycogen synthase kinase-3 inhibitors," Chinese Journal of Chemistry, 2007, 25(7):892-897.
Malinkova et al., "Cyclin-dependent Kinase Inhibitors for Cancer Therapy: A Patent Review (2009-2014)," Expert Opin Ther Pat., Jul. 10, 2015, 25(9):953-970.
Malumbres et al., "Mammalian cells cycle without the D-type cyclin-dependent kinases Cdk4 and Cdk6," Cell, Aug. 20, 2004, 118(4):493-504.
Markwalder et al., "Synthesis and biological evaluation of 1-aryl-4,5-dihydro-1H-pyrazolo[3,4-d]pyrimidin-4-one inhibitors of cyclin-dependent kinases," J Med Chem., 2004, 47(24):5894-5911.
McDonald et al., "Project Drive: A Compendium of Cancer Dependencies and Synthetic Lethal Relationships Uncovered by Large-Scale, Deep RNAi Screening," Cell, Jul. 27, 2017, 170(3):577-592.
Mendoza et al., "Selective cyclin-dependent kinase 2/cyclin A antagonists that differ from ATP site inhibitors block tumor growth," Cancer Res., 2003, 63(5):1020-1024.
Misra et al., "N-(cycloalkylamino)acyl-2-aminothiazole inhibitors of cyclin-dependent kinase 2. N-[5-[[[5-(1,1-dimethylethyl)-2-oxazolyl]methyl]thio]-2-thiazolyl]-4- piperidinecarboxamide (BMS-387032), a highly efficacious and selective antitumor agent," J Med Chem., 2004, 47(7):1719-1728.
Molenaar et al., "Inactivation of CDK2 is synthetically lethal to MYCN over-expressing cancer cells," Proc Natl Acad Sci USA., Aug. 4, 2009, 106(31):12968-12973.
Monzon et al., "CDKN2A mutations in multiple primary melanomas," New Eng J Med., 1998, 338(13):879-887.

(56) References Cited

OTHER PUBLICATIONS

Morgan., "Cyclin-dependent kinases: engines, clocks, and microprocessors," Annu Rev Cell Dev Biol., Nov. 1997, 13:261-291.
Najjar et al., "Computer-aided design, synthesis and biological characterization of novel inhibitors for PKMYT1," European Journal of Medicinal Chemistry, Jan. 1, 2019, 161:479-492.
Nakayama et al., "Gene amplification CCNE1 is related to poor survival and potential therapeutic target in ovarian cancer," Cancer, 2010, 116(11):2621-2634.
Nishino et al., "Reaction mechanism of 2-dimethoxymethyl-3-methoxypropionitrile with acetamidine. I. Revised structure of the intermediate," Bulletin of the Chemical Society of Japan, 1972, 45(4):1127-1132.
Nishino et al., "The Reaction of 2-dimethoxymethyl-3-methoxypropionitrile with acetamidine. Isolation of unusual products," Tetrahedron Letters, 1969, 10(23):1825-1828.
Noel et al., "Efficient Methodology for the Synthesis of 3-Amino-1,2,4-triazoles," Journal of Organic Chemistry, 2009, 74(19):7595-7597.
Norman, "The use of salt-inducible kinase inhibitors to treat autoimmune and inflammatory diseases: evaluation of WO 2013136070," Expert Opinion on Therapeutic Patents, 2014, 24(8):943-946.
Ohtsubo et al., "Human cyclin E, a nuclear protein essential for the G1-to-S phase transition," Mol Cell Biol., 1995, 15:2612-2624.
Okamoto et al., "Mutations and altered expression of p16INK4 in human cancer," PNAS, 1994, 91(23):11045-11049.
Park et al., "Homogeneous proximity tyrosine kinase assays: scintillation proximity assay versus homogeneous time-resolved fluorescence," Analytical Biochemistiy, 1999, 269(1):94-104.
Peturssion et al., "Protecting Groups in Carbohydrate Chemistry," J Chem Educ., 1997, 74(11):1297.
Pevarello et al., "3-Aminopyrazole inhibitors of CDK2/cyclin A as antitumor agents. 2. Lead optimization," J Med Chem., 2005, 48(8):2944-2956.
Platzer et al., "Identification of PKMYT1 inhibitors by screening the GSK published protein kinase inhibitor set I and II," Bioorganic & Medicinal Chemistry, 2018, 26(14):4014-4024.
Pollock et al., "Haplotype analysis of two recurrent CDKN2A mutations in 10 melanoma families: evidence for common founders and independent mutations," Hum Mutat., 1998, 11(6):424-431.
ProQinase, "CDK4/CycD1 cyclin dependent kinase 4," product # 0142-0143-1, 2 pages.
ProQinase, "CDK6/CycD1 cyclin dependent kinase 6,"product# 0051-0143-2, 2 pages.
Randerson-Moor et al., "A germline deletion of p14(ARF) but not CDKN2A in a melanoma-neural system tumour syndrome family," Hum Molec Genet., 2001, 10:55-62.
RefSNP Accession No. rsl04894094, dated Apr. 21, 2020, 14 pages.
RefSNP Accession No. rsl04894095, dated Apr. 21, 2020, 12 pages.
RefSNP Accession No. rsl04894097, dated Apr. 21, 2020, 12 pages.
RefSNP Accession No. rsl04894098, dated Apr. 21, 2020, 9 pages.
RefSNP Accession No. rsl04894104, dated Apr. 21, 2020, 10 pages.
RefSNP Accession No. rsl04894109, dated Apr. 21, 2020, 10 pages.
RefSNP Accession No. rsl13798404, dated Apr. 21, 2020, 10 pages.
RefSNP Accession No. rsl21913388, dated Apr. 21, 2020, 11 pages.
RefSNP Accession No. rsl37854599, dated Apr. 21, 2020, 10 pages.
RefSNP Accession No. rs587776716, dated Apr. 21, 2020, 9 pages.
RefSNP Accession No. rs587780668, dated Apr. 21, 2020, 12 pages.
Rosen et al., "Cyclin E expression is correlated with tumor progression and predicts a poor prognosis in patients with ovarian carcinoma," Cancer, 2006, 106(9):1925-1932.
Sanderson et al., "BI 885578, a Novel IGF1R/INSR Tyrosine Kinase Inhibitor with Pharmacokinetic Properties That Dissociate Antitumor Efficacy and Perturbation of Glucose Homeostasis," Molecular Cancer Therapeutics, 2015, 14(12):2762-2772.
Santamaria et al., "Cdk1 is sufficient to drive the mammalian cell cycle," Nature, 2007, 448(7155):811-815.
Scaltriti et al., "Cyclin E amplification/overexpression is a mechanism of trastuzumab resistance in HER2+breast cancer patients," Proc Natl Acad Sci USA., 2011, 108(9):3761-3766.

SciFinder Search A, dated Mar. 25, 2019, 99 pages.
SciFinder Search A, dated Aug. 2, 2019, 24 pages.
SciFinder Search A, dated Jan. 8, 2019, 833 pages.
SciFinder Search A, dated Mar. 13, 2019, 3 pages.
SciFinder Search B, dated Aug. 2, 2019 8 pages.
SciFinder Search B, dated Jan. 8, 2019, 97 pages.
SciFinder Search B, dated Jul. 15, 2019 16 pages.
SciFinder Search B, dated Mar. 13, 2019, 2 pages.
SciFinder Search B, dated Mar. 25, 2019 42 pages.
SciFinder Search C, dated Aug. 2, 2019, 20 pages.
SciFinder Search C, dated Jan. 8, 2019 92 pages.
SciFinder Search C, dated Mar. 25, 2019, 30 pages.
SciFinder Search D, dated Aug. 2, 2019, 149 pages.
SciFinder Search, dated Dec. 18, 2018 44 pages.
SciFinder Search, dated Mar. 8, 2019, 1 page.
SciFinder Search, dated Jul. 15, 2015, 63 pages.
Sherr, "Cancer cell cycles," Science, 1996, 274(5293):1672-1677.
Siemeister et al., "Molecular and pharmacodynamic characteristics of the novel multi-target tumor growth inhibitor ZK 304709," Biomed Pharmacother., 2006, 60(6):269-272.
Sonawane et al., "Cyclin Dependent Kinase 9 Inhibitors for Cancer Therapy," J Med Chem., 2016, 59:8667-8684.
Takada et al., "FBW7 Loss Promotes Chromosomal Instability and Tumorigenesis via Cyclin E1/CDK2-Mediated Phosphorylation of CENP-A," Cancer Res, 2017, 77(18):4881-4893.
Tan et al., "Development of Selective Covalent Janus Kinase 3 Inhibitors," Journal of Medicinal Chemistry, 2015, 58(16):6589-6606.
Tavares et al., "N-Phenyl-4-pyrazolo[l,5-b]pyridazin-3-ylpyrimidin-2-amines as Potent and Selective Inhibitors of Glycogen Synthase Kinase 3 with Good Cellular Efficacy," Journal of Medicinal Chemistry, 2004, 47(19):4716-4730.
Tong et al., "Pyrimidine-Based Tricyclic Molecules as Potent and Orally Efficacious Inhibitors of Wee 1 Kinase," ACS Med Chem Lett., Jan. 8, 2015, 6(1):58-62.
Toumi et al., "Concise, flexible syntheses of 4-(4-imidazolyl)pyrimidine cyclin-dependent kinase 2 (CDK2) inhibitors," Tetrahedron Letters, 2010, 51(47):6126-6128.
Turner et al., "Abstract CT039: Cyclin E1 (CCNE1) expression associates with benefit from palbociclib in metastatic breast cancer (MBC) in the PALOMA3 trial," Proceedings: AACR Annual Meeting, Apr. 14-18, 2018, Chicago, IL, 78(13):CT0139 (Abstract Only).
UniProtKB Accession No. P06400, "Retinoblastoma-associated protein," Jun. 17, 2020, 21 pages.
UniProtKB Accession No. P24864, "G1/S-specific cyclin-E1," dated Jun. 17, 2020, 7 pages.
UniProtKB Accession No. P42771, "Cyclin-dependent kinase inhibitor 2A," dated Jun. 17, 2020, 14 pages.
Wang et al., "2-Anilino-4-(thiazol-5-yl)pyrimidine CDK inhibitors: synthesis, SAR analysis, X-ray crystallography, and biological activity," J Med Chem., 2004, 47(7):1662-1675.
Ward et al., "Structure- and Reactivity-Based Development of Covalent Inhibitors of the Activating and Gatekeeper Mutant Forms of the Epidermal Growth Factor Receptor (EGFR)," Journal of Medicinal Chemistry, 2013, 56(17):7025-7048.
Wityak et al., "Lead Optimization toward Proof-of-Concept Tools for Huntington's Disease within a 4-(1H-Pyrazol-4-y1)pyrimidine Class of Pan-JNK Inhibitors," Journal of Medicinal Chemistry, 2015, 58(7):2967-2987.
Wyatt et al., "Identification of N-(4-piperidinyl)-4-(2,6-dichlorobenzoylamino)-1H-pyrazole-3-carboxamide (AT7519), a novel cyclin dependent kinase inhibitor using fragment-based X-ray crystallography and structure based drug design," J Med Chem., 2008, 51(16):4986-4999.
Xiao et al., "Inhibitory mode of N-phenyl-4-pyrazolo[1,5-b] pyridazin-3-ylpyrimidin-2-amine series derivatives against GSK-3: molecular docking and 3D-QSAR analyses," Protein Engineering, Design & Selection, 2006, 19(2)47-54.
Xu et al., "Design, synthesis and biological evaluation of deuterated nintedanib for improving pharmacokinetic properties," J Label Compd Radiopharm., 2015, 58(7):308-312.
Xu et al., "Mechanism of Cdk2/Cyclin E inhibition by p27 and p27 phosphorylation," Biochemistry, 1999, 38(27):8713-8722.

(56) References Cited

OTHER PUBLICATIONS

Yarbrough et al., "Biologic and biochemical analyses of p16(INK4a) mutations from primary tumors," Journal of the National Cancer Institute, 1999, 91(18):1569-1574.

Zhang et al., "AG-024322 is a multi-targeted CDK inhibitor with potent antitumor activity in vivo," Cancer Res., 2005, 65(9):1044-1045.

Zhang et al., "Quantitative RT-PCR Methods for Evaluating Toxicant-Induced Effects on Steroidogenesis Using the H295R Cell Line," Environ Sci Technol., 2005, 39(8):2777-2785.

Zhang et al., "4-(pyrimidin-2-ylamino)benzamide derivatives: design, synthesis, and hedgehog signaling pathway inhibition study," Youji Huaxue, 2014, 34(7):1407-1416 (English Abstract).

International Search Report and Written Opinion in International Application No. PCT/US2020/055033, dated Jan. 11, 2021, 18 pages.

Traquandi et al., "Identification of Potent Pyrazolo[4,3-h]quinazoline-3-carboxamides as Multi-Cyclin-Dependent Kinase Inhibitors," J Med Chem., 2010, 53(5):2171-2187.

Dong et al., "Increased expression of cyclin-dependent kinase inhibitor 2 (CDKN2A) gene product P16 INK4A in ovarian cancer is associated with progression and unfavourable prognosis," Int J Cancer, 1997, 74:57-63.

International Preliminary Report on Patentability in International Application No. PCT/US2020/018271, dated Aug. 10, 2021, 12 pages.

International Preliminary Report on Patentability in International Application No. PCT/US2020/018299, dated Aug. 10, 2021, 8 pages.

International Preliminary Report on Patentability in International Application No. PCT/US2020/020946, dated Aug. 25, 2021, 8 pages.

International Preliminary Report on Patentability in International Application No. PCT/US2020/025335, dated Sep. 28, 2021, 7 pages.

International Preliminary Report on Patentability in International Application No. PCT/US2020/030851, dated Nov. 2, 2021, 9 pages.

International Preliminary Report on Patentability in International Application No. PCT/US2020/030689, dated Nov. 2, 2021, 8 pages.

International Preliminary Report on Patentability in International Application No. PCT/US2020/046078, dated Feb. 8, 2022, 7 pages.

McMahon, "VEGF Receptor Signalling in Tumor Angiogenesis," Oncologist, 2000, 5(Suppl 1):3-10.

Pinedo et al., "Translational Research: The Role of VEGF in Tumor Angiogenesis," Oncologist, 2000, 5(Suppl 1):1-2.

Yang et al., "Cyclin-dependent kinase 2 is an ideal target for ovary tumors with elevated cyclin E1 expression," Oncotarget, 2015, 6(25):20801-20812.

| Cell line | Origins | CCNE1 Amplification | CCNE1 CN |
|---|---|---|---|
| COV318 | Ovary | + | 14 |
| OVCAR3_OVARY | Ovary | + | 10 |
| Fu-OV1 | Ovary | + | 10 |
| KLE | Uterus | + | 7 |
| COV504 | Ovary | - | 1 |
| OV56 | Ovary | - | 2 |
| Igrov1 | Ovary | - | 2 |

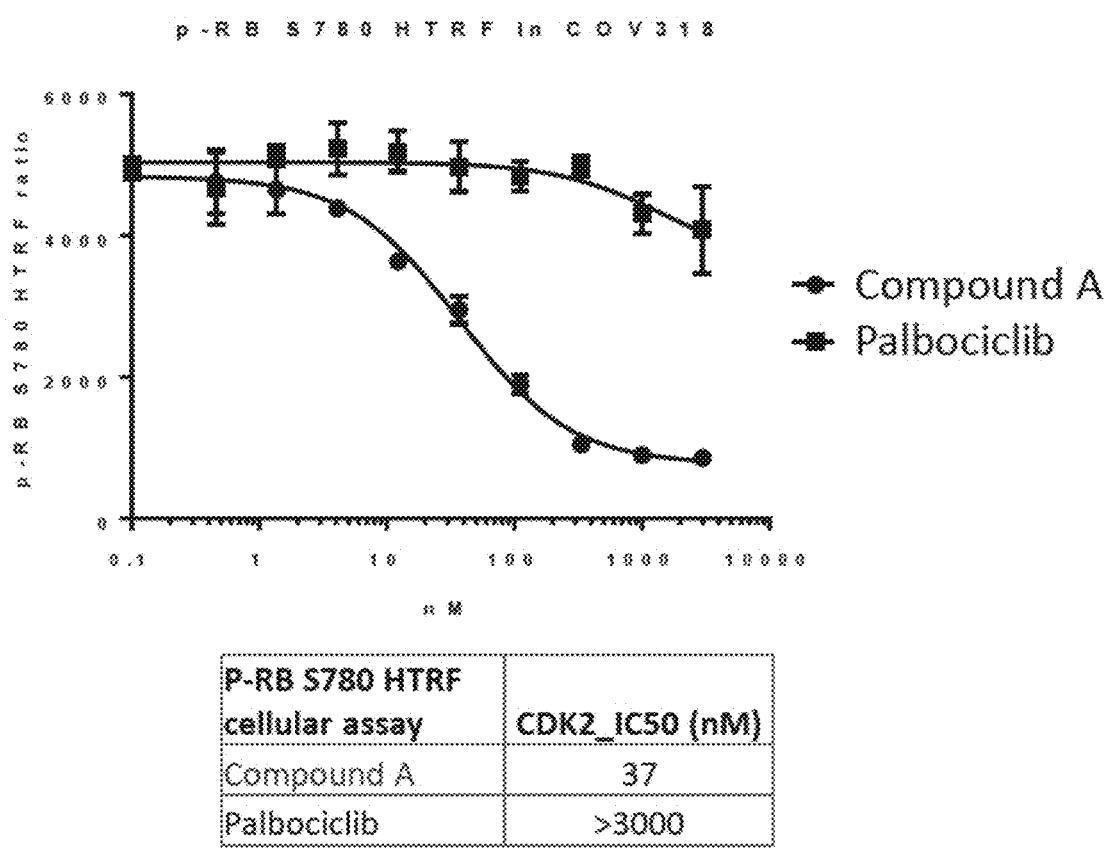

| | Mkn1 | Ags | NCIN87 |
|---|---|---|---|
| CCNE1 Amp | + | + | + |
| P16 Protein | Yes | No | No |

SEQUENCE LISTING

```
<160> NUMBER OF SEQ ID NOS: 8

<210> SEQ ID NO 1
<211> LENGTH: 156
<212> TYPE: PRT
<213> ORGANISM: Homo sapiens

<400> SEQUENCE: 1

Met Glu Pro Ala Ala Gly Ser Ser Met Glu Pro Ser Ala Asp Trp Leu
1               5                   10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60
```

```
Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Gly Gly Thr Arg Gly Ser Asn His Ala Arg
    130                 135                 140

Ile Asp Ala Ala Glu Gly Pro Ser Asp Ile Pro Asp
145                 150                 155
```

<210> SEQ ID NO 2
<211> LENGTH: 410
<212> TYPE: PRT
<213> ORGANISM: Homo sapiens

<400> SEQUENCE: 2

```
Met Pro Arg Glu Arg Arg Glu Arg Asp Ala Lys Glu Arg Asp Thr Met
1               5                   10                  15

Lys Glu Asp Gly Gly Ala Glu Phe Ser Ala Arg Ser Arg Lys Arg Lys
                20                  25                  30

Ala Asn Val Thr Val Phe Leu Gln Asp Pro Asp Glu Glu Met Ala Lys
            35                  40                  45

Ile Asp Arg Thr Ala Arg Asp Gln Cys Gly Ser Gln Pro Trp Asp Asn
        50                  55                  60

Asn Ala Val Cys Ala Asp Pro Cys Ser Leu Ile Pro Thr Pro Asp Lys
65                  70                  75                  80

Glu Asp Asp Arg Val Tyr Pro Asn Ser Thr Cys Lys Pro Arg Ile
                85                  90                  95

Ile Ala Pro Ser Arg Gly Ser Pro Leu Pro Val Leu Ser Trp Ala Asn
            100                 105                 110

Arg Glu Glu Val Trp Lys Ile Met Leu Asn Lys Glu Lys Thr Tyr Leu
        115                 120                 125

Arg Asp Gln His Phe Leu Glu Gln His Pro Leu Leu Gln Pro Lys Met
    130                 135                 140

Arg Ala Ile Leu Leu Asp Trp Leu Met Glu Val Cys Glu Val Tyr Lys
145                 150                 155                 160

Leu His Arg Glu Thr Phe Tyr Leu Ala Gln Asp Phe Phe Asp Arg Tyr
                165                 170                 175

Met Ala Thr Gln Glu Asn Val Val Lys Thr Leu Leu Gln Leu Ile Gly
            180                 185                 190

Ile Ser Ser Leu Phe Ile Ala Ala Lys Leu Glu Glu Ile Tyr Pro Pro
        195                 200                 205

Lys Leu His Gln Phe Ala Tyr Val Thr Asp Gly Ala Cys Ser Gly Asp
    210                 215                 220

Glu Ile Leu Thr Met Glu Leu Met Ile Met Lys Ala Leu Lys Trp Arg
225                 230                 235                 240

Leu Ser Pro Leu Thr Ile Val Ser Trp Leu Asn Val Tyr Met Gln Val
                245                 250                 255

Ala Tyr Leu Asn Asp Leu His Glu Val Leu Leu Pro Gln Tyr Pro Gln
            260                 265                 270

Gln Ile Phe Ile Gln Ile Ala Glu Leu Leu Asp Leu Cys Val Leu Asp
        275                 280                 285
```

```
Val Asp Cys Leu Glu Phe Pro Tyr Gly Ile Leu Ala Ser Ala Leu
    290                 295                 300

Tyr His Phe Ser Ser Ser Glu Leu Met Gln Lys Val Ser Gly Tyr Gln
305                 310                 315                 320

Trp Cys Asp Ile Glu Asn Cys Val Lys Trp Met Val Pro Phe Ala Met
                325                 330                 335

Val Ile Arg Glu Thr Gly Ser Ser Lys Leu Lys His Phe Arg Gly Val
            340                 345                 350

Ala Asp Glu Asp Ala His Asn Ile Gln Thr His Arg Asp Ser Leu Asp
        355                 360                 365

Leu Leu Asp Lys Ala Arg Ala Lys Lys Ala Met Leu Ser Glu Gln Asn
    370                 375                 380

Arg Ala Ser Pro Leu Pro Ser Gly Leu Leu Thr Pro Pro Gln Ser Gly
385                 390                 395                 400

Lys Lys Gln Ser Ser Gly Pro Glu Met Ala
                405                 410

<210> SEQ ID NO 3
<211> LENGTH: 928
<212> TYPE: PRT
<213> ORGANISM: Homo sapiens

<400> SEQUENCE: 3

Met Pro Pro Lys Thr Pro Arg Lys Thr Ala Ala Thr Ala Ala Ala Ala
1               5                   10                  15

Ala Ala Glu Pro Pro Ala Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
```

-continued

```
                245                 250                 255
Gln Asn Arg Ser Ala Arg Ile Ala Lys Gln Leu Glu Asn Asp Thr Arg
            260                 265                 270
Ile Ile Glu Val Leu Cys Lys Glu His Glu Cys Asn Ile Asp Glu Val
            275                 280                 285
Lys Asn Val Tyr Phe Lys Asn Phe Ile Pro Phe Met Asn Ser Leu Gly
            290                 295                 300
Leu Val Thr Ser Asn Gly Leu Pro Glu Val Glu Asn Leu Ser Lys Arg
305                 310                 315                 320
Tyr Glu Glu Ile Tyr Leu Lys Asn Lys Asp Leu Asp Ala Arg Leu Phe
                325                 330                 335
Leu Asp His Asp Lys Thr Leu Gln Thr Asp Ser Ile Asp Ser Phe Glu
            340                 345                 350
Thr Gln Arg Thr Pro Arg Lys Ser Asn Leu Asp Glu Val Asn Val
            355                 360                 365
Ile Pro Pro His Thr Pro Val Arg Thr Val Met Asn Thr Ile Gln Gln
370                 375                 380
Leu Met Met Ile Leu Asn Ser Ala Ser Asp Gln Pro Ser Glu Asn Leu
385                 390                 395                 400
Ile Ser Tyr Phe Asn Asn Cys Thr Val Asn Pro Lys Glu Ser Ile Leu
                405                 410                 415
Lys Arg Val Lys Asp Ile Gly Tyr Ile Phe Lys Glu Lys Phe Ala Lys
            420                 425                 430
Ala Val Gly Gln Gly Cys Val Glu Ile Gly Ser Gln Arg Tyr Lys Leu
            435                 440                 445
Gly Val Arg Leu Tyr Tyr Arg Val Met Glu Ser Met Leu Lys Ser Glu
            450                 455                 460
Glu Glu Arg Leu Ser Ile Gln Asn Phe Ser Lys Leu Leu Asn Asp Asn
465                 470                 475                 480
Ile Phe His Met Ser Leu Leu Ala Cys Ala Leu Glu Val Val Met Ala
                485                 490                 495
Thr Tyr Ser Arg Ser Thr Ser Gln Asn Leu Asp Ser Gly Thr Asp Leu
            500                 505                 510
Ser Phe Pro Trp Ile Leu Asn Val Leu Asn Leu Lys Ala Phe Asp Phe
            515                 520                 525
Tyr Lys Val Ile Glu Ser Phe Ile Lys Ala Glu Gly Asn Leu Thr Arg
            530                 535                 540
Glu Met Ile Lys His Leu Glu Arg Cys Glu His Arg Ile Met Glu Ser
545                 550                 555                 560
Leu Ala Trp Leu Ser Asp Ser Pro Leu Phe Asp Leu Ile Lys Gln Ser
                565                 570                 575
Lys Asp Arg Glu Gly Pro Thr Asp His Leu Glu Ser Ala Cys Pro Leu
            580                 585                 590
Asn Leu Pro Leu Gln Asn Asn His Thr Ala Ala Asp Met Tyr Leu Ser
            595                 600                 605
Pro Val Arg Ser Pro Lys Lys Lys Gly Ser Thr Thr Arg Val Asn Ser
            610                 615                 620
Thr Ala Asn Ala Glu Thr Gln Ala Thr Ser Ala Phe Gln Thr Gln Lys
625                 630                 635                 640
Pro Leu Lys Ser Thr Ser Leu Ser Leu Phe Tyr Lys Lys Val Tyr Arg
                645                 650                 655
Leu Ala Tyr Leu Arg Leu Asn Thr Leu Cys Glu Arg Leu Leu Ser Glu
            660                 665                 670
```

```
His Pro Glu Leu Glu His Ile Ile Trp Thr Leu Phe Gln His Thr Leu
            675                 680                 685
Gln Asn Glu Tyr Glu Leu Met Arg Asp Arg His Leu Asp Gln Ile Met
        690                 695                 700
Met Cys Ser Met Tyr Gly Ile Cys Lys Val Lys Asn Ile Asp Leu Lys
705                 710                 715                 720
Phe Lys Ile Ile Val Thr Ala Tyr Lys Asp Leu Pro His Ala Val Gln
                725                 730                 735
Glu Thr Phe Lys Arg Val Leu Ile Lys Glu Glu Tyr Asp Ser Ile
                740                 745                 750
Ile Val Phe Tyr Asn Ser Val Phe Met Gln Arg Leu Lys Thr Asn Ile
                755                 760                 765
Leu Gln Tyr Ala Ser Thr Arg Pro Pro Thr Leu Ser Pro Ile Pro His
            770                 775                 780
Ile Pro Arg Ser Pro Tyr Lys Phe Pro Ser Pro Leu Arg Ile Pro
785                 790                 795                 800
Gly Gly Asn Ile Tyr Ile Ser Pro Leu Lys Ser Pro Tyr Lys Ile Ser
                805                 810                 815
Glu Gly Leu Pro Thr Pro Thr Lys Met Thr Pro Arg Ser Arg Ile Leu
            820                 825                 830
Val Ser Ile Gly Glu Ser Phe Gly Thr Ser Glu Lys Phe Gln Lys Ile
            835                 840                 845
Asn Gln Met Val Cys Asn Ser Asp Arg Val Leu Lys Arg Ser Ala Glu
            850                 855                 860
Gly Ser Asn Pro Pro Lys Pro Leu Lys Lys Leu Arg Phe Asp Ile Glu
865                 870                 875                 880
Gly Ser Asp Glu Ala Asp Gly Ser Lys His Leu Pro Gly Glu Ser Lys
                885                 890                 895
Phe Gln Gln Lys Leu Ala Glu Met Thr Ser Thr Arg Thr Arg Met Gln
            900                 905                 910
Lys Gln Lys Met Asn Asp Ser Met Asp Thr Ser Asn Lys Glu Glu Lys
            915                 920                 925

<210> SEQ ID NO 4
<211> LENGTH: 1306
<212> TYPE: DNA
<213> ORGANISM: Artificial Sequence
<220> FEATURE:
<223> OTHER INFORMATION: Synthetic polynucleotide

<400> SEQUENCE: 4
cctcgaattc agctgcatgg agaacttcca aaaggtggaa agatcggag agggcacgta      60
cggagttgtg tacaaagcca gaaacaagtt gacgggagag gtggtggcgc ttaagaaaat     120
ccgcctggac actgagactg agggtgtgcc cagtactgcc atccgagaga tctctctgct     180
taaggagctt aaccatccta atattgtcaa gctgctggat gtcattcaca cagaaaataa     240
actctacctg gttttgaat tctgcaccca agatctcaag aaattcatgg atgcctctgc     300
tctcactggc attcctcttc ccctcatcaa gagctatctg ttccagctgc tccagggcct     360
agctttctgc cattctcatc gggtcctcca ccgagaccttt aaacctcaga atctgcttat     420
taacacagag ggggccatca agctagcaga ctttggacta gccagagctt tggagtacc     480
tgttcgtact tacacccatg aagtggtgac cctgtggtac cgagctcctg aaatcctcct     540
gggctgcaaa tattattcca cagctgtgga catctggagc ctgggctgca tctttgctga    600
```

-continued

```
gatggtgact cgccgggccc tattccctgg agattctgag attgaccagc tctttcggat    660
ctttcggact ctggggaccc cagatgaggt ggtgtggcca ggagttactt ctatgcctga    720
ttacaagcca agtttcccca agtgggcccg gcaagatttt agtaaagttg tacctccct    780 ggatgaagat ggacggagct tgttatcgca aatgctgcac tacgacccta acaagcggat    840
ttcggccaag gcagccctgg ctcacccttt cttccaggat gtgaccaagc cagtacccca    900
tcttcgactc ggagtgcagg tggaaaccat ctccccagga gacgggcgca ccttccccaa    960
gcgcggccag acctgcgtgg tgcactacac cgggatgctt gaagatggaa agaaagttga    1020
ttcctcccgg gacagaaaca agccctttaa gtttatgcta ggcaagcagg aggtgatccg    1080
aggctgggaa gaaggggttg cccagatgag tgtgggtcag agagccaaac tgactatatc    1140
tccagattat gcctatggtg ccactgggca cccaggcatc atcccaccac atgccactct    1200
cgtcttcgat gtggagcttc taaaactgga aggatacct tacgacgttc ctgattacgc    1260
ttacccttac gacgttcctg attacgctgg atcctaattc gaaagc              1306
```

```
<210> SEQ ID NO 5
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 5 gaattc                                                                6

<210> SEQ ID NO 6
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 6 ggatcc                                                                6

<210> SEQ ID NO 7
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 7 ttcgaa                                                                6

<210> SEQ ID NO 8
<211> LENGTH: 18
<212> TYPE: DNA
<213> ORGANISM: Homo sapiens

<400> SEQUENCE: 8
aagcagagat ctctcgga                                                  18
```

TRICYCLIC AMINE COMPOUNDS AS CDK2 INHIBITORS

This application claims the benefit of priority of U.S. Prov. Appl. No. 62/841,669, filed May 1, 2019, which is incorporated herein by reference in its entirety.

SEQUENCE LISTING

The instant application contains a Sequence Listing which has been filed electronically in ASCII format and is hereby incorporated by reference in its entirety. Said ASCII copy, created on Apr. 23, 2020, is named 20443-0606001_SL.txt and is 15.3 kilobytes in size.

TECHNICAL FIELD

This application is directed to tricyclic amine compounds which inhibit cyclin-dependent kinase 2 (CDK2) and are useful for treating cancer.

BACKGROUND

Cyclin-dependent kinases (CDKs) are a family of serine/threonine kinases. Heterodimerized with regulatory subunits known as cyclins, CDKs become fully activated and regulate key cellular processes including cell cycle progression and cell division (Morgan, D. O., *Annu Rev Cell Dev Biol*, 1997, 13:261-91). Uncontrolled proliferation is a hallmark of cancer cells. The deregulation of the CDK activity is associated with abnormal regulation of cell-cycle, and is detected in virtually all forms of human cancers (Sherr, C. J., *Science*, 1996, 274(5293):1672-7).

CDK2 is of particular interest because deregulation of CDK2 activity occurs frequently in a variety of human cancers. CDK2 plays a crucial role in promoting G1/S transition and S phase progression. In complex with cyclin E (CCNE), CDK2 phosphorylates retinoblastoma pocket protein family members (p107, p130, pRb), leading to de-repression of E2F transcription factors, expression of G1/S transition related genes and transition from G1 to S phase (Henley, S. A. and F. A. Dick, *Cell Div*, 2012, 7(1):10). This in turn enables activation of CDK2/cyclin A, which phosphorylates endogenous substrates that permit DNA synthesis, replication and centrosome duplication (Ekholm, S. V. and S. I. Reed, *Curr Opin Cell Biol*, 2000, 12(6):676-84). It has been reported that the CDK2 pathway influences tumorigenesis mainly through amplification and/or overexpression of CCNE1 and mutations that inactivate CDK2 endogenous inhibitors (e.g., p27), respectively (Xu, X., et al., *Biochemistry*, 1999, 38(27):8713-22).

CCNE1 copy-number gain and overexpression have been identified in ovarian, gastric, endometrial, breast and other cancers and been associated with poor outcomes in these tumors (Keyomarsi, K., et al., *N Engl J Med*, 2002, 347(20): 1566-75; Nakayama, N., et al., *Cancer*, 2010, 116(11):2621-34; Au-Yeung, G., et al., *Clin Cancer Res*, 2017, 23(7):1862-1874; Rosen, D. G., et al., *Cancer*, 2006, 106(9):1925-32). Amplification and/or overexpression of CCNE1 also reportedly contribute to trastuzumab resistance in HER2+ breast cancer and resistance to CDK4/6 inhibitors in estrogen receptor-positive breast cancer (Scaltriti, M., et al., *Proc Natl Acad Sci USA*, 2011, 108(9):3761-6; Herrera-Abreu, M. T., et al., *Cancer Res*, 2016, 76(8):2301-13). Various approaches targeting CDK2 have been shown to induce cell cycle arrest and tumor growth inhibition (Chen, Y N., et al., *Proc Natl Acad Sci USA*, 1999, 96(8):4325-9; Mendoza, N., et al., *Cancer Res*, 2003, 63(5):1020-4). Inhibition of CDK2 also reportedly restores sensitivity to trastuzumab treatment in resistant HER2+ breast tumors in a preclinical model (Scaltriti, supra).

These data provide a rationale for considering CDK2 as a potential target for new drug development in cancer associated with deregulated CDK2 activity. In the last decade there has been increasing interest in the development of CDK selective inhibitors. Despite significant efforts, there are no approved agents targeting CDK2 to date (Cicenas, J., et al., *Cancers (Basel)*, 2014, 6(4):2224-42). Therefore it remains a need to discover CDK inhibitors having novel activity profiles, in particular those targeting CDK2. This application is directed to this need and others.

SUMMARY

The present invention relates to, inter alia, compounds of Formula (I):

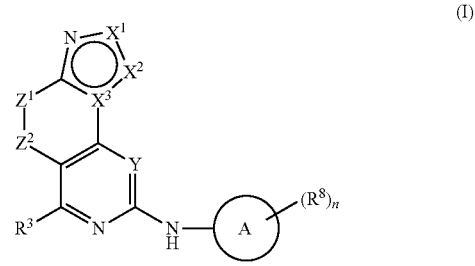

or a pharmaceutically acceptable salt thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting CDK2, comprising contacting the CDK2 with a compound of Formula (I), or a pharmaceutically acceptable salt thereof.

The present invention further provides methods of inhibiting CDK2 in a patient, comprising administering to the patient a compound of Formula (I), or a pharmaceutically acceptable salt thereof.

The present invention also provides methods of treating a disease or disorder associated with CDK2 in a patient, comprising administering to the patient a therapeutically effective amount of the compound described herein, or a pharmaceutically acceptable salt thereof.

The present invention further provides methods of treating a human subject having a disease or disorder associated with cyclin-dependent kinase 2 (CDK2), comprising administering to the human subject a compound described herein, or a pharmaceutically acceptable salt thereof, wherein the human subject has been previously determined to: (i) (a) have a nucleotide sequence encoding a p16 protein comprising the amino acid sequence of SEQ ID NO:1; and/or (b) have a cyclin dependent kinase inhibitor 2A (CDKN2A) gene lacking one or more inactivating nucleic acid substitutions and/or deletions; (ii) (a) have an amplification of the cyclin E1 (CCNE1) gene; and/or (b) have an expression level of CCNE1 in a biological sample obtained from the human subject that is higher than a control expression level of CCNE1.

The present invention additionally provides methods of treating a human subject having a disease or disorder associated with cyclin-dependent kinase 2 (CDK2), comprising: (i) identifying, in a biological sample obtained from the human subject: (a) a nucleotide sequence encoding a p16 protein comprising the amino acid sequence of SEQ ID NO:1; and/or (b) a cyclin dependent kinase inhibitor 2A (CDKN2A) gene lacking one or more inactivating nucleic acid substitutions; (ii) identifying, in a biological sample obtained from the human subject: (a) an amplification of the cyclin E1 (CCNE1) gene; and/or (b) an expression level of CCNE1 that is higher than a control expression level of CCNE1; and (iii) administering a compound described herein, or a pharmaceutically acceptable salt thereof, to the human subject.

The present invention also provides methods of evaluating the response of a human subject having a disease or disorder associated with cyclin-dependent kinase 2 (CDK2) to a compound described herein, or a pharmaceutically acceptable salt thereof, comprising: (a) administering the compound or the salt, to the human subject, wherein the human subject has been previously determined to have an amplification of the cyclin E1 (CCNE1) gene and/or an expression level of CCNE1 that is higher than a control expression level of CCNE1; (b) measuring, in a biological sample of obtained from the subject subsequent to the administering of step (a), the level of retinoblastoma (Rb) protein phosphorylation at the serine corresponding to amino acid position 780 of SEQ ID NO:3, wherein a reduced level of Rb phosphorylation at the serine corresponding to amino acid position 780 of SEQ ID NO:3, as compared to a control level of Rb phosphorylation at the serine corresponding to amino acid position 780 of SEQ ID NO:3, is indicative that the human subject responds to the compound or the salt.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DESCRIPTION OF DRAWINGS

FIG. 1A: Cell lines used for study included four cell lines with CCNE1 amplification and three cell lines with no CCNE1 amplification. CCNE1 amplification copy numbers are indicated. FIG. 1B: The expression of CCNE1 was determined by Western blot in indicated cell lines. This blot show cell lines with CCNE1 gain of function by copy number (CN>2) expressed higher levels of CCNE1 protein compared with cell lines with copy neutral or loss of function of the gene (CN≤2). GAPDH was detected as a loading control. Non-Amp, non-amplification; Amp, amplification.

FIG. 2A: CCNE1 amplified Fu-ov1 (upper) and KLE (lower) cells were harvested and subjected to cell cycle analysis 72 hours after transfection with either scrambled siRNAs ("Ctl") or CDK2 siRNAs. The cell cycle phase distribution was evaluated by FACS. Shown are representative images of three separate experiments. FIG. 2B: CDK2 knockdown was confirmed by Western blot analysis after transfection with CDK2 siRNA. GAPDH was used as a loading control.

FIG. 3A: CCNE1 non-amplified COV504 and Igrov1 cells were harvested and subjected to cell cycle analysis 72 hours after transfection with Ctl siRNAs and CDK2 siRNAs. The cell cycle phase distribution was evaluated by FACS. Shown are representative images of three separate experiments. FIG. 3B: CDK2 knockdown was confirmed by Western blot analysis after transfection with CDK2 siRNA. GAPDH was used as a loading control.

FIG. 7A: Four CCNE1 Amp cell lines, COV318, Fu-OV1, OVCAR3 and KLE cells, were transfected with CDK2 siRNAs for 72 hours. FIG. 7B: Three CCNE1 Non-Amp cell lines, COV504, OV56 and Igrov1, were transfected with CDK2 siRNAs for 72 hours. The total proteins were extracted from CDK2 siRNA or Ctl siRNA transfected cells and subjected to western blotting. GAPDH was used as a loading control.

FIG. 8A: CCNE1 Amp OVCAR3 and COV318 cells were treated at various concentrations of Palbociclib as indicated for 1 hour or 15 h. FIG. 8B: CCNE1 Non-Amp COV504 and OV56 were treated at various concentrations of Palbociclib as indicated for 1 hour or 15 h. The total proteins were extracted from these Palbociclib or DMSO (controls) treated cells and subjected to western blotting. p-RB, phosphorylated retinoblastoma protein. GAPDH was used as a loading control.

FIG. 9A: Chemical structure of dTAG. FIG. 9B: CDK2-FKBP12(F36V) degradation by CDK2-dTAG treatment for 14 hours inhibited RB phosphorylation at S780 in CDK2 knockout OVCAR3 (right, Cas9+, CDK2-FKBP12(F36V)-HA+, CDK2-gRNA) cells, but not in OVCAR3 cells with endogenous CDK2 (left, Cas9+, CDK2-FKBP12(F36V)-HA+, Ctl-gRNA).

FIGS. 10A-10B: p-RB S780 HTRF cellular Assay for identification of CDK2 inhibitors. FIG. 10A: $IC_{50}$ in CDK2 biochemical kinase activity assay. FIG. 10B: Concentration response analysis of reference compounds tested in the p-RB S780 HTRF cellular assay. HTRF, homogeneous time-resolved fluorescence. $IC_{50}$ from HTRF cellular Assay correlates with $IC_{50}$ in CDK2 enzymatic assay.

FIG. 11 shows the status of p16 in CDK2 sensitive verse insensitive cell lines. CCLE: Broad Institute Cancer Cell Line Encyclopedia (see Barretina, below).

FIG. 12A: Western blot analysis of p16 in three gastric cell lines with CCNE1 Amp. FIG. 12B: Percentage of cells at the S phase 3 days after transfection of CDK2 siRNAs, relative to Ctl siRNA. The cell cycle phase distribution was evaluated by FACS.

DETAILED DESCRIPTION

Compounds

Figures 1A, 1B:
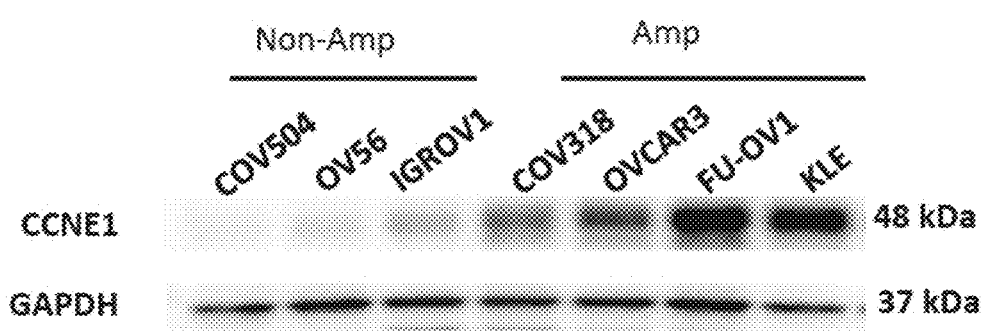
FIGS. 1A-1B: Characterization of ovarian and endometrial cell lines.

The present application provides, inter alia, a compound of Formula (I):

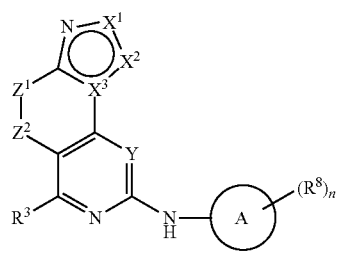

(I)

or a pharmaceutically acceptable salt thereof, wherein:
n is 0, 1, 2, 3, 4, 5, or 6;
$Z^1$ is $CR^4R^5$; and $Z^2$ is $NR^{6z}$, O, or S; or
$Z^1$ is $CR^4R^5$, $NR^6$, O, or S; and $Z^2$ is $CR^{4z}R^{5z}$;
Y is $CR^7$ or N;
$X^1$ is $NR^{1x}$, $CR^1$, N, or O;
$X^2$ is $NR^{2x}$, $CR^2$, N, or O;
$X^3$ is N or C;
wherein Ring

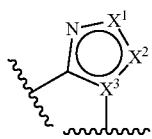

is an aromatic ring selected from:

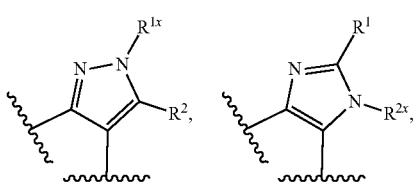

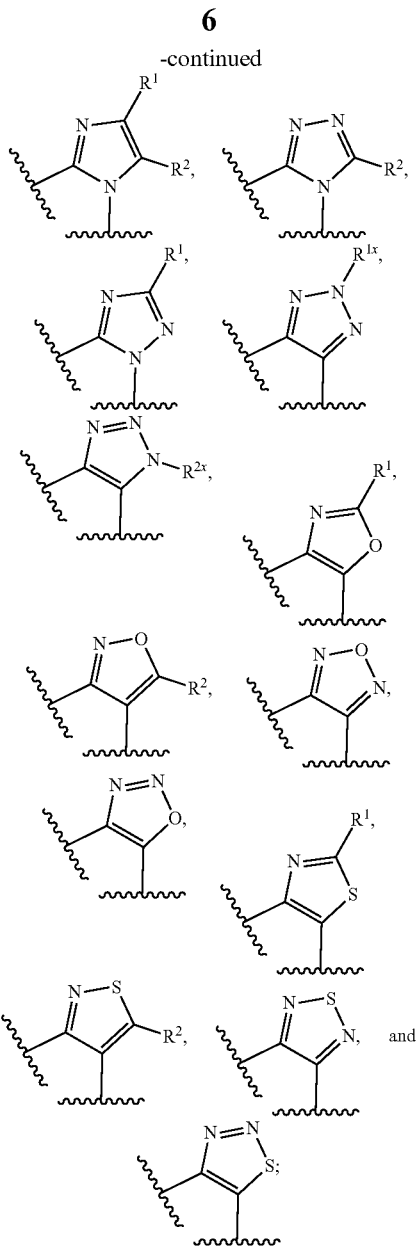

Ring moiety A is selected from (1) $C_{3-14}$ cycloalkyl, wherein 1, 2, 3, or 4 ring-forming carbon atoms of said $C_{3-14}$ cycloalkyl can be optionally substituted by one or more oxo or sulfido, and (2) 4-14 membered heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido; wherein Ring moiety A is attached to the —NH— group of Formula (I) at a ring member of a saturated or partially saturated ring of said $C_{3-14}$ cycloalkyl or said 4-14 membered heterocycloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)$ $NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{e1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{1A}$ substituents;

$R^{1x}$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $C(O)R^{b1}$, $C(O)NR^{c1}R^{d1}$, $C(O)NR^{c1}(OR^{a1})$, $C(O)OR^{a1}$, $C(=NR^{e1})R^{b1}$, $C(=NR^{e1})NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{1A}$ substituents;

$R^2$ is selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$ $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{2A}$ substituents;

$R^{2x}$ is selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $C(O)R^{b2}$, $C(O)NR^{c2}R^{d2}$, $C(O)NR^{c2}(OR^{a2})$, $C(O)OR^{a2}$, $C(=NR^{e2})R^{b2}$, $C(=NR^{e2})NR^{c2}R^{d2}$, $S(O)_2R^{b2}$, and $S(O)_2NR^{c2}R^{d2}$; wherein said $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{2A}$ substituents;

$R^3$ is selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, and $C_{3-4}$ cycloalkyl;

$R^4$, $R^{4z}$, $R^5$ and $R^{5z}$ are independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-3}$ alkyl, HO—$C_{1-3}$ alkyl, $C_{1-3}$ alkoxy-$C_{1-3}$ alkyl, and $C_{3-4}$ cycloalkyl;

or $R^4$ and $R^5$, together with the carbon atom to which they are attached, form a 3-7 membered cycloalkyl ring or a 4-7 membered heterocycloalkyl ring, which are each optionally substituted by 1, 2, 3, or 4 substituents independently selected from D, halo, CN, $C_{1-3}$ alkyl, $C_{1-3}$ haloalkyl, OH, $C_{1-3}$ alkoxy, $C_{1-3}$ haloalkoxy, amino, $C_{1-3}$ alkylamino, di($C_{1-3}$ alkyl)amino, cyano-$C_{1-3}$ alkyl, HO—$C_{1-3}$ alkyl, and $C_{1-3}$ alkoxy-$C_{1-3}$ alkyl;

or $R^{4z}$ and $R^{5z}$, together with the carbon atom to which they are attached, form a 3-7 membered cycloalkyl ring or a 4-7 membered heterocycloalkyl ring, which are each optionally substituted by 1, 2, 3, or 4 substituents independently selected from D, halo, CN, $C_{1-3}$ alkyl, $C_{1-3}$ haloalkyl, OH, $C_{1-3}$ alkoxy, $C_{1-3}$ haloalkoxy, amino, $C_{1-3}$ alkylamino, di($C_{1-3}$ alkyl)amino, cyano-$C_{1-3}$ alkyl, HO—$C_{1-3}$ alkyl, and $C_{1-3}$ alkoxy-$C_{1-3}$ alkyl;

$R^6$ and $R^{6z}$ are each independently selected from H, $C_{1-4}$ alkyl, $C_{1-4}$ haloalkyl, $C_{2-4}$ alkenyl, $C_{2-4}$ alkynyl, cyano-$C_{1-3}$ alkyl, HO—$C_{1-3}$ alkyl, $C_{1-3}$ alkoxy-$C_{1-3}$ alkyl, and $C_{3-4}$ cycloalkyl;

$R^7$ is selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-3}$ alkyl, HO—$C_{1-3}$ alkyl, $C_{1-3}$ alkoxy-$C_{1-3}$ alkyl, and $C_{3-4}$ cycloalkyl;

each $R^8$ is selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a8}$, $SR^{a8}$, $NHOR^{a8}$, $C(O)R^{b8}$, $C(O)NR^{c8}R^{d8}$, $C(O)NR^{c8}(OR^{a8})$, $C(O)OR^{a8}$, $OC(O)R^{b8}$, $OC(O)NR^{c8}R^{d8}$, $NR^{c8}R^{d8}$, $NR^{c8}NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR)NR^{c8}R^{d8}$, $NR^{c8}C(=NR^{e8})NR^{c8}R^{d8}$, $NR^{c8}C(=NR^{e8})R^{b8}$, $NR^{c8}S(O)NR^{c8}R^{d8}$, $NR^{c8}S(O)R^{b8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})R^{b8}$, $OS(O)_2R^{b8}$, $S(O)(=NR^{e8})R^{b8}$, $SF_5$, $P(O)R^{f8}R^{g8}$, $OP(O)(OR^{h8})(OR^{i8})$, $P(O)(OR^{h8})(OR^{i8})$, and $BR^{j8}R^{k8}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{8A}$ substituents;

each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, C(=NR$^{e11}$)NR$^{c11}$R$^{d11}$, NR$^{c11}$C(=NR$^{e11}$)NR$^{c11}$R$^{d11}$, NR$^{c11}$C(=NR$^{e11}$)R$^{b11}$, NR$^{c11}$S(O)NR$^{c11}$R$^{d11}$, NR$^{c11}$S(O)R$^{b11}$, NR$^{c11}$S(O)$_2$R$^{b11}$, NR$^{c11}$S(O)(=NR$^{e11}$)R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$, S(O)$_2$NR$^{c11}$R$^{d11}$, OS(O)(=NR$^{e11}$)R$^{b11}$, OS(O)$_2$R$^{b11}$, S(O)(=NR$^{e11}$)R$^{b11}$, SF$_5$, P(O)R$^{f11}$R$^{g11}$, OP(O)(OR$^{h11}$)(OR$^{i11}$), P(O)(OR$^{h11}$)(OR$^{i11}$) and BR$^{j11}$R$^{k11}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{1B}$ substituents;

each R$^{1B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a12}$, SR$^{a12}$, NHOR$^{a12}$, C(O)R$^{b12}$, C(O)NR$^{c12}$R$^{d12}$, C(O)NR$^{c12}$(OR$^{a12}$), C(O)OR$^{a12}$, OC(O)R$^{b12}$, OC(O)NR$^{c12}$R$^{d12}$, NR$^{c12}$R$^{d12}$, NR$^{c12}$NR$^{c12}$R$^{d12}$, NR$^{c12}$C(O)R$^{b12}$, NR$^{c12}$C(O)OR$^{a12}$, NR$^{c12}$C(O)NR$^{c12}$R$^{d12}$, C(=NR$^{e12}$)R$^{b12}$, C(=NR$^{e12}$)NR$^{c12}$R$^{d12}$, NR$^{c12}$C(=NR$^{e12}$)NR$^{c12}$R$^{d12}$, NR$^{c12}$C(=NR$^{e12}$)R$^{b12}$, NR$^{c12}$S(O)NR$^{c12}$R$^{d12}$, NR$^{c12}$S(O)R$^{b12}$, NR$^{c12}$S(O)$_2$R$^{b12}$, R$^{c12}$S(O)(=NR$^{e12}$)R$^{b12}$, NR$^{c12}$S(O)$_2$NR$^{c12}$R$^{d12}$, S(O)R$^{b12}$, S(O)NR$^{c12}$R$^{d12}$, S(O)$_2$R$^{b12}$, S(O)$_2$NR$^{c12}$R$^{d12}$, OS(O)(=NR$^{e12}$)R$^{b12}$, OS(O)$_2$R$^{b12}$, S(O)(=NR$^{e12}$)R$^{b12}$, SF$_5$, P(O)R$^{f12}$R$^{g12}$, OP(O)(OR$^{h12}$)(OR$^{i12}$), P(O)(OR$^{h12}$)(OR$^{i12}$), and BR$^{j12}$R$^{k12}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{2A}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a21}$, SR$^{a21}$, NHOR$^{a21}$, C(O)R$^{b21}$, C(O)NR$^{c21}$R$^{d21}$, C(O)NR$^{c21}$(OR$^{a21}$), C(O)OR$^{a21}$, OC(O)R$^{b21}$, OC(O)NR$^{c21}$R$^{d21}$, NR$^{c21}$R$^{d21}$, NR$^{c21}$NR$^{c21}$R$^{d21}$, NR$^{c21}$C(O)R$^{b21}$, NR$^{c21}$C(O)OR$^{a21}$, NR$^{c21}$C(O)NR$^{c21}$R$^{d21}$, C(=NR$^{e21}$)R$^{b21}$, C(=NR$^{e21}$)NR$^{c21}$R$^{d21}$, NR$^{c21}$C(=NR$^{e21}$)NR$^{c21}$R$^{d21}$, NR$^{c21}$C(=NR$^{e21}$)R$^{b21}$, NR$^{c21}$S(O)NR$^{c21}$R$^{d21}$, NR$^{c21}$S(O)R$^{b21}$, NR$^{c21}$S(O)$_2$R$^{b21}$, NR$^{c21}$S(O)(=NR$^{e21}$)R$^{b21}$, NR$^{c21}$S(O)$_2$NR$^{c21}$R$^{d21}$, S(O)R$^{b21}$, S(O)NR$^{c21}$R$^{d21}$, S(O)$_2$R$^{b21}$, S(O)$_2$NR$^{c21}$R$^{d21}$, OS(O)(=NR$^{e21}$)R$^{b21}$, OS(O)$_2$R$^{b21}$, S(O)(=NR$^{e21}$)R$^{b21}$, SF$_5$, P(O)R$^{f21}$R$^{g21}$, OP(O)(OR$^{h21}$)(OR$^{i21}$), P(O)(OR$^{h21}$)(OR$^{i21}$), and BR$^{j2}$R$^{k21}$, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{2B}$ substituents;

each R$^{2B}$ is independently selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a22}$, SR$^{a22}$, NHOR$^{a22}$, C(O)R$^{b22}$, C(O)NR$^{c22}$R$^{d22}$, C(O)NR$^{c22}$(OR$^{a22}$), C(O)OR$^{a22}$, OC(O)R$^{b22}$, OC(O)NR$^{c22}$R$^{d22}$, NR$^{c22}$R$^{d22}$, NR$^{c22}$NR$^{c22}$R$^{d22}$, NR$^{c22}$C(O)R$^{b22}$, NR$^{c22}$C(O)OR$^{a22}$, NR$^{c22}$C(O)NR$^{c22}$R$^{d22}$, C(=NR$^{e22}$)R$^{b22}$, C(=NR$^{e22}$)NR$^{c22}$R$^{d22}$, NR$^{c22}$C(=NR$^{e22}$)NR$^{c22}$R$^{d22}$, NR$^{c22}$C(=NR$^{e22}$)R$^{b22}$, NR$^{c22}$S(O)NR$^{c22}$R$^{d22}$, NR$^{c22}$S(O)R$^{b22}$, NR$^{c22}$S(O)$_2$R$^{b22}$, NR$^{c22}$S(O)(=NR$^{e22}$)R$^{b22}$, NR$^{c22}$S(O)$_2$NR$^{c22}$R$^{d22}$, S(O)R$^{b22}$, S(O)NR$^{c22}$R$^{d22}$, S(O)$_2$R$^{b22}$, S(O)$_2$NR$^{c22}$R$^{d22}$, OS(O)(=NR$^{e22}$)R$^{b22}$, OS(O)$_2$R$^{b22}$, S(O)(=NR$^{e22}$)R$^{b22}$, SF$_5$, P(O)R$^{f22}$R$^{g22}$, OP(O)(OR$^{h2}$)(OR$^{i22}$), P(O)(OR$^{h22}$)(OR$^{i22}$), and BR$^{j22}$R$^{k22}$, wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected R$^G$ substituents;

each R$^{8A}$ is selected from D, halo, CN, NO$_2$, C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, 5-10 membered heteroaryl-C$_{1-4}$ alkyl, OR$^{a81}$, SR$^{a81}$, NHOR$^{a81}$, C(O)R$^{b81}$, C(O)NR$^{c81}$R$^{d81}$, C(O)NR$^{c81}$(OR$^{a81}$), C(O)OR$^{a81}$, OC(O)R$^{b81}$, OC(O)NR$^{c81}$R$^{d81}$, NR$^{c81}$R$^{d81}$, NR$^{c81}$NR$^{c81}$R$^{d81}$, NR$^{c81}$C(O)R$^{b81}$, NR$^{c81}$C(O)OR$^{a81}$, NR$^{c81}$C(O)NR$^{c81}$R$^{d81}$, C(=NR$^{e81}$)R$^{b81}$, C(=NR$^{e81}$)NR$^{c81}$R$^{d81}$, NR$^{c81}$C(=NR$^{e81}$)NR$^{c81}$R$^{d81}$, NR$^{c81}$C(=NR$^{e81}$)R$^{b81}$, NR$^{c81}$S(O)NR$^{c81}$R$^{d81}$, NR$^{c81}$S(O)R$^{b81}$, NR$^{c81}$S(O)$_2$R$^{b81}$, NR$^{c81}$S(O)(=NR$^{e81}$)R$^{b81}$, NR$^{c81}$S(O)$_2$NR$^{c81}$R$^{d81}$, S(O)R$^{b81}$, S(O)NR$^{c81}$R$^{d81}$, S(O)$_2$R$^{b81}$, S(O)$_2$NR$^{c81}$R$^{d81}$, OS(O)(=NR$^{e81}$)R$^{b81}$, OS(O)$_2$R$^{b81}$, S(O)(=NR$^{e81}$)R$^{b81}$, SF$_5$, P(O)R$^{f81}$R$^{g81}$, OP(O)(OR$^{h81}$)(OR$^{i81}$), P(O)(OR$^{h81}$)(OR$^{i81}$), and BR$^{j81}$R$^{k81}$; wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted by 1, 2, 3, or 4 independently selected R$^{8B}$ substituents;

each R$^{8B}$ is selected from D, halo, CN, NO$_2$, C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a82}$, SR$^{a82}$, NHOR$^{a82}$, C(O)R$^{b82}$, C(O)NR$^{c82}$R$^{d82}$, C(O)NR$^{c82}$(OR$^{a82}$), C(O)OR$^{a82}$, OC(O)R$^{b82}$, OC(O)NR$^{c82}$R$^{d82}$, NR$^{c82}$R$^{d82}$, NR$^{c82}$NR$^{c82}$NR$^{d82}$, NR$^{c82}$C(O)R$^{b82}$, NR$^{c82}$C(O)OR$^{c82}$R$^{d82}$, C(O)NR$^{c82}$R$^{d82}$, C(=NR$^{e82}$)R$^{b82}$, C(=NR$^{e82}$)R$^{c82}$R$^{d82}$, NR$^{c82}$C(=NR$^{e82}$) NR$^{c82}$R$^{d82}$, NR$^{c82}$C(=NR$^{e82}$)R$^{b82}$, NR$^{c82}$S(O)NR$^{c82}$R$^{d82}$, NR$^{c82}$S(O)R$^{b82}$, NR$^{c82}$S(O)$_2$R$^{b82}$, NR$^{c82}$S(O)(=NR$^{e82}$) R$^{b82}$, NR$^{c82}$S(O)$_2$NR$^{c82}$R$^{d82}$, S(O)R$^{b82}$, S(O)NR$^{c82}$R$^{d82}$, S(O)$_2$R$^{b82}$, S(O)$_2$NR$^{c82}$R$^{d82}$, OS(O)(=NR$^{e82}$)R$^{b82}$, OS(O)$_2$ R$^{b82}$, S(O)(=NR$^{e82}$)R$^{b82}$, SF$_5$, P(O)R$^{f82}$R$^{g82}$, OP(O) (OR$^{h82}$)(OR$^{i82}$), P(O)(OR$^{h82}$)(OR$^{i82}$), and BR$^{j82}$R$^{k82}$; wherein said C$_{1-6}$ alkyl, C$_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^G$ substituents;

each $R^{a1}$, $R^{b1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{1A}$ substituents;

or, any $R^{c1}$ and $R^{d1}$ attached to the same N atom, together with the N atom to which they are attached, form a 4-10 membered heterocycloalkyl group, which is optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{1A}$ substituents;

each $R^{e1}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f1}$ and $R^{g1}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h1}$ and $R^{i1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j1}$ and $R^{k1}$ is independently selected from OH, $C_{1-6}$ alkoxy, and $C_{1-6}$ haloalkoxy;

or any $R^{j1}$ and $R^{k1}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{8B}$ substituents;

or, any $R^{c11}$ and $R^{d11}$ attached to the same N atom, together with the N atom to which they are attached, form a 4-7 membered heterocycloalkyl group, which is optionally substituted with 1, 2, 3, or 4 independently selected $R^{8B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{8B}$ substituents;

each $R^{e11}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f11}$ and $R^{g11}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h1}$ and $R^{i11}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j11}$ and $R^{k11}$ is independently selected from OH, $C_{1-6}$ alkoxy, and $C_{1-6}$ haloalkoxy;

or any $R^{j11}$ and $R^{k11}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a12}$, $R^{c12}$, and $R^{d12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, which is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, which is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f2}$ and $R^{g2}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{j1}$ and $R^{k2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2B}$ substituents;

or, any $R^{c21}$ and $R^{d21}$ attached to the same N atom, together with the N atom to which they are attached, form a 4-7 membered heterocycloalkyl group, which is optionally substituted with 1, 2, 3, or 4 independently selected $R^{2B}$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f21}$ and $R^{g21}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c22}$ and $R^{d22}$ attached to the same N atom, together with the N atom to which they are attached, form a 4-7 membered heterocycloalkyl group, which is optionally substituted with 1, 2, 3, or 4 independently selected $R^G$ substituents;

each $R^{b22}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f22}$ and $R^{g22}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h22}$ and $R^{i22}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j22}$ and $R^{k22}$ is independently selected from OH, $C_{1-6}$ alkoxy, and $C_{1-6}$ haloalkoxy;

or any $R^{j22}$ and $R^{k22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{8A}$ substituents;

or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j8}$ and $R^{k8}$ is independently selected from OH, $C_{1-6}$ alkoxy, and $C_{1-6}$ haloalkoxy;

or any $R^{j8}$ and $R^{k8}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{8B}$ substituents;

or, any $R^{c81}$ and $R^{d81}$ attached to the same N atom, together with the N atom to which they are attached, form a 4-7 membered heterocycloalkyl group, which is optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{8B}$ substituents;

each $R^{c81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{f81}$ and $R^{g81}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-membered heteroaryl-$C_{1-4}$ alkyl;

each $R^{h81}$ and $R^{i81}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j81}$ and $R^{k81}$ is independently selected from OH, $C_{1-6}$ alkoxy, and $C_{1-6}$ haloalkoxy;

or any $R^{j81}$ and $R^{k81}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a82}$, $R^{c82}$, and $R^{d82}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c82}$ and $R^{d82}$ attached to the same N atom, together with the N atom to which they are attached, form a 4-7 membered heterocycloalkyl group, which is optionally substituted with 1, 2, 3, or 4 independently selected $R^G$ substituents;

each $R^{b82}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e82}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f82}$ and $R^{g82}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h82}$ and $R^{i82}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j82}$ and $R^{k82}$ is independently selected from OH, $C_{1-6}$ alkoxy, and $C_{1-6}$ haloalkoxy;

or any $R^{j82}$ and $R^{k82}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamoyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, $X^1$ is $NR^{1x}$.
In some embodiments, $X^1$ is $CR^1$.
In some embodiments, $X^2$ is $NR^{2x}$.
In some embodiments, $X^2$ is $CR^2$.
In some embodiments, $X^3$ is C.
In some embodiments, Ring

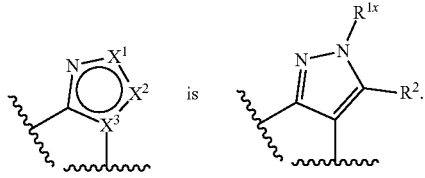

In some embodiments, Ring

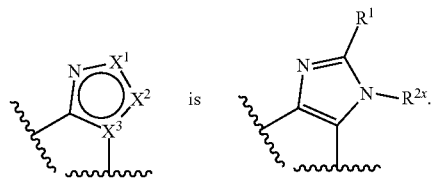

In some embodiments, $R^1$ is selected from H, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{1A}$ substituents.

In some embodiments, $R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{1A}$ substituents.

In some embodiments, $R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $OR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents.

In some embodiments, $R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{1A}$ substituents.

In some embodiments, $R^1$ is selected from H, halo, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents.

In some embodiments, $R^1$ is selected from H, halo, $C_{1-6}$ alkyl, phenyl, and 5-6 membered heteroaryl, wherein said $C_{1-6}$ alkyl, phenyl and 5-6 membered heteroaryl are each optionally substituted by 1 or 2 independently selected $R^{1A}$ substituents.

In some embodiments, $R^1$ is selected from H, Br, methyl, ethyl, isopropyl, phenyl, 2-fluorophenyl, 2,5-difluorophenyl, and 1,3-dimethylpyrazol-4-yl.

In some embodiments, $R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents.

In some embodiments, $R^{1x}$ is selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents.

In some embodiments, $R^{1x}$ is selected from H, $C_{1-6}$ alkyl, $C_{3-7}$ cycloalkyl, phenyl, and 4-7 membered heterocycloalkyl, wherein said $C_{1-6}$ alkyl, $C_{3-7}$ cycloalkyl, phenyl, and 4-7 membered heterocycloalkyl are each optionally substituted by 1 or 2 independently selected $R^{1A}$ substituents.

In some embodiments, RX is selected from methyl, —$CH_2CH_2OH$, cyclopropyl, 2,5-difluorophenyl, and tetrahydrofuran-3-yl.

In some embodiments:
each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{1A}$ substituents;

each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(O)R^{b11}$, $C(O)NR^{c11}R^{d11}$, $C(O)OR^{d11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{d11}$, $NR^{c11}C(O)NR^{c11}R^{d11}$, $NR^{c11}S(O)_2R^{b11}$, $NR^{c11}S(O)_2NR^{c11}R^{d11}$, $S(O)_2R^{b11}$, and $S(O)_2NR^{c11}R^{d11}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, and 5-10 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $NR^{c12}S(O)_2R^{b12}$, $NR^{c12}S(O)_2NR^{c12}R^{d12}$, $S(O)_2R^{b12}$, and $S(O)_2NR^{c12}R^{d12}$;

each $R^{a12}$, $R^{c12}$ and $R^{d12}$ is independently selected from H, $C_{1-6}$ alkyl, and $C_{1-6}$ haloalkyl; and each $R^{b12}$ is independently selected from $C_{1-6}$ alkyl and $C_{1-6}$ haloalkyl.

In some embodiments:

each $R^{a1}$, $R^{c1}$, and $R^{d1}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1A}$ substituents;

each $R^{1A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)_2R^{b11}$, $NR^{c11}S(O)_2NR^{c11}R^{d11}$, $S(O)_2R^{b11}$, and $S(O)_2NR^{c11}R^{d11}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from halo, CN, $NO_2$, $C_{1-6}$ alkyl, $C_{1-6}$ haloalkyl, $C_{3-4}$ cycloalkyl, 4-5 membered heterocycloalkyl, $OR^{a12}$, and $NR^{c12}R^{d12}$; and each $R^{a12}$, $R^{c12}$, and $R^{d12}$ is independently selected from H, $C_{1-6}$ alkyl, and $C_{1-6}$ haloalkyl.

In some embodiments:

each $R^{a1}$, $R^{c1}$, and $R^{d1}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1A}$ substituents;

each $R^{1A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)_2R^{b11}$, $NR^{c11}S(O)_2NR^{c11}R^{d11}$, $S(O)_2R^{b11}$, and $S(O)_2NR^{c11}R^{d11}$;

each $R^{a11}$, $R^{c11}$, and $R^{d11}$ is independently selected from H, $C_{1-6}$ alkyl and $C_{1-6}$ haloalkyl; and each $R^{b11}$ is independently selected from $C_{1-6}$ alkyl and $C_{1-6}$ haloalkyl.

In some embodiments:

each $R^{a1}$, $R^{c1}$, and $R^{d1}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{1A}$ substituents;

each $R^{b1}$ is independently selected from $C_{1-6}$ alkyl and $C_{1-6}$ haloalkyl, which are each optionally substituted with 1, 2, 3, or 4 independently selected $R^{1A}$ substituents;

each $R^{1A}$ is independently selected from halo, CN, $C_{1-6}$ alkyl, $C_{1-6}$ haloalkyl, $C_{3-7}$ cycloalkyl, $OR^{a1}$, and $NR^{c11}R^{d11}$; and each $R^{a11}$, $R^{c11}$, and $R^{d11}$ is independently selected from H, $C_{1-6}$ alkyl and $C_{1-6}$ haloalkyl.

In some embodiments, $R^2$ is selected from H, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{2A}$ substituents.

In some embodiments, $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2A}$ substituents.

In some embodiments, $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}S(O)_2R^{b2}$, $S(O)_2R^{b2}$, and $S(O)_2NR^{c2}R^{d2}$; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents.

In some embodiments, $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2A}$ substituents.

In some embodiments, $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents.

In some embodiments, $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, and 5-6 membered heteroaryl.

In some embodiments, $R^2$ is selected from H, $C_{1-6}$ alkyl, and $C_{3-7}$ cycloalkyl.

In some embodiments, $R^2$ is selected from H, methyl, isopropyl, and cyclopropyl.

In some embodiments, $R^{2x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents.

In some embodiments, $R^{2x}$ is selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents.

In some embodiments, $R^{2x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl.

In some embodiments, $R^{2x}$ is selected from H, $C_{1-6}$ alkyl, $C_{3-7}$ cycloalkyl, and phenyl-$C_{1-3}$ alkyl.

In some embodiments, $R^{2x}$ is selected from H, methyl, isopropyl, cyclopropyl, and benzyl.

In some embodiments:

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{2A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, and 5-10 membered heteroaryl-$C_{1-4}$ alkyl are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2B}$ substituents;

each $R^{2B}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a22}$, $SR^{a22}$, $C(O)R^{b22}$, $C(O)NR^{c22}R^{d22}$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)_2R^{b22}$, $NR^{c22}S(O)_2NR^{c22}R^{d22}$, $S(O)_2R^{b22}$, and $S(O)_2NR^{c22}R^{d22}$;

each $R^{a22}$, $R^{c22}$, and $R^{d22}$ is independently selected from H, $C_{1-6}$ alkyl, and $C_{1-6}$ haloalkyl; and each $R^{b22}$ is independently selected from $C_{1-6}$ alkyl and $C_{1-6}$ haloalkyl.

In some embodiments:

each $R^{a2}$, $R^{c2}$, and $R^{d2}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2A}$ substituents;

each $R^{2A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{b21}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2B}$ substituents;

each $R^{2B}$ is independently selected from halo, CN, $NO_2$, $C_{1-6}$ alkyl, $C_{1-6}$ haloalkyl, $C_{3-4}$ cycloalkyl, 4-5 membered heterocycloalkyl, $OR^{a22}$, and $NR^{c22}R^{d22}$; and each $R^{a22}$, $R^{c22}$, and $R^{d22}$ is independently selected from H, $C_{1-6}$ alkyl, and $C_{1-6}$ haloalkyl.

In some embodiments:

each $R^{a2}$, $R^{c2}$, and $R^{d2}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2A}$ substituents;

each $R^{2A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$.

each $R^{a21}$, $R^{c21}$, and $R^{d21}$ is independently selected from H, $C_{1-6}$ alkyl and $C_{1-6}$ haloalkyl; and each $R^{b21}$ is independently selected from $C_{1-6}$ alkyl and $C_{1-6}$ haloalkyl.

In some embodiments:

each $R^{a2}$, $R^{c2}$, and $R^{d2}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, 3, or 4 independently selected $R^{2A}$ substituents;

each $R^{b2}$ is independently selected from $C_{1-6}$ alkyl and $C_{1-6}$ haloalkyl, which are each optionally substituted with 1, 2, 3, or 4 independently selected $R^{2A}$ substituents;

each $R^{2A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, $OR^{a21}$, and $NR^{c21}R^{d21}$; and each $R^{a21}$, $R^{c21}$, and $R^{d21}$ is independently selected from H, $C_{1-6}$ alkyl and $C_{1-6}$ haloalkyl.

In some embodiments, $R^3$ is selected from H, halo, CN, $C_{1-3}$ alkyl, and $C_{1-3}$ haloalkyl.

In some embodiments, $R^3$ is selected from H, F, $CH_3$, and $CF_3$.

In some embodiments, $R^3$ is H.

In some embodiments, Y is N.

In some embodiments, Y is $CR^7$.

In some embodiments, $R^7$ is selected from H, halo, CN, $C_{1-3}$ alkyl, and $C_{1-3}$ haloalkyl.

In some embodiments, $R^7$ is selected from H, F, $CH_3$, and $CF_3$.

In some embodiments, $R^7$ is H.

In some embodiments, $Z^1$ is $CR^4R^5$; and $Z^2$ is $CR^{4z}R^{5z}$ or O.

In some embodiments, $Z^1$ is $CH_2$; and $Z^2$ is $CH_2$ or O.

In some embodiments, $Z^1$ is $CR^4R^5$ or O; and $Z^2$ is $CR^{4z}R^{5z}$.

In some embodiments, $Z^1$ is $CH_2$ or O; and $Z^2$ is $CH_2$.

In some embodiments:

$R^4$, $R^{4z}$, $R^5$ and $R^{5z}$ are independently selected from H, halo, CN, $C_{1-3}$ alkyl, and $C_{1-3}$ haloalkyl;

or $R^4$ and $R^5$, together with the carbon atom to which they are attached, form a cyclopropyl or cyclobutyl ring;

or $R^{4z}$ and $R^{5z}$, together with the carbon atom to which they are attached, form a 3 cyclopropyl or cyclobutyl ring.

In some embodiments, $R^4$, $R^{4z}$, $R^5$ and $R^{5z}$ are independently selected from H, F, $CH_3$ and $CF_3$; or $R^4$ and $R^5$, together with the carbon atom to which they are attached, form a cyclopropyl ring.

In some embodiments, $R^4$, $R^{4z}$, $R^5$ and $R^{5z}$ are each independently selected from H and $C_{1-3}$ alkyl.

In some embodiments, $R^4$, $R^{4z}$, $R^5$ and $R^{5z}$ are each H.

In some embodiments, $R^6$ and $R^{6z}$ are each independently selected from H, $C_{1-3}$ alkyl, and $C_{1-3}$ haloalkyl.

In some embodiments, $R^6$ and $R^{6z}$ are each independently selected from H, $CH_3$, and $CF_3$.

In some embodiments, Ring moiety A is monocyclic or bicyclic 4-10 membered heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido, wherein said heterocycloalkyl does not comprise an aromatic ring.

In some embodiments, Ring moiety A is monocyclic $C_{3-7}$ cycloalkyl.

In some embodiments, Ring moiety A is monocyclic 4-7 membered heterocycloalkyl having 1 or 2 ring-forming heteroatoms independently selected from N, O, and S, wherein 1, 2 or 3 ring-forming carbon or heteroatoms can be optionally substituted by one or more oxo or sulfido.

In some embodiments, Ring moiety A is an azetidine ring, a pyrrolidine ring, a piperidine ring, or an azepane ring.

In some embodiments, Ring moiety A is azetidin-3-yl, piperidin-3-yl, or piperidin-4-yl.

In some embodiments, Ring moiety A is a piperidine ring.

In some embodiments, Ring moiety A is piperidin-4-yl.

In some embodiments, n is 1, 2, 3, or 4.

In some embodiments, n is 1, 2, or 3.

In some embodiments, n is 1 or 2.

In some embodiments, n is 2.

In some embodiments, n is 1.

In some embodiments, $R^8$ is selected from H, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a8}$, $SR^{a8}$, $NHOR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}S(O)_2R^{b8}$, $NR^{c8}S(O)_2NR^{c8}R^{d8}$, $S(O)_2R^{b8}$, and $S(O)_2NR^{c8}R^{d8}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{8A}$ substituents.

In some embodiments, $R^8$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}S(O)_2R^{b8}$, $NR^{c8}S(O)_2NR^{c8}R^{d8}$, $S(O)_2R^{b8}$, and $S(O)_2NR^{c8}R^{d8}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{8A}$ substituents.

In some embodiments, at least one $R^8$ is $S(O)_2R^{b8}$.

In some embodiments, one $R^8$ is $S(O)_2R^{b8}$; and each remaining $R^8$ is independently selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}CR^{d8}$, $NR^{c8}S(O)_2R^{b8}$, $NR^{c8}S(O)_2NR^{c8}R^{d8}$, $S(O)_2R^{b8}$, and $S(O)_2NR^{c8}R^{d8}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{8A}$ substituents.

In some embodiments, one $R^8$ is $S(O)_2R^{b8}$; and each remaining $R^8$ is independently selected from halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, $OR^{a8}$, and $NR^{c8}R^{d8}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{8A}$ substituents.

In some embodiments, one $R^8$ is $S(O)_2R^{b8}$; and each remaining $R^8$ is independently selected from halo, CN, $C_{1-6}$ alkyl, $C_{1-6}$ haloalkyl, $OR^{a8}$, and $NR^{c8}R^{d8}$; wherein said $C_{1-6}$ alkyl and $C_{1-6}$ haloalkyl are each optionally substituted by 1, 2, 3, or 4 independently selected $R^{8A}$ substituents.

In some embodiments, one $R^8$ is $S(O)_2R^{b8}$; and each remaining $R^8$ is independently selected from $C_{1-6}$ alkyl and $C_{1-6}$ haloalkyl.

In some embodiments, one $R^8$ is $S(O)_2R^{b8}$, wherein $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8A}$ substituents.

In some embodiments, one $R^8$ is halo or $C_{1-6}$ alkyl and one $R^8$ is $S(O)_2R^{b8}$, wherein $R^{b8}$ is selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{8A}$ substituents.

In some embodiments, one $R^8$ is $S(O)_2R^{b8}$, wherein $R^{b8}$ is independently selected from selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{8A}$ substituents.

In some embodiments, one $R^8$ is $S(O)_2R^{b8}$, wherein $R^{b8}$ is selected from methyl, ethyl, cyclopropyl, 3-cyanophenyl, pyrazol-4-yl, 1,2-dimethyl-1H-imidazol-4-yl, 1-methyl-1H-imidazol-4-yl, 6-(4-methylpiperazin-1-yl)pyridin-2-yl, 2-[(3-hydroxy)pyrrolidinyl]-pyridin-5-yl, and 1-methyl-pyrazol-4-yl.

In some embodiments, one $R^8$ is $S(O)_2R^{b8}$, wherein $R^{b8}$ is selected from methyl, ethyl, cyclopropyl, 3-cyanophenyl, pyrazol-4-yl, 1,2-dimethyl-1H-imidazol-4-yl and 1-methyl-pyrazol-4-yl.

In some embodiments, one $R^8$ is halo or $C_{1-6}$ alkyl and one $R^8$ is $S(O)_2R^{b8}$, wherein $R^{b8}$ is selected from methyl, ethyl, cyclopropyl, 3-cyanophenyl, pyrazol-4-yl, 1,2-dimethyl-1H-imidazol-4-yl, 1-methyl-1H-imidazol-4-yl, 6-(4-methylpiperazin-1-yl)pyridin-2-yl, 2-[(3-hydroxy)pyrrolidinyl]-pyridin-5-yl, and 1-methyl-pyrazol-4-yl.

In some embodiments, one R is $C_{1-6}$ alkyl and one $R^8$ is $S(O)_2R^{b8}$, wherein $R^{b8}$ is selected from methyl, ethyl, cyclopropyl, 3-cyanophenyl, pyrazol-4-yl, 1,2-dimethyl-1H-imidazol-4-yl, 1-methyl-1H-imidazol-4-yl, 6-(4-methylpiperazin-1-yl)pyridin-2-yl, 2-[(3-hydroxy)pyrrolidinyl]-pyridin-5-yl, and 1-methyl-pyrazol-4-yl.

In some embodiments, one $R^8$ is methyl and one $R^8$ is $S(O)_2R^{b8}$, wherein $R^{b8}$ is selected from methyl, ethyl, cyclopropyl, 3-cyanophenyl, pyrazol-4-yl, 1,2-dimethyl-1H-imidazol-4-yl, 1-methyl-1H-imidazol-4-yl, 6-(4-methylpiperazin-1-yl)pyridin-2-yl, 2-[(3-hydroxy)pyrrolidinyl]-pyridin-5-yl, and 1-methyl-pyrazol-4-yl.

In some embodiments:
each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{8A}$ substituents;

each $R^{8A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a81}$, $SR^{a81}$, $C(O)R^{b81}$, $C(O)NR^{c81}R^{d81}$, $C(O)OR^{a81}$, $OC(O)R^{a81}$, $OC(O)NR^{c81}R^{d81}$, $NR^{c81}R^{d81}$, $NR^{c81}C(O)R^{b81}$, $NR^{c81}C(O)OR^{a81}$, $NR^{c81}C(O)NR^{c81}R^{d81}$, $NR^{c81}S(O)_2R^{b81}$, $NR^{c81}S(O)_2NR^{c81}R^{d81}$, $S(O)_2R^{b81}$, and $S(O)_2NR^{c81}R^{d81}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{a81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8B}$ substituents;

each $R^{8B}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a82}$, $SR^{a82}$, $C(O)R^{b82}$, $C(O)NR^{c82}R^{d82}$, $C(O)OR^{a82}$, $OC(O)R^{b82}$, $OC(O)NR^{c82}R^{d82}$, $NR^{c82}R^{d82}$, $NR^{c82}C(O)R^{b82}$, $NR^{c82}C(O)OR^{a82}$, $NR^{c82}C(O)NR^{c82}R^{d82}$, $NR^{c82}S(O)_2R^{b82}$, $NR^{c82}S(O)_2NR^{c82}R^{d82}$, $S(O)_2R^{b82}$, and $S(O)_2NR^{c82}R^{d82}$;

each $R^{a82}$, $R^{c82}$, and $R^{d82}$ is independently selected from H, $C_{1-6}$ alkyl, and $C_{1-6}$ haloalkyl; and each $R^{b82}$ is independently selected from $C_{1-6}$ alkyl and $C_{1-6}$ haloalkyl.

In some embodiments:
each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8A}$ substituents;

each $R^{8A}$ is independently selected from halo, CN, NO$_2$, C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a81}$, SR$^{a81}$, C(O)R$^{b81}$, C(O)NR$^{c81}$R$^{d81}$, C(O)OR$^{a81}$, OC(O)R$^{a81}$, OC(O)NR$^{c81}$R$^{d81}$, NR$^{c81}$R$^{d81}$, NR$^{c81}$C(O)R$^{b81}$, NR$^{c11}$C(O)OR$^{a81}$, R$^{c81}$C(O)NR$^{c81}$R$^{d81}$, NR$^{c81}$S(O)$_2$R$^{b81}$, NR$^{c81}$S(O)$_2$NR$^{c81}$R$^{d81}$, S(O)$_2$R$^{b81}$, and S(O)$_2$NR$^{c81}$R$^{d81}$, wherein said C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected RB substituents;

each $R^{a81}$, $R^{c81}$, and $R^{d81}$ is independently selected from H, C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected $R^{8B}$ substituents;

each $R^{b81}$ is independently selected from C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected $R^{8B}$ substituents;

each $R^{8B}$ is independently selected from halo, CN, NO$_2$, C$_{1-6}$ alkyl, C$_{1-6}$ haloalkyl, C$_{3-4}$ cycloalkyl, 4-5 membered heterocycloalkyl, OR$^{b82}$, and NR$^{c82}$R$^{d82}$; and each $R^{a82}$, $R^{c82}$, and $R^{d82}$ is independently selected from H, C$_{1-6}$ alkyl, and C$_{1-6}$ haloalkyl.

In some embodiments:

each $R^{a8}$, $R^{c8}$, and $R^{d8}$ is independently selected from H, C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected $R^{8A}$ substituents;

each $R^{b8}$ is independently selected from C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected $R^{8A}$ substituents;

each $R^{8A}$ is independently selected from halo, CN, NO$_2$, C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, 5-6 membered heteroaryl-C$_{1-4}$ alkyl, OR$^{a81}$, SR$^{a81}$, C(O)R$^{b81}$, C(O)NR$^{c81}$R$^{d81}$, C(O)OR$^{a81}$, OC(O)R$^{a81}$, OC(O)NR$^{c81}$R$^{d81}$, NR$^{c81}$R$^{d81}$, NR$^{c81}$C(O)R$^{b81}$, NR$^{c81}$C(O)OR$^{a81}$ NR$^{c81}$C(O)NR$^{c81}$R$^{d81}$, NR$^{c81}$S(O)$_2$R$^{b81}$, NR$^{c81}$S(O)$_2$NR$^{c81}$R$^{d81}$, S(O)$_2$R$^{b811}$, and S(O)$_2$NR$^{c81}$R$^{d81}$;

each $R^{a81}$, $R^{c81}$, and $R^{d81}$ is independently selected from H, C$_{1-6}$ alkyl and C$_{1-6}$ haloalkyl; and each $R^{b81}$ is independently selected from C$_{1-6}$ alkyl and C$_{1-6}$ haloalkyl.

In some embodiments:

each $R^{8A}$ is independently selected from halo, CN, C$_{1-6}$ alkyl, C$_{1-6}$ haloalkyl, and 4-7 membered heterocycloalkyl; wherein said C$_{1-6}$ alkyl, C$_{1-6}$ haloalkyl, and 4-7 membered heterocycloalkyl are each optionally substituted by 1 or 2 independently selected $R^{8B}$ substituents;

each $R^{8B}$ is selected from C$_{1-6}$ alkyl and OR$^{a82}$; and each $R^{a82}$ is independently selected from H and C$_{1-6}$ alkyl.

In some embodiments:

each $R^{a8}$, $R^{c8}$, and $R^{d8}$ is independently selected from H, C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, wherein said C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted with 1, 2, 3, or 4 independently selected $R^{8A}$ substituents;

each $R^{b8}$ is independently selected from C$_{1-6}$ alkyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl, which are each optionally substituted with 1, 2, 3, or 4 independently selected $R^{8A}$ substituents;

each $R^{8A}$ is independently selected from halo, CN, NO$_2$, C$_{1-6}$ alkyl, C$_{2-6}$ alkenyl, C$_{2-6}$ alkynyl, C$_{1-6}$ haloalkyl, C$_{3-4}$ cycloalkyl, OR$^{a81}$, and NR$^{c81}$R$^{d81}$; and each $R^{a81}$, $R^{c81}$, and $R^{d81}$ is independently selected from H, C$_{1-6}$ alkyl and C$_{1-6}$ haloalkyl.

In some embodiments:

n is 1, 2, 3, or 4;

$Z^1$ is CR$^4$R$^5$; and $Z^2$ is NR$^{6z}$, O, or S; or $Z^1$ is CR$^4$R$^5$, NR$^6$, O, or S; and $Z^2$ is CR$^{4z}$R$^{5z}$;

Y is CR$^7$ or N;

$X^1$ is NR$^{1x}$ or CR$^1$;

$X^2$ is NR$^{2x}$ or CR$^2$;

$X^3$ is N or C;

wherein Ring

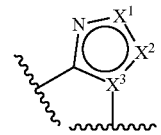

is an aromatic ring selected from:

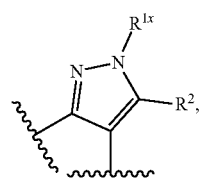 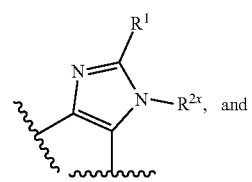 and

-continued

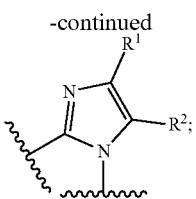

Ring moiety A is monocyclic or bicyclic 4-10 membered heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido, wherein said heterocycloalkyl does not comprise an aromatic ring;

$R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{1A}$ substituents;

$R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents;

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2A}$ substituents;

$R^{2x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

$R^3$ is selected from H, halo, CN, $C_{1-3}$ alkyl, and $C_{1-3}$ haloalkyl;

$R^4$, $R^{4z}$, $R^5$ and $R^{5z}$ are independently selected from H, halo, CN, $C_{1-3}$ alkyl, and $C_{1-3}$ haloalkyl;

or $R^4$ and $R^5$, together with the carbon atom to which they are attached, form a cyclopropyl or cyclobutyl ring;

or $R^{4z}$ and $R^{5z}$, together with the carbon atom to which they are attached, form a 3 cyclopropyl or cyclobutyl ring;

$R^7$ is selected from H, halo, CN, $C_{1-3}$ alkyl, and $C_{1-3}$ haloalkyl;

$R^8$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}S(O)_2R^{b8}$, $NR^{c8}S(O)_2NR^{c8}R^{d8}$, $S(O)_2R^{b8}$, and $S(O)_2NR^{c8}R^{d8}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{8A}$ substituents;

each $R^{a1}$, $R^{c1}$, and $R^{d1}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1A}$ substituents;

each $R^{1A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)_2R^{b11}$, $NR^{c11}S(O)_2NR^{c11}R^{d11}$, $S(O)_2R^{b11}$, and $S(O)_2NR^{c11}R^{d11}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from halo, CN, $NO_2$, $C_{1-6}$ alkyl, $C_{1-6}$ haloalkyl, $C_{3-4}$ cycloalkyl, 4-5 membered heterocycloalkyl, $OR^{a12}$, and $NR^{c12}R^{d12}$;

each $R^{a12}$, $R^{c12}$, and $R^{d12}$ is independently selected from H, $C_{1-6}$ alkyl, and $C_{1-6}$ haloalkyl;

each $R^{a2}$, $R^{c2}$, and $R^{d2}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2A}$ substituents;

each $R^{2A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{b21}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2B}$ substituents;

each $R^{2B}$ is independently selected from halo, CN, $NO_2$, $C_{1-6}$ alkyl, $C_{1-6}$ haloalkyl, $C_{3-4}$ cycloalkyl, 4-5 membered heterocycloalkyl, $OR^{a22}$, and $NR^{c22}R^{d22}$ each $R^{a22}$, $R^{c22}$, and $R^{d22}$ is independently selected from H, $C_{1-6}$ alkyl, and $C_{1-6}$ haloalkyl;

each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8A}$ substituents;

each $R^{8A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a81}$, $SR^{a81}$, $C(O)R^{b81}$, $C(O)NR^{c81}R^{d81}$, $C(O)OR^{a81}$, $OC(O)R^{a81}$, $OC(O)NR^{c81}R^{d81}$, $NR^{c81}R^{d81}$, $NR^{c81}C(O)R^{b11}$, $NR^{c11}C(O)OR^{a81}$, $NR^{c81}C(O)NR^{c81}R^{d81}$, $NR^{c81}S(O)_2R^{b81}$, $NR^{c81}S(O)_2NR^{c81}R^{d81}$, $S(O)_2R^{b81}$, and $S(O)_2NR^{c81}R^{d81}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected RB substituents;

each $R^{a81}$, $R^{c81}$, and $R^{d81}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8B}$ substituents;

each $R^{8B}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a82}$, $SR^{a82}$, $C(O)R^{b82}$, $C(O)NR^{c82}R^{b82}$, $C(O)OR^{a82}$, $OC(O)R^{b82}$, $OC(O)NR^{c82}R^{d82}$, $NR^{c82}R^{d82}$, $NR^{c82}C(O)R^{b82}$, $NR^{c82}C(O)OR^{a82}$, $NR^{c2}C(O)NR^{c82}R^{d82}$, $NR^{c82}S(O)_2R^{b82}$, $NR^{c82}S(O)_2NR^{c82}R^{d82}$, $S(O)_2R^{b82}$, and $S(O)_2NR^{c82}R^{d82}$;

each $R^{a82}$, $R^{c82}$, and $R^{d82}$ is independently selected from H, $C_{1-6}$ alkyl, and $C_{1-6}$ haloalkyl; and each $R^{b82}$ is independently selected from $C_{1-6}$ alkyl and $C_{1-6}$ haloalkyl.

In some embodiments:

n is 1, 2, or 3;

$Z^1$ is $CR^4R^5$; and $Z^2$ is O; or $Z^1$ is $CR^4R^5$ or O; and $Z^2$ is $CR^{4z}R^{5z}$;

Y is N or CH;

$X^1$ is $NR^{1x}$ or $CR^1$;

$X^2$ is $NR^{2x}$ or $CR^2$;

$X^3$ is N or C;

wherein Ring

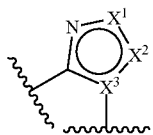

is an aromatic ring selected from:

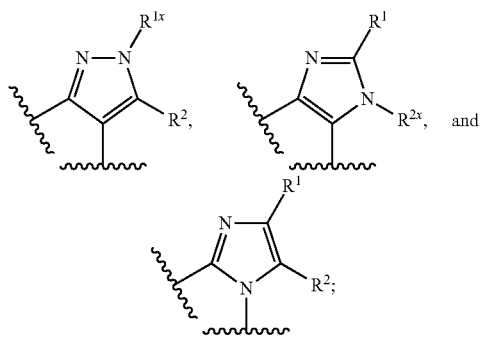

Ring moiety A is monocyclic 4-7 membered heterocycloalkyl having 1 or 2 ring-forming heteroatoms independently selected from N, O, and S, wherein 1, 2, or 3 ring-forming carbon or heteroatoms can be optionally substituted by one or more oxo or sulfido;

$R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{1A}$ substituents;

$R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents;

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2A}$ substituents;

$R^{2x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

$R^3$ is selected from H, F, $CH_3$, and $CF_3$;

$R^4$, $R^{4z}$, $R^5$ and $R^{5z}$ are independently selected from H, F, $CH_3$ and $CF_3$; or $R^4$ and $R^5$, together with the carbon atom to which they are attached, form a cyclopropyl ring;

at least one $R^8$ is $S(O)_2RV$; and each remaining $R^8$ is independently selected from halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, and $NR^{c8}R^{d8}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{8A}$ substituents;

each $R^{1A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(O)R^{b1}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)_2R^{b11}$, $NR^{c11}S(O)_2R^{c11}R^{d11}$, $S(O)_2R^{b11}$, and $S(O)_2NR^{c11}R^{d11}$.

each $R^{a11}$, $R^{c11}$, and $R^{d11}$ is independently selected from H, $C_{1-6}$ alkyl and $C_{1-6}$ haloalkyl; and each $R^{b11}$ is independently selected from $C_{1-6}$ alkyl and $C_{1-6}$ haloalkyl.

each $R^{2A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)_2R^{b21}$, $NR^{c21}S(O)_2R^{c21}R^{d21}$, $S(O)_2R^{b21}$, and $S(O)_2NR^{c21}R^{d21}$.

each $R^{a21}$, $R^{c21}$, and $R^{d21}$ is independently selected from H, $C_{1-6}$ alkyl and $C_{1-6}$ haloalkyl;

each $R^{b21}$ is independently selected from $C_{1-6}$ alkyl and $C_{1-6}$ haloalkyl;

each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8A}$ substituents;

each $R^{8A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a81}$, $C(O)R^{a81}$, $C(O)NR^{c81}R^{d81}$, $C(O)OR^{a81}$, $OC(O)R^{b81}$, $NR^{c81}R^{d81}$, $NR^{c81}C(O)R^{b81}$, $S(O)_2R^{b81}$, and $S(O)_2NR^{c81}R^{d81}$;

each $R^{a81}$, $R^{c81}$, and $R^{d81}$ is independently selected from H, $C_{1-6}$ alkyl and $C_{1-6}$ haloalkyl; and each $R^{b81}$ is independently selected from $C_{1-6}$ alkyl and $C_{1-6}$ haloalkyl.

In some embodiments:
n is 1 or 2;
$Z^1$ is $CR^4R^5$; and $Z^2$ is O; or
$Z^1$ is $CR^4R^5$ or O; and $Z^2$ is $CR^{4z}R^{5z}$;
Y is N or CH;
$X^1$ is $NR^{1x}$ or $CR^1$;
$X^2$ is $NR^{2x}$ or $CR^2$;
$X^3$ is N or C;
wherein Ring

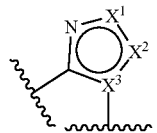

is an aromatic ring selected from:

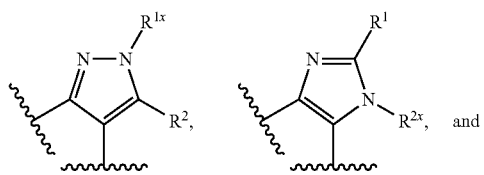

Ring moiety A is an azetidine ring, a pyrrolidine ring, a piperidine ring, or an azepane ring;

$R^1$ is selected from H, halo, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents;

$R^{1x}$ is selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents.

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents;

$R^{2x}$ is selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents;

$R^3$ is selected from H;

$R^4$, $R^{4z}$, $R^5$ and $R^{5z}$ are independently selected from H; or $R^4$ and $R^5$, together with the carbon atom to which they are attached, form a cyclopropyl ring;

one $R^8$ is $S(O)_2R^{b8}$; and each remaining $R^8$ is independently selected from H, halo, CN, $C_{1-6}$ alkyl, $C_{1-6}$ haloalkyl, $OR^{a8}$, and $NR^{c8}R^{d8}$; wherein said $C_{1-6}$ alkyl and $C_{1-6}$ haloalkyl are each optionally substituted by 1, 2, 3, or 4 independently selected $R^{8A}$ substituents;

each $R^{1A}$ is independently selected from halo, CN, $C_{1-6}$ alkyl, $C_{1-6}$ haloalkyl, $C_{3-7}$ cycloalkyl, $OR^{a11}$, and $NR^{c11}R^{d11}$;

each $R^{a11}$, $R^{c11}$, and $R^{d11}$ is independently selected from H, $C_{1-6}$ alkyl and $C_{1-6}$ haloalkyl;

each $R^{2A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, $OR^{a21}$, and $NR^{c21}R^{d21}$;

each $R^{a21}$, $R^{c21}$, and $R^{d21}$ is independently selected from H, $C_{1-6}$ alkyl and $C_{1-6}$ haloalkyl;

each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8A}$ substituents;

each $R^{8A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-4}$ cycloalkyl, $OR^{a81}$, and $NR^{c81}R^{d81}$; and each $R^{a81}$, $R^{c81}$, and $R^{d81}$ is independently selected from H, $C_{1-6}$ alkyl and $C_{1-6}$ haloalkyl.

In some embodiments:

n is 1 or 2;

$Z^1$ is $CR^4R^5$; and $Z^2$ is O; or $Z^1$ is $CR^4R^5$; and $Z^2$ is $CR^{4z}R^{5z}$;

$R^4$ and $R^5$ are each independently selected from H and $C_{1-3}$ alkyl;

or $R^4$ and $R^5$, together with the carbon atom to which they are attached, form a cyclopropyl or cyclobutyl ring;

$R^{4z}$ and $R^{5z}$ are each H;

Y is N;

$X^1$ is $NR^{1x}$ or $CR^1$;

$X^2$ is $NR^{2x}$ or $CR^2$;

$X^3$ is C;

wherein Ring

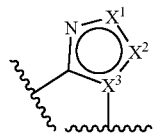

is an aromatic ring selected from:

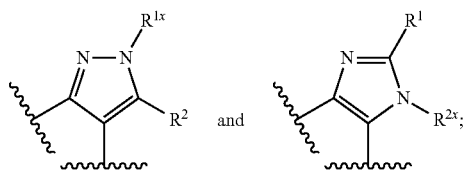

Ring moiety A is azetinidin-3-yl, pyrrolidin-3-yl, piperidin-3-yl, or piperidin-4-yl;

$R^1$ is selected from H, halo, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents;

$R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents;

each $R^{1A}$ is independently selected from halo, CN, $C_{1-6}$ alkyl, $C_{1-6}$ haloalkyl, $C_{3-4}$ cycloalkyl, $OR^{a11}$, and $NR^{c11}R^{d11}$;

each $R^{a11}$, $R^{c11}$, and $R^{d11}$ is independently selected from H and $C_{1-6}$ alkyl;

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

$R^{2x}$ is selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

each $R^{2A}$ is independently selected from halo, CN, $C_{1-6}$ alkyl, $C_{1-6}$ haloalkyl, $C_{3-4}$ cycloalkyl, $OR^{a21}$, and $NR^{c21}R^{d21}$;

each $R^{a21}$, $R^{c21}$, and $R^{d21}$ is independently selected from H and $C_{1-6}$ alkyl;

one $R^8$ is $S(O)_2R^{b8}$;

the remaining $R^8$ is selected from halo or $C_{1-3}$ alkyl;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, or 3 independently selected $R^{8A}$ substituents;

each $R^{8A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a81}$, $SR^{a81}$, $C(O)R^{b81}$, $C(O)NR^{c81}R^{d81}$, $C(O)OR^{a81}$, $OC(O)R^{a81}$, $OC(O)NR^{c81}R^{d81}$, $NR^{c81}R^{d81}$, $NR^{c81}C(O)R^{b81}$, $NR^{c11}C(O)OR^{a81}$, $NR^{c81}C(O)NR^{c81}R^{d81}$, $NR^{c81}S(O)_2R^{b81}$, $NR^{c81}S(O)_2NR^{c81}R^{d81}$, $S(O)_2R^{b81}$, and $S(O)_2NR^{c81}R^{d81}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{a81}$, $R^{c81}$, and $R^{d81}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8B}$ substituents;

each $R^{8B}$ is independently selected from halo, CN, $C_{1-6}$ alkyl, $C_{1-6}$ haloalkyl, $C_{3-4}$ cycloalkyl, $OR^{a82}$, $SR^{a82}$, $C(O)R^{b82}$, $C(O)NR^{c82}R^{b82}$, $C(O)OR^{a82}$, $OC(O)R^{b82}$, $OC(O)NR^{c82}R^{d82}$, $NR^{c82}R^{d82}$, $NR^{c82}C(O)R^{b82}$, $NR^{c82}C(O)OR^{a82}$, $NR^{c82}C(O)NR^{c82}R^{d82}$, $NR^{c82}S(O)_2R^{b82}$, $NR^{c82}S(O)_2NR^{c82}R^{d82}$, $S(O)_2R^{b82}$, and $S(O)_2NR^{c82}R^{d82}$;

each $R^{a82}$, $R^{c82}$, and $R^{d82}$ is independently selected from H, $C_{1-6}$ alkyl, and $C_{1-6}$ haloalkyl; and each $R^{b82}$ is independently selected from $C_{1-6}$ alkyl and $C_{1-6}$ haloalkyl.

In some embodiments:

n is 1 or 2;

$Z^1$ is $CR^4R^5$; and $Z^2$ is O; or $Z^1$ is $CR^4R^5$; and $Z^2$ is $CH_2$;

$R^4$ and $R^5$ are each independently selected from H and methyl;

$R^{4z}$ and $R^{5z}$ are each H;

Y is N;

$X^1$ is $NR^{1x}$ or $CR^1$;

$X^2$ is $NR^{2x}$ or $CR^2$;

$X^3$ is C;

wherein Ring

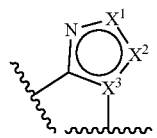

is an aromatic ring selected from:

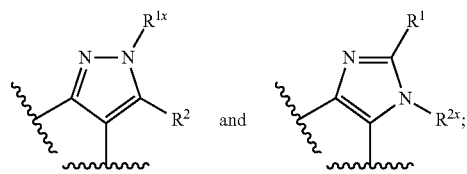

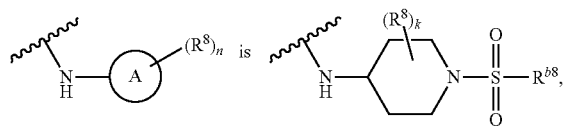

wherein k is n−1;

$R^1$ is selected from H, halo, $C_{1-6}$ alkyl, phenyl, and 5-6 membered heteroaryl, wherein said $C_{1-6}$ alkyl, phenyl and 5-6 membered heteroaryl are each optionally substituted by 1 or 2 independently selected $R^{14}$ substituents;

$R^{1x}$ is selected from H, $C_{1-6}$ alkyl, $C_{3-7}$ cycloalkyl, phenyl, and 4-7 membered heterocycloalkyl, wherein said $C_{1-6}$ alkyl, $C_{3-7}$ cycloalkyl, phenyl, and 4-7 membered heterocycloalkyl are each optionally substituted by 1 or 2 independently selected $R^{14}$ substituents;

each $R^{14}$ is independently selected from halo, CN, $C_{1-6}$ alkyl, $C_{1-6}$ haloalkyl, $C_{3-4}$ cycloalkyl, $OR^{a11}$, and $NR^{c11}R^{d11}$;

each $R^{a11}$, $R^{c11}$, and $R^{d11}$ is independently selected from H and $C_{1-6}$ alkyl;

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, and 5-6 membered heteroaryl;

$R^{2x}$ is selected from H, $C_{1-6}$ alkyl, $C_{3-7}$ cycloalkyl, and phenyl-$C_{1-3}$ alkyl;

$R^8$ is $C_{1-3}$ alkyl;

each $R^{b8}$ is independently selected from $C_{1-6}$ alkyl, $C_{3-7}$ cycloalkyl, phenyl, 4-7 membered heterocycloalkyl, and 5-6 membered heteroaryl, which are each optionally substituted with 1 or 2 independently selected $R^{8A}$ substituents;

each $R^{8A}$ is independently selected from halo, CN, $C_{1-6}$ alkyl, $C_{1-6}$ haloalkyl, and 4-7 membered heterocycloalkyl; wherein said $C_{1-6}$ alkyl, $C_{1-6}$ haloalkyl, and 4-7 membered heterocycloalkyl are each optionally substituted by 1 or 2 independently selected $R^{8B}$ substituents;

each $R^{8B}$ is selected from $C_{1-6}$ alkyl and $OR^{a82}$; and each $R^{a82}$ is independently selected from H and $C_{1-6}$ alkyl.

In some embodiments, the compound is a compound of Formula (IIa):

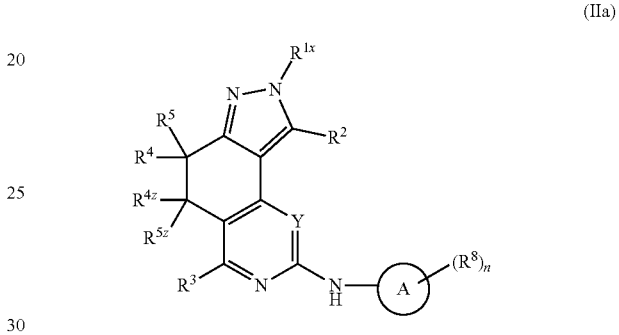

or a pharmaceutically acceptable salt thereof.

In some embodiments, the compound is a compound of Formula (IIb):

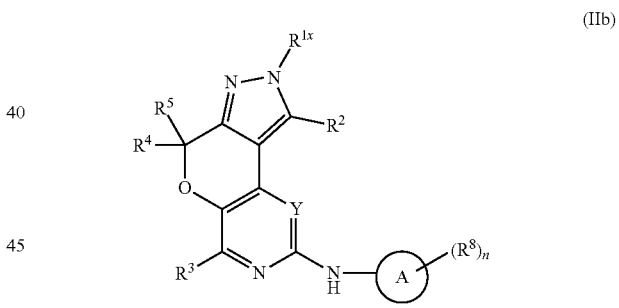

or a pharmaceutically acceptable salt thereof.

In some embodiments, the compound is a compound of Formula (IIc):

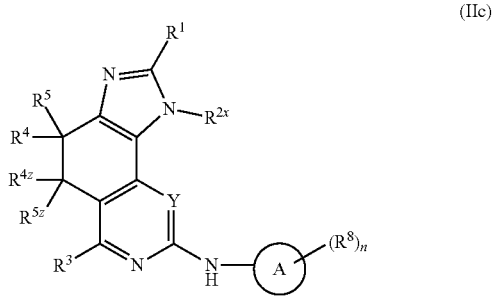

or a pharmaceutically acceptable salt thereof.

In some embodiments, the compound is a compound of Formula (IId):

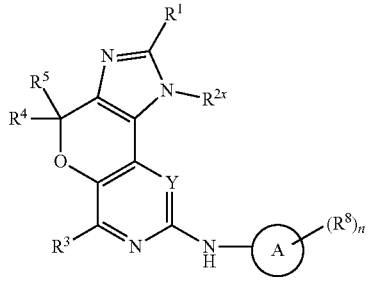

(IId)

or a pharmaceutically acceptable salt thereof.

In some embodiments, the compound is a compound of Formula (IIIa):

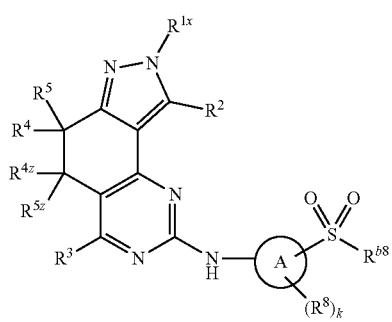

(IIIa)

or a pharmaceutically acceptable salt thereof, wherein k is n−1.

In some embodiments, the compound is a compound of Formula (IIIb):

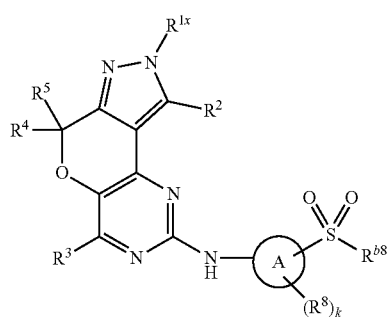

(IIIb)

or a pharmaceutically acceptable salt thereof, wherein k is n−1.

In some embodiments, the compound is a compound of Formula (IIIc):

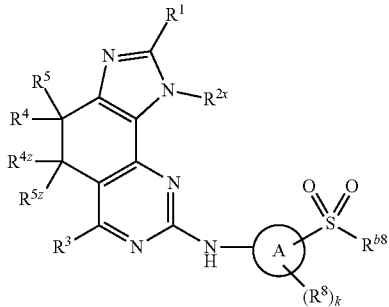

(IIIc)

or a pharmaceutically acceptable salt thereof, wherein k is n−1.

In some embodiments, the compound is a compound of Formula (IIId):

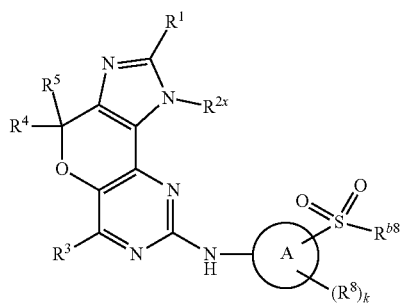

(IIId)

or a pharmaceutically acceptable salt thereof, wherein k is n−1.

In some embodiments, the compound is a compound of Formula (IVa):

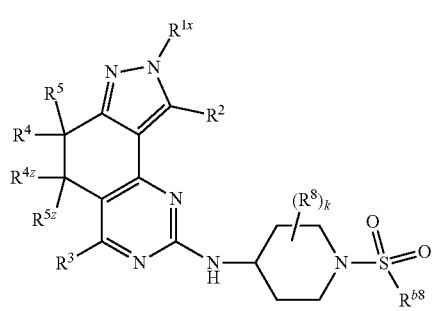

(IVa)

or a pharmaceutically acceptable salt thereof, wherein k is n−1.

In some embodiments, the compound is a compound of Formula (IVb):

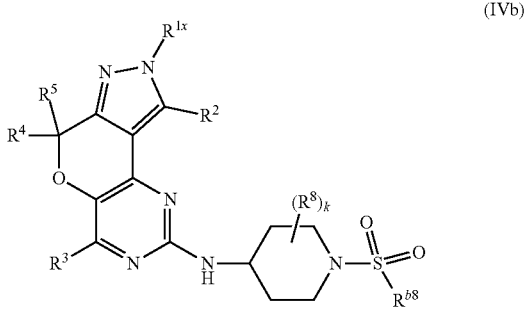

(IVb)

or a pharmaceutically acceptable salt thereof, wherein k is n−1.

In some embodiments, the compound is a compound of Formula (IVc):

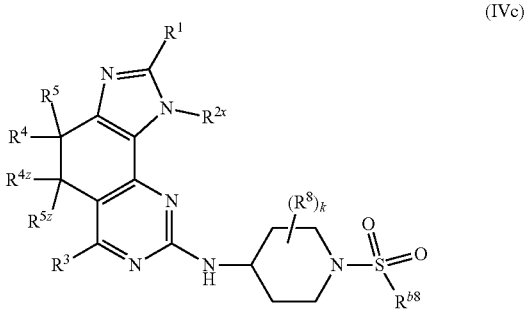

(IVc)

or a pharmaceutically acceptable salt thereof, wherein k is n−1.

In some embodiments, the compound is a compound of Formula (IVd):

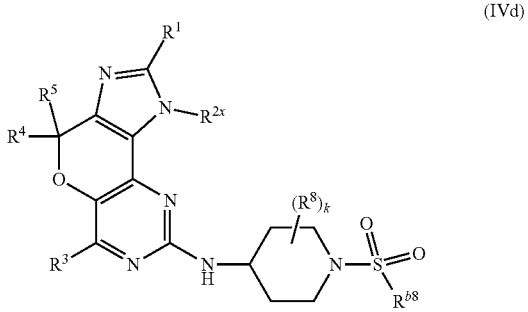

(IVd)

or a pharmaceutically acceptable salt thereof, wherein k is n−1.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-4}$ alkyl-" and "alkylene" linking groups, as described herein, are optionally replaced by deuterium atoms.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

When an embodiment that recites "one $R^8$ is $S(O)_2R^{b8}$; and each remaining $R^8$ is independently selected from" is combined through multiple dependencies with a formula showing a floating —$S(O)_2R$ substituent (e.g., Formula (IIIa)), then the floating —$S(O)_2RV$ substituent on the formula replaces the "one $R^8$ is $S(O)_2R^{b8}$" phrase. In the case of such an embodiment combined with Formula (IIIa), one of the $R^8$ substituents (of n possible $R^8$ substituents) is replaced by the $S(O)_2R$ substituent on Formula (IIIa), wherein each of the remaining $R^8$ substituents (there being k remaining $R^8$ substituents) is independently selected from the "each remaining $R^8$" list.

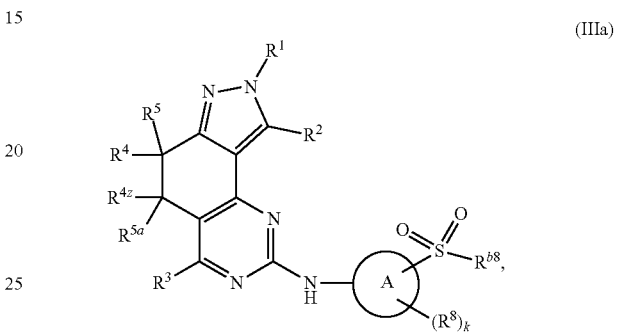

(IIIa)

wherein k is n−1.

At various places in the present specification, divalent linking substituents are described. Unless otherwise specified, it is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency, that the designated atom's normal valency is not exceeded, and that the substitution results in a stable compound.

As used herein, the term "independently selected from" means that each occurrence of a variable or substituent are independently selected at each occurrence from the applicable list.

When any variable (e.g., $R^G$) occurs more than one time in any constituent or formula for a compound, its definition at each occurrence is independent of its definition at every other occurrence. Thus, for example, if a group is shown to be substituted with 1, 2, 3, or 4 $R^G$, then said group may optionally be substituted with up to four $R^G$ groups and $R^G$ at each occurrence is selected independently from the definition of $R^G$. Also, combinations of substituents and/or variables are permissible only if such combinations result in stable compounds.

In some embodiments, when an optionally multiple substituent is designated in the form:

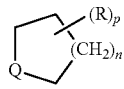

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is said to be $CH_2$, NH, etc., any floating substituent such as R in the above example, can replace a hydrogen of the Q variable as well as a hydrogen in any other non-variable component of the ring.

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (i-Pr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2 or 3 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, the aryl group has from 6 to 10 carbon atoms.

In some embodiments, the aryl group is phenyl or naphthyl. In some embodiments, the aryl is phenyl.

As used herein, "halo" refers to F, Cl, Br, or I. In some embodiments, halo is F, Cl, or Br. In some embodiments, halo is F or Cl. In some embodiments, halo is F. In some embodiments, halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "$C_{n-m}$ fluoroalkyl" refers to an alkyl group having from one fluoro atom to 2s+1 fluoro atoms, where "s" is the number of carbon atoms in the alkyl group, wherein the alkyl group has n to m carbon atoms. In some embodiments, the alkyl group has 1 to 6, 1 to 4, or 1 to 3 carbon atoms. Example haloalkyl groups include $CF_3$, $C_2F_5$, $CHF_2$, $CH_2F$, and the like.

As used herein, the term "thio" refers to a group of formula —SH.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonylamino" refers to a group of formula —NHC(O)O($C_{n-m}$ alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamoyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-$C_{n-m}$ alkyl" refers to a group of formula —($C_{n-m}$ alkylene)-CN, wherein the alkylene group has n to m carbon atoms. As used herein, the term "cyano-$C_{1-3}$ alkyl" refers to a group of formula —($C_{1-3}$ alkylene)-CN.

As used herein, the term "HO—$C_{n-m}$ alkyl" refers to a group of formula $C_{n-m}$ alkylene)-OH, wherein the alkylene group has n to m carbon atoms. As used herein, the term "HO—$C_{1-3}$ alkyl" refers to a group of formula —($C_{1-3}$ alkylene)-OH.

As used herein, the term "$C_{n-m}$ alkoxy-$C_{o-p}$ alkyl" refers to a group of formula —($C_{n-m}$ alkylene)-O($C_{o-p}$ alkyl), wherein the alkylene group has n to m carbon atoms and the alkyl group has o to p carbon atoms. As used herein, the term "$C_{1-3}$ alkoxy-$C_{1-3}$ alkyl" refers to a group of formula —($C_{1-3}$ alkylene)-O($C_{1-3}$ alkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms.

In some embodiments, each alkyl group independently has 1 to 6, 1 to 4, or 1 to 3 carbon atoms.

As used herein, the term "$C_{n-m}$ alkylcarbonyloxy" is a group of formula —OC(O)— alkyl, wherein the alkyl group has n to m carbon atoms. In some embodiments, the alkyl group has 1 to 6, 1 to 4, or 1 to 3 carbon atoms.

As used herein, "aminocarbonyloxy" is a group of formula —OC(O)—NH$_2$.

As used herein, "$C_{n-m}$ alkylaminocarbonyloxy" is a group of formula —OC(O)—NH— alkyl, wherein the alkyl group has n to m carbon atoms. In some embodiments, the alkyl group has 1 to 6, 1 to 4, or 1 to 3 carbon atoms.

As used herein, "di($C_{n-m}$alkyl)aminocarbonyloxy" is a group of formula —OC(O)—N(alkyl)$_2$, wherein each alkyl group has, independently, n to m carbon atoms. In some embodiments, each alkyl group independently has 1 to 6, 1 to 4, or 1 to 3 carbon atoms.

As used herein $C_{n-m}$ alkoxycarbonylamino refers to a group of formula —NHC(O)—O-alkyl, wherein the alkyl group has n to m carbon atoms.

As used herein, the term "carbamyl" to a group of formula —C(O)NH$_2$.

As used herein, the term "carbonyl", employed alone or in combination with other terms, refers to a —C(O)— group.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13 or 14 ring-forming carbons (i.e., $C_{3-14}$). In some embodiments, cycloalkyl is $C_{3-14}$ cycloalkyl, wherein 1, 2, 3, or 4 ring-forming carbon atoms of said $C_{3-14}$ cycloalkyl can be optionally substituted by one or more oxo or sulfido. In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-14}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a monocyclic, bicyclic, or tricyclic 5-14 membered heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, and S. In some embodiments, the heteroaryl is a 5-6 monocyclic heteroaryl having 1 or 2 heteroatom ring members independently selected from N, O, and S. In some embodiments, the heteroaryl group contains 5 to 14, 5 to 10, 5 to 6, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridyl, pyrimidinyl, pyrazinyl, pyridazinyl, pyrrolyl, pyrazolyl, azolyl, oxazolyl, isoxazolyl, thiazolyl, isothiazolyl, imidazolyl, furyl, thienyl, triazolyl (e.g., 1,2,3-triazolyl, 1,2,4-triazolyl, 1,3,4-triazolyl), tetrazolyl, thiadiazolyl (e.g., 1,2,3-thiadiazolyl, 1,2,4-thiadiazolyl, 1,3,4-thiadiazolyl), quinolinyl, isoquinolinyl, indolyl, benzothienyl, benzofuran, benzisoxazole, imidazo[1, 2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, and oxadiazolyl (e.g., 1,2,3-oxadiazolyl, 1,2,4-oxadiazolyl, 1,3,4-oxadiazolyl).

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 4-14, 4-12, 4-10, 5-7, 4-7, 4-6, and 5-6-membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 4 to 14 ring-forming atoms, 4 to 10 ring-forming atoms, 4 to 7 ring-forming atoms, 4 to 6 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom.

In some embodiments, the heterocycloalkyl is a 4-14 membered monocyclic, bicyclic, or tricyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-10 membered monocyclic, bicyclic, or tricyclic heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido. In some embodiments, the heterocycloalkyl is a 4-7 membered monocyclic heterocycloalkyl having 1 or 2 ring-forming heteroatoms independently selected from N, O, and S, and wherein 1, 2 or 3 ring-forming carbon or heteroatoms can be optionally substituted by one or more oxo or sulfido. In some embodiments, the heterocycloalkyl is a monocyclic 4-6 membered heterocycloalkyl having 1 or 2 heteroatoms independently selected from N, O, and S and having one or more oxidized ring members. Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl, and the like.

As used herein, "$C_{o-p}$ cycloalkyl-$C_{n-m}$ alkyl-" refers to a group of formula cycloalkyl-alkylene-, wherein the cycloalkyl has o to p carbon ring members and the alkylene linking group has n to m carbon atoms.

As used herein "$C_{o-p}$ aryl-$C_{n-m}$ alkyl-" refers to a group of formula aryl-alkylene-, wherein the aryl has o to p carbon ring members and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

At certain places, the definitions or embodiments refer to specific rings (e.g., an azetidine ring, a pyridine ring, etc.).

Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes, such as those provided in the in the Schemes below.

The reactions for preparing compounds described herein can be carried out in suitable solvents which can be readily selected by one of skill in the art of organic synthesis.

Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, e.g., Wuts et al., *Protective Groups in Organic Synthesis,* 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of formula 1-4 can be prepared by the general synthetic procedure illustrated in Scheme 1. Appropriately substituted compounds of formula 1-1 can react with 1-tert-butoxy-N,N,N',N'-tetramethylmethanediamine to provide compounds of formula 1-2. Compounds of formula 1-2 can then be converted into compounds of formula 1-4 via reaction with appropriately substituted compounds of formula 1-3 in the presence of a suitable base such as NaOEt.

Scheme 1

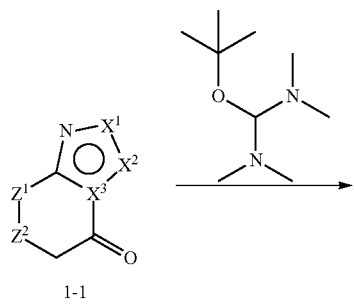

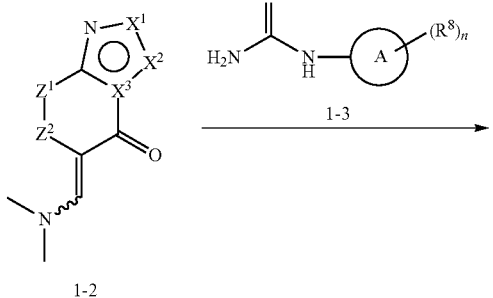

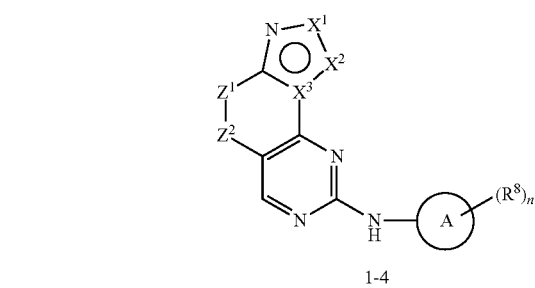

Compounds of formula 2-7 with a variety of substitution can be prepared using the processes illustrated in Scheme 2. As shown in Scheme 2, appropriately substituted compounds of formula 2-1 can react with appropriately substituted compounds of formula 2-2 in the presence of a suitable base such as DIPEA to provide compounds of formula 2-3. Compounds of formula 2-3 can then be converted into compounds of formula 2-4 via rearrangement reaction in the presence of a suitable Lewis acid such as AlCl$_3$. Compounds of formula 2-5 can be accessed via the reaction of compounds of formula 2-4 with oxalyl chloride. Compounds of formula 2-5 can react with appropriately substituted compounds of formula 2-6 in the presence of a suitable base such as DIPEA to yield compounds of formula 2-7. Alternatively, compounds of formula 2-5 can react with appropriately substituted compounds of formula 2-8 in the presence of a suitable base such as DIPEA to provide compounds of formula 2-9 which can be then converted into compounds of formula 2-7 by deprotection of Boc protecting group under acidic condition.

Scheme 2

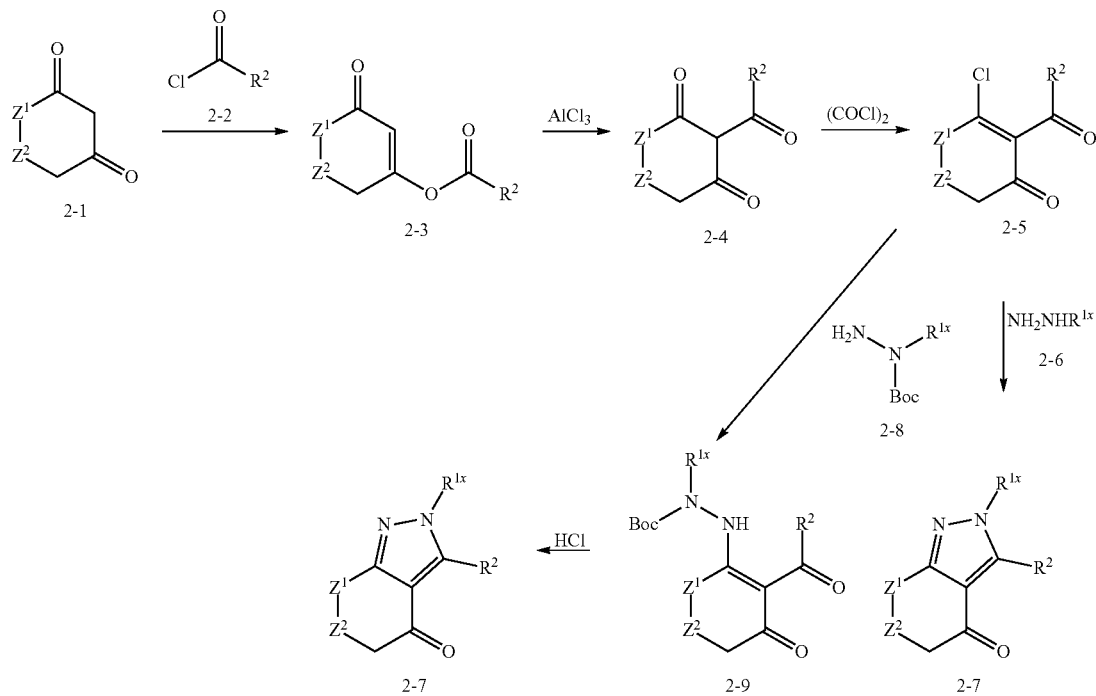

Compounds of formula 3-7 with a variety of substitution can be prepared using the processes illustrated in Scheme 3. As shown in Scheme 3, appropriately substituted compounds of formula 3-1 can react with NBS to provide compounds of formula 3-2. Compounds of formula 3-4 can be accessed via the reaction of compounds of formula 3-2 with appropriately substituted compounds of formula 3-3 and a suitable base such as $K_2CO_3$. Compounds of formula 3-4 can then be converted into compounds of formula 3-7 by a number of methods, e.g., by nucleophilic substitution with appropriately substituted halides of formula 3-6 (X=Cl, Br or I) in a suitable solvent (e.g., DMSO, DMF, 1,4-dioxane) with or without a suitable base (e.g., triethylamine, N,N-diisopropylethylamine, or $Cs_2CO_3$), or by a suitable C—N cross-coupling, including Chan-Lam coupling with appropriately substituted boronic acids of formula 3-5 (e.g., in the presence of a copper catalyst such as $Cu(OAc)_2$, a ligand such as 2,2'-bipyridine and a base such as $K_2CO_3$) in a suitable solvent (e.g., 1,4-dioxane or 1,2-dichloroethane).

Scheme 3

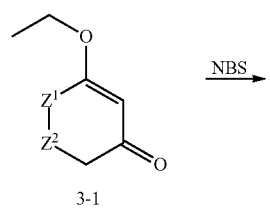

-continued

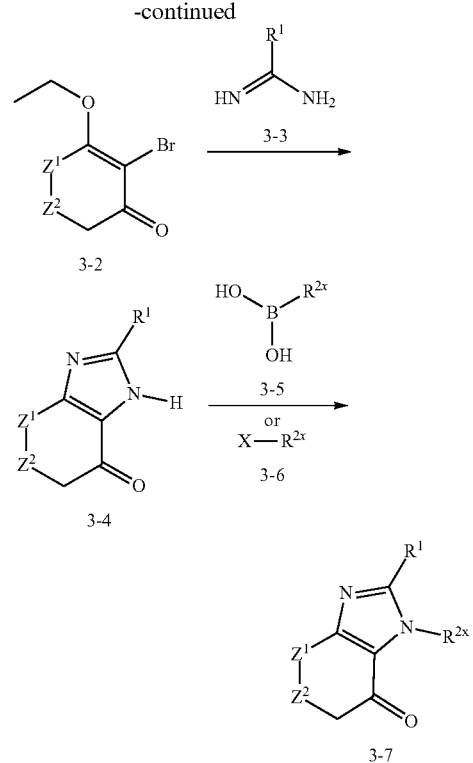

Alternatively, compounds of formula 3-7 with a variety of substitution can also be prepared using the processes illustrated in Scheme 4. As shown in Scheme 4, appropriately substituted compounds of formula 4-1 can react with appropriately substituted compounds of formula 4-2 in the presence of a suitable base such as Et₃N to provide compounds of formula 4-3. Compounds of formula 4-3 can then be converted into compounds of formula 3-7 by reacting with appropriately substituted compounds of formula 3-2 in the presence of a suitable base such as Et₃N.

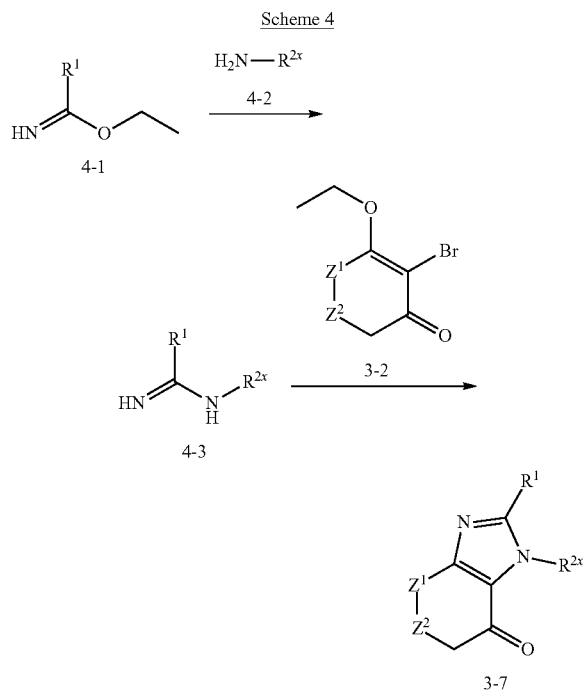

Compounds of formula 1-3 with a variety of substitution can be prepared using the processes illustrated in Scheme 5. Appropriately substituted compounds of formula 5-1 can react with 1H-pyrazole-1-carboximidamide hydrochloride in the presence of a suitable base such as DIPEA to provide compounds of formula 1-3.

Methods of Use

Compounds of the present disclosure can inhibit CDK2 and therefore are useful for treating diseases wherein the underlying pathology is, wholly or partially, mediated by CDK2. Such diseases include cancer and other diseases with proliferation disorder. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors with aberrations that activate the CDK2 kinase activity. These include, but not limited to, disease (e.g., cancers) that are characterized by amplification or overexpression of CCNE1 such as ovarian cancer, uterine carcinosarcoma and breast cancer and p27 inactivation such as breast cancer and melanomas. Accordingly, in some embodiments of the methods, the patient has been previously determined to have an amplification of the cyclin E1 (CCNE1) gene and/or an expression level of CCNE1 in a biological sample obtained from the human subject that is higher than a control expression level of CCNE1. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells with CCNE1 amplification and overexpression in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method of inhibiting CDK2, comprising contacting the CDK2 with a compound of Formula (I) or any of the formulas as described herein, a compound as recited in any of the claims and described herein, or a salt thereof. In some embodiments, provided herein is a method of inhibiting CDK2 in a patient, comprising administering to the patient a compound of Formula (I) or any of the formulas as described herein, a compound as recited in any of the claims and described herein, or a salt thereof.

In some embodiments, provided herein is a method for treating cancer. The method includes administering to a patient (in need thereof), a therapeutically effective amount of a compound of Formula (I) or any of the formulas as described herein, a compound as recited in any of the claims and described herein, or a salt thereof. In another embodiment, the cancer is characterized by amplification or overexpression of CCNE1. In some embodiments, the cancer is ovarian cancer or breast cancer, characterized by amplification or overexpression of CCNE1.

In some embodiments, provided herein is a method of treating a disease or disorder associated with CDK2 in a patient, comprising administering to the patient a therapeutically effective amount of a compound of Formula (I) or any of the formulas as described herein, a compound as recited in any of the claims and described herein, or a salt thereof. In some embodiments, the disease or disorder associated with CDK2 is associated with an amplification of the cyclin E1 (CCNE1) gene and/or overexpression of CCNE1.

In some embodiments, the disease or disorder associated with CDK2 is N-myc amplified neuroblastoma cells (See Molenaar et al., *Proc Natl Acad Sci USA*, 106(31):12968-12973), K-Ras mutant lung cancers (see Hu, S., et al., *Mol Cancer Ther*, 2015, 14(11):2576-85, and cancers with FBW7 mutation and CCNE1 overexpression (see Takada, et al., *Cancer Res*, 2017, 77(18):4881-4893).

In some embodiments, the disease or disorder associated with CDK2 is lung squamous cell carcinoma, lung adenocarcinoma, pancreatic adenocarcinoma, breast invasive carcinoma, uterine carcinosarcoma, ovarian serous cystadenocarcinoma, stomach adenocarcinoma, esophageal carcinoma, bladder urothelial carcinoma, mesothelioma, or sarcoma.

In some embodiments, the disease or disorder associated with CDK2 is lung adenocarcinoma, breast invasive carcinoma, uterine carcinosarcoma, ovarian serous cystadenocarcinoma, or stomach adenocarcinoma.

In some embodiments, the disease or disorder associated with CDK2 is an adenocarcinoma, carcinoma, or cystadenocarcinoma.

In some embodiments, the disease or disorder associated with CDK2 is uterine cancer, ovarian cancer, stomach cancer, esophageal cancer, lung cancer, bladder cancer, pancreatic cancer, or breast cancer.

In some embodiments, the disease or disorder associated with CDK2 is a cancer.

In some embodiments, the cancer is characterized by amplification or overexpression of CCNE1. In some embodiments, the cancer is ovarian cancer or breast cancer, characterized by amplification or overexpression of CCNE1.

In some embodiments, the breast cancer is chemotherapy or radiotherapy resistant breast cancer, endocrine resistant breast cancer, trastuzumab resistant breast cancer, or breast cancer demonstrating primary or acquired resistance to CDK4/6 inhibition. In some embodiments, the breast cancer is advanced or metastatic breast cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma, BRAF and HSP90 inhibition-resistant melanoma), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer, urothelial cancer (e.g., bladder) and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer (SCLC), bronchogenic carcinoma, squamous cell, undifferentiated small cell, undifferentiated large cell, adenocarcinoma, alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, Merkel cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK2-associated diseases, disorders or conditions. Other agents such as therapeutic antibodies can be used in combination with the compounds of the present disclosure for treatment of CDK2-associated diseases, disorders or conditions. The one or more additional pharmaceutical agents can be administered to a patient simultaneously or sequentially.

In some embodiments, the CDK2 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein.

Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-DR, PKA, PKG, PKC, CaM-kinase, phosphorylase kinase, MEKK, ERK, MAPK, mTOR$^{a1}$, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, fit-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib or baricitinib; JAK1, e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3K6 inhibitor and the like. The compounds can be administered in combination with one or more anti-cancer drugs, such as a chemotherapeutic agent. Examples of chemotherapeutics include any of abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a CDK2 inhibitor of the present disclosure with an additional agent.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *Chlamydia*, rickettsial bacteria, mycobacteria, staphylococci, streptococci, pneumococci, meningococci and conococci, *Klebsiella, Proteus, Serratia, Pseudomonas, Legionella,* diphtheria, *Salmonella,* bacilli, cholera, tetanus, botulism, anthrax, plague, leptospirosis, and Lyme's disease bacteria.

Pathogenic fungi causing infections treatable by methods of the disclosure include, but are not limited to, *Candida (albicans, krusei, glabrata, tropicalis,* etc.), *Cryptococcus neoformans, Aspergillus (fumigatus, niger,* etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD122, CD96, CD73, CD47, GITR, CSF1R, JAK, PI3K delta, PI3K gamma, TAM, arginase, HPK1, CD137 (also known as 4-1B), ICOS, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1B).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g., urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736. In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration.

Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating CDK2 in tissue samples, including human, and for identifying CDK2 activators by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes CDK2 assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups of the disclosed Formulas (e.g., Formula (I)) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene and alkynylene linking groups, as described herein, are optionally replaced by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et al. J. Med. Chem. 2011, 54, 201-210; R. Xu et al. J. Label Compd. Radiopharm. 2015, 58, 308-312). In particular, substitution at one or more metabolism sites may afford one or more of the therapeutic advantages.

The radionuclide that is incorporated in the instant radiolabeled compounds will depend on the specific application of that radio-labeled compound. For example, for in vitro CDK2 labeling and competition assays, compounds that incorporate $^3$H, $^{14}$C, $^{82}$Br, $^{125}$I, $^{131}$I, or $^{35}$S can be useful. For radio-imaging applications $^{11}$C, $^{18}$F, $^{125}$I, $^{123}$I, $^{124}$I, $^{131}$I, $^{75}$Br, $^{76}$Br, or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S, and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind activate CDK2 by monitoring its concentration variation when contacting with CDK2, through tracking of the labeling. For example, a test compound (labeled) can be evaluated for its ability to reduce binding of another compound which is known to inhibit CDK2 (i.e., standard compound). Accordingly, the ability of a test compound to compete with the standard compound for binding to CDK2 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of CDK2-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Biomarkers and Pharmacodynamics Markers

The disclosure further provides predictive markers (e.g., biomarkers and pharmacodynamic markers, e.g., gene copy number, gene sequence, expression levels, or phosphorylation levels) to identify those human subjects having, suspected of having, or at risk of developing a disease or disorder associated with CDK2 for whom administering a CDK2 inhibitor ("a CDK2 inhibitor" as used herein refers to a compound of the disclosure, or a pharmaceutically acceptable salt thereof) is likely to be effective. The disclosure also provides pharmacodynamic markers (e.g., phosphorylation levels) to identify those human subjects having, suspected of having, or at risk of developing a disease or disorder associated with CDK2 whom are responding to a CDK2 inhibitor.

The methods are based, at least in part, on the discovery that the functional status of cyclin dependent kinase inhibitor 2A ("CDKN2A"; also referred to as "p16") is a biomarker for predicting sensitivity to CDK2-targeting therapies in G1/S-specific cyclin-E1-("CCNE1-") amplified cells suitable for use in patient stratification. In addition, the present invention is based, at least in part, on the discovery that, in CCNE1-amplified cell lines, the level of human retinoblastoma associated protein ("Rb") phosphorylation at the serine corresponding to amino acid position 780 of SEQ ID NO:3 is a pharmacodynamic marker for CDK2 activity and is suitable for use in measuring CDK2 enzymatic activity in cellular assay or preclinical and clinical applications, such as, e.g., monitoring the progress of or responsiveness to treatment with a CDK2 inhibitor.

CCNE1 and p16

CCNE1 and p16 have been identified in the Examples as genes, in combination, useful in predicting responsiveness (e.g., improvement in disease as evidenced by disease remission/resolution) of a subject having a disease or disorder associated with CDK2 to a CDK2 inhibitor.

p16 (also known as cyclin-dependent kinase inhibitor 2A, cyclin-dependent kinase 4 inhibitor A, multiple tumor suppressor 1, and p16-INK4a) acts as a negative regulator of the proliferation of normal cells by interacting with CDK4 and CDK6. p16 is encoded by the cyclin dependent kinase inhibitor 2A ("CDKN2A") gene (GenBank Accession No. NM_000077). The cytogenic location of the CDKN2A gene is 9p21.3, which is the short (p) arm of chromosome 9 at position 21.3. The molecular location of the CDKN2A gene is base pairs 21,967,752 to 21,995,043 on chromosome 9 (Homo sapiens Annotation Release 109, GRCh38.p12). Genetic and epigenetic abnormalities in the gene encoding p16 are believed to lead to escape from senescence and cancer formation (Okamoto et al., 1994, PNAS 91(23): 11045-9). Nonlimiting examples of genetic abnormalities in the gene encoding p16 are described in Table A, below. The amino acid sequence of human p16 is provided below (GenBank Accession No. NP_000068/UniProtKB Accession No. P42771):

```
                                          (SEQ ID NO: 1)
  1 MEPAAGSSME PSADWLATAA ARGRVEEVRA LLEAGALPNA

PNSYGRRPIQ VMMMGSARVA

61 ELLLLHGAEP NCADPATLTR PVHDAAREGF LDTLVVLHRA

GARLDVRDAW GRLPVDLAEE

121 LGHRDVARYL RAAAGGTRGS NHARIDAAEG PSDIPD
```

CCNE1 is a cell cycle factor essential for the control of the cell cycle at the G1/S transition (Ohtsubo et al., 1995, Mol. Cell. Biol. 15:2612-2624). CCNE1 acts as a regulatory subunit of CDK2, interacting with CDK2 to form a serine/threonine kinase holoenzyme complex. The CCNE1 subunit of this holoenzyme complex provides the substrate specificity of the complex (Honda et al., 2005, EMBO 24:452-463). CCNE1 is encoded by the cyclin E1 ("CCNE1") gene (GenBank Accession No. NM_001238). The amino acid sequence of human CCNE1 is provided below (GenBank Accession No. NP_001229/UniProtKB Accession No. P24864):

```
                                          (SEQ ID NO: 2)
  1 mprerrerda kerdtmkedg gaefsarsrk rkanvtvflq dpdeemakid rtardqcgsq 61 pwdnnavcad pcsliptpdk edddrvypns tckpriiaps rgsplpvlsw anreevwkim 121 lnkektylrd qhfleghpll qpkmrailld wlmevcevyk lhretfylaq dffdrymatq 181 envvktllql igisslfiaa kleeiyppkl hqfayvtdga csgdeiltme lmimkalkwr 241 lspltivswl nvymqvayln dlhevllpqy pqqifiqiae lldlcvldvd clefpygila 301 asalyhfsss elmqkvsgyq wcdiencvkw mvpfamvire tgssklkhfr gvadedahni 361 qthrdsldll dkarakkaml seqnrasplp sglltppqsg kkqssgpema.
```

The Examples demonstrate CDK2-knockdown inhibits proliferation of CCNE1-amplified cell lines, but not of CCNE-non-amplified cell lines. Conversely, the Examples show that CDK4/6 inhibition inhibits proliferation of CCNE1-non-amplified cell lines, but not of CCNE-amplified cell lines. The Examples further demonstrate that presence of a normal (e.g., non-mutated or non-deleted) p16 gene is required for the observed inhibition of cell proliferation in CCNE1-amplified cells treated with a CDK2-inhibitor. Accordingly, CCNE1 and p16 are, together, a combination biomarker: cells that respond to treatment with a CDK2 inhibitor display an amplification of the CCNE1 gene and/or an expression level of CCNE1 that is higher than a control expression level of CCNE1, and have a nucleotide sequence (e.g., a gene or an mRNA) that encodes the p16 protein (e.g., a p16 protein comprising the amino acid sequence of SEQ ID NO:1) and/or have p16 protein present, while control cells that do not respond to treatment with a CDK2 inhibitor do not have an amplification of the CCNE1 gene and/or an expression level of CCNE1 that is higher than a control expression level of CCNE1, and tend to have a mutated or deleted gene that encodes the p16 protein and/or lack expression of p16 protein.

Thus, the disclosure provides a method of treating a human subject having, suspected of having, or at risk of developing a disease or disorder associated with CDK2, comprising administering to the human subject a CDK2 inhibitor, wherein the human subject has been previously determined to: (i) (a) have a nucleotide sequence encoding a p16 protein comprising the amino acid sequence of SEQ ID NO:1, (b) have a CDKN2A gene lacking one or more inactivating nucleic acid substitutions and/or deletions, and/or (c) express a p16 protein, and (ii) (a) have an amplification of the CCNE1 gene and/or (b) have an expression level of CCNE1 in a biological sample obtained from the human subject that is higher than a control expression level of CCNE1. In certain embodiments, the predictive methods described herein predict that the subject will respond to treatment with the CDK2 inhibitor with at least 50%, at least 60%, at least 70%, at least 80%, at least 90%, at least 95%, at least 98% or 100% accuracy. For example, in some embodiments, if the predictive methods described herein are applied to 10 subjects having, suspected of having, or at risk of developing a disease or disorder associated with CDK2, and 8 of those 10 subjects are predicted to respond to treatment with a CDK2 inhibitor based on a predictive method described herein, and 7 of those 8 subjects do indeed respond to treatment with a CDK2 inhibitor, then the predictive method has an accuracy of 87.5% (7 divided by 8). A subject is considered to respond to the CDK2 inhibitor if the subject shows any improvement in disease status as evidenced by, e.g., reduction or alleviation in symptoms, disease remission/resolution, etc.

In some embodiments, the subject has a disease or disorder associated with CDK2. In some embodiments, the human subject has been previously determined to: (i) (a) have a nucleotide sequence encoding a p16 protein comprising the amino acid sequence of SEQ ID NO:1 and/or (b) a CDKN2A gene lacking one or more inactivating nucleic acid substitutions and/or deletions, and (ii) have an amplification of the CCNE1 gene in a biological sample obtained from the human subject. In some embodiments, the CDKN2A gene encodes a protein comprising the amino acid sequence of SEQ ID NO:1. In specific embodiments, the CDKN2A gene encodes a protein comprising the amino acid sequence of SEQ ID NO:1.

In specific embodiments, the one or more inactivating nucleic acid substitutions and/or deletions in the CDKN2A gene is as described in Table A. In specific embodiments, the one or more inactivating nucleic acid substitutions and/or deletions in the CDKN2A gene is as described in Yarbrough et al., Journal of the National Cancer Institute, 91(18):1569-1574, 1999; Liggett and Sidransky, Biology of Neoplasia, Journal of Oncology, 16(3):1197-1206, 1998, and Cairns et al., Nature Genetics, 11:210-212, 1995, each of which is incorporated by reference herein in its entirety.

TABLE A

CDKN2A gene substitutions, deletions, and modifications

| Description | Reference(s) |
| --- | --- |
| C to T transition converting codon 232 of the CDKN2A gene from an arginine codon to a stop codon | RefSNP Accession No. rs121913388; Kamb et al., Science 264: 436-440, 1994 |
| 19-basepair germline deletion at nucleotide 225 causing a reading-frame shift predicted to severely truncate p16 protein | RefSNP Accession No. rs587776716; Gruis et al., Nature Genet. 10: 351-353, 1995 |
| 6-basepair deletion at nucleotides 363-368 of the CDKN2A gene | ClinVar Accession No. RCV000010017.2; Liu et al., Oncogene 11: 405-412, 1995 |
| Mutation at chromosome 9:21971058 predicted to substitute glycine corresponding to amino acid position 101 of SEQ ID NO: 1 with a tryptophan | RefSNP Accession No. rs104894094; Ciotti et al., Am. J. Hum. Genet. 67: 311-319, 2000 |
| Germline mutation constituting an in-frame 3-basepair duplication at nucleotide 332 in exon 2 of the CDKN2A gene | ClinVar Accession No. RCV000010020.3; Borg et al., Cancer Res. 56: 2497-2500, 1996 |
| Mutation predicted to substitute methionine corresponding to amino acid position 53 of SEQ ID NO: 1 with an isoleucine | RefSNP Accession No. rs104894095; Harland et al., Hum. Molec. Genet. 6: 2061-2067, 1997 |
| Mutation predicted to substitute arginine corresponding to amino acid position 24 of SEQ ID NO: 1 with a proline | RefSNP Accession No. rs104894097; Monzon et al., New Eng. J. Med. 338: 879-887, 1998 |
| 24-basepair repeat inserted at chromosome 9 between 21974795 and 21974796 (forward strand) | RefSNP Accession No. rs587780668; Pollock et al., Hum. Mutat. 11: 424-431, 1998) |
| G-to-T transversion at nucleotide −34 of the CDKN2A gene | ClinVar Accession No. RCV000010024.5; Liu et al., Nature Genet. 21: 128-132, 1999 |
| Deletion of the p14(ARF)-specific exon 1-beta of CDKN2A | ClinVar Accession No. RCV000010026.2; Randerson-Moor et al., Hum. Molec. Genet. 10: 55-62, 2001 |
| Mutation predicted to substitute valine corresponding to amino acid position 126 of SEQ ID NO: 1 with an isoleucine | RefSNP Accession No. rs104894098; Goldstein et al., Brit. J. Cancer 85: 527-530, 2001 |
| Transition (IVS2-105 A-G) in intron 2 of the CDKN2A gene creating a false GT splice donor site 105 bases 5-prime of exon 3 resulting in aberrant splicing of the mRNA | ClinVar Accession No. RCV000010028.3; Harland et al., Hum. Molec. Genet. 10: 2679-2686, 2001 |
| Mutation predicted to result in substitution of glycine corresponding to amino acid position 122 of SEQ ID NO: 1 with an arginine | RefSNP Accession No. rs113798404; Hewitt et al., Hum. Molec. Genet. 11: 1273-1279, 2002 |
| Mutation predicted to result in substitution of valine corresponding to amino acid position 59 of SEQ ID NO: 1 with an arginine | RefSNP Accession No. rs113798404; Yakobson et al., Melanoma Res. 11: 569-570, 2001 |
| Tandem germline339G-C transversion and a 340C-T transition in the CDKN2A gene resulting in substitution of proline corresponding to amino acid position 114 of SEQ ID NO: 1 with a serine | RefSNP Accession Nos. rs113798404 and rs104894104; Kannengiesser et al., Genes Chromosomes Cancer 46: 751-760, 2007 |
| Mutation predicted to result in substitution of serine corresponding to amino acid position 56 of SEQ ID NO: 1 with an isoleucine | RefSNP Accession No. rs104894109; Kannengiesser et al., Genes Chromosomes Cancer 46: 751-760, 2007 |

TABLE A-continued

CDKN2A gene substitutions, deletions, and modifications

| Description | Reference(s) |
|---|---|
| Mutation predicted to result in substitution of glycine corresponding to amino acid position 89 of SEQ ID NO: 1 with an aspartic acid | RefSNP Accession No. rs137854599; Goldstein et al., J. Med. Genet. 45: 284-289, 2008 |
| Heterozygous A-to-G transition in exon 1B of the CDKN2A gene, affecting splicing of the p14(ARF) isoform | ClinVar Accession no. RCV000022943.3; Binni et al., Clin. Genet. 77: 581-586, 2010 |
| Heterozygous 5-bp duplication (19_23dup) in the CDKN2A gene, resulting in a frameshift and premature termination | ClinVar Accession No. RCV000030680.6; Harinck, F., Kluijt et al., J. Med. Genet. 49: 362-365, 2012 |
| Mutation predicted to result in substitution of aspartic acid corresponding to amino acid position 84 of SEQ ID NO: 1 with a valine | Yarbrough et al., Journal of the National Cancer Institute, 91(18): 1569-1574 |
| Mutation predicted to result in substitution of aspartic acid corresponding to amino acid position 84 of SEQ ID NO: 1 with a glycine | Yarbrough et al., Journal of the National Cancer Institute, 91(18): 1569-1574 |
| Mutation predicted to result in substitution of arginine corresponding to amino acid position 87 of SEQ ID NO: 1 with a proline | Yarbrough et al., Journal of the National Cancer Institute, 91(18): 1569-1574 |
| Mutation predicted to result in substitution of proline corresponding to amino acid position 48 of SEQ ID NO: 1 with a leucine | Yarbrough et al., Journal of the National Cancer Institute, 91(18): 1569-1574 |
| Mutation predicted to result in substitution of aspartic acid corresponding to amino acid position 74 of SEQ ID NO: 1 with a asparagine | Yarbrough et al., Journal of the National Cancer Institute, 91(18): 1569-1574 |
| Mutation predicted to result in substitution of arginine corresponding to amino acid position 87 of SEQ ID NO: 1 with a leucine | Yarbrough et al., Journal of the National Cancer Institute, 91(18): 1569-1574 |
| Mutation predicted to result in substitution of asparagine corresponding to amino acid position 71 of SEQ ID NO: 1 with a serine | Yarbrough et al., Journal of the National Cancer Institute, 91(18): 1569-1574 |
| Mutation predicted to result in substitution of arginine corresponding to amino acid position 80 of SEQ ID NO: 1 with a leucine | Yarbrough et al., Journal of the National Cancer Institute, 91(18): 1569-1574 |
| Mutation predicted to result in substitution of histidine corresponding to amino acid position 83 of SEQ ID NO: 1 with a tyrosine | Yarbrough et al., Journal of the National Cancer Institute, 91(18): 1569-1574 |

The disclosure also features a method of treating a human subject having, suspected of having, or at risk of developing a disease or disorder associated with CDK2, comprising: (i) identifying, in a biological sample obtained from the human subject: (a) a nucleotide sequence encoding a p16 protein comprising the amino acid sequence of SEQ ID NO:1, (b) a CDKN2A gene lacking one or more inactivating nucleic acid substitutions, and/or (c) the presence of a p16 protein; (ii) identifying, in a biological sample obtained from the human subject: (a) an amplification of the CCNE1 gene and/or (b) an expression level of CCNE1 that is higher than a control expression level of CCNE1; and (iii) administering a CDK2 inhibitor to the human subject. In some embodiments, the subject has a disease or disorder associated with CDK2. In some embodiments, the subject is suspected of having or is at risk of developing a disease or disorder associated with CDK2. In some embodiments, the method comprises: (i) identifying, in a biological sample obtained from the human subject: (a) a nucleotide sequence encoding a p16 protein comprising the amino acid sequence of SEQ ID NO:1, (b) a CDKN2A gene lacking one or more inactivating nucleic acid substitutions and/or deletions, and/or (c) the presence of a p16 protein; (ii) identifying, in a biological sample obtained from the human subject: (a) an amplification of the CCNE1 gene; and (iii) administering a CDK2 inhibitor to the human subject.

The disclosure also features a method of predicting the response of a human subject having, suspected of having, or at risk of developing a disease or disorder associated with CDK2 to a CDK2 inhibitor, comprising: (i) determining, from a biological sample obtained from the human subject: (a) the nucleotide sequence of a CDKN2A gene, (b) the presence of a CDKN2A gene lacking one or more inactivating nucleic acid substitutions and/or deletions, and/or (c) the presence of a p16 protein; and (ii) determining, from a biological sample obtained from the human subject: (a) the copy number of the CCNE1 gene and/or (b) the expression level of CCNE1, wherein (1) (a) the presence of a CDKN2A gene encoding a p16 protein comprising the amino acid sequence of SEQ ID NO:1, (b) the presence of a CDKN2A gene lacking one or more inactivating nucleic acid substitutions and/or deletions, and/or (c) the presence of a p16 protein, and (2) (a) an amplification of the CCNE1 gene and/or (b) an expression level of CCNE1 that is higher than a control expression level of CCNE1, is predictive that the human subject will respond to the CDK2 inhibitor. In some embodiments, the subject has a disease or disorder associated with CDK2. In some embodiments, the subject is suspected of having or is at risk of developing a disease or disorder associated with CDK2. In some embodiments, the method comprises: (i) determining, from a biological sample obtained from the human subject: (a) the nucleotide sequence of a CDKN2A gene and/or (b) the presence of a CDKN2A gene lacking one or more inactivating nucleic acid substitutions and/or deletions; and (ii) determining, from a biological sample obtained from the human subject: (a) the copy number of the CCNE1 gene, wherein (1) (a) the presence of a CDKN2A gene encoding a p16 protein comprising the amino acid sequence of SEQ ID NO:1 and/or (b) the presence of a CDKN2A gene lacking one or more inactivating nucleic acid substitutions and/or deletions, and (2) (a) an amplification of the CCNE1 gene, is predictive that the human subject will respond to the CDK2 inhibitor.

In specific embodiments, the (i) determining of (a) the nucleotide sequence of a CDKN2A gene, (b) the presence of a CDKN2A gene lacking one or more inactivating nucleic acid substitutions and/or deletions, and/or (c) the presence of a p16 protein is performed before (e.g., at least 1 day, at least 2 days, at least 3 days, at least 4 days, at least 5 days, at least 6 days, at least 7 days, at least 2 weeks, at least 3 weeks, or at least 4 weeks, or from 6 hours to 16 hours, from 6 hours to 20 hours, or from 6 hours to 24 hours, from 2 days to 3 days, from 2 days to 4 days, from 2 days to 5 days, from 2 days to 6 days, from 2 days to 7 days, from 1 week to 2 weeks, from 1 week to 3 weeks, or from 1 week to 4 weeks before) administering to the human subject the CDK2 inhibitor. In specific embodiments, the (ii) determining of (a) the copy number of the CCNE1 gene and/or (b) the expression level of CCNE1 in the biological sample obtained from the human subject is performed before (e.g., at least 1 day, at least 2 days, at least 3 days, at least 4 days, at least 5 days, at least 6 days, at least 7 days, at least 2 weeks, at least 3 weeks, or at least 4 weeks, or from 6 hours to 16 hours, from 6 hours to 20 hours, or from 6 hours to 24 hours, from 2 days to 3 days, from 2 days to 4 days, from 2 days to 5 days, from 2 days to 6 days, from 2 days to 7 days, from 1 week to 2 weeks, from 1 week to 3 weeks, or from 1 week to 4 weeks before) administering to the human subject the CDK2 inhibitor.

An amplification of the CCNE1 gene and/or an expression level of CCNE1 that is higher than a control expression level of CCNE1, combined with the presence of a CDKN2A gene encoding a p16 protein comprising the amino acid sequence of SEQ ID NO:1, the presence of a CDKN2A gene lacking one or more inactivating nucleic acid substitutions and/or deletions, and/or the presence of a p16 protein (e.g., a p16 protein comprising the amino acid sequence of SEQ ID NO:1), is indicative/predictive that a human subject having, suspected of having, or at risk of developing a disease or disorder associated with CDK2 will respond to a CDK2 inhibitor.

In some embodiments, the CCNE1 gene is amplified to a gene copy number from 3 to 25. In specific embodiments, the CCNE1 gene is amplified to a gene copy number of at least 3. In specific embodiments, the CCNE1 gene is amplified to a gene copy number of at least 5. In specific embodiments, the CCNE1 gene is amplified to a gene copy number of at least 7. In specific embodiments, the CCNE1 gene is amplified to a gene copy number of at least 10. In specific embodiments, the CCNE1 gene is amplified to a gene copy number of at least 12. In specific embodiments, the CCNE1 gene is amplified to a gene copy number of at least 14. In specific embodiments, the CCNE1 gene is amplified to a gene copy number of at least 21.

In specific embodiments, the expression level of CCNE1 is the level of CCNE1 mRNA. In specific embodiments, the expression level of CCNE1 is the level of CCNE1 protein.

In some embodiments of the foregoing methods, the control expression level of CCNE1 is a pre-established cut-off value. In some embodiments of the foregoing methods, the control expression level of CCNE1 is the expression level of CCNE1 in a sample or samples obtained from one or more subjects that have not responded to treatment with the CDK2 inhibitor.

In some embodiments of the foregoing methods, the expression level of CCNE1 is the expression level of CCNE1 mRNA. In some embodiments of the foregoing methods, the expression level of CCNE1 is the expression level of CCNE1 protein. In some embodiments in which the expression level of CCNE1 is the expression level of CCNE1 mRNA, the expression level of CCNE1 is measured by RNA sequencing, quantitative polymerase chain reaction (PCR), in situ hybridization, nucleic acid array or RNA sequencing. In some embodiments in which the expression level of CCNE1 is the expression level of CCNE1 protein, the expression level of CCNE1 is measured by western blot, enzyme-linked immunosorbent assay, or immunohistochemistry staining.

Rb S780

The disclosure also features a method for assessing the CDKN2A gene and the CCNE1 gene, comprising determining, from a biological sample or biological samples obtained from a human subject having a disease or disorder associated with CDK2, (i) (a) the nucleotide sequence of a CDKN2A gene or (b) the presence of a CDKN2A gene lacking one or more inactivating nucleic acid substitutions and/or deletions, and (ii) the copy number of the CCNE1 gene.

The disclosure also features a method of evaluating the response of a human subject having, suspected of having, or at risk of developing a disease or disorder associated with CDK2 to a CDK2 inhibitor, comprising: (a) administering a CDK2 inhibitor to the human subject, wherein the human subject has been previously determined to have an amplification of the CCNE1 gene and/or an expression level of CCNE1 that is higher than a control expression level of CCNE1; (b) measuring, in a biological sample of obtained from the subject subsequent to the administering of step (a), the level of retinoblastoma (Rb) protein phosphorylation at the serine corresponding to amino acid position 780 of SEQ ID NO:3, wherein a reduced level of Rb phosphorylation at the serine corresponding to amino acid position 780 of SEQ ID NO:3, as compared to a control level of Rb phosphorylation at the serine corresponding to amino acid position 780 of SEQ ID NO:3, is indicative that the human subject responds to the CDK2 inhibitor. In some embodiments, the subject has a disease or disorder associated with CDK2. In some embodiments, the subject is suspected of having or is at risk of developing a disease or disorder associated with CDK2. In some embodiments, the biological sample comprises a blood sample or a tumor biopsy sample.

Phosphorylation of Rb at the serine corresponding to amino acid position 780 of SEQ ID NO:3 (referred to herein as "Ser780" or "S780") has been identified in the Examples as a pharmacodynamic marker useful in assessing responsiveness (e.g., inhibition by CDK2) of a human subject having a disease or disorder having CCNE1 amplification to a CDK2 inhibitor.

Rb is a regulator of the cell cycle and acts as a tumor suppressor. Rb is activated upon phosphorylation by cyclin D-CDK4/6 at Ser780 and Ser795 and by cyclin E/CDK2 at Ser807 and Ser811. Rb is encoded by the RB transcriptional corepressor 1 ("RB1") gene (GenBank Accession No. NM_000321). The amino acid sequence of human Rb is provided below (GenBank Accession No. NP_000312/UniProtKB Accession No. P06400) (S780 is in bold and underlined):

(SEQ ID NO: 3)
1   MPPKTPRKTA ATAAAAAAEP PAPPPPPPPE EDPEQDSGPE

DLPLVRLEFE ETEEPDFTAL

```
          -continued
 61  CQKLKIPDHV RERAWLTWEK VSSVDGVLGG YIQKKKELWG

ICIFIAAVDL DEMSFTFTEL

121  QKNIEISVHK FFNLLKEIDT STKVDNAMSR LLKKYDVLFA

LFSKLERTCE LIYLTQPSSS

181  ISTEINSALV LKVSWITFLL AKGEVLQMED DLVISFQLML

CVLDYFIKLS PPMLLKEPYK

241  TAVIPINGSP RTPRRGQNRS ARIAKQLEND TRIIEVLCKE

HECNIDEVKN VYFKNFIPFM

301  NSLGLVTSNG LPEVENLSKR YEEIYLKNKD LDARLFLDHD

KTLQTDSIDS FETQRTPRKS

361  NLDEEVNVIP PHTPVRTVMN TIQQLMMILN SASDQPSENL

ISYFNNCTVN PKESILKRVK

421  DIGYIFKEKF AKAVGQGCVE IGSQRYKLGV RLYYRVMESM

LKSEEERLSI QNFSKLLNDN

481  IFHMSLLACA LEVVMATYSR STSQNLDSGT DLSFPWILNV

LNLKAFDFYK VIESFIKAEG

541  NLTREMIKHL ERCEHRIMES LAWLSDSPLF DLIKQSKDRE

GPTDHLESAC PLNLPLQNNH

601  TAADMYLSPV RSPKKKGSTT RVNSTANAET QATSAFQTQK

PLKSTSLSLF YKKVYRLAYL

661  RLNTLCERLL SEHPELEHII WTLFQHTLQN EYELMRDRHL

DQIMMCSMYG ICKVKNIDLK

721  FKIIVTAYKD LPHAVQETFK RVLIKEEEYD SIIVFYNSVF

MQRLKTNILQ YASTRPPTLS

781  PIPHIPRSPY KFPSSPLRIP GGNIYISPLK SPYKISEGLP

TPTKMTPRSR ILVSIGESFG

841  TSEKFQKINQ MVCNSDRVLK RSAEGSNPPK PLKKLRFDIE

GSDEADGSKH LPGESKFQQK

901  LAEMTSTRTR MQKQKMNDSM DTSNKEEK
```

As stated above, the Examples demonstrate CDK2-knockdown inhibits proliferation in CCNE1-amplified cell lines, but not in CCNE1-non-amplified cell lines. The Examples further demonstrate CDK2-knockdown or inhibition blocks Rb phosphorylation at the S780 in CCNE1-amplified cell lines, but not in CCNE1-non-amplified cell lines. Accordingly, Rb phosphorylation at the serine corresponding to amino acid position 780 of SEQ ID NO:3 is a pharmacodynamic marker for assessing response to CDK2 inhibition in CCNE1 amplified cancer cells or patients with diseases or disorders having CCNE1 amplification. Thus, provided herein are methods relating to the use of the level of Rb phosphorylation at the serine corresponding to amino acid position 780 of SEQ ID NO:3 in a human subject having, suspected of having, or at risk of developing a disease or disorder associated with CDK2 as a marker for indicating the response of the human subject to a CDK2 inhibitor, wherein the human subject has an increased expression level of CCNE1.

Thus, the disclosure features a method for measuring the amount of a protein in a sample, comprising: (a) providing a biological sample obtained from a human subject having a disease or disorder associated with CDK2; and (b) measuring the level of Rb protein phosphorylation at the serine corresponding to amino acid position 780 of SEQ ID NO:3 in the biological sample. In some embodiments, the biological sample comprises a blood sample or a tumor biopsy sample. In a specific embodiment, provided herein is a method of evaluating the response of a human subject having, suspected of having, or at risk of developing a disease or disorder associated with CDK2 to a CDK2 inhibitor, comprising: (a) administering a CDK2 inhibitor to the human subject, wherein the human subject has been previously determined to have an amplification of the CCNE1 gene and/or an expression level of CCNE1 that is higher than a control expression level of CCNE1; and (b) measuring, in a biological sample obtained from the human subject subsequent to the administering of step (a), the level of Rb phosphorylation at the serine corresponding to amino acid position 780 of SEQ ID NO:3, wherein a reduced level of Rb phosphorylation at the serine corresponding to amino acid position 780 of SEQ ID NO:3, as compared to a control level of Rb phosphorylation at the serine corresponding to amino acid position 780 of SEQ ID NO:3, is indicative that the human subject responds to the CDK2 inhibitor. In specific embodiments, the human subject has a disease or disorder associated with CDK2.

A reduced level of Rb phosphorylation at the serine corresponding to amino acid position 780 of SEQ ID NO:3, as compared to a control level of Rb phosphorylation at the serine corresponding to amino acid position 780 of SEQ ID NO:3, combined with an amplification of the CCNE1 gene and/or an expression level of CCNE1 that is higher than a control expression level of CCNE1, is indicative that a human subject having, suspected of having, or at risk of developing a disease or disorder associated with CDK2 responds to a CDK2 inhibitor. For example, in a subject having an amplification of the CCNE1 gene and/or an expression level of CCNE1 that is higher than a control expression level of CCNE1, a biological sample, obtained from the subject after treatment with a CDK2 inhibitor, having low (e.g., reduced as compared to a control) or undetectable levels of Rb phosphorylation at serine corresponding to amino acid position 780 of SEQ ID NO:3 is indicative that the subject responds to the CDK2 inhibitor.

A biological sample, obtained from a subject after administration of a CDK2 inhibitor to the subject, having a reduced level of Rb phosphorylation at the serine corresponding to amino acid position 780 of SEQ ID NO:3, as compared to a control level of Rb phosphorylation at the serine corresponding to amino acid position 780 of SEQ ID NO:3, combined with: (i) an amplification of the CCNE1 gene and/or an expression level of CCNE1 that is higher than a control expression level of CCNE1, and (ii) presence of a CDKN2A gene encoding a p16 protein comprising the amino acid sequence of SEQ ID NO:1, presence of a CDKN2A gene lacking one or more inactivating nucleic acid substitutions and/or deletions, and/or presence of a p16 protein (e.g., a p16 protein comprising the amino acid sequence of SEQ ID NO:1), is indicative that a human subject having, suspected of having, or at risk of developing a disease or disorder associated with CDK2 responds to a CDK2 inhibitor. For example, in a human subject having (i) an amplification of the CCNE1 gene and/or an expression level of CCNE1 that is higher than a control expression level of CCNE1, and (ii) the presence of a CDKN2A gene encoding a p16 protein comprising the amino acid sequence of SEQ ID NO:1, the presence of a CDKN2A gene lacking one or more inactivating nucleic acid substitutions and/or deletions, and/or the presence of a p16 protein (e.g., a p16 protein comprising the amino acid sequence of SEQ ID NO:1), a biological sample, obtained from the human subject after administration of a CDK2 inhibitor to the subject, having low (e.g., reduced as compared to a control) or undetectable levels of Rb phosphorylation at the serine corresponding to amino acid position 780 of SEQ ID NO:3 is indicative that the human subject responds to the CDK2 inhibitor In some embodiments, the CCNE1 gene is amplified to a gene copy number from 3 to 25. In specific embodiments, the CCNE1 gene is amplified to a gene copy number of at least 3. In specific embodiments, the CCNE1 gene is amplified to a gene copy number of at least 5. In specific embodiments, the CCNE1 gene is amplified to a gene copy number of at least 7. In specific embodiments, the CCNE1 gene is amplified to a gene copy number of at least 10. In specific embodiments, the CCNE1 gene is amplified to a gene copy number of at least 12. In specific embodiments, the CCNE1 gene is amplified to a gene copy number of at least 14. In specific embodiments, the CCNE1 gene is amplified to a gene copy number of at least 21. In specific embodiments, the expression level of CCNE1 is the level of CCNE1 mRNA. In specific embodiments, the expression level of CCNE1 is the level of CCNE1 protein.

Controls

As described above, the methods related to biomarkers and pharmacodynamic markers can involve, measuring one or more markers (e.g., a biomarker or a pharmacodynamics marker, e.g., the amplification of the CCNE1 gene, the expression level of CCNE1, the presence of a CDKN2A gene encoding a p16 protein comprising the amino acid sequence of SEQ ID NO:1, the presence of a CDKN2A gene lacking one or more inactivating nucleic acid substitutions and/or deletions, the presence of a p16 protein (e.g., a p16 protein comprising the amino acid sequence of SEQ ID NO:1), and Rb phosphorylation at the serine corresponding to amino acid position 780 of SEQ ID NO:3) in a biological sample from a human subject having, suspected of having or at risk of developing a disease or disorder associated with CDK2. In specific embodiments, the human subject has a disease or disorder associated with CDK2. In specific embodiments, the human subject is suspected of having or is at risk of developing a disease or disorder associated with CDK2. In certain aspects, the level (e.g., amplification (e.g., for the CCNE1 gene), expression level (e.g., for CCNE1 or p16 protein), or phosphorylation level (e.g., for Rb)) of one or more biomarkers, compared to a control level of the one or more biomarkers, predicts/indicates the response of a human subject to treatment comprising a CDK2 inhibitor. In certain embodiments, when (i) the CCNE1 gene is amplified and/or an expression level of CCNE1 that is higher than a control expression level of CCNE1, and (ii) a CDKN2A gene encoding a p16 protein comprising the amino acid sequence of SEQ ID NO:1 is present, a CDKN2A gene lacking one or more inactivating nucleic acid substitutions and/or deletions is present, and/or a p16 protein (e.g., a p16 protein comprising the amino acid sequence of SEQ ID NO:1) is present, the human subject is identified as likely to respond to a CDK2 inhibitor. In other embodiments, when (i) the CCNE1 gene is amplified and/or an expression level of CCNE1 that is higher than a control expression level of CCNE1, and (ii) in a biological sample from the human subject after the human subject has been administered a CDK2 inhibitor, the level of Rb phosphorylation at the serine corresponding to amino acid position 780 of SEQ ID NO:3 is less than the control level of Rb phosphorylation at the serine corresponding to amino acid position 780 of SEQ ID NO:3, the human subject is identified as responding to a CDK2 inhibitor. In yet another embodiment, when (i) the CCNE1 gene is amplified and/or an expression level of CCNE1 that is higher than a control expression level of CCNE1, (ii) a CDKN2A gene encoding a p16 protein comprising the amino acid sequence of SEQ ID NO:1 is present, a CDKN2A gene lacking one or more inactivating nucleic acid substitutions and/or deletions is present, and/or a p16 protein (e.g., a p16 protein comprising the amino acid sequence of SEQ ID NO:1) is present, and (iii) in a biological sample from the human subject after the human subject has been administered a CDK2 inhibitor, the level of Rb phosphorylation at the serine corresponding to amino acid position 780 of SEQ ID NO:3 is less than the control level of Rb phosphorylation at the serine corresponding to amino acid position 780 of SEQ ID NO:3, the human subject is identified as responding to a CDK2 inhibitor. In this context, the term "control" includes a sample (from the same tissue type) obtained from a human subject who is known to not respond to a CDK2 inhibitor. The term "control" also includes a sample (from the same tissue type) obtained in the past from a human subject who is known to not respond to a CDK2 inhibitor and used as a reference for future comparisons to test samples taken from human subjects for which therapeutic responsiveness is to be predicted. The "control" level (e.g., gene copy number, expression level, or phosphorylation level) for a particular biomarker (e.g., CCNE1, p16, or Rb phosphorylation) in a particular cell type or tissue may be pre-established by an analysis of biomarker level (e.g., expression level or phosphorylation level) in one or more (e.g., 2, 3, 4, 5, 6, 7, 8, 9, 10, 15, 20, 25, 30, 35, or 40 or more) human subjects that have not responded to treatment with a CDK2 inhibitor. This pre-established reference value (which may be an average or median level (e.g., gene copy number, expression level, or phosphorylation level) taken from multiple human subjects that have not responded to the therapy) may then be used for the "control" level of the biomarker (e.g., CCNE, p16, or Rb phosphorylation) in the comparison with the test sample. In such a comparison, the human subject is predicted to respond to a CDK2 inhibitor if the CCNE1 gene is amplified and/or the expression level of CCNE is higher than the pre-established reference, and a CDKN2A gene encoding a p16 protein comprising the amino acid sequence of SEQ ID NO:1 is present, a CDKN2A gene lacking one or more inactivating nucleic acid substitutions and/or deletions is present, and/or a p16 protein (e.g., a p16 protein comprising the amino acid sequence of SEQ ID NO:1) is present. In another such a comparison, the human subject is predicted to respond to a CDK2 inhibitor if (i) CCNE1 gene is amplified and/or the expression level of CCNE is higher than the pre-established reference, and (ii) after administering to the human subject a CDK2 inhibitor, the level of Rb phosphorylation at the serine corresponding to amino acid position 780 of SEQ ID NO:3 is lower than the pre-established reference. In yet another such a comparison, the human subject is indicated to respond to a CDK2 inhibitor if (i) CCNE1 gene is amplified and/or the expression level of CCNE is higher than the pre-established reference, (ii) a CDKN2A gene encoding a p16 protein comprising the amino acid sequence of SEQ ID NO:1 is present, a CDKN2A gene lacking one or more inactivating nucleic acid substitutions and/or deletions is present, and/or a p16 protein (e.g., a p16 protein comprising the amino acid sequence of SEQ ID NO:1) is present, and (iii) after administering to the human subject a CDK2 inhibitor, the level of Rb phosphorylation at the serine corresponding to amino acid position 780 of SEQ ID NO:3 is lower than the pre-established reference.

The "control" level for a particular biomarker in a particular cell type or tissue may alternatively be pre-established by an analysis of biomarker level in one or more human subjects that have responded to treatment with a CDK2 inhibitor. This pre-established reference value (which may be an average or median level (e.g., expression level or phosphorylation level) taken from multiple human subjects that have responded to the therapy) may then be used as the "control" level (e.g., expression level or phosphorylation level) in the comparison with the test sample. In such a comparison, the human subject is indicated to respond to a CDK2 inhibitor if the level (e.g., copy number of the CCNE1 gene, expression level of CCNE1, expression level of p16, or phosphorylation level of Rb at the serine corresponding to amino acid position 780 of SEQ ID NO:3) of the biomarker being analyzed is equal or comparable to (e.g., at least 85% but less than 115% of), the pre-established reference.

In certain embodiments, the "control" is a pre-established cut-off value. A cut-off value is typically a level (e.g., a copy number, an expression level, or a phosphorylation level) of a biomarker above or below which is considered predictive of responsiveness of a human subject to a therapy of interest. Thus, in accordance with the methods and compositions described herein, a reference level (e.g., of CCNE1 gene copy number, CCNE1 expression, p16 expression, or Rb phosphorylation at the serine corresponding to amino acid position 780 of SEQ ID NO:3) is identified as a cut-off value, above or below of which is predictive of responsiveness to a CDK2 inhibitor. Cut-off values determined for use in the methods described herein can be compared with, e.g., published ranges of concentrations but can be individualized to the methodology used and patient population.

In some embodiments, the expression level of CCNE1 is increased as compared to the expression level of CCNE1 in a control. For example, the expression level of CCNE1 analyzed can be at least 1.5, at least 2, at least 3, at least 4, at least 5, at least 6, at least 7, at least 8, at least 9, at least 10, at least 20, at least 25, at least 50, at least 75, or at least 100 times higher, or at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1,000%, at least 1,500%, at least 2,000%, at least 2,500%, at least 3,000%, at least 3,500%, at least 4,000%, at least 4,500%, or at least 5,000% higher, than the expression level of CCNE1 in a control.

A p16 protein is present if the protein is detectable by any assay known in the art or described herein, such as, for example, western blot, immunohistochemistry, fluorescence-activated cell sorting, and enzyme-linked immunoassay. In some embodiments, a p16 protein is present at an expression level that is within at least 5%, at least 10%, at least 20%, or at least 30% of the p16 expression level in a healthy control.

In some embodiments, the level of Rb phosphorylation at the serine corresponding to amino acid position 780 of SEQ ID NO:3 being analyzed is reduced as compared to the level of Rb phosphorylation at the serine corresponding to amino acid position 780 of SEQ ID NO:3 in a control. For example, the level of the Rb phosphorylation at the serine corresponding to amino acid position 780 of SEQ ID NO:3 being analyzed can be at least 1.5, at least 2, at least 3, at least 4, at least 5, at least 6, at least 7, at least 8, at least 9, at least 10, at least 20, at least 25, at least 50, at least 75, or at least 100 times lower, or at least 10%, at least 20%, at least 30%, at least 40%, at least 50%, at least 60%, at least 70%, at least 80%, at least 90%, or 100% lower, than the level of Rb phosphorylation at the serine corresponding to amino acid position 780 of SEQ ID NO:3 in a control.

Biological Samples

Suitable biological samples for the methods described herein include any sample that contains blood or tumor cells obtained or derived from the human subject in need of treatment. For example, a biological sample can contain tumor cells from biopsy from a patient suffering from a solid tumor. A tumor biopsy can be obtained by a variety of means known in the art. Alternatively, a blood sample can be obtained from a patients suffering from a hematological cancer.

A biological sample can be obtained from a human subject having, suspected of having, or at risk of developing, a disease or disorder associated with CDK2. In some embodiments, the disease or disorder associated with CDK2 is a cancer (such as those described supra).

Methods for obtaining and/or storing samples that preserve the activity or integrity of molecules (e.g., nucleic acids or proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Evaluating Biomarkers and Pharmacodynamic Markers

Expression levels of CCNE1 or p16 can be detected as, e.g., RNA expression of a target gene (i.e., the genes encoding CCNE1 or p16). That is, the expression level (amount) of CCNE1 or p16 can be determined by detecting and/or measuring the level of mRNA expression of the gene encoding CCNE1. Alternatively, expression levels of CCNE1 or p16 can be detected as, e.g., protein expression of target gene (i.e., the genes encoding CCNE1 or p16). That is, the expression level (amount) of CCNE1 or p16 can be determined by detecting and/or measuring the level of protein expression of the genes encoding CCNE1 or p16.

In some embodiments, the expression level of CCNE1 or p16 is determined by measuring RNA levels. A variety of suitable methods can be employed to detect and/or measure the level of mRNA expression of a gene. For example, mRNA expression can be determined using Northern blot or dot blot analysis, reverse transcriptase-PCR (RT-PCR; e.g., quantitative RT-PCR), in situ hybridization (e.g., quantitative in situ hybridization), nucleic acid array (e.g., oligonucleotide arrays or gene chips) and RNA sequencing analysis. Details of such methods are described below and in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; Gibson et al. (1999) Genome Res., 6(10):995-1001; and Zhang et al. (2005) Environ. Sci. Technol., 39(8):2777-2785; U.S. Publication No. 2004086915; European Patent No. 0543942; and U.S. Pat. No. 7,101,663; Kukurba et al. (2015) Cold Spring Harbor Protocols., 2015 (11): 951-69; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled-polynucleotide probes, complementary to the mRNA sequence of interest, which bind to and thus render detectable their corresponding mRNA populations. Detectable-labels include, e.g., fluorescent (e.g., umbelliferone, fluorescein, fluorescein isothiocyanate, rhodamine, dichlorotriazinylamine fluorescein, dansyl chloride, allophycocyanin, or phycoerythrin), luminescent (e.g., europium, terbium, Qdot™ nanoparticles supplied by the Quantum Dot Corporation, Palo Alto, Calif.), radiological (e.g., 125I, 131I, 35S, 32P, 33P, or 3H), and enzymatic (horseradish peroxidase, alkaline phosphatase, beta-galactosidase, or acetylcholinesterase) labels.

In some embodiments, the expression level of CCNE1 or p16 is determined by measuring protein levels. A variety of suitable methods can be employed to detect and/or measure the level of protein expression of target genes. For example, CCNE1 or p16 protein expression can be determined using western blot, enzyme-linked immunosorbent assay ("ELISA"), fluorescence activated cell sorting, or immunohistochemistry analysis (e.g., using a CCNE1-specific or p16-specific antibody, respectively). Details of such methods are described below and in, e.g., Sambrook et al., supra.

In one example, the presence or amount of one or more discrete protein populations (e.g., CCNE1 or p16) in a biological sample can be determined by western blot analysis, e.g., by isolating total protein from the biological sample (see, e.g., Sambrook et al. (supra)) and subjecting the isolated protein to agarose gel electrophoresis to separate the protein by size. The size-separated proteins are then transferred (e.g., by diffusion) to a solid support such as a nitrocellulose membrane. The presence or amount of one or more protein populations in the biological sample can then be determined using one or more antibody probes, e.g., a first antibody specific for the protein of interest (e.g., CCNE1 or p16), and a second antibody, detectably labeled, specific for the first antibody, which binds to and thus renders detectable the corresponding protein population. Detectable-labels suitable for use in western blot analysis are known in the art.

Methods for detecting or measuring gene expression (e.g., mRNA or protein expression) can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburgh, Pa.).

In some embodiments, the presence of a CDKN2A gene encoding a p16 protein comprising the amino acid sequence of SEQ ID NO:1 and/or the presence of a CDKN2A gene lacking one or more inactivating nucleic acid substitutions and/or deletions is determined by evaluating the DNA sequence of the CDKN2A gene (e.g., genomic DNA or cDNA) or by evaluating the RNA sequence of the CDKN2A gene (e.g., RNA, e.g., mRNA). Methods of performing nucleic acid sequencing analyses are known in the art and described above. Nonlimiting examples of inactivating nucleic acid substitutions and/or deletions preventing the CDKN2A gene from encoding a protein comprising the amino acid sequence of SEQ ID NO:1 are described in Table A, above. In specific embodiments, the one or more inactivating nucleic acid substitutions and/or deletions in the CDKN2A gene is as described in Yarbrough et al., Journal of the National Cancer Institute, 91(18):1569-1574, 1999; Liggett and Sidransky, Biology of Neoplasia, Journal of Oncology, 16(3):1197-1206, 1998, and Cairns et al., Nature Genetics, 11:210-212, 1995, each of which is incorporated by reference herein in its entirety.

In some embodiments, the expression level of a gene or the presence of a gene lacking one or more inactivating nucleic acid substitutions or deletions is determined by evaluating the copy number variation (CNV) of the gene. The CNV of genes (e.g., the CCNE1 gene and/or the CDKN2A gene) can be determined/identified by a variety of suitable methods. For example, CNV can be determined using fluorescent in situ hybridization (FISH), multiplex ligation dependent probe amplification (MLPA), array comparative genomic hybridization (aCGH), single-nucleotide polymorphisms (SNP) array, and next-generation sequencing (NGS) technologies.

In one example, the copy number variation of one or more discrete genes in a biological sample can be determined by MLPA, e.g., by extracting DNA specimens from the biological sample (see, e.g., Sambrook et al. (supra) and U.S. Pat. No. 6,812,341), and amplifying DNA sequence of interest (e.g., CCNE1 or CDKN2A) using a mixture of MLPA probes. Each MLPA probe consists of two oligonucleotides that hybridize to immediately adjacent target DNA sequence (e.g., CCNE1 or CDKN2A) in order to be ligated into a single probe. Ligated probes are amplified though PCR with one PCR primer fluorescently labeled, enabling the amplification products to be visualized during fragment separation by capillary electrophoresis. The presence, absence or amplification of one or more genes of interest in the biological sample is calculated by measuring PCR derived fluorescence, quantifying the amount of PCR product after normalization and comparing it with control DNA samples.

The level of Rb phosphorylation at the serine corresponding to amino acid position 780 of SEQ ID NO:3 can be detected by a variety of suitable methods. For example, phosphorylation status can be determined using western blot, ELISA, fluorescence activated cell sorting, or immunohistochemistry analysis. Details of such methods are described below and in, e.g., Sambrook et al., supra.

As with the methods for detecting or measuring gene expression (above), methods for detecting or measuring the level of Rb phosphorylation at the serine corresponding to amino acid position 780 of SEQ ID NO:3 can optionally be performed in formats that allow for rapid preparation, processing, and analysis of multiple samples.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g., "Two-Pump at-Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J Combi. Chem.*, 5, 670 (2003); and "Preparative LC-MS Purification: Improved Compound Specific Method Optimization", K. Blom, B. Glass, R. Sparks, A. Combs, *J Combi. Chem.*, 6, 874-883 (2004). The separated compounds were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature (see "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with the 30×100 mm column was 60 mL/minute.

pH=10 purifications: Waters XBridge $C_{18}$ 5 μm particle size, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature (See "Preparative LCMS Purification: Improved Compound Specific Method Optimization", K. Blom, B. Glass, R. Sparks, A. Combs, *J. Comb. Chem.*, 6, 874-883 (2004)). Typically, the flow rate used with 30×100 mm column was 60 mL/minute.

Intermediate 1. 2-Methyl-3,5,6,7-tetrahydro-4H-benzo[d]imidazol-4-one

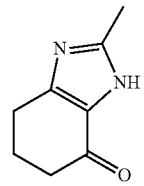

Step 1: 2-Bromo-3-ethoxycyclohex-2-en-1-one

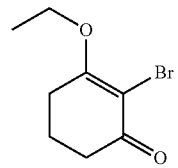

In a flask with a stir bar, a mixture of 3-ethoxycyclohex-2-en-1-one (Alfa Aesar, 9.84 g, 70.2 mmol) and N-bromosuccinimide (13.1 g, 73.6 mmol) in CH$_2$Cl$_2$ (140 mL) was stirred at room temperature for 36 hours. The resultant mixture was quenched by saturated aqueous NaHCO$_3$, extracted by CH$_2$Cl$_2$ (500 mL×2), and the combined organic layers were dried over anhydrous Na$_2$SO$_4$, filtered, and concentrated. The residue was then slurry washed by hexanes, and filtered. The filtrate was discarded. The solid was dried in vacuo to afford crude 2-bromo-3-ethoxycyclohex-2-en-1-one (15.3 g), which was used next reaction without further purification. LCMS calculated for $C_8H_{12}BrO_2$ (M+H)$^+$: m/z=219.0; Found 219.0.

Step 2: 2-Methyl-3,5,6,7-tetrahydro-4H-benzo[d]imidazol-4-one

In a flask with a stir bar, a mixture of 2-bromo-3-ethoxycyclohex-2-en-1-one (15.3 g), acetimidamide hydrochloride (7.96 g, 84.2 mmol), and potassium carbonate (35.0 g, 253 mmol) in DMF (150 ml) was stirred at 110° C. for 2 hours. The solution was concentrated under reduced pressure, and the mixture was then purified via flash column chromatography (Agela Flash Column Silica-CS (120 g), eluting with a gradient of 0 to 20% CH$_2$Cl$_2$/methanol) to afford 2-methyl-3,5,6,7-tetrahydro-4H-benzo[d]imidazol-4-one (3.34 g, 22.2 mmol, 32% yield). LCMS calculated for $C_8H_{11}N_2O$ (M+H)$^+$: m/z=151.1; Found 151.0.

Intermediate 2. 2,3-Dimethyl-3,5,6,7-tetrahydro-4H-benzo[d]imidazol-4-one

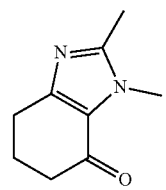

In a flask with a stir bar, a mixture of 2-methyl-3,5,6,7-tetrahydro-4H-benzo[d]imidazol-4-one (1.75 g, 11.7 mmol) and Cs$_2$CO$_3$ (4.18 g, 12.8 mmol) in DMF (140 ml) was stirred at room temperature for 10 min. MeI (2 M in tert-BuOMe, 5.85 mL, 11.7 mmol) was added to the solution, and stirred at 0° C. for 3 hours. Then saturated aqueous NH$_4$Cl solution was added to the mixture, and the resultant mixture was extracted by CH$_2$Cl$_2$ (600 mL×2), combined organic layers were washed with brine (100 mL), dried over anhydrous Na$_2$SO$_4$, and concentrated. The residue was purified via flash column chromatography (Agela Flash Column Silica-CS (120 g), eluting with a gradient of 0 to 20% CH$_2$Cl$_2$/methanol) to afford 2,3-dimethyl-3,5,6,7-tetrahydro-4H-benzo[d]imidazol-4-one (1.15 g, 7.00 mmol, 60.1% yield). LCMS calculated for C$_9$H$_{13}$N$_2$O (M+H)$^+$: m/z=165.1; Found 165.1.

Intermediate 3. tert-Butyl 4-((1,2-dimethyl-4,5-dihydro-1H-imidazo[4,5-h]quinazolin-8-yl)amino)piperidine-1-carboxylate

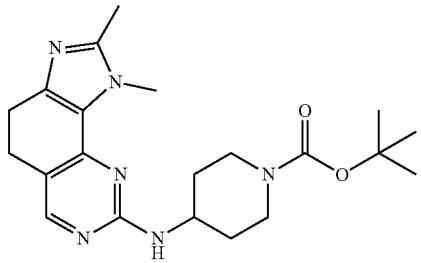 [SMILES: Cc1nc2c(n1C)-c1nc(NC3CCN(C(=O)OC(C)(C)C)CC3)ncc1CC2]

A mixture of 2,3-dimethyl-3,5,6,7-tetrahydro-4H-benzo[d]imidazol-4-one (490 mg, 2.98 mmol) and 1-tert-butoxy-N,N,N',N'-tetramethylmethanediamine (4.0 mL, 19 mmol) was purged with nitrogen and irradiated in a microwave reactor at 140° C. for 1 hour. After the resultant mixture was quenched by MeOH, the mixture was concentrated in vacuo. The residue was added to tert-butyl 4-guanidinopiperidine-1-carboxylate hydrochloride (723 mg, 2.98 mmol) in EtOH (2 mL), and the mixture was purged with nitrogen and irradiated in a microwave reactor at 120° C. for 1 hour. The resultant mixture was filtered and concentrated in vacuo. The residue was purified via flash column chromatography (Agela Flash Column Silica-CS (40 g), eluting with a gradient of 0 to 3% CH$_2$Cl$_2$/methanol) to afford tert-butyl 4-((1,2-dimethyl-4,5-dihydro-1H-imidazo[4,5-h]quinazolin-8-yl)amino)piperidine-1-carboxylate (440 mg, 1.10 mmol, 37% yield). LCMS calculated for C$_{21}$H$_{31}$N$_6$O$_2$ (M+H)$^+$: m/z=399.3; Found 399.5.

Intermediate 4. 1-(1-(Methylsulfonyl)piperidin-4-yl)guanidine hydrochloride

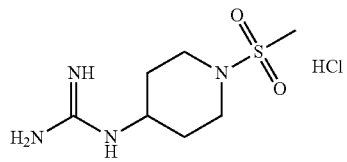

A mixture of 1H-pyrazole-1-carboximidamide hydrochloride (13.9 g, 95 mmol), 1-(methylsulfonyl)piperidin-4-amine (16.90 g, 95 mmol) and DIPEA (16.56 mL, 95 mmol) in DMF (60 mL) was stirred at 60° C. for 18 h. Et$_2$O (400 mL) was added to precipitate the desired product as white solid. LCMS calculated for C$_7$H$_{17}$N$_4$O$_2$S (M–HCl+H)$^+$: m/z=221.1; Found 221.0.

Example 1. N-(1-(Ethylsulfonyl)piperidin-4-yl)-1,2-dimethyl-4,5-dihydro-1H-imidazo[4,5-h]quinazolin-8-amine

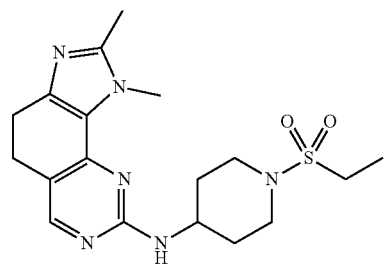 [SMILES: CCS(=O)(=O)N1CCC(Nc2ncc3c(n2)-c2c(nc(C)n2C)CC3)CC1]

In a screw-cap vial equipped with a magnetic stir bar, trifluoroacetic acid (3 mL) was added to tert-butyl 4-((1,2-dimethyl-4,5-dihydro-1H-imidazo[4,5-h]quinazolin-8-yl)amino)piperidine-1-carboxylate (440 mg, 1.104 mmol). After stirring at room temperature for 1 hour, trifluoroacetic acid was removed under reduced pressure to afford crude 1,2-dimethyl-N-(piperidin-4-yl)-4,5-dihydro-1H-imidazo[4,5-h]quinazolin-8-amine as the trifluoroacetic acid salt. To a solution of the obtained crude material (100 mg) in CH$_2$Cl$_2$ (3 mL) was added N,N-diisopropylethylamine (0.75 mL, 4.3 mmol) and ethanesulfonyl chloride. After the mixture was stirred at room temperature for 1 hour, the solution was quenched by MeOH, and the resulting solution was concentrated. The residue was dissolved in acetonitrile for prep-LCMS (XBridge C18 column, eluting with a gradient of acetonitrile/water containing 0.1% NH$_4$OH, at flow rate of 60 m/min). LCMS calculated for C$_{18}$H$_{27}$N$_6$O$_2$S (M+H)$^+$: m/z=391.2; Found 391.1.

Example 2. N-(1-(Cyclopropylsulfonyl)piperidin-4-yl)-1,2-dimethyl-4,5-dihydro-1H-imidazo[4,5-h]quinazolin-8-amine

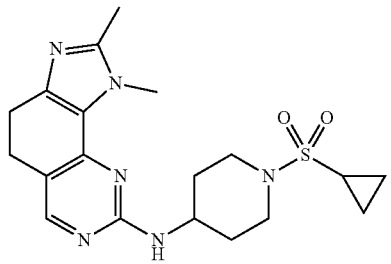 [SMILES: Cc1nc2c(n1C)-c1nc(NC3CCN(S(=O)(=O)C4CC4)CC3)ncc1CC2]

This compound was prepared according to the procedures described in Example 1, using cyclopropanesulfonyl chloride instead of ethanesulfonyl chloride as starting material. CMS calculated for C$_{19}$H$_{27}$N$_6$O$_2$S (M+H)$^+$: m/z=403.2; Found 403.1.

Example 3. 1,2-Dimethyl-N-(1-((1-methyl-1H-pyrazol-4-yl)sulfonyl)piperidin-4-yl)-4,5-dihydro-1H-imidazo[4,5-h]quinazolin-8-amine

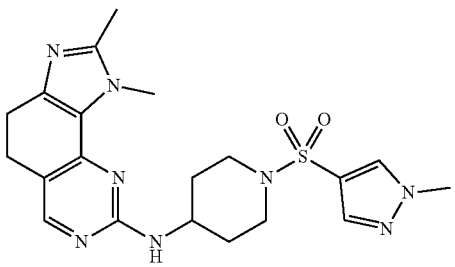 [SMILES: Cc1nc2c(n1C)-c1nc(NC3CCN(S(=O)(=O)c4cnn(C)c4)CC3)ncc1CC2]

This compound was prepared according to the procedures described in Example 1, using 1-methyl-1H-pyrazole-4-sulfonyl chloride instead of ethanesulfonyl chloride as starting material. LCMS calculated for $C_２H_{27}N_8O_2S$ (M+H)$^+$: m/z=443.2; Found 443.3.

Example 4. N-(1-((1H-Pyrazol-4-yl)sulfonyl)piperidin-4-yl)-1,2-dimethyl-4,5-dihydro-1H-imidazo[4,5-h]quinazolin-8-amine

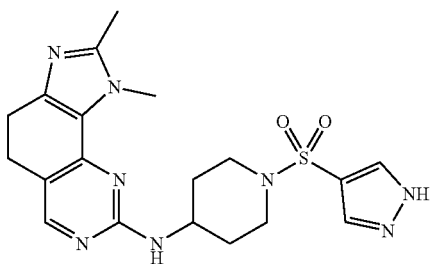 [SMILES: Cc1nc2c(n1C)-c1nc(NC3CCN(S(=O)(=O)c4cn[nH]c4)CC3)ncc1CC2]

This compound was prepared according to the procedures described in Example 1, using 1H-pyrazole-4-sulfonyl chloride instead of ethanesulfonyl chloride as starting material. LCMS calculated for $C_{19}H_{25}N_8O_2S$ (M+H)$^+$: m/z=429.2; Found 429.1.

Example 5. 3-((4-((1,2-Dimethyl-4,5-dihydro-1H-imidazo[4,5-h]quinazolin-8-yl)amino)piperidin-1-yl)sulfonyl)benzonitrile

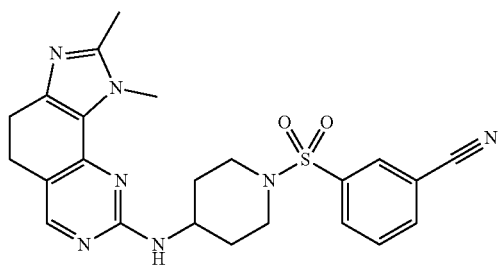 [SMILES: Cc1nc2c(n1C)-c1nc(NC3CCN(S(=O)(=O)c4cccc(C#N)c4)CC3)ncc1CC2]

This compound was prepared according to the procedures described in Example 1, using 3-cyanobenzenesulfonyl chloride instead of ethanesulfonyl chloride as starting material. LCMS calculated for $C_{23}H_{26}N_7O_2S$ (M+H)$^+$: m/z=464.2; Found 464.1.

Example 6. N-(1-((1,2-Dimethyl-1H-imidazol-4-yl)sulfonyl)piperidin-4-yl)-1,2-dimethyl-4,5-dihydro-1H-imidazo[4,5-h]quinazolin-8-amine

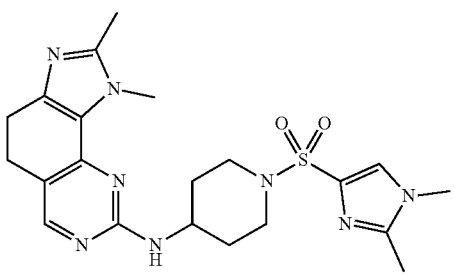 [SMILES: Cc1nc(S(=O)(=O)N2CCC(Nc3ncc4c(n3)-c3c(nc(C)n3C)CC4)CC2)cn1C]

This compound was prepared according to the procedures described in Example 1, using 1,2-dimethyl-1H-imidazole-4-sulfonyl chloride instead of ethanesulfonyl chloride as starting material. LCMS calculated for $C_{21}H_{29}N_8O_2S$ (M+H)$^+$: m/z=457.2; Found 457.5.

Example 7. 2-Methyl-N-(1-(methylsulfonyl)piperidin-4-yl)-4,5-dihydro-1H-imidazo[4,5-h]quinazolin-8-amine

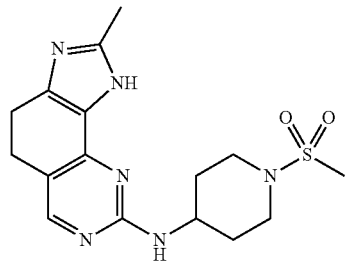 [SMILES: Cc1nc2c([nH]1)-c1nc(NC3CCN(S(C)(=O)=O)CC3)ncc1CC2]

A mixture of 2-methyl-3,5,6,7-tetrahydro-4H-benzo[d]imidazol-4-one (90 mg, 0.60 mmol) and 1-tert-butoxy-N,N,N',N'-tetramethylmethanediamine (2.0 mL, 9.7 mmol) was purged with nitrogen and irradiated in a microwave reactor at 140° C. for 1 hour. After the resultant mixture was quenched by MeOH, the mixture was concentrated in vacuo. The residue was then dissolved in EtOH (1 mL), and the solution was added to a mixture of sodium ethoxide (21 wt % in ethanol, 0.19 mL, 0.57 mmol) and 1-(1-(methylsulfonyl)piperidin-4-yl)guanidine hydrochloride (129 mg, 0.599 mmol). The solution was purged with nitrogen and irradiated in a microwave reactor at 120° C. for 1 hour. The resultant mixture was filtered and concentrated in vacuo. The residue was dissolved in acetonitrile and purified by prep-LCMS (Sunfire C18 column, eluting with gradient of acetonitrile/water containing 0.1% TFA, at flow rate of 60 mL/min). The fractions containing product were then concentrated and further purified by prep-LCMS (XBridge C18 column, eluting with a gradient of acetonitrile/water containing 0.1% NH$_4$OH, at flow rate of 60 mL/min). LCMS calculated for $C_{16}H_{23}N_6O_2S$ (M+H)$^+$: m/z=363.2; Found 363.1.

Example 8. 1-Benzyl-2-methyl-N-(1-(methylsulfonyl)piperidin-4-yl)-4,5-dihydro-1H-imidazo[4,5-h]quinazolin-8-amine

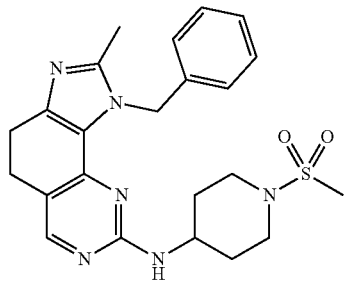 [SMILES: Cc1nc2c(n1Cc1ccccc1)-c1nc(NC3CCN(S(C)(=O)=O)CC3)ncc1CC2]

Step 1: 3-Benzyl-2-methyl-3,5,6,7-tetrahydro-4H-benzo[d]imidazol-4-one

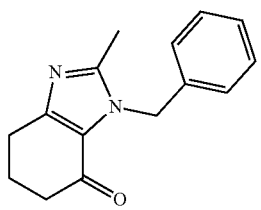 [SMILES: Cc1nc2c(n1Cc1ccccc1)C(=O)CCC2]

A screw-cap vial equipped with a magnetic stir bar was charged with 2-methyl-3,5,6,7-tetrahydro-4H-benzo[d]imidazol-4-one (300 mg, 2.00 mmol) and $Cs_2CO_3$ (716 mg, 2.20 mmol) in DMF (5 mL). Benzyl chloride (0.25 mL, 2.2 mmol) and sodium iodide (59.9 mg, 0.400 mmol) were added to the solution respectively, and stirred at room temperature for 24 hours. Then saturated aqueous $NH_4Cl$ sol. (20 mL) was added to the mixture, and the resultant mixture was extracted by $CH_2Cl_2$ (50 mL×2), and the combined organic layers were washed with brine (50 mL), dried with anhydrous $Na_2SO_4$, and concentrated. The residue was purified via flash column chromatography (Agela Flash Column Silica-CS (40 g), eluting with a gradient of 0 to 20% $CH_2C_2$/methanol) to afford two isomers of 3-benzyl-2-methyl-3,5,6,7-tetrahydro-4H-benzo[d]imidazol-4-one and 1-benzyl-2-methyl-1,5,6,7-tetrahydro-4H-benzo[d]imidazol-4-one (Total: 480 mg, 2.00 mmol, 100% yield). LCMS calculated for $C_{15}H_{17}N_2O$ $(M+H)^+$: m/z=241.1; Found 241.2.

Step 2: 1-Benzyl-2-methyl-N-(1-(methylsulfonyl)piperidin-4-yl)-4,5-dihydro-1H-imidazo[4,5-h]quinazolin-8-amine A mixture of 3-benzyl-2-methyl-3,5,6,7-tetrahydro-4H-benzo[d]imidazol-4-one and 1-benzyl-2-methyl-1,5,6,7-tetrahydro-4H-benzo[d]imidazol-4-one (Total: 120 mg, 0.499 mmol) and 1-tert-butoxy-N,N,N',N'-tetramethylmethanediamine (2.0 mL, 9.7 mmol) was purged with nitrogen and irradiated in a microwave reactor at 140° C. for 1 hour. After the resultant mixture was quenched by MeOH, the mixture was concentrated in vacuo. The residue was then dissolved in EtOH (10 ml), and the solution was added to a mixture of sodium ethoxide (21 wt % in ethanol, 0.16 mL, 0.50 mmol) and 1-(1-(methylsulfonyl)piperidin-4-yl)guanidine hydrochloride (128 mg, 0.499 mmol). The solution was purged with nitrogen and irradiated in a microwave reactor at 120° C. for 1 hour. The resultant mixture was filtered and concentrated in vacuo. The residue was dissolved in acetonitrile and purified by prep-LCMS (XBridge column, eluting with a gradient of acetonitrile/water containing 0.1% $NH_4OH$, at flow rate of 60 m/min). Fractions containing the desired product were then concentrated, and the material obtained was dissolved in acetonitrile and purified by prep-LCMS (Sunfire C18 column, eluting with a gradient of acetonitrile/water containing 0.1% TFA, at flow rate of 60 mL/min). $^1H$ NMR (TFA salt, 600 MHz, DMSO-$d_6$, 343 K) δ 8.13 (s, 1H), 7.38 (m, 2H), 7.31 (m, 1H), 7.21 (m, 2H), 5.96 (s, 2H), 3.59 (m, 1H), 3.42 (m, 2H), 2.91 (m, 4H), 2.80 (s, 3H), 2.55-2.45 (m, 2H), 2.43 (s, 3H), 1.77 (m, 2H), 1.46 (m, 2H). LCMS calculated for $C_{23}H_{29}N_6O_2S$ $(M+H)^+$: m/z=453.2; Found 453.2.

Example 9. 8-Methyl-N-(1-(methylsulfonyl)piperidin-4-yl)-6,8-dihydro-5H-pyrazolo[3,4-h]quinazolin-2-amine

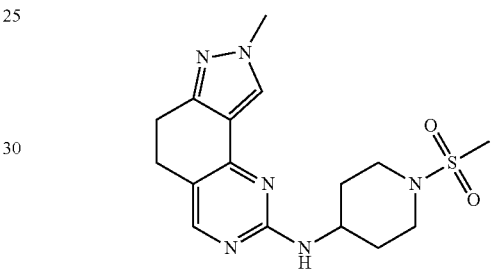

Step 1: 8-Methyl-6,8-dihydro-5H-pyrazolo[3,4-h]quinazolin-2-amine

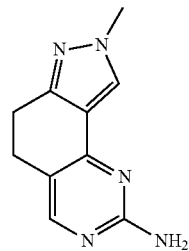

A solution of cyclohexane-1,3-dione (147 mg, 1.31 mmol) and methylhydrazine (0.069 mL, 1.31 mmol) in THF (1 mL) was stirred at RT for 2 h. 1,1-Dimethoxy-N,N-dimethylmethanamine (1562 mg, 13.11 mmol) was added at RT. The mixture was purged with nitrogen and irradiated in a microwave reactor at 120° C. for 30 min. Then, the resultant mixture was concentrated and added guanidine hydrochloride (1252 mg, 13.11 mmol) and NaOEt in EtOH (21 wt %, 4.89 mL, 13.11 mmol). The mixture was purged with nitrogen and irradiated in a microwave reactor at 140° C. for 30 min. The resultant mixture was then purified by prep-LCMS (XBridge C18 column, eluting with a gradient of acetonitrile/water containing 0.1% $NH_4OH$, at flow rate of 60 m/min). LCMS calculated for $C_{10}H_{12}N_5$ $(M+H)^+$: m/z=202.1; Found 202.1.

Step 2: 8-Methyl-N-(1-(methylsulfonyl)piperidin-4-yl)-6,8-dihydro-5H-pyrazolo[3,4-h]quinazolin-2-amine A mixture of 8-methyl-6,8-dihydro-5H-pyrazolo[3,4-h]quinazolin-2-amine (10 mg, 0.050 mmol), 4-bromo-1-(methylsulfonyl)piperidine (120 mg, 0.497 mmol) and cesium carbonate (162 mg, 0.497 mmol) in DMF (1 mL) was stirred at 100° C. for 18 h. The resultant mixture was then purified by prep-LCMS (Sunfire C18 column, eluting with a gradient of acetonitrile/water containing 0.1% TFA, at flow rate of 60 mL/min). LCMS calculated for $C_{16}H_{23}N_6O_2S$ (M+H)$^+$: m/z=363.2; Found 363.1.

Example 10. 8-Methyl-N-(1-(methylsulfonyl)piperidin-4-yl)-6,8-dihydropyrazolo[4',3':4,5]pyrano[3,2-d]pyrimidin-2-amine

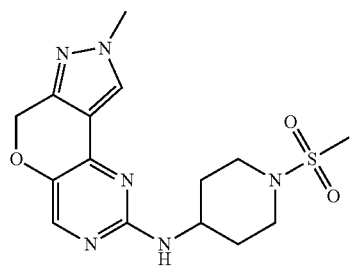 [SMILES: Cn1cc2c(n1)COc1cnc(NC3CCN(S(C)(=O)=O)CC3)nc1-2]

This compound was prepared according to the procedures described in Example 9, using 2H-pyran-3,5(4H,6H)-dione instead of cyclohexane-1,3-dione as starting material. LCMS calculated for $C_{15}H_{21}N_6O_3S$ (M+H)$^+$: m/z=365.1; Found 365.0.

Example 11. 8-(2,6-Difluorophenyl)-9-methyl-N-(1-(methylsulfonyl)piperidin-4-yl)-6,8-dihydro-5H-pyrazolo[3,4-h]quinazolin-2-amine

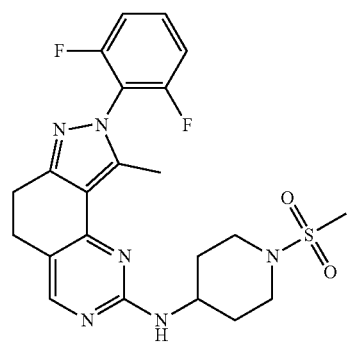 [SMILES: Cc1c2c(nn1-c1c(F)cccc1F)CCc1cnc(NC3CCN(S(C)(=O)=O)CC3)nc1-2]

Step 1: 2-(2,6-Difluorophenyl)-3-methyl-2,5,6,7-tetrahydro-4H-indazol-4-one

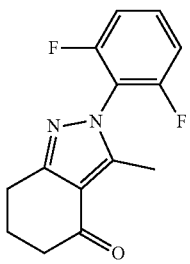 [SMILES: Cc1c2c(nn1-c1c(F)cccc1F)CCCC2=O]

A solution of cyclohexane-1,3-dione (160 mg, 1.42 mmol) and (2,6-difluorophenyl)hydrazine (206 mg, 1.42 mmol) in THF (1 mL) was stirred at RT for 2 h. Then 1,1-dimethoxy-N,N-dimethylethan-1-amine (417 μL, 2.85 mmol) was added. The mixture was purged with nitrogen and irradiated in a microwave reactor at 120° C. for 30 min. The resultant mixture was then purified by prep-LCMS (XBridge C18 column, eluting with a gradient of acetonitrile/water containing 0.1% NH$_4$OH, at flow rate of 60 mL/min). LCMS calculated for $C_{14}H_{13}F_2N_2O$ (M+H)$^+$: m/z=263.1; Found 263.2.

Step 2: 8-(2,6-Difluorophenyl)-9-methyl-N-(1-(methylsulfonyl)piperidin-4-yl)-6,8-dihydro-5H-pyrazolo[3,4-h]quinazolin-2-amine This compound was prepared according to the procedures described in Example 7, using 2-(2,6-difluorophenyl)-3-methyl-2,5,6,7-tetrahydro-4H-indazol-4-one instead of 2-methyl-3,5,6,7-tetrahydro-4H-benzo[d]imidazol-4-one as starting material. LCMS calculated for $C_{22}H_{25}F_2N_6O_2S$ (M+H)$^+$: m/z=475.2; Found 475.0.

Example 12. 9-Cyclopropyl-8-methyl-N-(1-(methylsulfonyl)piperidin-4-yl)-6,8-dihydro-5H-pyrazolo[3,4-h]quinazolin-2-amine

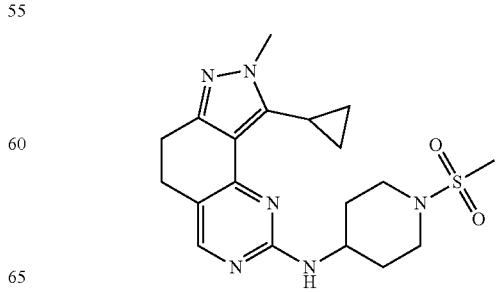

Step 1: 3-Oxocyclohex-1-en-1-yl cyclopropanecarboxylate

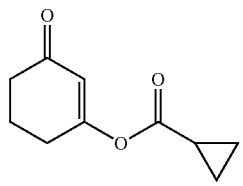 [SMILES: O=C1C=C(OC(=O)C2CC2)CCC1]

To a solution of cyclohexane-1,3-dione (1.83 g, 16.3 mmol) and triethylamine (2.96 mL, 21.2 mmol) in THF (15 mL) was added cyclopropanecarbonyl chloride (1.64 mL, 17.95 mmol) at RT. The mixture was stirred at RT for 2 h. The resultant mixture was concentrated under reduced pressure, and purified via flash column chromatography to give the desired product. LCMS calculated for $C_{10}H_{13}O_3$ (M+H)$^+$: m/z=181.1; Found 181.0.

Step 2: 2-(Cyclopropanecarbonyl)cyclohexane-1,3-dione

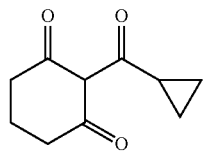 [SMILES: O=C1CCCC(=O)C1C(=O)C1CC1]

To a solution of 3-oxocyclohex-1-en-1-yl cyclopropanecarboxylate (2.62 g, 14.5 mmol) in DCM (15 mL) was added aluminum chloride (3.88 g, 29.1 mmol) at 0° C. The mixture was stirred at RT for 2 h and then aq. HCl (1.0 M, 20 mL) was added. Using a separatory funnel, the aqueous layer was extracted with DCM (20 mL×3). The combined organic fractions were dried over $Na_2SO_4$, concentrated under reduced pressure, and purified via flash column chromatography to give the desired product. LCMS calculated for $C_{10}H_{13}O_3$ (M+H)$^+$: m/z=181.1; Found 181.0.

Step 3: tert-Butyl 2-(2-(cyclopropanecarbonyl)-3-oxocyclohex-1-en-1-yl)-1-methylhydrazine-1-carboxylate

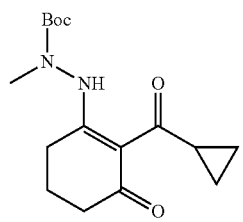 [SMILES: CN(NC1=C(C(=O)C2CC2)C(=O)CCC1)C(=O)OC(C)(C)C]

To a solution of 2-(cyclopropanecarbonyl)cyclohexane-1,3-dione (178 mg, 0.988 mmol) in DCM (2 mL) was added oxalyl chloride (0.173 mL, 1.976 mmol) at RT. The mixture was stirred at RT for 18 h and then concentrated under reduced pressure. The crude material and tert-butyl 1-methylhydrazine-1-carboxylate (0.147 mL, 0.988 mmol), triethylamine (0.275 mL, 1.976 mmol) were dissolved in THF (2 mL). The resultant mixture was stirred at RT for 18 h and then water (5 mL) was added. Using a separatory funnel, the aqueous layer was extracted with DCM (20 mL×3). The combined organic fractions were dried over $Na_2SO_4$, concentrated under reduced pressure, and purified via flash column chromatography to give the desired product. LCMS calculated for $C_{16}H_{25}N_2O_4$ (M+H)$^+$: m/z=309.2; Found 309.1.

Step 4: 3-Cyclopropyl-2-methyl-2,5,6,7-tetrahydro-4H-indazol-4-one

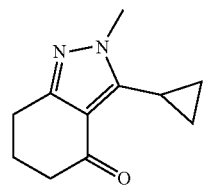

To tert-butyl 2-(2-(cyclopropanecarbonyl)-3-oxocyclohex-1-en-1-yl)-1-methylhydrazine-1-carboxylate (from Step 3) was added HCl in dioxane (4 M, 3 mL) at RT. The resultant solution was stirred at RT overnight. The resultant mixture was concentrated under reduced pressure and the crude product was used directly for the next step. LCMS calculated for $C_{11}H_{15}N_2O$ (M+H)$^+$: m/z=191.1; Found 191.0.

Step 5: 9-Cyclopropyl-8-methyl-N-(1-(methylsulfonyl)piperidin-4-yl)-6,8-dihydro-5H-pyrazolo[3,4-h]quinazolin-2-amine This compound was prepared according to the procedures described in Example 7, using 3-cyclopropyl-2-methyl-2,5,6,7-tetrahydro-4H-indazol-4-one instead of 2-methyl-3,5,6,7-tetrahydro-4H-benzo[d]imidazol-4-one as starting material. LCMS calculated for $C_{19}H_{27}N_6O_2S$ (M+H)$^+$: m/z=403.2; Found 403.0.

Example 13. 9-Isopropyl-8-methyl-N-(1-(methylsulfonyl)piperidin-4-yl)-6,8-dihydro-5H-pyrazolo[3,4-h]quinazolin-2-amine

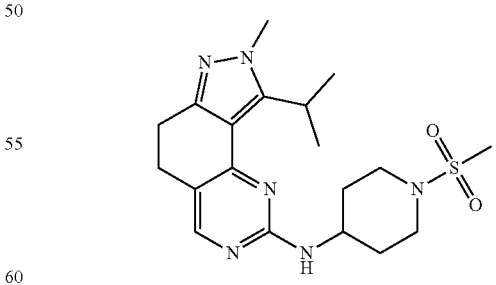

This compound was prepared according to the procedures described in Example 12, using isobutyryl chloride instead of cyclopropanecarbonyl chloride as starting material. LCMS calculated for $C_{19}H_{29}N_6O_2S$ (M+H)$^+$: m/z=405.2; Found 405.1. $^1$H NMR (TFA salt, 500 MHz, DMSO-d$_6$) δ 8.10 (s, 1H), 3.95 (m, 1H), 3.87 (s, 3H), 3.75 (m, 1H), 3.62

(d, J=12.3 Hz, 2H), 2.93 (s, 3H), 2.87-2.75 (m, 4H), 2.71 (t, J=6.8 Hz, 2H), 2.01 (d, J=10.5 Hz, 2H), 1.64 (td, J=15.0, 4.0 Hz, 2H), 1.43 (d, J=7.1 Hz, 6H).

Example 14. 9-Cyclopropyl-N-(1-(methylsulfonyl)piperidin-4-yl)-8-(tetrahydrofuran-3-yl)-6,8-dihydro-5H-pyrazolo[3,4-h]quinazolin-2-amine

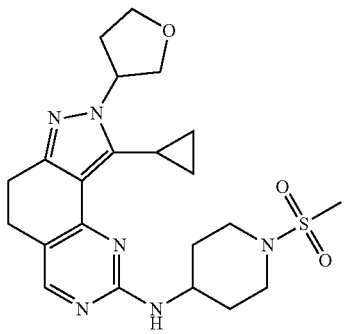 [SMILES: CS(=O)(=O)N1CCC(Nc2ncc3c(n2)-c2c(nn(C4CCOC4)c2C2CC2)CC3)CC1]

This compound was prepared according to the procedures described in Example 12, using tert-butyl 1-(tetrahydrofuran-3-yl)hydrazine-1-carboxylate instead of tert-butyl 1-methylhydrazine-1-carboxylate as starting material. LCMS calculated for $C_{22}H_{31}N_6O_3S$ (M+H)$^+$: m/z=459.2; Found 459.0.

Example 15. 2-(9-Cyclopropyl-2-((1-(methylsulfonyl)piperidin-4-yl)amino)-5,6-dihydro-8H-pyrazolo[3,4-h]quinazolin-8-yl)ethan-1-ol

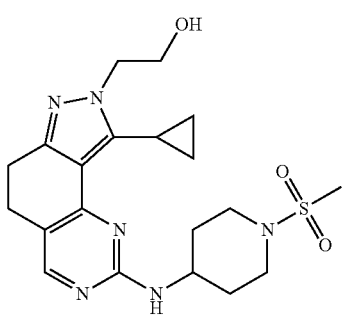 [SMILES: CS(=O)(=O)N1CCC(Nc2ncc3c(n2)-c2c(nn(CCO)c2C2CC2)CC3)CC1]

This compound was prepared according to the procedures described in Example 12, using tert-butyl 1-(2-hydroxyethyl)hydrazine-1-carboxylate instead of tert-butyl 1-methylhydrazine-1-carboxylate as starting material. LCMS calculated for $C_2H_{29}N_6O_3S$ (M+H)$^+$: m/z=433.2; Found 433.0.

Example 16. 8,9-Dicyclopropyl-N-(1-(methylsulfonyl)piperidin-4-yl)-6,8-dihydro-5H-pyrazolo[3,4-h]quinazolin-2-amine

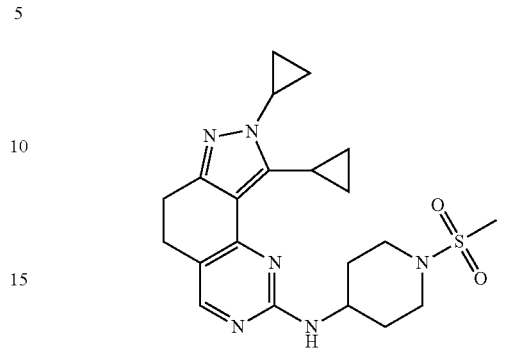

This compound was prepared according to the procedures described in Example 12, using tert-butyl 1-cyclopropylhydrazine-1-carboxylate instead of tert-butyl 1-methylhydrazine-1-carboxylate as starting material. LCMS calculated for $C_{21}H_{29}N_6O_2S$ (M+H)$^+$: m/z=429.2; Found 429.0.

Example 17. 1,2-Dimethyl-N-(1-(methylsulfonyl)piperidin-4-yl)-4,5-dihydro-1H-imidazo[4,5-h]quinazolin-8-amine

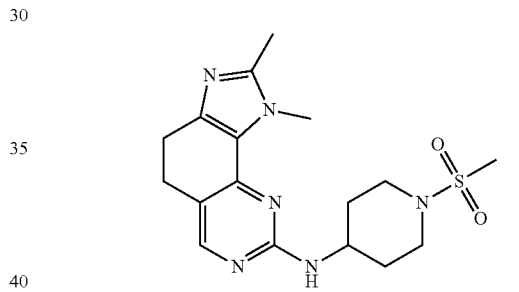

This compound was prepared according to the procedures described in Example 7, using 2,3-dimethyl-3,5,6,7-tetrahydro-4H-benzo[d]imidazol-4-one instead of 2-methyl-3,5,6,7-tetrahydro-4H-benzo[d]imidazol-4-one as starting material. LCMS calculated for $C_{17}H_{25}N_6O_2S$ (M+H)$^+$: m/z=377.2; Found 377.0.

Example 18. 2-Isopropyl-1-methyl-N-(1-(methylsulfonyl)piperidin-4-yl)-4,5-dihydro-1H-imidazo[4,5-h]quinazolin-8-amine

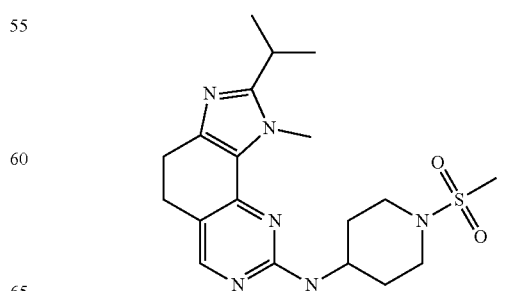

Step 1: 2-Isopropyl-3,5,6,7-tetrahydro-4H-benzo[d]imidazol-4-one

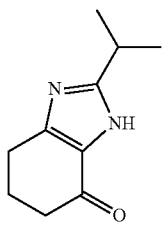

This compound was prepared according to the procedures described in Intermediate 1, using isobutyrimidamide hydrochloride instead of acetimidamide hydrochloride as starting material. LCMS calculated for $C_{10}H_{15}N_2O$ (M+H)$^+$: m/z=179.1; Found 179.0.

Step 2: 2-Isopropyl-1-methyl-N-(1-(methylsulfonyl)piperidin-4-yl)-4,5-dihydro-1H-imidazo[4,5-h]quinazolin-8-amine This compound was prepared according to the procedures described in Intermediate 2 and Example 7, using 2-isopropyl-3,5,6,7-tetrahydro-4H-benzo[d]imidazol-4-one instead of 2-methyl-3,5,6,7-tetrahydro-4H-benzo[d]imidazol-4-one as starting material. LCMS calculated for $C_{19}H_{29}N_6O_2S$ (M+H)$^+$: m/z=405.2; Found 405.1.

Example 19. 1-Cyclopropyl-2-methyl-N-(1-(methylsulfonyl)piperidin-4-yl)-4,5-dihydro-1H-imidazo[4,5-h]quinazolin-8-amine

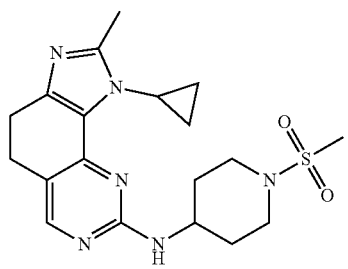 [SMILES: Cc1nc2c(n1C1CC1)-c1nc(NC3CCN(S(C)(=O)=O)CC3)ncc1CC2]

Step 1:3-Cyclopropyl-2-methyl-3,5,6,7-tetrahydro-4H-benzo[d]imidazol-4-one

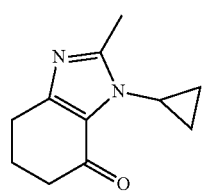

A solution of copper (II) acetate (48.4 mg, 0.266 mmol) and 2,2'-bipyridine (41.6 mg, 0.266 mmol) in 1,2-dichloroethane (2 mL) was stirred at 60° C. for 15 min. Then the resultant mixture was added to a solution of 2-methyl-3,5,6,7-tetrahydro-4H-benzo[d]imidazol-4-one (40 mg, 0.266 mmol), cyclopropylboronic acid (34.3 mg, 0.400 mmol) and potassium carbonate (73.6 mg, 0.533 mmol) in 1,2-dichloroethane (2 mL) at RT. The mixture was stirred under air at 60° C. for 18 h. The resultant mixture was then purified by prep-LCMS (XBridge C18 column, eluting with a gradient of acetonitrile/water containing 0.1% NH$_4$OH, at flow rate of 60 m/min). LCMS calculated for $C_{11}H_{15}N_2O$ (M+H)$^+$: m/z=191.1; Found 191.1.

Step 2: 1-Cyclopropyl-2-methyl-N-(1-(methylsulfonyl)piperidin-4-yl)-4,5-dihydro-H-imidazo[4,5-h]quinazolin-8-amine This compound was prepared according to the procedures described in Example 7, using 3-cyclopropyl-2-methyl-3,5,6,7-tetrahydro-4H-benzo[d]imidazol-4-one instead of 2-methyl-3,5,6,7-tetrahydro-4H-benzo[d]imidazol-4-one as starting material. LCMS calculated for $C_{19}H_{27}N_6O_2S$ (M+H)$^+$: m/z=403.2; Found 403.2. $^1$H NMR (TFA salt, 500 MHz, DMSO-d$_6$) δ 8.16 (s, 1H), 3.95 (m, 1H), 3.56 (m, 3H), 2.89 (s, 3H), 2.87 (m, 6H), 2.65 (s, 3H), 1.99 (d, J=10.1 Hz, 2H), 1.60 (m, 2H), 1.27 (m, 2H), 1.06 (m, 2H).

Example 20. 1-Cyclopropyl-N-(1-(methylsulfonyl)piperidin-4-yl)-4,5-dihydro-1H-imidazo[4,5-h]quinazolin-8-amine

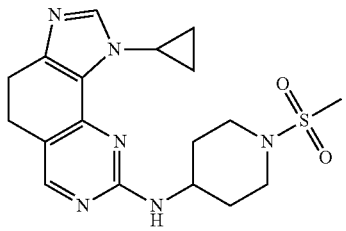 [SMILES: CS(=O)(=O)N1CCC(Nc2ncc3c(n2)-c2c(ncn2C2CC2)CC3)CC1]

Step 1: 3-Cyclopropyl-3,5,6,7-tetrahydro-4H-benzo[d]imidazol-4-one

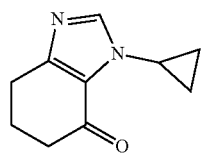 [SMILES: O=C1CCCc2ncn(C3CC3)c21]

To a solution of ethyl formimidate hydrochloride (0.90 g, 8.22 mmol) in iPrOH (10 mL) was added triethylamine (2.29 mL, 16.43 mmol) at 0° C. The mixture was stirred at RT for 15 min. Cyclopropanamine (0.569 mL, 8.22 mmol) was added at 0° C. The mixture was stirred at RT for 2 h. 2-Bromo-3-ethoxycyclohex-2-en-1-one (1.44 g, 6.57 mmol) was added at RT. The mixture was stirred at 80° C. for 18 h. The resultant mixture was concentrated under reduced pressure, and purified via flash column chromatography to give the desired product. LCMS calculated for $C_{10}HN_2O$ (M+H)$^+$: m/z=177.1; Found 177.0.

Step 2: 1-Cyclopropyl-N-(1-(methylsulfonyl)piperidin-4-yl)-4,5-dihydro-H-imidazo[4,5-h]quinazolin-8-amine This compound was prepared according to the procedures described in Example 7, using 3-cyclopropyl-3,5,6,7-tetrahydro-4H-benzo[d]imidazol-4-one instead of 2-methyl-3,5,6,7-tetrahydro-4H-benzo[d]imidazol-4-one as starting material. LCMS calculated for $C_{18}H_{25}N_6O_2S$ (M+H)+: m/z=389.2; Found 389.1.

Example 21. 2-Bromo-1-cyclopropyl-N-(1-(methylsulfonyl)piperidin-4-yl)-4,5-dihydro-1H-imidazo[4,5-h]quinazolin-8-amine

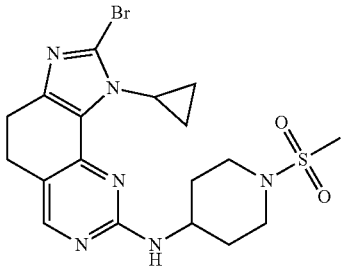 [SMILES: CS(=O)(=O)N1CCC(Nc2ncc3c(n2)-c2c(nc(Br)n2C2CC2)CC3)CC1]

In a vial wrapped by aluminum foil, to a solution of 1-cyclopropyl-N-(1-(methylsulfonyl)piperidin-4-yl)-4,5-dihydro-1H-imidazo[4,5-h]quinazolin-8-amine (7.2 mg, 0.019 mmol) in acetonitrile (1 mL) was added NBS (3.30 mg, 0.019 mmol) at RT. The mixture was stirred at RT for 2 h. The resultant mixture was purified by prep-LCMS (Sunfire C18 column, eluting with a gradient of acetonitrile/water containing 0.1% TFA, at flow rate of 60 mL/min). LCMS calculated for $C_{18}H_{24}BrN_6O_2S$ (M+H)+: m/z=467.1; Found 467.2.

Example 22. 1-Cyclopropyl-N-(1-(methylsulfonyl)piperidin-4-yl)-2-phenyl-4,5-dihydro-1H-imidazo[4,5-h]quinazolin-8-amine

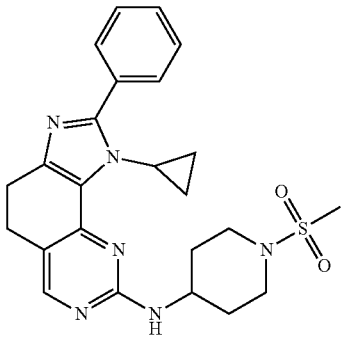 [SMILES: CS(=O)(=O)N1CCC(Nc2ncc3c(n2)-c2c(nc(-c4ccccc4)n2C2CC2)CC3)CC1]

A solution of 2-bromo-1-cyclopropyl-N-(1-(methylsulfonyl)piperidin-4-yl)-4,5-dihydro-1H-imidazo[4,5-h]quinazolin-8-amine (15 mg, 0.032 mmol), phenylboronic acid (7.83 mg, 0.064 mmol), Pd(dppf)Cl2 (11.74 mg, 0.016 mmol) and Na3PO4 (20.44 mg, 0.096 mmol) in dioxane (1 mL) and water (0.2 mL) was stirred at 80° C. for 1 h. The resultant mixture was purified by prep-LCMS (Sunfire C18 column, eluting with a gradient of acetonitrile/water containing 0.1% TFA, at flow rate of 60 mL/min). LCMS calculated for $C_{24}H_{29}N_6O_2S$ (M+H)+: m/z=465.2; Found 465.0.

Example 23. 1-Cyclopropyl-2-(2-fluorophenyl)-N-(1-(methylsulfonyl)piperidin-4-yl)-4,5-dihydro-1H-imidazo[4,5-h]quinazolin-8-amine

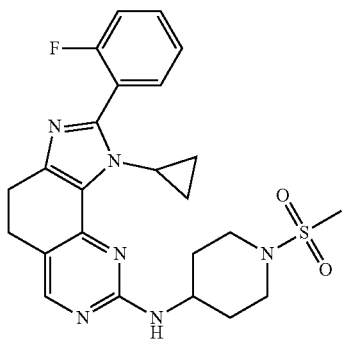 [SMILES: CS(=O)(=O)N1CCC(Nc2ncc3c(n2)-c2c(nc(-c4ccccc4F)n2C2CC2)CC3)CC1]

This compound was prepared according to the procedures described in Example 22, using (2-fluorophenyl)boronic acid instead of phenylboronic acid as starting material. LCMS calculated for $C_{24}H_{28}FN_6O_2S$ (M+H)+: m/z=483.2; Found 483.1.

Example 24. 1-Cyclopropyl-2-(1,3-dimethyl-1H-pyrazol-4-yl)-N-(1-(methylsulfonyl)piperidin-4-yl)-4,5-dihydro-1H-imidazo[4,5-h]quinazolin-8-amine

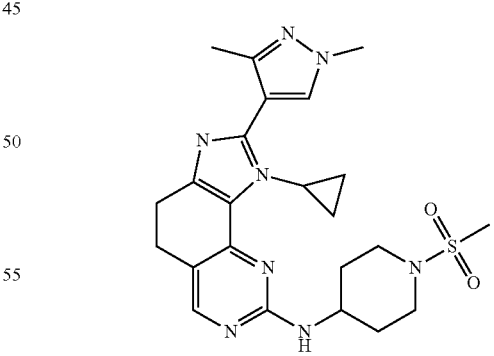

This compound was prepared according to the procedures described in Example 22, using 1,3-dimethyl-4-(4,4,5,5-tetramethyl-1,3,2-dioxaborolan-2-yl)-1H-pyrazole instead of phenylboronic acid as starting material. LCMS calculated for $C_{23}H_{31}N_8O_2S$ (M+H)+: m/z=483.2; Found 483.0.

Example 25. 1-Cyclopropyl-2,4,4-trimethyl-N-(1-(methylsulfonyl)piperidin-4-yl)-4,5-dihydro-1H-imidazo[4,5-h]quinazolin-8-amine

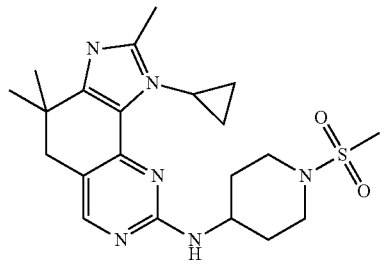

Step 1:
3-Methoxy-4,4-dimethylcyclohex-2-en-1-one

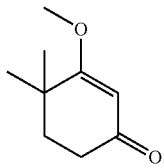

A solution of 4,4-dimethylcyclohexane-1,3-dione (1.23 g, 8.76 mmol) and p-toluenesulfonic acid monohydrate (0.083 g, 0.438 mmol) in methanol (15 mL) was stirred at 80° C. for 1 h. The resultant mixture was concentrated under reduced pressure, and purified via flash column chromatography to give the desired product. LCMS calculated for $C_9H_{15}O_2$ $(M+H)^+$: m/z=155.1; Found 155.0.

Step 2: 1-Cyclopropyl-2,4,4-trimethyl-N-(1-(methylsulfonyl)piperidin-4-yl)-4,5-dihydro-1H-imidazo[4,5-h]quinazolin-8-amine This compound was prepared according to the procedures described in Intermediate 1 and Example 19, using 3-methoxy-4,4-dimethylcyclohex-2-en-1-one instead of 3-ethoxycyclohex-2-en-1-one as starting material. LCMS calculated for $C_{21}H_{31}N_6O_2S$ $(M+H)^+$: m/z=431.2; Found 431.0.

Example 26. 1-Cyclopropyl-N-(1-(methylsulfonyl)piperidin-4-yl)-1,4-dihydroimidazo[4',5':4,5]pyrano[3,2-d]pyrimidin-8-amine

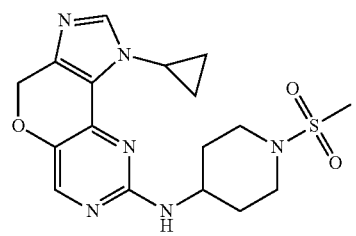 [SMILES: CS(=O)(=O)N1CCC(Nc2ncc3c(n2)-c2c(ncn2C2CC2)CO3)CC1]

This compound was prepared according to the procedures described in Example (Step 1), Intermediate 1 (Step 1) and Example 20, using 2H-pyran-3,5(4H,6H)-dione instead of 4,4-dimethylcyclohexane-1,3-dione as starting material. LCMS calculated for $C_{17}H_{23}N_6O_3S$ $(M+H)^+$: m/z=391.2; Found 391.0.

Example 27. 1-Isopropyl-2-methyl-N-(1-(methylsulfonyl)piperidin-4-yl)-4,5-dihydro-1H-imidazo[4,5-h]quinazolin-8-amine

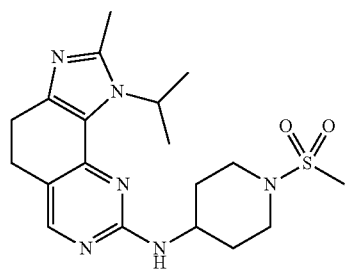 [SMILES: Cc1nc2c(n1C(C)C)-c1nc(NC3CCN(S(C)(=O)=O)CC3)ncc1CC2]

Step 1: 3-Isopropyl-2-methyl-3,5,6,7-tetrahydro-4H-benzo[d]imidazol-4-one

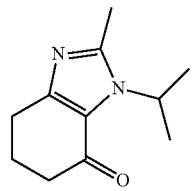

This compound was prepared according to the procedures described in Intermediate 2, using 2-iodopropane instead of MeI (2 M in tert-BuOMe) as starting material. LCMS calculated for $C_{11}H_{17}N_2O$ $(M+H)^+$: m/z=193.1; Found 193.1.

Step 2: 1-Isopropyl-2-methyl-N-(1-(methylsulfonyl)piperidin-4-yl)-4,5-dihydro-1H-imidazo[4,5-h]quinazolin-8-amine This compound was prepared according to the procedures described in Example 7, using 3-isopropyl-2-methyl-3,5,6,7-tetrahydro-4H-benzo[d]imidazol-4-one instead of 2-methyl-3,5,6,7-tetrahydro-4H-benzo[d]imidazol-4-one as starting material. LCMS calculated for $C_{19}H_{29}N_6O_2S$ $(M+H)^+$: m/z=405.2; Found 405.1.

Example 28. 1,2-Dimethyl-N-((3R,4S)-3-methyl-1-((1-methyl-1H-imidazol-4-yl)sulfonyl)piperidin-4-yl)-4,5-dihydro-1H-imidazo[4,5-h]quinazolin-8-amine

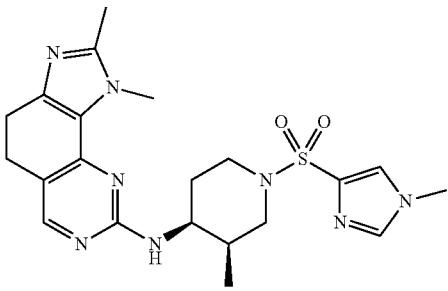 [SMILES: Cc1nc2c(n1C)-c1nc(N[C@H]3CCN(S(=O)(=O)c4cn(C)cn4)C[C@H]3C)ncc1CC2]

Step 1: tert-Butyl (3R,4S)-4-guanidino-3-methylpiperidine-1-carboxylate hydrochloride

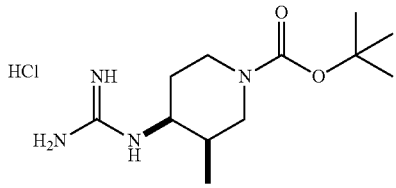 [SMILES: Cl ; C[C@@H]1CN(C(=O)OC(C)(C)C)CC[C@@H]1NC(=N)N]

This compound was prepared according to the procedures described in Intermediate 4, using tert-butyl (3R,4S)-4-amino-3-methylpiperidine-1-carboxylate instead of 1-(methylsulfonyl)piperidin-4-amine as starting material. LCMS calculated for $C_{12}H_{25}N_4O_2$ (M−HCl+H)$^+$: m/z=257.2; Found 257.2.

Step 2: tert-Butyl (3R,4S)-4-((1,2-dimethyl-4,5-dihydro-H-imidazo[4,5-h]quinazolin-8-yl)amino)-3-methylpiperidine-1-carboxylate

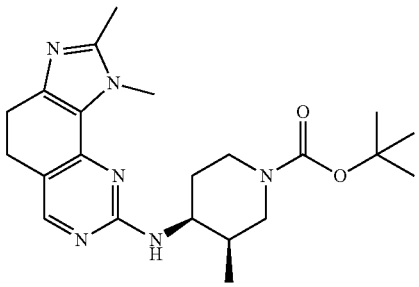 [SMILES: Cc1nc2c(n1C)-c1nc(N[C@H]3CCN(C(=O)OC(C)(C)C)C[C@H]3C)ncc1CC2]

This compound was prepared according to the procedures described in Intermediate 3, using tert-butyl (3R,4S)-4-guanidino-3-methylpiperidine-1-carboxylate hydrochloride instead of tert-butyl 4-guanidinopiperidine-1-carboxylate hydrochloride as starting material. LCMS calculated for $C_{22}H_{33}N_6O_2$ (M+H)$^+$: m/z=413.3; Found 413.2.

Step 3: 1,2-Dimethyl-N-((3R,4S)-3-methyl-1-((1-methyl-1H-imidazol-4-yl)sulfonyl)piperidin-4-yl)-4,5-dihydro-1H-imidazo[4,5-h]quinazolin-8-amine This compound was prepared according to the procedures described in Example 1, using tert-butyl (3R,4S)-4-((1,2-dimethyl-4,5-dihydro-1H-imidazo[4,5-h]quinazolin-8-yl)amino)-3-methylpiperidine-1-carboxylate instead of tert-butyl 4-((1,2-dimethyl-4,5-dihydro-1H-imidazo[4,5-h]quinazolin-8-yl)amino)piperidine-1-carboxylate, and 1-methyl-1H-imidazole-4-sulfonyl chloride instead of ethanesulfonyl chloride as starting material. $^1$H NMR (TFA salt, 500 MHz, DMSO-$d_6$) δ 8.16 (brs, 1H), 7.82 (d, J=1.4 Hz, 1H), 7.79 (d, J=1.4 Hz, 1H), 7.61 (brs, 1H), 4.06 (brs, 3H), 3.93 (m, 1H), 3.71 (s, 3H), 3.29 (m, 1H), 3.17 (m, 1H), 3.02-2.79 (m, 6H), 2.58 (s, 3H), 2.20 (m, 1H), 1.84 (m, 1H), 1.69 (m, 1H), 0.90 (d, J=6.9 Hz, 3H). LCMS calculated for $C_{21}H_{29}N_8O_2S$ (M+H)$^+$: m/z=457.2; Found 457.1.

Example 29. 1,2-Dimethyl-N-((3R,4S)-3-methyl-1-((6-(4-methylpiperazin-1-yl)pyridin-2-yl)sulfonyl)piperidin-4-yl)-4,5-dihydro-1H-imidazo[4,5-h]quinazolin-8-amine

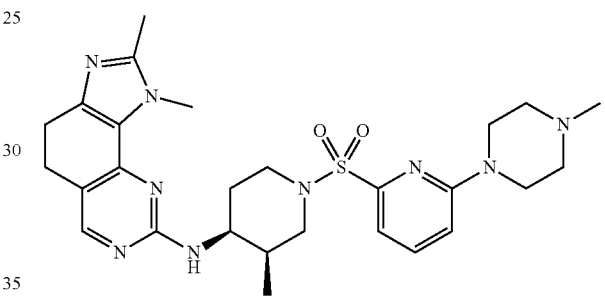

Step 1: N-((3R,4S)-1-((6-Bromopyridin-2-yl)sulfonyl)-3-methylpiperidin-4-yl)-1,2-dimethyl-4,5-dihydro-1H-imidazo[4,5-h]quinazolin-8-amine

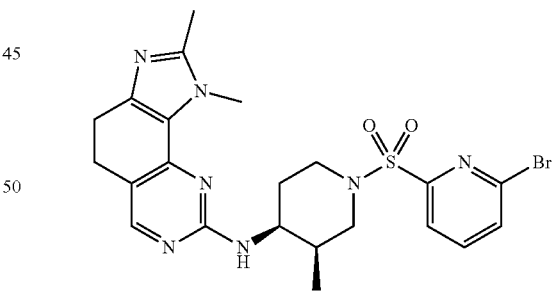

This compound was prepared according to the procedures described in Example 28, using 6-bromopyridine-2-sulfonyl chloride instead of 1-methyl-1H-imidazole-4-sulfonyl chloride as starting material. LCMS calculated for $C_{22}H_{27}BrN_7O_2S$ (M+H)$^+$: m/z=532.1; Found 532.2.

Step 2: 1,2-Dimethyl-N-((3R,4S)-3-methyl-1-((6-(4-methylpiperazin-1-yl)pyridin-2-yl)sulfonyl)piperidin-4-yl)-4,5-dihydro-1H-imidazo[4,5-h]quinazolin-8-amine A solution of N-((3R,4S)-1-((6-bromopyridin-2-yl)sulfonyl)-3-methylpiperidin-4-yl)-1,2-dimethyl-4,5-dihydro-1H- imidazo[4,5-h]quinazolin-8-amine and 1-methylpiperazine in DMF (1 mL) was heated at 100° C. for an hour. The resultant mixture was diluted with MeOH and purified by prep-LCMS (XBridge C18 column, eluting with a gradient of acetonitrile/water containing 0.1% NH$_4$OH, at flow rate of 60 mL/min) to afford the desired product. LCMS calculated for $C_{27}H_3N_9O_2S$ (M+H)$^+$: m/z=552.3; Found 552.4.

Example 30. (R)-1-(5-(((3R,4S)-4-((1,2-Dimethyl-4,5-dihydro-1H-imidazo[4,5-h]quinazolin-8-yl)amino)-3-methylpiperidin-1-yl)sulfonyl)pyridin-2-yl)pyrrolidin-3-ol

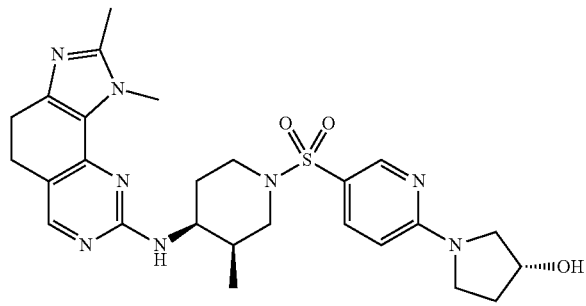 [SMILES: Cc1nc2c(n1C)-c1nc(N[C@H]3CCN(S(=O)(=O)c4ccc(N5CC[C@@H](O)C5)nc4)C[C@H]3C)ncc1CC2]

This compound was prepared according to the procedures described in Example 29, using 6-chloropyridine-3-sulfonyl chloride instead of 6-bromopyridine-2-sulfonyl chloride, and (R)-pyrrolidin-3-ol instead of 1-methylpiperazine as starting material. LCMS calculated for $C_{26}H_{35}N_8O_3S$ (M+H)$^+$: m/z=539.3; Found 539.4.

Example 31. 1-Cyclopropyl-2-methyl-N-((3R,4S)-3-methyl-1-((1-methyl-1H-imidazol-4-yl)sulfonyl)piperidin-4-yl)-4,5-dihydro-1H-imidazo[4,5-h]quinazolin-8-amine

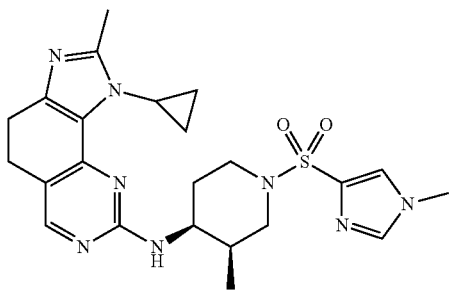 [SMILES: Cc1nc2c(n1C1CC1)-c1nc(N[C@H]3CCN(S(=O)(=O)c4cn(C)cn4)C[C@H]3C)ncc1CC2]

This compound was prepared according to the procedures described in Example 28, using 3-cyclopropyl-2-methyl-3,5,6,7-tetrahydro-4H-benzo[d]imidazol-4-one instead of 2,3-dimethyl-3,5,6,7-tetrahydro-4H-benzo[d]imidazol-4-one as starting material. LCMS calculated for $C_{23}H_{31}N_8O_2S$ (M+H)$^+$: m/z=483.2; Found 483.2.

Example 32. 1-Cyclopropyl-2-methyl-N-((3R,4S)-3-methyl-1-((1-methyl-1H-pyrazol-4-yl)sulfonyl)piperidin-4-yl)-4,5-dihydro-1H-imidazo[4,5-h]quinazolin-8-amine

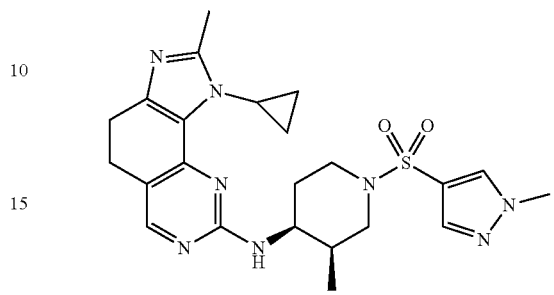

This compound was prepared according to the procedures described in Example 31, using 1-methyl-1H-pyrazole-4-sulfonyl chloride instead of 1-methyl-1H-imidazole-4-sulfonyl chloride as starting material. LCMS calculated for $C_{23}H_{31}N_8O_2S$ (M+H)$^+$: m/z=483.2; Found 483.2.

Example A. CDK2/Cyclin E1 HTRF Enzyme Activity Assay

CDK2/Cyclin E1 enzyme activity assays utilize full-length human CDK2 co-expressed as N-terminal GST-tagged protein with FLAG-Cyclin E1 in a baculovirus expression system (Carna Product Number 04-165). Assays are conducted in white 384-well polystyrene plates in a final reaction volume of 8 μL. CDK2/Cyclin E1 (0.25 nM) is incubated with compounds (40 nL serially diluted in DMSO) in the presence of ATP (50 μM or 1 mM) and 50 nM ULight™-labeled eIF4E-binding protein 1 (THR37/46) peptide (PerkinElmer) in assay buffer (containing 50 mM HEPES pH 7.5, 1 mM EGTA, 10 mM MgCl$_2$, 2 mM DTT, 0.05 mg/ml BSA, and 0.01% Tween 20) for 60 minutes at room temperature. The reactions are stopped by the addition of EDTA and Europium-labeled anti-phospho-4E-BP1 antibody (PerkinElmer), for a final concentration of 15 mM and 1.5 nM, respectively. HTRF signals are read after 1 hour at room temperature on a PHERAstar FS plate reader (BMG Labtech). Data is analyzed with IDBS XLFit and GraphPad Prism 5.0 software using a three or four parameter dose response curve to determine IC$_{50}$ for each compound. The IC$_{50}$ data as measured for the Examples at 1 mM ATP in the assay of Example A is shown in Table 1.

TABLE 1

| Example | IC$_{50}$ (nM) |
|---|---|
| 1 | + |
| 2 | + |
| 3 | + |
| 4 | + |
| 5 | + |
| 6 | + |
| 7 | ++ |
| 8 | + |
| 9 | ++ |
| 10 | +++ |
| 11 | + |
| 12 | + |
| 13 | + |
| 14 | + |

TABLE 1-continued

| Example | IC$_{50}$ (nM) |
|---|---|
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |

+ refers to ≤50 nM
++ refers to >50 nM to 200 nM
+++ refers to >200 nM to 500 nM
++++ refers to >500 nM to 1000 nM

Example B1. Characterization of Cyclin E1 in Ovarian and Endometrial Cancer Cell Lines The cyclin E1 ("CCNE1") gene was evaluated in various ovarian and endometrial cancer cell lines (FIGS. 1A and 1). CCNE1 was amplified in COV318, OVCAR3 OVARY, Fu-OV1, and KLE cells, each of which displayed a CCNE1 gain of function by copy number (copy number ("CN") >2) (FIG. 1A). In contrast, CCNE1 was not amplified in COV504, OV56, or Igrov1 cells, each of which displayed copy neutral (2) or loss of function of the gene (CN≤2). CN was obtained from the Broad Institute Cancer Cell Line Encyclopedia ("CCLE") database (Barretina, et al., *Nature*, 2012, 483(7391):603-7, which is incorporated herein by reference in its entirety).

Western blot analysis was performed on protein samples from COV318, OVCAR3_OVARY, Fu-OV1, KLE, COV504, OV56, and Igrov1 cells to evaluate CCNE1 protein levels. CCNE1 protein levels were higher in cell lines with CCNE1 gain of function by copy number (CN >2; i.e., COV318, OVCAR3 OVARY, Fu-OV1, and KLE cells) compared to cell lines with copy neutral or loss of function of the gene (CN≤2; i.e., COV504, OV56, and Igrov1 cells).

Figure 2A:
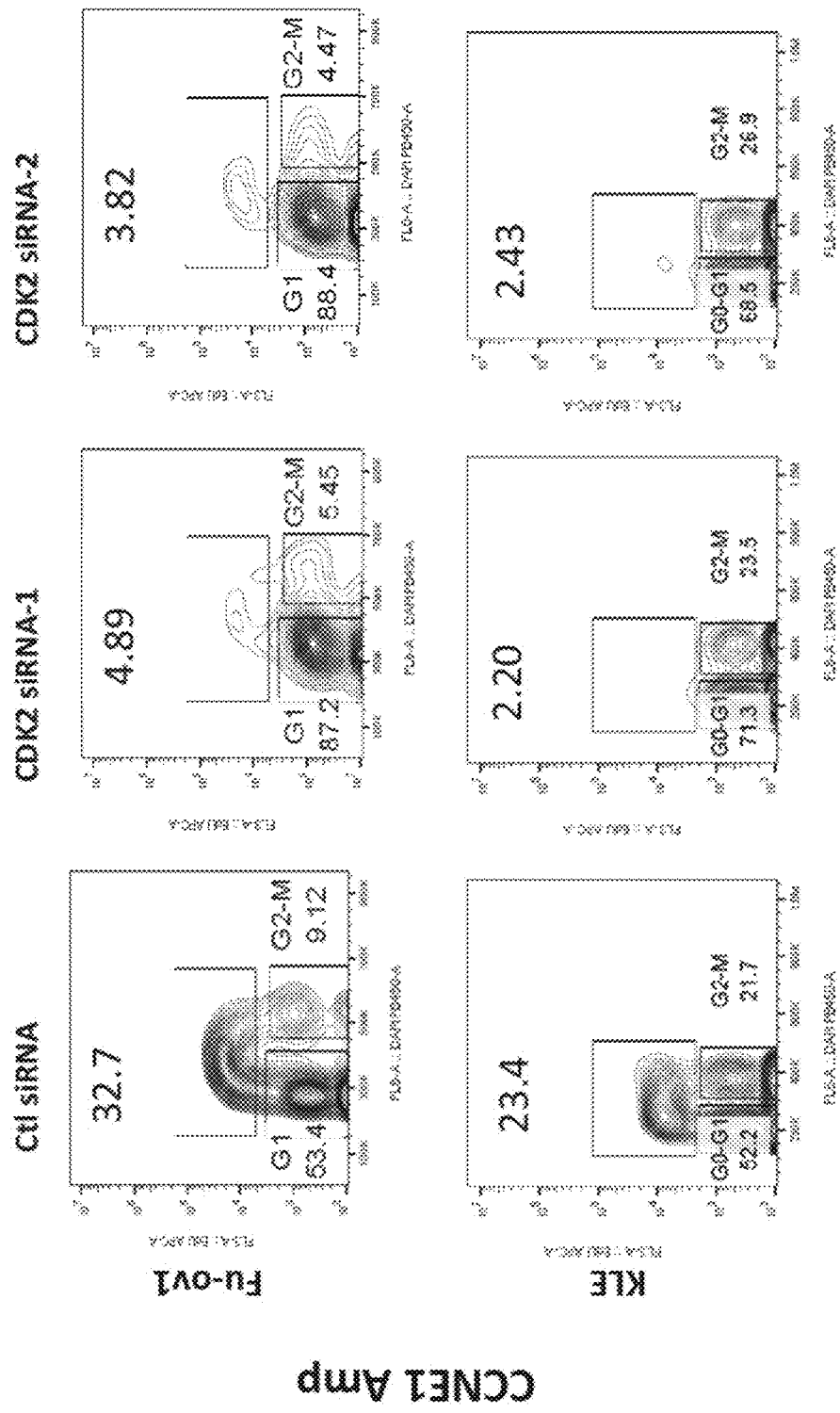
FIGS. 2A-2B: siRNA mediated CDK2 knockdown inhibits proliferation in CCNE1 amplified cell lines.
Figure 2B:
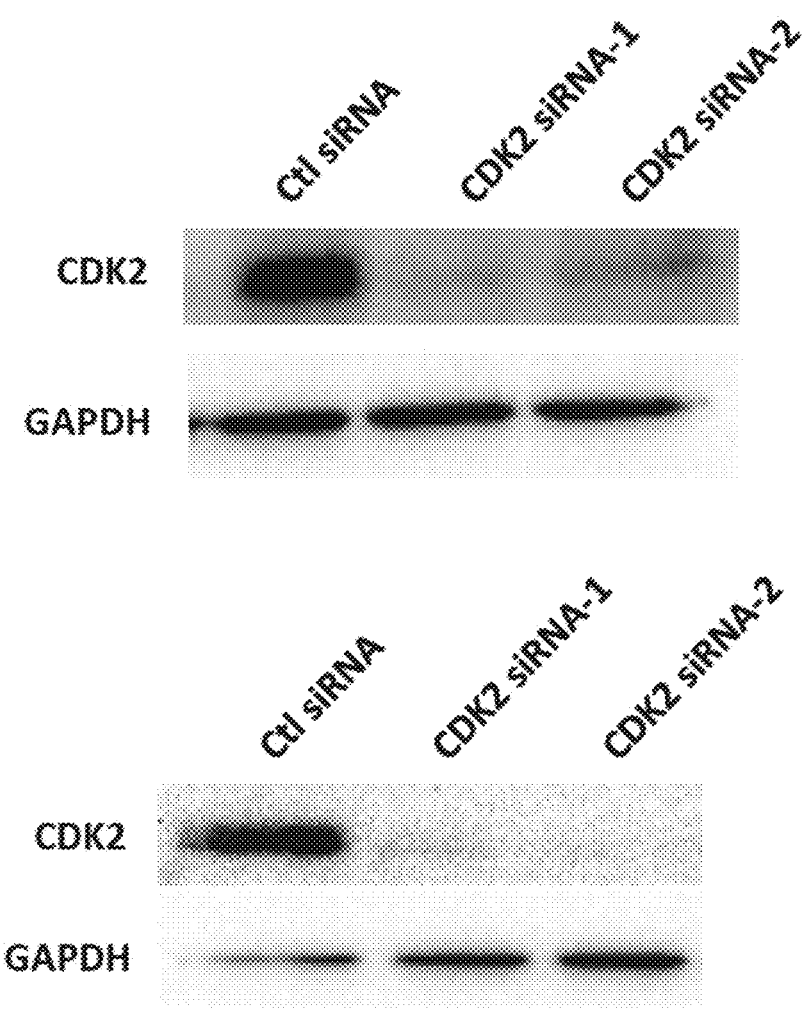
Figure 3A:
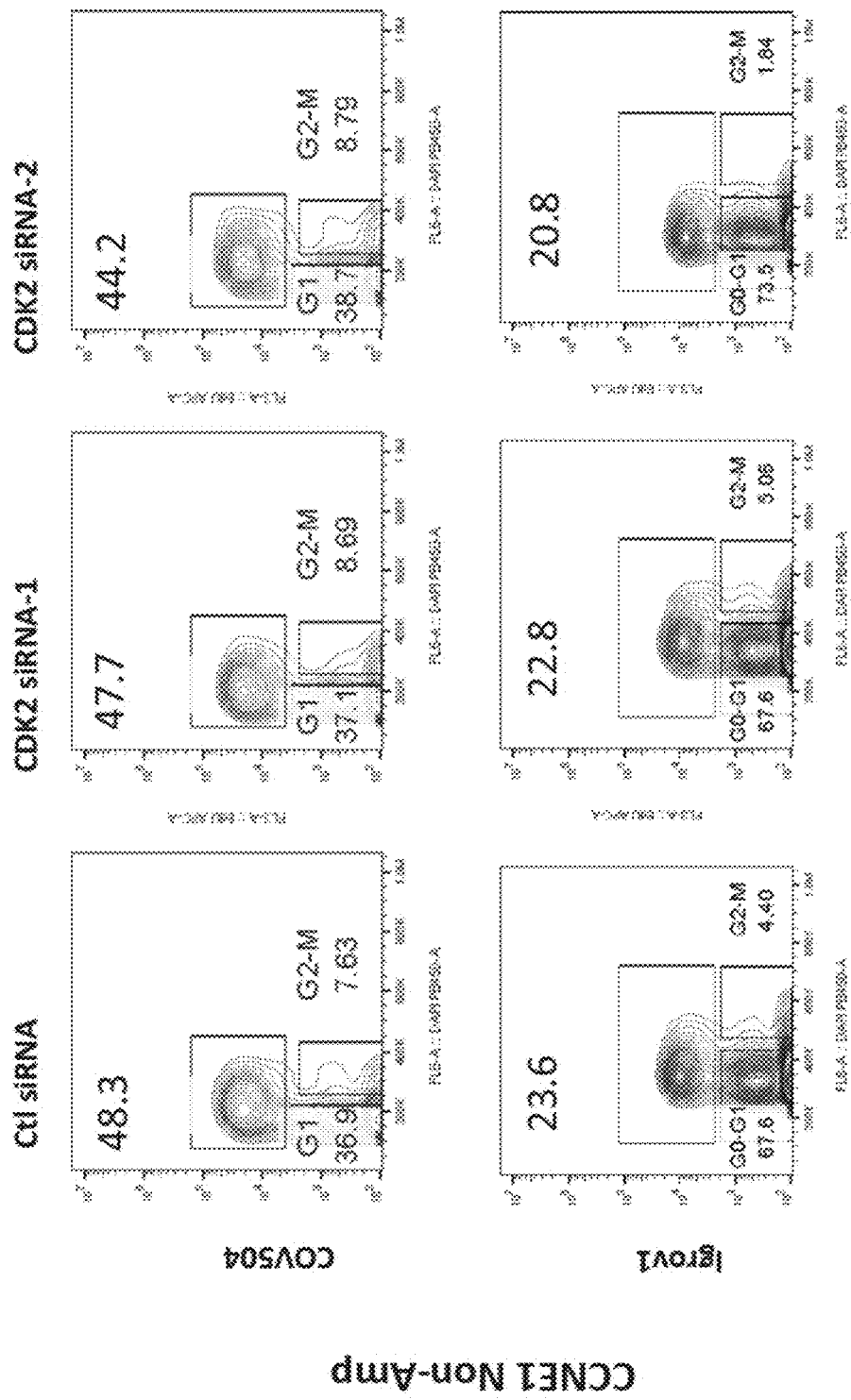
FIGS. 3A-3B: CDK2 knockdown does not inhibit proliferation in CCNE1 Non-Amp lines.
Figure 3B:
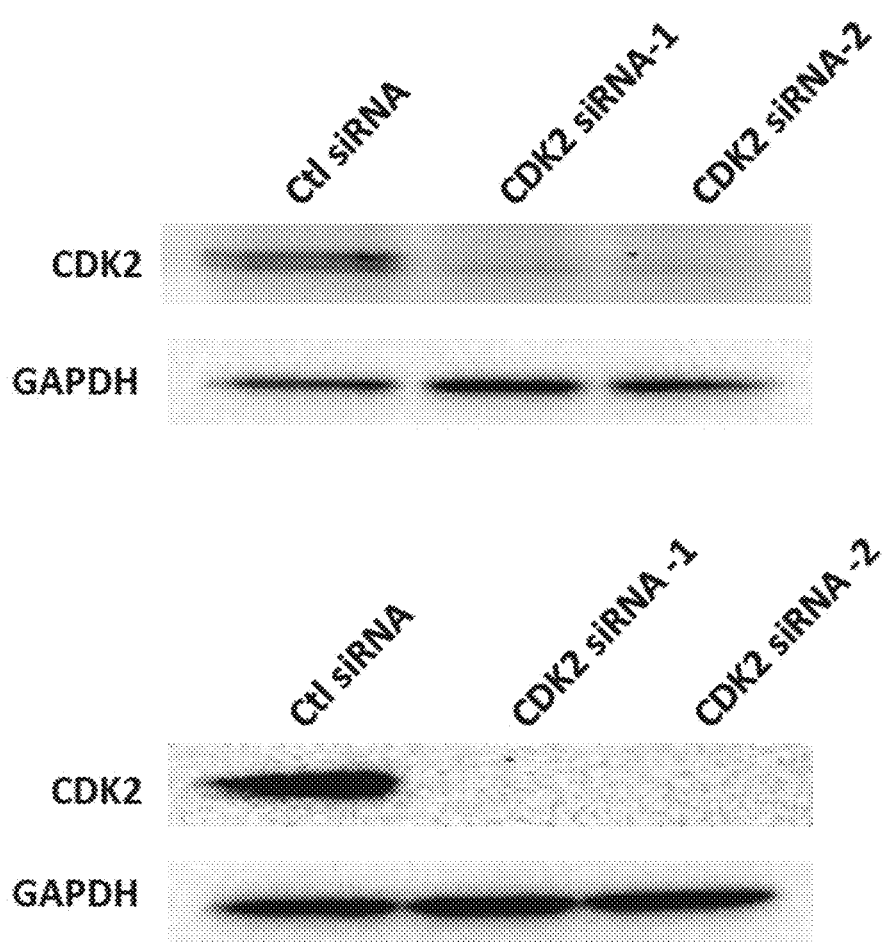

Example B2. CDK2-Knockdown by siRNA Inhibits Proliferation in CCNE1-Amplified, but not CCNE1-Non-Amplified Human Cancer Cell Lines The effect of CDK2-knockdown in CCNE1-amplified versus CCNE1-non-amplified cell lines was evaluated. CCNE1-amplified cell lines (Fu-OV1 and KLE) or CCNE1-non-amplified cell lines (COV504 and Igrov1) were treated with a control ("ctrl") or CDK2-specific small interfering RNAs ("siRNAs") ("CDK2 siRNA-1" and "CDK2 siRNA-2") (FIGS. 2A and 2B and 3A and 3B). Seventy-two hours after transfection with the siRNAs, the cells were harvested and subjected to cell cycle analysis by fluorescence activated cell sorting ("FACS") (FIGS. 2A and 3A). Knockdown of CDK2 was confirmed by western blot (FIGS. 2B and 3B). CDK2-knockdown inhibited proliferation in CCNE1-amplified cell lines, but not in CCNE1-non-amplified cell lines (FIGS. 2A and 3A).

Figure 4:
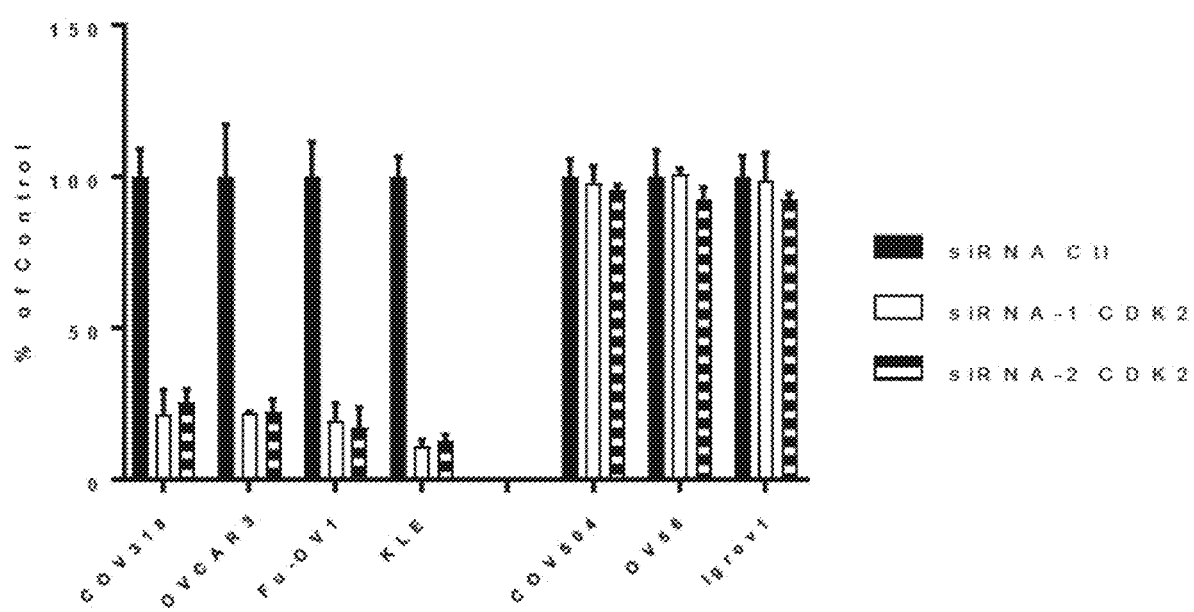
FIG. 4: CDK2 knockdown by siRNA inhibits proliferation in CCNE1 amplified, but not in CCNE1 non-amplified, human cancer cell lines. Percentage of cells at the S phase 3 days after transfection of CDK2 siRNAs, relative to Ctl siRNA. The cell cycle phase distribution was evaluated by FACS. Means represent three independent experiments in four CCNE1 Amp cell lines and three Non-Amp lines.

A similar experiment was performed in additional CCNE1-amplified cell lines (COV318, OVCAR3, Fu-OV1, and KLE) and CCNE1-non-amplified cell lines (COV504, OV56, and Igrov1) (FIG. 4). The percentage of cells at the S phase three days after treatment with CDK2-specific siRNAs was significantly decreased in CCNE1-amplified cell lines as compared to treatment with control siRNA (FIG. 4). Consistent with the results of FIGS. 2A and 3A, the percentage of cells at the S phase three days after treatment with CDK2-specific siRNAs was not significantly different in CCNE1-non-amplified cell lines as compared to treatment with control siRNA (FIG. 4).

Figure 5:
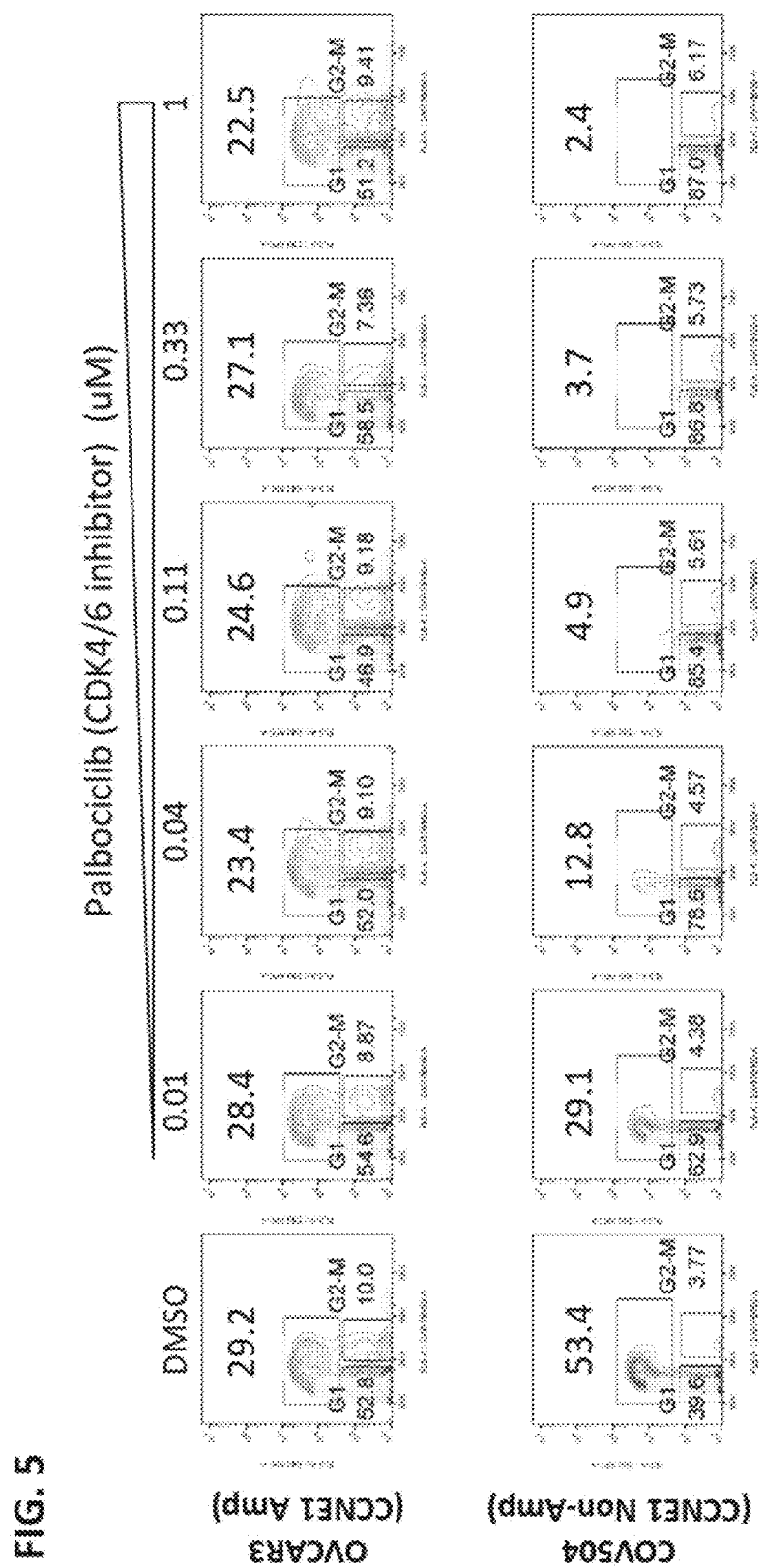
FIG. 5: Palbociclib treatment induces dose-dependent inhibition of proliferation in CCNE1 non-amplified, but not in amplified cell lines. Cell cycle analysis of CCNE1 non-amplified cell line COV504 (upper) and CCNE1 amplified OVCAR3 cells (lower) after Palbociclib treatment for 16 hours. The cell cycle phase distribution was evaluated by FACS.

Example B3. Proliferation in CCNE1 Amplified and CCNE-Non-Amplified Cell Lines Upon CDK4/6 Inhibition The effect of CDK4/6-inhibition in CCNE1-amplified versus CCNE1-non-amplified cell lines was evaluated. CCNE1-amplified cells (OVCAR3) or CCNE1-non-amplified cells (COV504) were treated with dimethyl sulfoxide ("DMSO") control or increasing concentrations of CDK4/6 inhibitor palbociclib (FIG. 5). Sixteen hours after treatment with DMSO or palbociclib, the cells were harvested and subjected to cell cycle analysis by FACS (FIG. 5). CDK4/6-inhibition resulted in dose-dependent inhibition of the proliferation in CCNE1-non-amplified cells, but not in CCNE1-amplified cells (FIG. 5).

Figure 6:
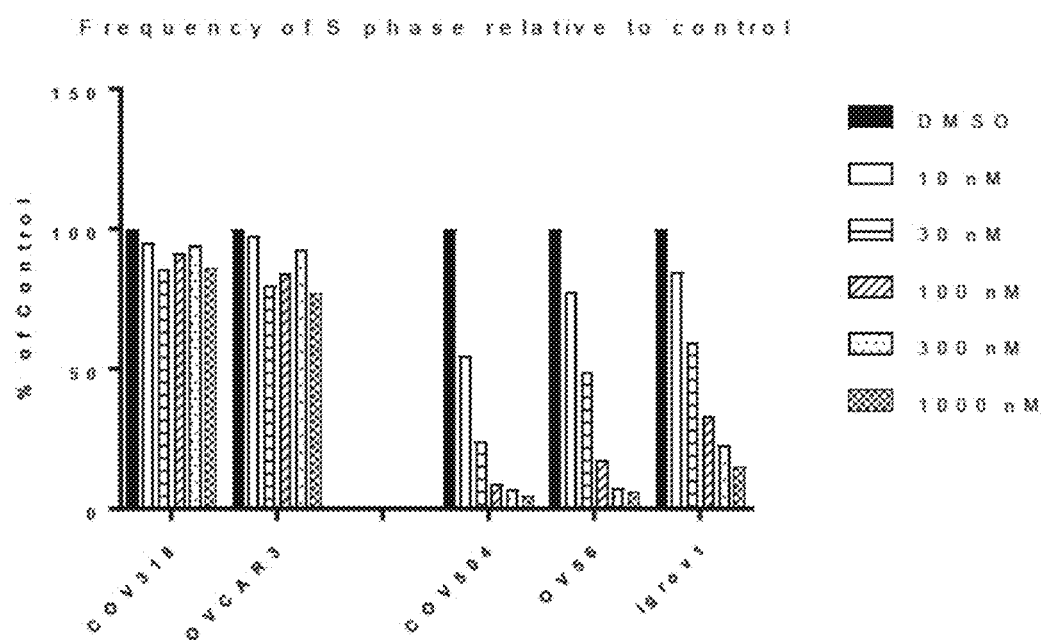
FIG. 6: Palbociclib treatment selectively inhibits proliferation in CCNE1 non-amplified cancer cell lines. Percentage of cells at the S phase after 16 hours of Palbociclib with the indicated doses, relative to DMSO.

A similar experiment was performed in a larger set of CCNE1-amplified cell lines (COV318 and OVCAR3) and CCNE1-non-amplified cell lines (COV504, OV56, and Igrov1) (FIG. 6). The percentage of cells at the S phase 16 hours after treatment with palbociclib was decreased in CCNE1-non-amplified cell lines in a dose-dependent fashion as compared to treatment with DMSO (FIG. 6). Consistent with the results of FIG. 5, the percentage of cells at the S phase 16 hours after treatment with palbociclib was not significantly different in CCNE1-amplified cell lines as compared to treatment with DMSO (FIG. 6).

Figure 7A:
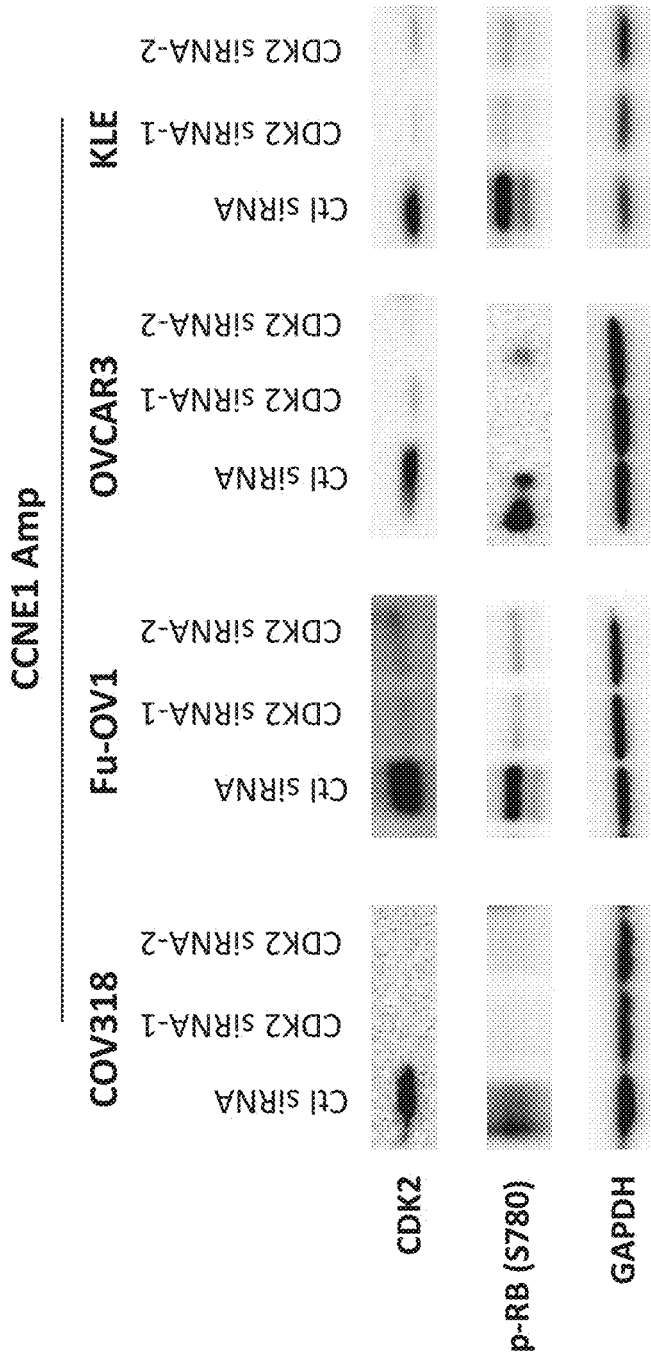
FIGS. 7A-7B: CDK2 knockdown by siRNAs blocks RB phosphorylation at S780 in CCNE1 amplified, but not in non-amplified ovarian cells.
Figure 7B:
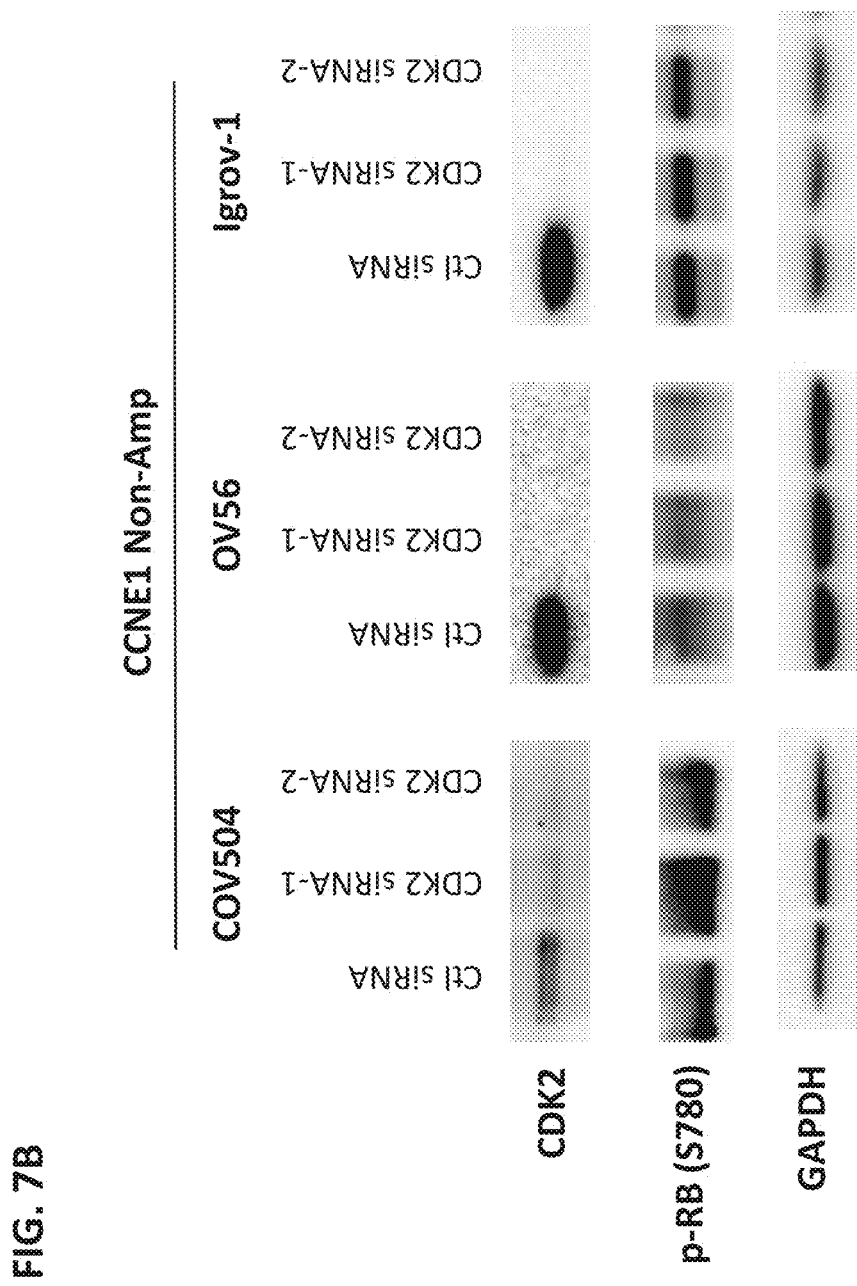

Example B4. CDK2-Knockdown Blocks Rb Phosphorylation at S780 in CCNE1-Amplified, but not in CCNE1-Non-Amplified, Cell Lines The effect of CDK2-knockdown on Rb phosphorylation at Ser-780 of SEQ ID NO:3 ("S780") in CCNE1-amplified versus CCNE1-non-amplified cell lines was evaluated. CCNE1-amplified cell lines (COV318, Fu-OV1 and KLE) or CCNE1-non-amplified cell lines (COV504, OV56 and Igrov1) were treated with ctrl or CDK2-specific siRNAs (FIGS. 7A and 7B). 72 hours after transfection with the siRNAs, the cells were harvested and total protein was extracted and analyzed by western blot. Knockdown of CDK2 was confirmed by western blot. CDK2-knockdown blocked Rb phosphorylation at S780 in CCNE1-amplified cell lines (FIG. 7A), but not in CCNE-non-amplified cell lines (FIG. 7B).

Figure 8A:
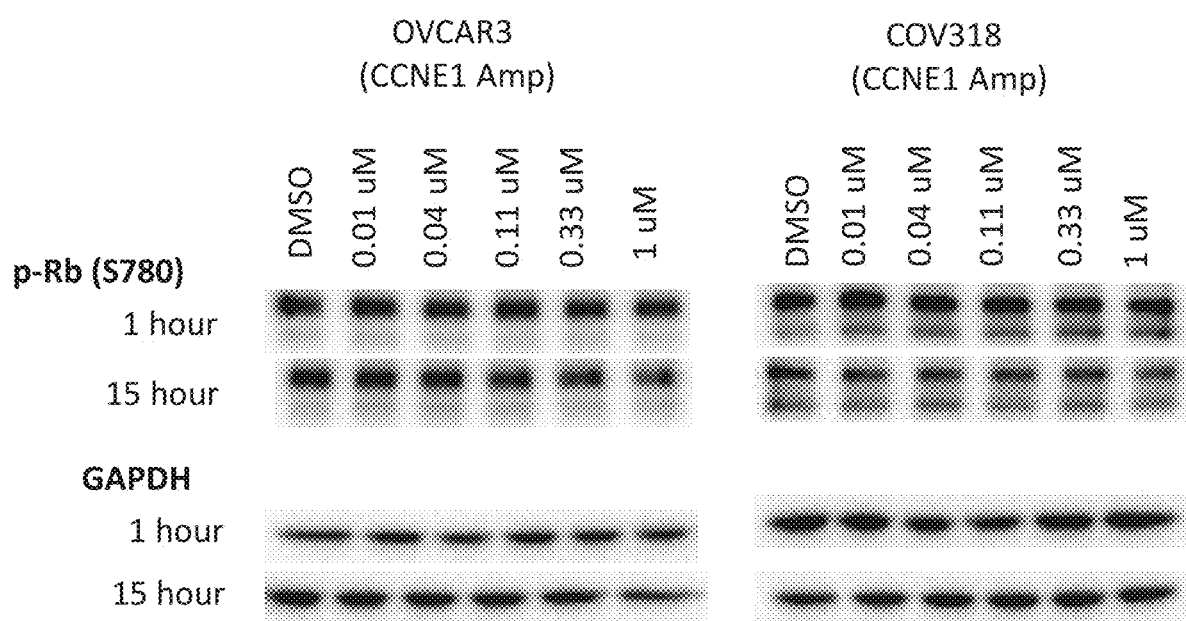
FIGS. 8A-8B: Palbociclib blocks RB phosphorylation at S780 in CCNE1 non-amplified, but not in amplified ovarian cells.
Figure 8B:
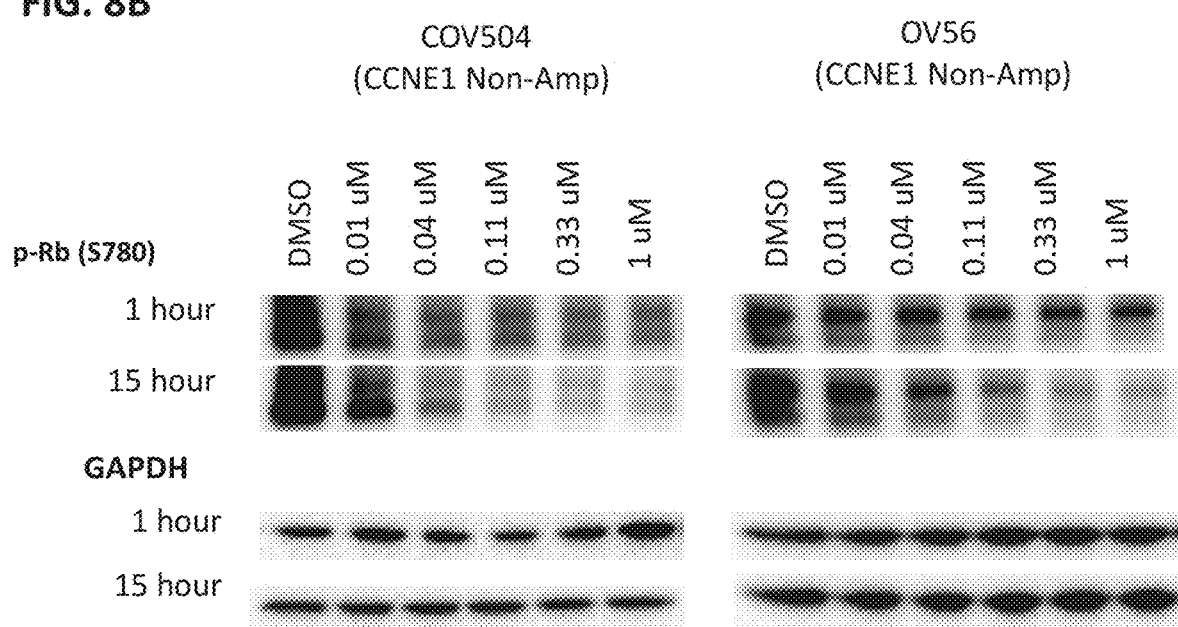

Example B5. Palbociclib Blocks Rb Phosphorylation at S780 in CCNE1 Non-Amplified, but not in CCNE1-Amplified, Cell Lines The effect of CDK4/6-inhibition on Rb phosphorylation at S780 in CCNE1-amplified versus CCNE1-non-amplified cell lines was evaluated. CCNE1-amplified cell lines (OVCAR3 and COV318) or CCNE1-non-amplified cell lines (COV504 and OV56) were treated with DMSO or various doses of palbociclib (FIGS. 8A and 8B). One or 15 hours after treatment, the cells were harvested and total protein was extracted and analyzed by western blot (FIG. 8). Palbociclib treatment blocked Rb phosphorylation at 5780 in CCNE1-non-amplified cell lines (FIG. 8B), but not in CCNE1-amplified cell lines (FIG. 8A).

Example B6. CDK2 Degradation by dTAG Decreases Rb Phosphorylation at S780

To further confirm that CDK2 knockdown decreases Rb phosphorylation at S780 in CCNE1-amplified cells (see Example B4), the dTAG system was used to degrade CDK2 and the level of 5780-phosphorylated Rb was evaluated (Erb et al., Nature, 2017, 543(7644):270-274, which is incorporated herein by reference in its entirety). Briefly, OVCAR3 cells were engineered to express Cas9 by lentiviral transduction of Cas9 construct. The OVCAR3-Cas9 cells were then engineered to express CDK2-FKBP12F36V-HA fusion protein by lentiviral transduction of CDK2-FKBP12F36V-HA expression construct. Next, to engineer the line to have endogenous CDK2 inactivated, OVCAR3 (Cas9, CDK2-FKBP12F36V-HA) cells were transduced with CDK2 sgRNA ("CDK2-gRNA"); OVCAR3 (Cas9, CDK2-FKBP12F36V-HA) cells transduced with non-targeting sgRNA ("Ctl-gRNA"; Cellecta) served as a control cell line.

Figure 9A:
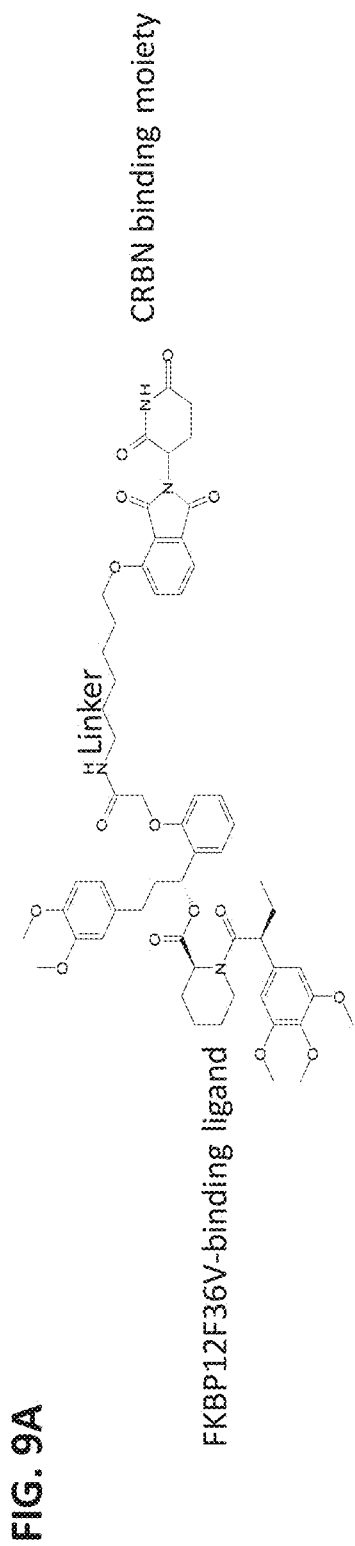
FIGS. 9A-9B: CDK2 degradation by dTAG decreases RB phosphorylation at 5780.
Figure 9B:
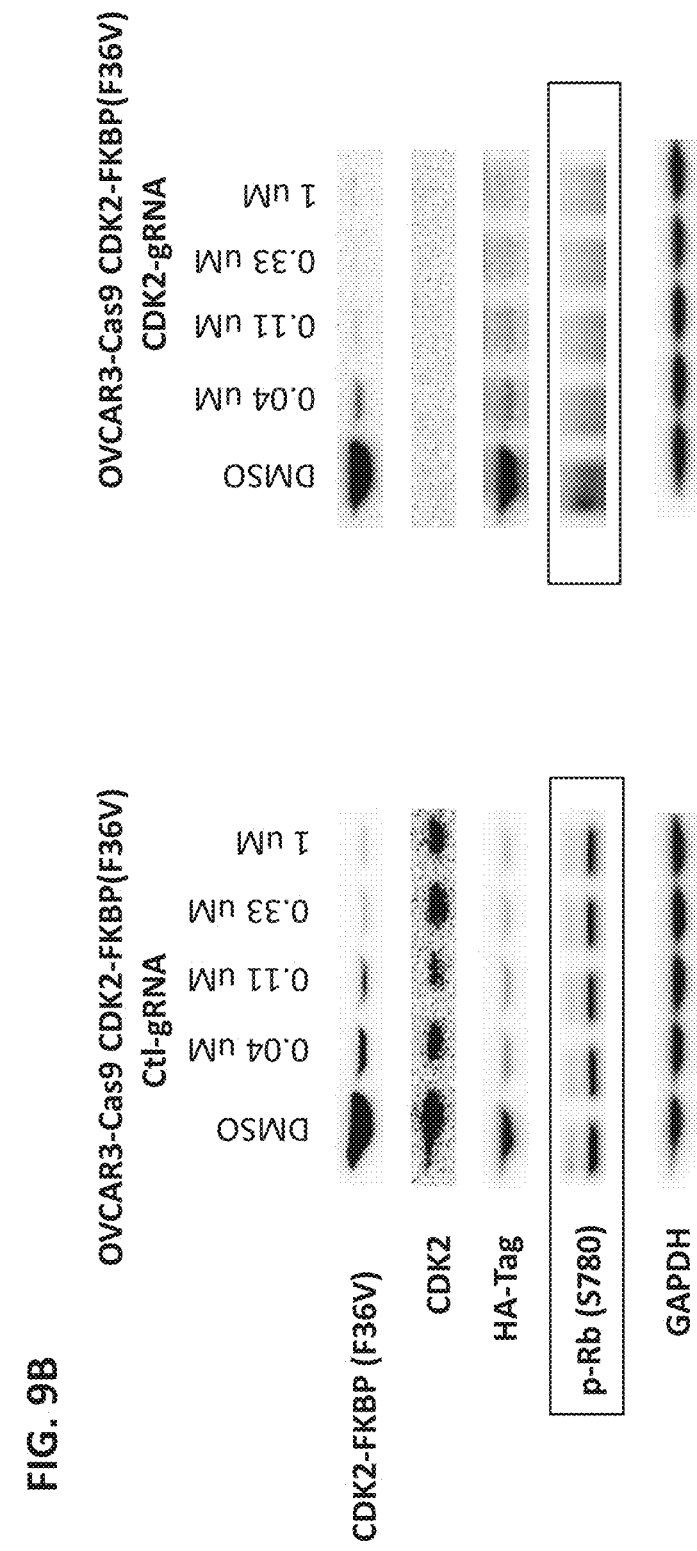

To degrade CDK2-FKBP12F36V-HA protein by dTAG (FIG. 9A), cells were treated with DMSO or with a titration of concentrations of dTAG for 14 hours. Cells were collected and processed for Western blot (FIG. 9B). A dose-responsive degradation of CDK2-FKBP12(F36V) was detected by western blot after treatment with dTAG in both control- and CDK2-gRNA treated cells (FIG. 9B). Degradation was further confirmed by western blot for HA-Tag. Endogenous CDK2 protein was detected in OVCAR3 cells treated with control gRNA, but not with CDK2-gRNA (FIG. 9B). CDK2-FKBP12(F36V) degradation inhibited Rb phosphorylation at S780 in CDK2 knockout OVCAR3 cells, but not in OVCAR3 cells with endogenous CDK2 expression.

Example B7. p-Rb S780 HTRF Cellular Assay for Identification of CDK2 Inhibitors

An in vitro CDK2/CCNE1 enzyme activity assay was used to measure phosphorylation of a peptide substrate using homogenous time-resolved energy transfer ("HTRF"). First, the specificity of 8-((1R,2R)-2-hydroxy-2-methylcyclopentyl)-2-((1-(methylsulfonyl)piperidin-4-yl)amino)pyrido[2,3-d]pyrimidin-7(8H)-one (Compound A; see US Patent Application Publication No. 2018/0044344 at page 51, paragraph [0987], which is incorporated by reference herein in its entirety) for CDK2 inhibition was confirmed via a kinase activity assay (FIG. 10A). To this end, the LANCE® Ultra kinase assay was used with a ULight™-labeled EIF4E-binding protein 1 (Thr37/46) peptide (PerkinElmer, TRF0128-M) as substrate and an Europium-labeled anti-phospho-EIF4E binding protein1 (Thr37/46) antibody (PerkinElmer, TRF0216-M). A ratio of fluorescence transferred to the labeled substrate (665 nm) relative to fluorescence of the Europium donor (620 nm) represents the extent of phosphorylation. The $IC_{50}$ for Compound A was determined to be 1.1 nM (FIG. 10A). In contrast, the $IC_{50}$ for the CDK4/6 inhibitor palbociclib was 10,000 nM (FIG. 10A).

Next, a CDK2 pRb (S780) HTRF cellular assay was performed, enabling the quantitative detection of Rb phosphorylated on serine 780 in CCNE1 amplified COV318 cells upon treatment with Compound A or palbociclib (FIG. 10B). Treatment with Compound A, but not palbociclib, inhibited Rb phosphorylation on serine 780 in CCNE1 amplified cells (FIG. 10B). The $IC_{50}$ for Compound A in this assay was 37 nM, while the $IC_{50}$ for palbociclib was >3,000 nM (FIG. 10B).

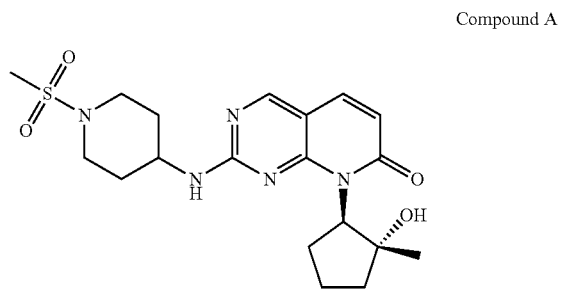

Compound A

Example B8. Bioinformatics Analysis of CCLE Dataset Reveals the Sensitivity to CDK2 Inhibition in CCNE1 Amplified Cells Relies on Functional p16

In an attempt to identify a biomarker for predicting sensitivity to CDK2-inhibition in CCNE1-amplified cells, 460 cell lines from CCLE were analyzed (Barretina, supra). First, the cell lines were filtered based on CCNE1 copy number and expression and CDK2 sensitive score based on shRNA knockdown data. A total of 41 cell lines were identified as having CCNE1 copy number of >3 and CCNE1 expression score (CCLE: >3). Of these 41 cell lines, 18 (44%) were sensitive to CDK2 inhibition (CDK2 sensitive score ≤−3), while 23 (56%) were insensitive to CDK2 inhibition (CDK2 sensitive score >−3).

Figure 11:
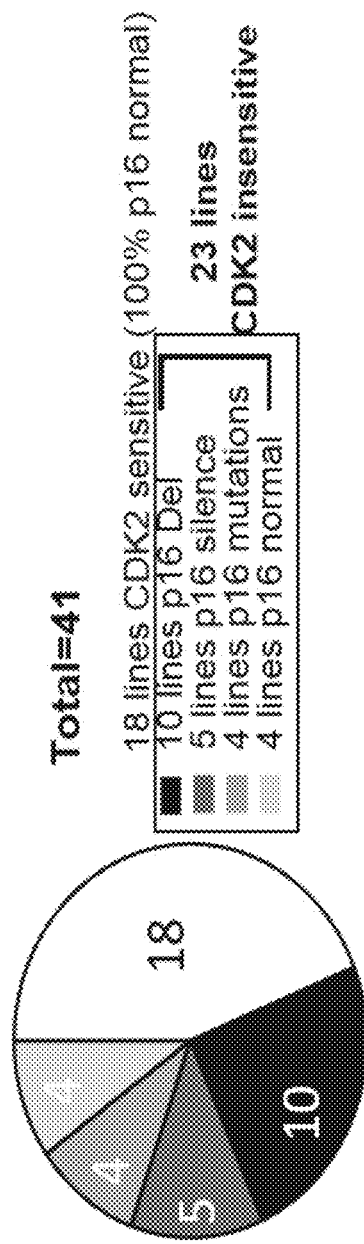
FIG. 11: Bioinformatics analysis of CCLE dataset reveals the sensitivity to CDK2 inhibition in CCNE1 amplified cells relies on functional p16.

Next, the p16 status was evaluated in the CDK2-sensitive and CDK2-insensitive cell lines (FIG. 11). Of the 18 cell lines that were sensitive to CDK2-inhibition, 100% expressed normal p16 gene (FIG. 11). In contrast, only 4 of the 23 CDK2-insensitive cell lines expressed normal p16 gene (FIG. 11). The majority of the 23 CDK2-insensitive cell lines displayed dysfunctional p16 gene expression: the p16 gene was deleted in 10 of 23 cell lines; the p16 gene was silenced in 5 of the 23 cell lines, and the p16 gene was mutated in 4 of the 23 cell lines (FIG. 11).

A summary of CDK2 sensitivity and CDKN2A/p16 status in CCNE1 amplified cell lines is provided in Table 2, below.

TABLE 2

Cell lines with CDK2 sensitive Score ≤3 counted as CDK2 Sensitive lines; ≥3 as CDK2 insensitive line. Cell lines verified in experiments are in bold. NCIN87_STOMACH showed no CDKN2A/P16 protein expression in western blot. CCNE1 and CDKN2A/P16 copy number were calculated based on CCLE dataset. Expression Score <0 counted as gene silencing.

| Cell Lines | CDK2 sensitive Score | CCNE1 Copy No. | CDKN2A Copy No. | CDKN2A/p16 mRNA Expression Score | CDKN2a/p16 Dysfunction |
|---|---|---|---|---|---|
| HCC1569_BREAST | −9.6 | 16 | 2 | 5.11 | |
| OVISE_OVARY | −9.4 | 3 | 2 | 4.17 | |
| MKN1_STOMACH | −8.9 | 5 | 1 | 4.28 | |
| EFE184_ENDOMETRIUM | −8.7 | 3 | 2 | 3.97 | |
| KURAMOCHI_OVARY | −8.2 | 3 | 2 | 3.60 | |
| MKN7_STOMACH | −7.7 | 21 | 1 | 4.37 | |
| MDAMB157_BREAST | −7.6 | 6 | 2 | 5.01 | |
| HCC70_BREAST | −7.6 | 4 | 4 | 4.88 | |
| NIHOVCAR3_OVARY | −7.4 | 10 | 2 | 4.15 | |
| FUOV1_OVARY | −7 | 10 | 3 | 5.19 | |
| KLE_ENDOMETRIUM | −7 | 7 | 2 | 6.24 | |
| COV318_OVARY | −7 | 14 | 2 | 5.09 | |
| CAOV4_OVARY | −6.7 | 3 | 2 | 3.59 | |
| MFE280_ENDOMETRIUM | −6.3 | 4 | 2 | 4.97 | |
| NCIH661_LUNG | −6.2 | 5 | 2 | 3.73 | |
| OVCAR4_OVARY | −4.3 | 4 | 1 | 4.77 | |
| SNU8_OVARY | −3.8 | 5 | 3 | 5.35 | |
| OVCAR8_OVARY | −3.7 | 3 | 2 | 5.21 | |
| RMUGS_OVARY | −2.8 | 4 | 1 | −0.08 | Silencing |
| NCCSTCK140_STOMACH | −2.7 | 3 | 0 | −4.70 | Deletion |
| NCIH2286_LUNG | −1.6 | 3 | 1 | 3.63 | Mutation |
| HOP62_LUNG | −1.4 | 4 | 0 | −1.21 | Deletion |
| LN340_CENTRAL_NERVOUS_SYSTEM | −1.0 | 3 | 0 | −5.47 | Deletion |
| NCIH1339_LUNG | −0.8 | 3 | 2 | 2.42 | Unknown |
| NCIN87_STOMACH | 0.1 | 3 | 2 | 4.67 | No protein |
| U2OS_BONE | 0.4 | 3 | 1 | −5.72 | Silencing |
| SF172_CENTRAL_NERVOUS_SYSTEM | 0.5 | 3 | 0 | −2.35 | Deletion |
| CAL120_BREAST | 0.6 | 4 | 1 | 4.86 | |
| RMGI_OVARY | 0.9 | 3 | 0 | −3.33 | Deletion |
| OV90_OVARY | 0.9 | 3 | 1 | 3.95 | Mutation |
| SNU601_STOMACH | 1.1 | 4 | 2 | −3.79 | Silencing |
| EW8_BONE | 1.5 | 5 | 1 | 3.11 | |
| JHESOAD1_OESOPHAGUS | 1.7 | 5 | 0 | −5.52 | Deletion |
| HCC1806_BREAST | 1.9 | 8 | 0 | −4.61 | Deletion |
| NCIH2170_LUNG | 2.0 | 3 | 0 | −3.73 | Deletion |
| HCC1428_BREAST | 2.3 | 3 | 2 | 2.28 | |
| A549_LUNG | 2.5 | 4 | 0 | −6.13 | Deletion |
| LXF289_LUNG | 2.6 | 4 | 3 | 4.10 | Mutation |
| AGS_STOMACH | 3.0 | 3 | 2 | −5.56 | Silencing |
| NCIH647_LUNG | 3.0 | 4 | 0 | −5.07 | Deletion |
| HLF_LIVER | 3.9 | 3 | 2 | 3.40 | |

Figure 12A:
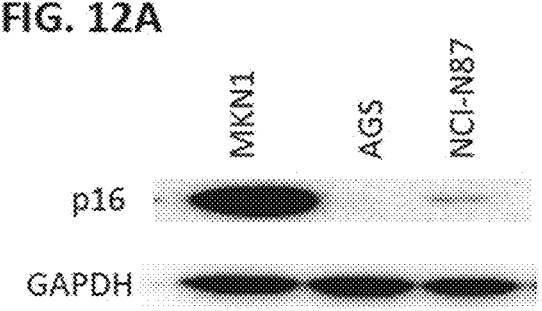
FIGS. 12A-12B: CCNE1 amplified cells with dysfunctional p16 do not respond to CDK2 inhibition.

Example B9. CCNE1 Amplified Cells with Dysfunctional p16 do not Respond to CDK2 Inhibition To further evaluate the role of p16 in CDK2-sensitivity in CCNE-amplified cells, p16 protein expression in three gastric cell lines with CCNE1-amplification was evaluated by western blot. AGS and NCI-N87 cells displayed absent or dramatically reduced levels of p16 (FIG. 12A). In contrast, p16 protein was detected in MKN1 cellular protein extracts (FIG. 12A).

Next, the impact of CDK2-knockdown in these cells was evaluated. Mkn1, Ags, and NCI-N87 cells were treated with control or CDK2-specific siRNA. Three days-post-siRNA transfection, cell cycle phase distribution of the cells was evaluated by FACS.

Figure 12B:
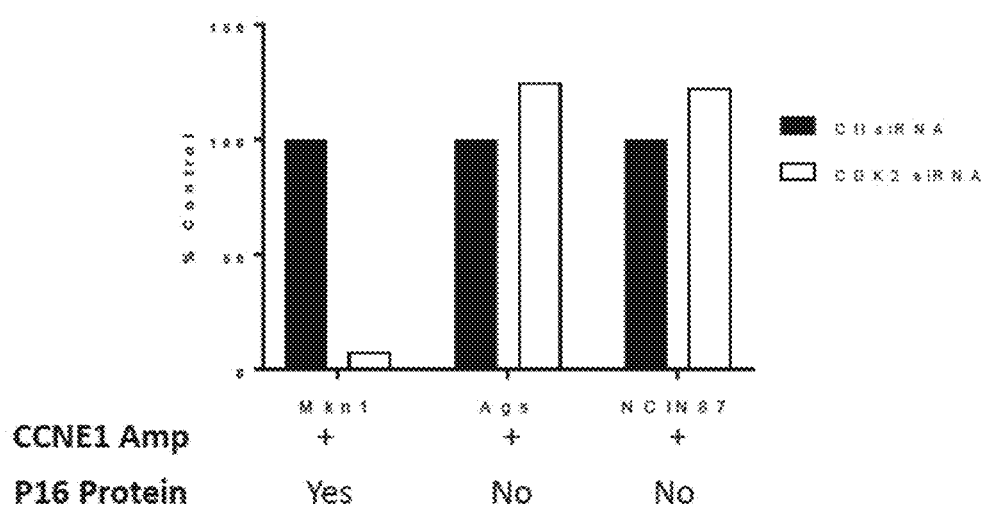

The percentage of cells at the S phase in the Mkn1 cells (CCNE-amplified, p16 protein detected) was significantly decreased in the CDK2 siRNA-treated cells as compared to control (FIG. 12B). In contrast, the percentage of cells at the S phase was not significantly decreased in Ags and NCI-N87 cells (CCNE1-amplified, dysfunctional p16 protein levels) after treatment with CDK2 siRNA as compared to control (FIG. 12B).

Figure 13:
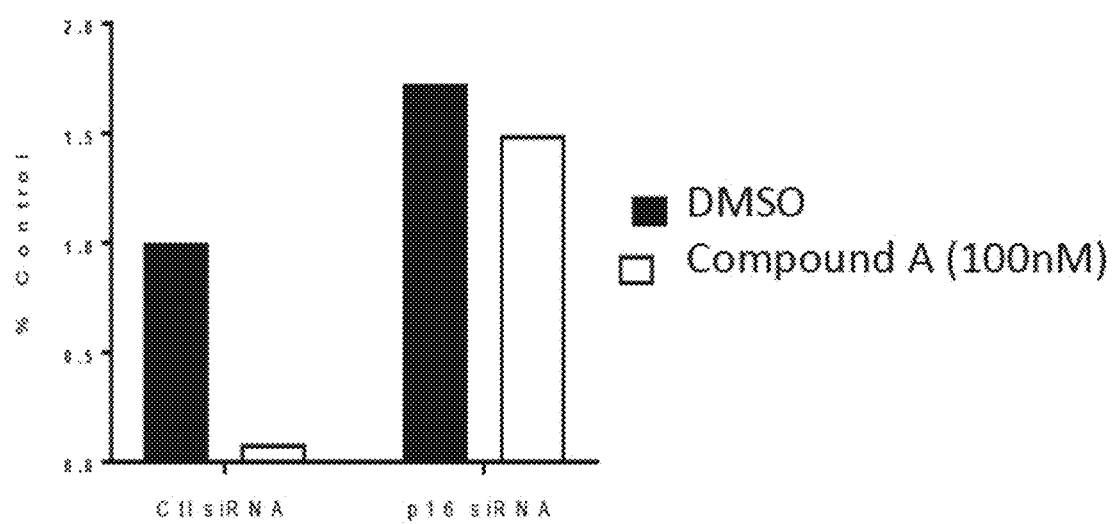
FIG. 13: p16 knockdown by siRNA abolishes CDK2 inhibition induced cell cycle suppression in CCNE1 amplified cells. The percentage of S phase cells following p16 knockdown and CDK2 inhibitor treatment, normalized to cell with Ctl siRNA and DMSO treatment. CCNE1 amplified COV318 cells were transfected with either Ctl siRNAs or p16 siRNA. 72 hours after transfection, cells were treated with 100 nM CDK2 inhibitor Compound A. Cells were harvested and subjected to cell cycle analysis 16 hours after treatment.

Example B10. p16 Knockdown by siRNA Abolishes CDK2 Inhibition Induced Cell Cycle Suppression in CCNE1 Amplified Cells To confirm the role of p16 in CDK2-sensitivity of CCNE-amplified cells, COV318 cells were treated with control or p16-specific siRNA. Seventy-two hours after transfection, cells were treated with DMSO (control) or 100 nM of Compound A. Sixteen hours after treatment with DMSO or the CDK2-inhibitor, cells were harvested and subjected to cell cycle analysis by FACS. Consistent with the results described above, the percentage of S phase cells significantly decreased in the control siRNA-treated cells treated with CDK2-inhibitor (Compound A), but not with the DMSO control (FIG. 13). In contrast, the percentage of S phase cells was not significantly decreased after treatment with the CDK2-inhibitor (Compound A) in p16 knocked down cells as compared to DMSO control (FIG. 13).

Materials and Methods Used in Examples B1-B10

Cell Culture and Transfection

Human cyclin E1 (CCNE1) amplified ovarian cell lines OVCAR3, COV318, Fu-OV1, endometrial cell line KLE, gastric cell lines MKN1, AGS, NCIN87, and CCNE1 non-amplified ovarian cell lines COV504, OV56, Igrov1 were cultured in RPMI 1640 medium. The complete growth medium was supplemented with 10% FBS, 0.1 mM non-essential amino acids, 2 mM L-glutamine, 100 units/mL penicillin G and 100 µg/mL streptomycin in 37° C. humidified incubator and an atmosphere of 5% $CO_2$ in air. Fu-OV1 line was purchased from Leibniz-Institute DSMZ—German Collection of Microorganisms and Cell Cultures; MKN1 was purchased from Japanese Cancer Research Resources Bank; and the rest of cell lines were purchased from American Type Culture Collection. For transfection, cells were seeded into 6-well for 24 hours and transiently transfected by Lipofectamine 2000 Reagent (Thermo Fisher, 11668027). ON-TARGETplus Human CKD2 siRNAs (GE Healthcare Dharmacon, J-003236-11-0002 and J-003236-12-0002) and ON-TARGETplus Human CDKN2A/p16 siR-NAs (GE Healthcare Dharmacon, J-011007-08-0002) were used to knockdown the endogenous CDK2 and CDKN2A/p16. ON-TARGETplus Non-targeting Pool (GE Healthcare Dharmacon, D-001810-10-20) was used as a negative control.

Western Blot Analysis

Whole cell extracts were prepared using RIPA buffer (Thermo Scientific, 89900) with a Halt Protease and Phosphatase Inhibitor Cocktail (Thermo Scientific, 78440). Protein concentration was quantified with a BCA Protein Assay Kit (Thermo Scientific, 23225) and 40 g of protein lysates were loaded for SDS-PAGE using precast gradient gels (Bio-Rad, Hercules, No. 456-1094). Samples were diluted in 5× Laemmli buffer (300 mM Tris-HCl pH 6.8, 10% SDS (w/v), 5% 2-mercaptoethanol, 25% glycerol (v/v), 0.1% bromophenol blue w/v) and boiled for 5 minutes. 35 g of proteins were separated by 8-15% SDS-PAGE and transferred onto polyvinylidene fluoride (PVDF) membranes. Unspecific binding sites on the PVDF membranes were blocked with 5% non-fat milk in TBST (20 mM Tris-HCl, pH 7.6, 137 mM NaCl, 1% Tween-20). Membranes were hybridized with antibodies against anti-CDKN2A/p16 (Cell Signaling Technology, 92803S), anti-Cas9 (Cell Signaling Technology, 97982S), anti-HA (Cell Signaling Technology, 3724S), anti-Rb (Cell Signaling Technology, 9309S), anti-phospho-Rb (Ser780) (Cell Signaling Technology, 8180S), anti-CDK2 (Cell Signaling Technology, 2546S), anti-CCNE1 (Cell Signaling Technology, 20808S) and anti-GAPDH (Cell Signaling Technology, 8884S) for overnight at 4° C., followed by incubation with horseradish peroxidase (HRP)-conjugated secondary antibodies for 1 hour at room temperature. The membranes were then developed using Immobilon Western chemiluminescence HRP substrates (Millipore, WBKLS0500). Images were captured by Luminescence/Fluorescence Imaging System Odyssey CLx Imager (LI-COR).

Cell Cycle Analysis

Cells were seeded in six-well tissue culture plates and 24 hours later were treated with a titration of concentrations of Palbociclib or Compound A. After overnight treatment, cells exposed to 10 M EdU for 3 hours before detection of EdU-DNA by Click-iT AlexaFluor® 647 azide kit (Life Technology, C10424) following the manufacturer's instructions. Bulk DNA was stained with DAPI. Compound-treated and DMSO treated control cells were acquired with Cyto-Flex (Beckman Coulter) and were analyzed using the FlowJo software. For cell cycle analysis of cells with siRNA knockdown, 72 hours after siRNA transfection, cells exposed to 10 M EdU for 3 hours before detection of Click-iT Alexa Fluor® 647 azide kit.

Plasmids

LentiCas9 plasmid pRCCH-CMV-Cas9-2A (Cellecta, SVC9-PS) was used for Cas9 expression. sgRNA-CDK2 lentiviral construct, designed to target AAGCAGAGATCTCTCGGA (SEQ ID NO:8) of CDK2, was cloned into sgRNA expression vector pRSG-U6 and purchased from Cellecta (93661). For CDK2-FKBP12F36V-HA expression, a 1306 base pair DNA fragment encoding CDK2 and FKBP12F36V-2xHA tag at the C-terminus was synthesized and cloned into EcoRI and BamHI digested pCDH-EF1α-MCS-T2A-Puro lentivector (Systembio, CD527A-1).

```
Sequence of 1306 bp DNA fragment:
                                          (SEQ ID NO: 4)
CCTCGAATTCAGCTGCATGGAGAACTTCCAAAAGGTGGAAAAGATCGGAG

AGGGCACGTACGGAGTTGTGTACAAAGCCAGAAACAAGTTGACGGGAGA

GGTGGTGGCGCTTAAGAAAATCCGCCTGGACACTGAGACTGAGGGTGTG

CCCAGTACTGCCATCCGAGAGATCTCTCTGCTTAAGGAGCTTAACCATCC

TAATATTGTCAAGCTGCTGGATGTCATTCACACAGAAAATAAACTCTACC

TGGTTTTTGAATTTCTGCACCAAGATCTCAAGAAATTCATGGATGCCTCT

GCTCTCACTGGCATTCCTCTTCCCCTCATCAAGAGCTATCTGTTCCAGCT

GCTCCAGGGCCTAGCTTTCTGCCATTCTCATCGGGTCCTCCACCGAGACC

TTAAACCTCAGAATCTGCTTATTAACACAGAGGGGCCATCAAGCTAGCA

GACTTTGGACTAGCCAGAGCTTTTGGAGTACCTGTTCGTACTTACACCCA

TGAAGTGGTGACCCTGTGGTACCGAGCTCCTGAAATCCTCCTGGGCTGCA

AATATTATTCCACAGCTGTGGACATCTGGAGCCTGGGCTGCATCTTTGC

TGAGATGGTGACTCGCCGGGCCCTATTCCCTGGAGATTCTGAGATTGACC

AGCTCTTTCGGATCTTTCGGACTCTGGGGACCCCAGATGAGGTGGTGTGG

CCAGGAGTTACTTCTATGCCTGATTACAAGCCAAGTTTCCCCAAGTGGGC

CCGGCAAGATTTTAGTAAAGTTGTACCTCCCCTGGATGAAGATGGACGGA

GCTTGTTATCGCAAATGCTGCACTACGACCCTAACAAGCGGATTTCGGCC

AAGGCAGCCCTGGCTCACCCTTTCTTCCAGGATGTGACCAAGCCAGTAC

CCCATCTTCGACTCGGAGTGCAGGTGGAAACCATCTCCCCAGGAGACGGG

CGCACCTTCCCCAAGCGCGGCCAGACCTGCGTGGTGCACTACACCGGGAT

GCTTGAAGATGGAAAGAAAGTTGATTCCTCCCGGGACAGAAACAAGCCCT

TTAAGTTTATGCTAGGCAAGCAGGAGGTGATCCGAGGCTGGGAAGAAGGG

GTTGCCCAGATGAGTGTGGGTCAGAGAGCCAAACTGACTATATCTCCAGA

TTATGCCTATGGTGCCACTGGGCACCCAGGCATCATCCCACCACATGCCA

CTCTCGTCTTCGATGTGGAGCTTCTAAAACTGGAAGGATACCCTTACGAC

GTTCCTGATTACGCTTACCCTTACGACGTTCCTGATTACGCTGGATCCTA

ATTCGAAAGC
```

GAATTC (SEQ ID NO:5; EcoRI), GGATCC (SEQ ID NO:6; BamHI) and TTCGAA (SEQ ID NO:7; BstBI) restriction enzyme sites were underlined. Sequence encoding CDK2 is in bold and sequence of FKBP12F36V-HA is in italics. Three nucleic acids underlined within the CDK2 sequence indicated modifications that abolished PAM sites to avoided CRISPR knockout effect. These changes did not change amino acids encoded.

Lentivirus Production

Production of lentivirus was performed in 293T cells by co-transfection of Lentiviral Packaging Mix (Sigma, SHP001), and a given lentiviral expression plasmid using Lipofectamine 2000. Viral supernatants were collected 48 and 72 hours after transfection, filtered through a 0.22 μm membrane. All cells lines were transduced by spinoculation at 2000 revolutions per minute (rpm) for 1 hour at room temperature with 8 μg/mL polybrene (Santa Cruz, sc-134220).

CDK2-dTAG Cells

OVCAR3 cells were first engineered to express Cas9 by lentiviral transduction of Cas9 construct. Cells were selected and maintained in 100 μg/mL hygromycin (Life Technologies, 10687010) and verified to express Cas9 by immunoblot. OVCAR3-Cas9 cells were then engineered to express CDK2-FKBP12F36V-HA fusion protein by lentiviral transduction of CDK2-FKBP12F36V-HA expression construct and selection with 2 μg/mL puromycin dihydrochloride (Life Technologies, A1113803). Expression of CDK2-FKBP12F36V-HA was verified by immunoblot using anti-CDK2 and anti-HA antibodies. Next, to engineer the line to have endogenous CDK2 inactivated, OVCAR3 (Cas9, CDK2-FKBP12F36V-HA) cells were transduced with CDK2 sgRNA and selected by 50 μg/mL Zeocin (Life Technologies, R25001). Inactivated expression of endogenous CDK2 in the expanded clones was tested by immunoblotting. OVCAR3 (Cas9, CDK2-FKBP12F36V-HA) cells transduced with non-targeting sgRNA (Cellecta) were served as a control cell line.

To degrade CDK2-FKBP12F36V-HA protein by dTAG, 200,000 cells were seeded in 1 mL media in triplicate in a 24-well plate and treated with dimethyl sulfoxide (DMSO) or with a titration of concentrations of dTAG for 14 hours. Cells were collected and processed for Western blot.

CDK2 CCNE1 Enzymatic Assay

In vitro CDK2/CCNE1 enzyme activity assay measures phosphorylation of a peptide substrate using homogeneous time-resolved energy transfer (HTRF). The LANCE® Ultra kinase assay used a ULight™-labeled EIF4E-binding protein 1 (Thr37/46) peptide (PerkinElmer, TRF0128-M) as substrate and an Europium-labeled anti-phospho-EIF4E binding protein1 (Thr37/46) antibody (PerkinElmer, TRF0216-M). A ratio of fluorescence transferred to the labeled substrate (665 nm) relative to fluorescence of the Europium donor (620 nm) represents the extent of phosphorylation. Ratios for treated wells are normalized to DMSO only (100% activity) and no enzyme (0% activity) controls. Normalized data is analyzed using a four parameter dose response curve to determine $IC_{50}$ for each compound.

CDK2 pRb (S780) HTRF Cellular Assay

CDK2 pRb (S780) HTRF cellular assay enables the quantitative detection of Rb phosphorylated on serine 780 in CCNE1 amplified COV318 cells. The assay comprised two antibodies: Europium cryptate labeled anti-Phospho-Rb S780 antibody (donor) and d2 labeled anti-Rb antibody (acceptor). In brief, COV318 cells were seeded into the wells of 96-well plate at a density of 25,000 per well with 9-point, 3-fold serial diluted compounds and cultured overnight at 37 degree with 5% $CO_2$. The final concentrations of compounds start from 3 μM. The next day cells were lysed in 70 μL 1× Phospho-total protein lysis buffer #2 (Cisbio), supplemented with 0.7 μL blocking buffer (Cisbio) and 1.4 μL protease inhibitor cocktail set III, EDTA-free (Calbiochem, 539134). 16 μL of cell lysates were mixed with 4 μL of the fluorophore-conjugated antibodies to a final concentration of 0.188 nM cryptate-labeled anti-Phospho-Rb S780 antibody and 0.14 nM d2 labeled anti-Rb antibody. After 2 h of incubation at room temperature, HTRF signals were measured on the PHERAstar microplate reader (BMG Labtech), using 340 nm as excitation wavelength, a 620 nm filter for the Europium donor fluorescence, and a 665-nm filter for the acceptor fluorescence detection. HTRF signals were calculated as the HTRF ratio (ratio of fluorescence measured at 665 nm and 620 nm)×10000.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

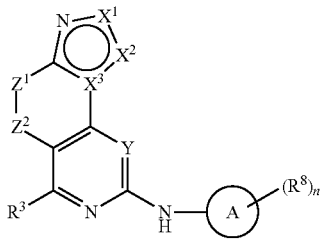
(I)

or a pharmaceutically acceptable salt thereof, wherein:

n is 0, 1, 2, 3, 4, 5, or 6;

$Z^1$ is $CR^4R^5$; and $Z^2$ is $NR^{6z}$, O, or S; or $Z^1$ is $CR^4R^5$, $NR^6$, O, or S; and $Z^2$ is $CR^{4z}R^{5z}$;

Y is $CR^7$ or N;

$X^1$ is $NR^{1x}$, $CR^1$, N, or O;

$X^2$ is $NR^{2x}$, $CR^2$, N, or O;

$X^3$ is N or C;

wherein Ring

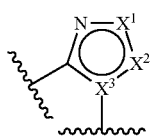

is an aromatic ring selected from:

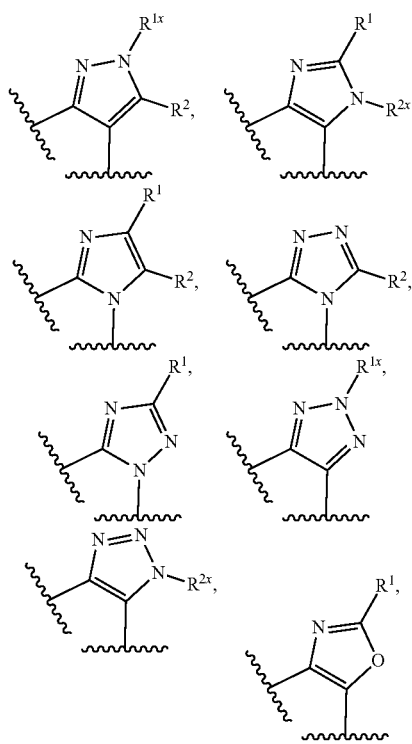

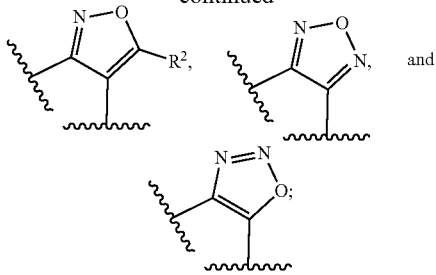

Ring moiety A is selected from (1) $C_{3-14}$ cycloalkyl, wherein 1, 2, 3, or 4 ring-forming carbon atoms of said $C_{3-14}$ cycloalkyl can be optionally substituted by one or more oxo or sulfido, and (2) 4-14 membered heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido; wherein Ring moiety A is attached to the —NH— group of Formula (I) at a ring member of a saturated or partially saturated ring of said $C_{3-14}$ cycloalkyl or said 4-14 membered heterocycloalkyl;

$R^1$ is selected from H, D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a1}$, $SR^{a1}$, $NHOR^{a1}$, $C(O)R^{b1}$, $C(O)NR^{c1}R^{d1}$, $C(O)NR^{c1}(OR^{a1})$, $C(O)OR^{a1}$, $OC(O)R^{b1}$, $OC(O)NR^{c1}R^{d1}$, $NR^{c1}R^{d1}$, $NR^{c1}NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}C(=NR^{e1})R^{b1}$, $NR^{c1}S(O)NR^{c1}R^{d1}$, $NR^{c1}S(O)R^{b1}$, $NR^{c1}S(O)_2R^{b1}$, $NR^{c1}S(O)(=NR^{e1})R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $OS(O)(=NR^{e1})R^{b1}$, $OS(O)_2R^{b1}$, $S(O)(=NR^{e1})R^{b1}$, $SF_5$, $P(O)R^{f1}R^{g1}$, $OP(O)(OR^{h1})(OR^{i1})$, $P(O)(OR^{h1})(OR^{i1})$, and $BR^{j1}R^{k1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{14}$ substituents;

$R^{1x}$ is selected from H, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $C(O)R^{b1}$, $C(O)NR^{c1}R^{d1}$, $C(O)NR^{c1}(OR^{a1})$, $C(O)OR^{a1}$, $C(=NR^{e1})R^{b1}$, $C(=NR^{e1})NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{1A}$ substituents;

$R^2$ is selected from H, D, halo, $NO_2$, CN, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a2}$, $SR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $OC(O)R^{b2}$, $OC(O)NR^{c2}R^{d2}$, $NR^{c2}R^{d2}$, $NR^{c2}NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}C(=NR^{e2})R^{b2}$, $NR^{c2}S(O)NR^{c2}R^{d2}$, $NR^{c2}S(O)R^{b2}$, $NR^{c2}S(O)_2R^{b2}$, $NR^{c2}S(O)(=NR^{e2})R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$, $OS(O)(=NR^{e2})R^{b2}$, $OS(O)_2R^{b2}$, $S(O)(=NR^{e2})R^{b2}$, $SF_5$, $P(O)R^{f2}R^{g2}$, $OP(O)(OR^{h2})(OR^{i2})$, $P(O)(OR^{h2})(OR^{i2})$, and $BR^{j2}R^{k2}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{2A}$ substituents;

$R^{2x}$ is selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $C(O)R^{b2}$, $C(O)NR^{c2}R^{d2}$, $C(O)NR^{c2}(OR^{a2})$, $C(O)OR^{a2}$, $C(=NR^{e2})R^{b2}$, $C(=NR^{e2})NR^{c2}R^{d2}$, $S(O)_2R^{b2}$, and $S(O)_2NR^{c2}R^{d2}$; wherein said $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{2A}$ substituents;

$R^3$ is selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, and $C_{3-4}$ cycloalkyl;

$R^4$, $R^{4z}$, $R^5$ and $R^{5z}$ are independently selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-3}$ alkyl, HO—$C_{1-3}$ alkyl, $C_{1-3}$ alkoxy-$C_{1-3}$ alkyl, and $C_{3-4}$ cycloalkyl;

or $R^4$ and $R^5$, together with the carbon atom to which they are attached, form a 3-7 membered cycloalkyl ring or a 4-7 membered heterocycloalkyl ring, which are each optionally substituted by 1, 2, 3, or 4 substituents independently selected from D, halo, CN, $C_{1-3}$ alkyl, $C_{1-3}$ haloalkyl, OH, $C_{1-3}$ alkoxy, $C_{1-3}$ haloalkoxy, amino, $C_{1-3}$ alkylamino, di($C_{1-3}$ alkyl) amino, cyano-$C_{1-3}$ alkyl, HO—$C_{1-3}$ alkyl, and $C_{1-3}$ alkoxy-$C_{1-3}$ alkyl;

or $R^{4z}$ and $R^{5z}$, together with the carbon atom to which they are attached, form a 3-7 membered cycloalkyl ring or a 4-7 membered heterocycloalkyl ring, which are each optionally substituted by 1, 2, 3, or 4 substituents independently selected from D, halo, CN, $C_{1-3}$ alkyl, $C_{1-3}$ haloalkyl, OH, $C_{1-3}$ alkoxy, $C_{1-3}$ haloalkoxy, amino, $C_{1-3}$ alkylamino, di($C_{1-3}$ alkyl) amino, cyano-$C_{1-3}$ alkyl, HO—$C_{1-3}$ alkyl, and $C_{1-3}$ alkoxy-$C_{1-3}$ alkyl;

$R^6$ and $R^{6z}$ are each independently selected from H, $C_{1-4}$ alkyl, $C_{1-4}$ haloalkyl, $C_{2-4}$ alkenyl, $C_{2-4}$ alkynyl, cyano-$C_{1-3}$ alkyl, HO—$C_{1-3}$ alkyl, $C_{1-3}$ alkoxy-$C_{1-3}$ alkyl, and $C_{3-4}$ cycloalkyl;

$R^7$ is selected from H, D, halo, CN, $C_{1-4}$ alkyl, $C_{1-4}$ haloalkyl, $C_{2-4}$ alkenyl, $C_{2-4}$ alkynyl, OH, $C_{1-3}$ alkoxy, $C_{1-3}$ haloalkoxy, amino, $C_{1-3}$ alkylamino, di($C_{1-3}$ alkyl)amino, cyano-$C_{1-3}$ alkyl, HO—$C_{1-3}$ alkyl, $C_{1-3}$ alkoxy-$C_{1-3}$ alkyl, and $C_{3-4}$ cycloalkyl;

each $R^8$ is selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a8}$, $SR^{a8}$, $NHOR^{a8}$, $C(O)R^{b8}$, $C(O)NR^{c8}R^{d8}$, $C(O)NR^{c8}(OR^{a8})$, $C(O)OR^{a8}$, $OC(O)R^{b8}$, $OC(O)NR^{c8}R^{d8}$, $NR^{c8}R^{d8}$, $NR^{c8}NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NR^{e8})NR^{c8}R^{d8}$, $NR^{c8}C(=NR^{e8})NR^{c8}R^{d8}$, $NR^{c8}C(=NR^{e8})R^{b8}$, $NR^{c8}S(O)NR^{c8}R^{d8}$, $NR^{c8}S(O)R^{b8}$, $NR^{c8}S(O)_2R^{b8}$, $NR^{c8}S(O)(=NR^{e8})R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$, $OS(O)(=NR^{e8})R^{b8}$, $OS(O)_2R^{b8}$, $S(O)(=NR^{e8})R^{b8}$, $SF_5$, $P(O)R^{f8}R^{g8}$, $OP(O)(OR^{h8})(OR^{i8})$, $P(O)(OR^{h8})(OR^{i8})$, and $BR^{j8}R^{k8}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{8A}$ substituents;

each $R^{1A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a11}$, $SR^{a11}$, $NHOR^{a11}$, $C(O)R^{b11}$, $C(O)NR^{c11}R^{d11}$, $C(O)NR^{c11}(OR^{a11})$, $C(O)OR^{a11}$, $OC(O)R^{b11}$, $OC(O)NR^{c11}R^{d11}$, $NR^{c11}R^{d11}$, $NR^{c11}NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NR^{e11})NR^{c11}R^{d11}$, $NR^{c11}C(=NR^{e11})NR^{c11}R^{d11}$, $NR^{c11}C(=NR^{e11})R^{b11}$, $NR^{c11}S(O)NR^{c11}R^{d11}$, $NR^{c11}S(O)R^{b11}$, $NR^{c11}S(O)_2R^{b11}$, $NR^{c11}S(O)(=NR^{e11})R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$, $OS(O)(=NR^{e11})R^{b11}$, $OS(O)_2R^{b11}$, $S(O)(=NR^{e11})R^{b11}$, $SF_5$, $P(O)R^{f11}R^{g11}$, $OP(O)(OR^{h11})(OR^{i11})$, $P(O)(OR^{h11})(OR^{i11})$ and $BR^{j11}R^{k11}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{1B}$ substituents;

each $R^{1B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a12}$, $SR^{a12}$, $NHOR^{a12}$, $C(O)R^{b12}$, $C(O)NR^{c12}R^{d12}$, $C(O)NR^{c12}(OR^{a12})$, $C(O)OR^{a12}$, $OC(O)R^{b12}$, $OC(O)NR^{c12}R^{d12}$, $NR^{c12}R^{d12}$, $NR^{c12}NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NR^{e12})NR^{c12}R^{d12}$, $NR^{c12}C(=NR^{e12})NR^{c12}R^{d12}$, $NR^{c12}C(=NR^{e12})R^{b12}$, $NR^{c12}S(O)NR^{c12}R^{d12}$, $NR^{c12}S(O)R^{b12}$, $NR^{c12}S(O)_2R^{b12}$, $NR^{c12}S(O)(=NR^{e12})R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$, $OS(O)(=NR^{e12})R^{b12}$, $OS(O)_2R^{b12}$, $S(O)(=NR^{e12})R^{b12}$, $SF_5$, $P(O)R^{f12}R^{g12}$, $OP(O)(OR^{h12})(OR^{i12})$, $P(O)(OR^{h12})(OR^{i12})$, and $BR^{j12}R^{k12}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{2A}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})$ $NR^{c21}R^{d21}$, $NR^{c21}C(=NR^{e21})R^{b21}$, $NR^{c21}S(O)NR^{c21}R^{d21}$, $NR^{c21}S(O)R^{b21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, $OS(O)_2R^{b21}$, $S(O)(=NR^{e21})R^{b21}$, $SF_5$, $P(O)R^{f21}R^{g21}$, $OP(O)(OR^{h21})(OR^{i21})$, $P(O)(OR^{h21})(OR^{i21})$, and $BR^{j21}R^{k21}$, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2B}$ substituents;

each $R^{2B}$ is independently selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)NR^{c22}R^{d22}$, $NR^{c22}S(O)R^{b22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, $OS(O)(=NR^{e22})R^{b22}$, $OS(O)_2R^{b22}$, $S(O)(=NR^{e22})R^{b22}$, $SF_5$, $P(O)R^{f22}R^{g22}$, $OP(O)(OR^{h22})(OR^{i22})$, $P(O)(OR^{h22})(OR^{i22})$, and $BR^{j22}R^{k22}$, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

each $R^{8A}$ is selected from D, halo, CN, $NO_2$, $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, 5-10 membered heteroaryl-$C_{1-4}$ alkyl, $OR^{a81}$, $SR^{a81}$, $NHOR^{a81}$, $C(O)R^{b81}$, $C(O)NR^{c81}R^{d81}$, $C(O)NR^{c81}(OR^{a81})$, $C(O)OR^{a81}$, $OC(O)R^{b81}$, $OC(O)NR^{c81}R^{d81}$, $NR^{c81}R^{d81}$, $NR^{c81}NR^{c81}R^{d81}$, $NR^{c81}C(O)R^{b81}$, $NR^{c81}C(O)OR^{a81}$, $NR^{c81}C(O)NR^{c81}R^{d81}$, $C(=NR^{e81})R^{b81}$, $C(=NR^{e81})NR^{c81}R^{d81}$, $NR^{c81}C(=NR^{e81})NR^{c81}R^{d81}$, $NR^{c81}C(=NR^{e81})R^{b81}$, $NR^{c81}S(O)NR^{c81}R^{d81}$, $NR^{c81}S(O)R^{b81}$, $NR^{c81}S(O)_2R^{b81}$, $NR^{c81}S(O)(=NR^{e81})R^{b81}$, $NR^{c81}S(O)_2NR^{c81}R^{d81}$, $S(O)R^{b81}$, $S(O)NR^{c81}R^{d81}$, $S(O)_2R^{b81}$, $S(O)_2NR^{c81}R^{d81}$, $OS(O)(=NR^{e81})R^{b81}$, $OS(O)_2R^{b81}$, $S(O)(=NR^{e81})R^{b81}$, $SF_5$, $P(O)R^{f81}R^{g81}$, $OP(O)(OR^{h81})(OR^{i81})$, $P(O)(OR^{h81})(OR^{i81})$, and $BR^{j81}R^{k81}$; wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted by 1, 2, 3, or 4 independently selected $R^{8B}$ substituents;

each $R^{8B}$ is selected from D, halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a82}$, $SR^{a82}$, $NHOR^{a82}$, $C(O)R^{b82}$, $C(O)NR^{c82}R^{d82}$, $C(O)NR^{c82}(OR^{a82})$, $C(O)OR^{a82}$, $OC(O)R^{b82}$, $OC(O)NR^{c82}R^{d82}$, $NR^{c82}R^{d82}$, $NR^{c82}NR^{c82}R^{d82}$, $NR^{c82}C(O)R^{b82}$, $NR^{c82}C(O)OR^{a82}$, $NR^{c82}C(O)NR^{c82}R^{d82}$, $C(=NR^{e82})R^{b82}$, $C(=NR^{e82})NR^{c82}R^{d82}$, $NR^{c82}C(=NR^{e82})NR^{c82}R^{d82}$, $NR^{c82}C(=NR^{e82})R^{b82}$, $NR^{c82}S(O)NR^{c82}R^{d82}$, $NR^{c82}S(O)R^{b82}$, $NR^{c82}S(O)_2R^{b82}$, $NR^{c82}S(O)(=NR^{e82})R^{b82}$, $NR^{c82}S(O)_2NR^{c82}R^{d82}$, $S(O)R^{b82}$, $S(O)NR^{c82}R^{d82}$, $S(O)_2R^{b82}$, $S(O)_2NR^{c82}R^{d82}$, $OS(O)(=NR^{e82})R^{b82}$, $OS(O)_2R^{b82}$, $S(O)(=NR^{e82})R^{b82}$, $SF_5$, $P(O)R^{f82}R^{g82}$, $OP(O)(OR^{h82})(OR^{i82})$, $P(O)(OR^{h82})(OR^{i82})$, and $BR^{j82}R^{k82}$; wherein said $C_{1-6}$ alkyl, $C_{2-6}$ alkenyl, C$_{2-6}$ alkynyl, C$_{1-6}$ haloalkyl, C$_{3-7}$ cycloalkyl, phenyl, 4-7 membered heterocycloalkyl, 5-6 membered heteroaryl, C$_{3-7}$ cycloalkyl-C$_{1-4}$ alkyl, phenyl-C$_{1-4}$ alkyl, 4-7 membered heterocycloalkyl-C$_{1-4}$ alkyl, and 5-6 membered heteroaryl-C$_{1-4}$ alkyl are each optionally substituted by 1, 2, 3, or 4 independently selected R$^G$ substituents;

each R$^{a1}$, R$^{c1}$, and R$^{d1}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{1A}$ substituents;

or, any R$^{c1}$ and R$^{d1}$ attached to the same N atom, together with the N atom to which they are attached, form a 4-10 membered heterocycloalkyl group, which is optionally substituted with 1, 2, 3, or 4 independently selected R$^{1A}$ substituents;

each R$^{b1}$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, which are each optionally substituted with 1, 2, 3, or 4 independently selected R$^{1A}$ substituents;

each R$^{e1}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{f1}$ and R$^{g1}$ are independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{h1}$ and R$^{i1}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{j1}$ and R$^{k1}$ is independently selected from OH, C$_{1-6}$ alkoxy, and C$_{1-6}$ haloalkoxy;

or any R$^{j1}$ and R$^{k1}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{a11}$, R$^{c11}$, and R$^{d11}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, wherein said C$_{1-6}$ alkyl, C$_{2-6}$ alkenyl, C$_{2-6}$ alkynyl, C$_{1-6}$ haloalkyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl are each optionally substituted with 1, 2, 3, or 4 independently selected R$^{1B}$ substituents;

or, any R$^{c11}$ and R$^{d11}$ attached to the same N atom, together with the N atom to which they are attached, form a 4-7 membered heterocycloalkyl group, which is optionally substituted with 1, 2, 3, or 4 independently selected R$^{1B}$ substituents;

each R$^{b11}$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl, which are each optionally substituted with 1, 2, 3, or 4 independently selected R$^{1B}$ substituents;

each R$^{e11}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{f11}$ and R$^{g11}$ are independently selected from H, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{h11}$ and R$^{i11}$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, 6-10 membered aryl, 4-10 membered heterocycloalkyl, 5-10 membered heteroaryl, C$_{3-10}$ cycloalkyl-C$_{1-4}$ alkyl, 6-10 membered aryl-C$_{1-4}$ alkyl, 4-10 membered heterocycloalkyl-C$_{1-4}$ alkyl, and 5-10 membered heteroaryl-C$_{1-4}$ alkyl;

each R$^{j11}$ and R$^{k11}$ is independently selected from OH, C$_{1-6}$ alkoxy, and C$_{1-6}$ haloalkoxy;

or any R$^{j11}$ and R$^{k11}$ attached to the same B atom, together with the B atom to which they are attached, form a 5- or 6-membered heterocycloalkyl group optionally substituted with 1, 2, 3, or 4 substituents independently selected from C$_{1-6}$ alkyl and C$_{1-6}$ haloalkyl;

each R$^{a12}$, R$^{c12}$, and R$^{d12}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c12}$ and $R^{d12}$ attached to the same N atom, together with the N atom to which they are attached, form a 4-7 membered heterocycloalkyl group, which is optionally substituted with 1, 2, 3, or 4 independently selected $R^G$ substituents;

each $R^{b12}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e12}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f12}$ and $R^{g12}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h12}$ and $R^{i12}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j12}$ and $R^{k12}$ is independently selected from OH, $C_{1-6}$ alkoxy, and $C_{1-6}$ haloalkoxy;

or any $R^{j12}$ and $R^{k12}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2A}$ substituents;

or, any $R^{c2}$ and $R^{d2}$ attached to the same N atom, together with the N atom to which they are attached, form a 4-10 membered heterocycloalkyl group, which is optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2A}$ substituents;

each $R^{e2}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f2}$ and $R^{g2}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h2}$ and $R^{i2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j2}$ and $R^{k2}$ is independently selected from OH, $C_{1-6}$ alkoxy, and $C_{1-6}$ haloalkoxy;

or any $R^{j2}$ and $R^{k2}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{2B}$ substituents;

or, any $R^{c21}$ and $R^{d21}$ attached to the same N atom, together with the N atom to which they are attached, form a 4-7 membered heterocycloalkyl group, which is optionally substituted with 1, 2, 3, or 4 independently selected $R^{2B}$ substituents;

each $R^{b21}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f21}$ and $R^{g21}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h21}$ and $R^{i21}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j21}$ and $R^{k21}$ is independently selected from OH, $C_{1-6}$ alkoxy, and $C_{1-6}$ haloalkoxy;

or any $R^{j21}$ and $R^{k21}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c22}$ and $R^{d22}$ attached to the same N atom, together with the N atom to which they are attached, form a 4-7 membered heterocycloalkyl group, which is optionally substituted with 1, 2, 3, or 4 independently selected $R^G$ substituents;

each $R^{b22}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f22}$ and $R^{g22}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h22}$ and $R^{i22}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j22}$ and $R^{k22}$ is independently selected from OH, $C_{1-6}$ alkoxy, and $C_{1-6}$ haloalkoxy;

or any $R^{j22}$ and $R^{k22}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a8}$, $R^{c8}$, and $R^{d8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{8A}$ substituents;

or, any $R^{c8}$ and $R^{d8}$ attached to the same N atom, together with the N atom to which they are attached, form a 4-10 membered heterocycloalkyl group, which is optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{8A}$ substituents;

each $R^{e8}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f8}$ and $R^{g8}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h8}$ and $R^{i8}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j8}$ and $R^{k8}$ is independently selected from OH, $C_{1-6}$ alkoxy, and $C_{1-6}$ haloalkoxy;

or any $R^{j8}$ and $R^{k8}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a81}$, $R^{c81}$, and $R^{d81}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl are each optionally substituted with 1, 2, 3, or 4 independently selected $R^{8B}$ substituents;

or, any $R^{c81}$ and $R^{d81}$ attached to the same N atom, together with the N atom to which they are attached, form a 4-7 membered heterocycloalkyl group, which is optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl, which are each optionally substituted with 1, 2, 3, or 4 independently selected $R^{8B}$ substituents;

each $R^{e81}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{f81}$ and $R^{g81}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{h81}$ and $R^{i81}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, 6-10 membered aryl, 4-10 membered heterocycloalkyl, 5-10 membered heteroaryl, $C_{3-10}$ cycloalkyl-$C_{1-4}$ alkyl, 6-10 membered aryl-$C_{1-4}$ alkyl, 4-10 membered heterocycloalkyl-$C_{1-4}$ alkyl, and 5-10 membered heteroaryl-$C_{1-4}$ alkyl;

each $R^{j81}$ and $R^{k81}$ is independently selected from OH, $C_{1-6}$ alkoxy, and $C_{1-6}$ haloalkoxy;

or any $R^{j81}$ and $R^{k81}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^{a82}$, $R^{c82}$, and $R^{d82}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^G$ substituents;

or, any $R^{c82}$ and $R^{d82}$ attached to the same N atom, together with the N atom to which they are attached, form a 4-7 membered heterocycloalkyl group, which is optionally substituted with 1, 2, 3, or 4 independently selected $R^G$ substituents;

each $R^{b82}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^G$ substituents;

each $R^{e82}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{f82}$ and $R^{g82}$ are independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{h82}$ and $R^{i82}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl;

each $R^{j82}$ and $R^{k82}$ is independently selected from OH, $C_{1-6}$ alkoxy, and $C_{1-6}$ haloalkoxy;

or any $R^{j82}$ and $R^{k82}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^G$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl) amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonyloxy, $C_{1-3}$ alkylcarbonylamino, $C_{1-3}$ alkoxycarbonylamino, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino wherein "cycloalkyl" refers to a non-aromatic monocyclic or bicyclic hydrocarbon, including cyclized alkyl and alkenyl groups, which may be fused, spirocyclic, or bridged, which may contain one or more fused aromatic rings, wherein the ring-forming carbon atoms of a cycloalkyl group can be optionally substituted by oxo or sulfido (C(O) or C(S));

wherein "heterocycloalkyl" refers to monocyclic or bicyclic heterocycle, having at least one non-aromatic ring (saturated or partially unsaturated ring), which may contain a fused aromatic ring, wherein the ring-forming carbon atoms and heteroatoms of the heterocycloalkyl group can be optionally substituted by one or more oxo or sulfido (C(O), S(O), C(S), or S(O)$_2$, and wherein 1, 2, 3, or 4 of the ring-forming atoms are independently selected from N, O, S, and B; and wherein "heteroaryl" refers to a monocyclic or bicyclic aromatic heterocycle, wherein 1, 2, 3, or 4 of the ring-forming atoms are independently selected from N, O, S, and B, and wherein any ring-forming N in a heteroaryl moiety can be an N-oxide.

2. The compound of claim 1, or a pharmaceutically acceptable salt thereof, wherein Ring

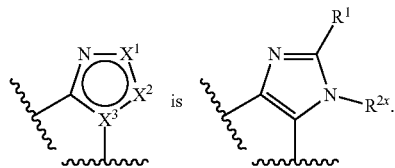

3. The compound of claim 2, or a pharmaceutically acceptable salt thereof, wherein $R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{1A}$ substituents.

4. The compound of claim 2, or a pharmaceutically acceptable salt thereof, wherein $R^1$ is selected from H, halo, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents.

5. The compound of claim 2, or a pharmaceutically acceptable salt thereof, wherein $R^1$ is selected from H, halo, $C_{1-6}$ alkyl, phenyl, and 5-6 membered heteroaryl, wherein said $C_{1-6}$ alkyl, phenyl and 5-6 membered heteroaryl are each optionally substituted by 1 or 2 independently selected $R^{1A}$ substituents.

6. The compound of claim 2, or a pharmaceutically acceptable salt thereof, wherein $R^{2x}$ is selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl, wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents.

7. The compound of claim 2, or a pharmaceutically acceptable salt thereof, wherein $R^{2x}$ is selected from H, $C_{1-6}$ alkyl, $C_{3-7}$ cycloalkyl, and phenyl-$C_{1-3}$ alkyl.

8. The compound of claim 1, or a pharmaceutically acceptable salt thereof, wherein Ring

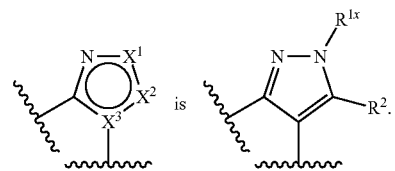

9. The compound of claim 8, or a pharmaceutically acceptable salt thereof, wherein $R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents.

10. The compound of claim 8, or a pharmaceutically acceptable salt thereof, wherein $R^{1x}$ is selected from H, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{1A}$ substituents.

11. The compound of claim 8, or a pharmaceutically acceptable salt thereof, wherein $R^{1x}$ is selected from H, $C_{1-6}$ alkyl, $C_{3-7}$ cycloalkyl, phenyl, and 4-7 membered heterocycloalkyl, wherein said $C_{1-6}$ alkyl, $C_{3-7}$ cycloalkyl, phenyl, and 4-7 membered heterocycloalkyl are each optionally substituted by 1 or 2 independently selected $R^{14}$ substituents.

12. The compound of claim 8, or a pharmaceutically acceptable salt thereof, wherein $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2A}$ substituents.

13. The compound of claim 8, or a pharmaceutically acceptable salt thereof, wherein $R^2$ is selected from H, halo, CN, $C_{1-6}$ alkyl, $C_{1-6}$ haloalkyl, $C_{3-7}$ cycloalkyl, phenyl, 4-7 membered heterocycloalkyl, and 5-6 membered heteroaryl; wherein said $C_{1-6}$ alkyl, $C_{1-6}$ haloalkyl, $C_{3-7}$ cycloalkyl, phenyl, 4-7 membered heterocycloalkyl, and 5-6 membered heteroaryl are each optionally substituted by 1, 2, or 3 independently selected $R^{2A}$ substituents.

14. The compound of claim 8, or a pharmaceutically acceptable salt thereof, wherein $R^2$ is selected from H, $C_{1-6}$ alkyl, and $C_{3-7}$ cycloalkyl.

15. The compound of claim 1, or a pharmaceutically acceptable salt thereof, wherein $R^3$ is H.

16. The compound of claim 1, or a pharmaceutically acceptable salt thereof, wherein Y is N.

17. The compound of claim 1, or a pharmaceutically acceptable salt thereof, wherein $Z^1$ is $CR^4R^5$; and $Z^2$ is $CR^{4z}R^{5z}$ or O.

18. The compound of claim 1, or a pharmaceutically acceptable salt thereof, wherein $R^4$, $R^{4z}$, $R^5$ and $R^{5z}$ are each independently selected from H and $C_{1-3}$ alkyl.

19. The compound of claim 1, or a pharmaceutically acceptable salt thereof, wherein Ring moiety A is piperidin-4-yl.

20. The compound of claim 1, or a pharmaceutically acceptable salt thereof, wherein n is 1 or 2.

21. The compound of claim 1, or a pharmaceutically acceptable salt thereof, wherein one $R^8$ is halo or $C_{1-6}$ alkyl and one $R^8$ is $S(O)_2R^{b8}$, wherein $R^{b8}$ is selected from $C_{1-6}$ alkyl, $C_{1-6}$ haloalkyl, $C_{3-7}$ cycloalkyl, phenyl, 4-7 membered heterocycloalkyl, and 5-6 membered heteroaryl, each of which is optionally substituted by 1, 2, 3, or 4 independently selected $R^{8A}$ substituents.

22. The compound of claim 1, or a pharmaceutically acceptable salt thereof, wherein:
n is 1, 2, 3, or 4;
$Z^1$ is $CR^4R^5$; and $Z^2$ is $NR^{6z}$, O, or S; or
$Z^1$ is $CR^4R^5$, $NR^6$, O, or S; and $Z^2$ is $CR^{4z}R^{5z}$;
Y is $CR^7$ or N;
$X^1$ is $NR^{1x}$ or $CR^1$;
$X^2$ is $NR^{2x}$ or $CR^2$;
$X^3$ is N or C;
wherein Ring

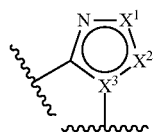

is an aromatic ring selected from:

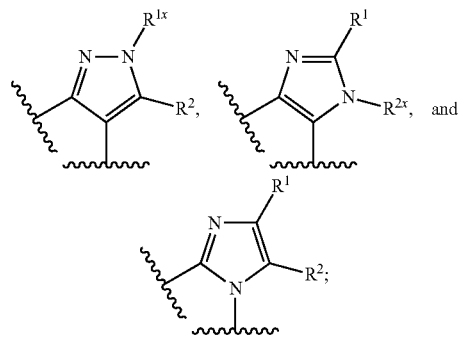

Ring moiety A is monocyclic or bicyclic 4-10 membered heterocycloalkyl having 1, 2, 3, or 4 ring-forming heteroatoms independently selected from N, O, and S, wherein 1, 2, 3, or 4 ring-forming carbon or heteroatoms can be optionally substituted by one or more oxo or sulfido, wherein said heterocycloalkyl does not comprise an aromatic ring;

$R^1$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$, and $S(O)_2NR^{c1}R^{d1}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{14}$ substituents;

$R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{14}$ substituents;

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{2A}$ substituents;

$R^{2x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

$R^3$ is selected from H, halo, CN, $C_{1-3}$ alkyl, and $C_{1-3}$ haloalkyl;

$R^4$, $R^{4z}$, $R^5$ and $R^{5z}$ are independently selected from H, halo, CN, $C_{1-3}$ alkyl, and $C_{1-3}$ haloalkyl;

or $R^4$ and $R^5$, together with the carbon atom to which they are attached, form a cyclopropyl or cyclobutyl ring;

or $R^{4z}$ and $R^{5z}$, together with the carbon atom to which they are attached, form a 3 cyclopropyl or cyclobutyl ring;

$R^7$ is selected from H, halo, CN, $C_{1-3}$ alkyl, and $C_{1-3}$ haloalkyl;

$R^8$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $NR^{c8}S(O)_2R^{b8}$, $NR^{c8}S(O)_2NR^{c8}R^{d8}$, $S(O)_2R^{b8}$, and $S(O)_2NR^{c8}R^{d8}$; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, 3, or 4 independently selected $R^{8A}$ substituents;

each $R^{a1}$, $R^{c1}$, and $R^{d1}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1A}$ substituents;

each $R^{b1}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1A}$ substituents;

each $R^{1A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $NR^{c11}S(O)_2R^{b11}$, $NR^{c11}S(O)_2NR^{c11}R^{d11}$, $S(O)_2R^{b11}$, and $S(O)_2NR^{c11}R^{d11}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{a11}$, $R^{c11}$, and $R^{d11}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{1B}$ substituents;

each $R^{b11}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{1B}$ substituents;

each $R^{1B}$ is independently selected from halo, CN, $NO_2$, $C_{1-6}$ alkyl, $C_{1-6}$ haloalkyl, $C_{3-4}$ cycloalkyl, 4-5 membered heterocycloalkyl, $OR^{a12}$, and $NR^{c12}R^{d12}$;

each $R^{a12}$, $R^{c12}$, and $R^{d12}$ is independently selected from H, $C_{1-6}$ alkyl, and $C_{1-6}$ haloalkyl;

each $R^{a2}$, $R^{c2}$, and $R^{d2}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2A}$ substituents;

each $R^{b2}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2A}$ substituents;

each $R^{2A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a21}$, $SR^{a21}$, $C(O)R^{b21}$, $C(O)NR^{c21}R^{d21}$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)$ $OR^{a21}$, $NR^{c21}C(O)NR^{c21}R^{d21}$, $NR^{c21}S(O)_2R^{b21}$, $NR^{c21}S(O)_2NR^{c21}R^{d21}$, $S(O)_2R^{b21}$, and $S(O)_2NR^{c21}R^{d21}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{2B}$ substituents;

each $R^{b21}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{2B}$ substituents;

each $R^{2B}$ is independently selected from halo, CN, $NO_2$, $C_{1-6}$ alkyl, $C_{1-6}$ haloalkyl, $C_{3-4}$ cycloalkyl, 4-5 membered heterocycloalkyl, $OR^{a22}$, and $NR^{c22}R^{d22}$;

each $R^{a22}$, $R^{c22}$, and $R^{d22}$ is independently selected from H, $C_{1-6}$ alkyl, and $C_{1-6}$ haloalkyl;

each $R^{a8}$, $R^{c8}$, and $R^{d8}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{14}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8A}$ substituents;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8A}$ substituents;

each $R^{8A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a81}$, $SR^{a81}$, $C(O)R^{b81}$, $C(O)NR^{c81}R^{d81}$, $C(O)OR^{a81}$, $OC(O)R^{b81}$, $OC(O)NR^{c81}R^{d81}$, $NR^{c81}C(O)OR^{a81}$, $NR^{c81}C(O)NR^{c81}R^{d81}$, $NR^{c81}S(O)_2R^{b81}$, $NR^{c81}S(O)_2NR^{c81}R^{d81}$, $S(O)_2R^{b81}$, and $S(O)_2NR^{c81}R^{d81}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{a81}$, $R^{c81}$, and $R^{d81}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8B}$ substituents;

each $R^{8B}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a82}$, $SR^{a82}$, $C(O)R^{b82}$, $C(O)NR^{c82}R^{d82}$, $C(O)OR^{a82}$, $OC(O)R^{b82}$, $OC(O)NR^{c82}R^{d82}$, $NR^{c82}R^{d82}$, $NR^{c82}C(O)R^{b82}$, $NR^{c82}C(O)OR^{a82}$, $NR^{c82}C(O)NR^{c82}R^{d82}$, $NR^{c82}S(O)_2R^{b82}$, $NR^{c82}S(O)_2NR^{c82}R^{d82}$, $S(O)_2R^{b82}$, and $S(O)_2NR^{c82}R^{d82}$;

each $R^{a82}$, $R^{c82}$, and $R^{d82}$ is independently selected from H, $C_{1-6}$ alkyl, and $C_{1-6}$ haloalkyl; and each $R^{b82}$ is independently selected from $C_{1-6}$ alkyl and $C_{1-6}$ haloalkyl.

23. The compound of claim 1, or a pharmaceutically acceptable salt thereof, wherein:

n is 1 or 2;

$Z^1$ is $CR^4R^5$; and $Z^2$ is O; or $Z^1$ is $CR^4R^5$; and $Z^2$ is $CR^{4z}R^{5z}$;

$R^4$ and $R^5$ are each independently selected from H and $C_{1-3}$ alkyl;

or $R^4$ and $R^5$, together with the carbon atom to which they are attached, form a cyclopropyl or cyclobutyl ring;

$R^{4z}$ and $R^{5z}$ are each H;

Y is N;

$X^1$ is $NR^{1x}$ or $CR^1$;

$X^2$ is $NR^{2x}$ or $CR^2$;

$X^3$ is C;

wherein Ring

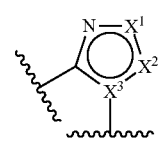

is an aromatic ring selected from:

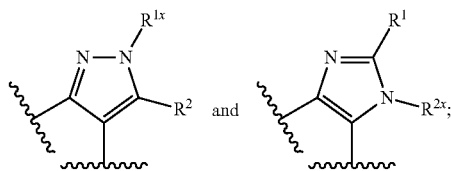

Ring moiety A is azetinidin-3-yl, pyrrolidin-3-yl, piperidin-3-yl, or piperidin-4-yl;

$R^1$ is selected from H, halo, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents;

$R^{1x}$ is selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{1A}$ substituents;

each $R^{1A}$ is independently selected from halo, CN, $C_{1-6}$ alkyl, $C_{1-6}$ haloalkyl, $C_{3-4}$ cycloalkyl, $OR^{a11}$, and $NR^{c11}R^{d11}$;

each $R^{a11}$, $R^{c11}$, and $R^{d11}$ is independently selected from H and $C_{1-6}$ alkyl;

$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

$R^{2x}$ is selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl; wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted by 1, 2, or 3 independently selected $R^{2A}$ substituents;

each $R^{2A}$ is independently selected from halo, CN, $C_{1-6}$ alkyl, $C_{1-6}$ haloalkyl, $C_{3-4}$ cycloalkyl, $OR^{a21}$, and $NR^{c21}R^{d21}$;

each $R^{a21}$, $R^{c21}$, and $R^{d21}$ is independently selected from H and $C_{1-6}$ alkyl;

one $R^8$ is $S(O)_2R^{b8}$;

the remaining $R^8$ is selected from halo or $C_{1-3}$ alkyl;

each $R^{b8}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, or 3 independently selected $R^{8A}$ substituents;

each $R^{8A}$ is independently selected from halo, CN, $NO_2$, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, 5-6 membered heteroaryl-$C_{1-4}$ alkyl, $OR^{a81}$, $SR^{a81}$, $C(O)R^{b81}$, $C(O)NR^{c81}R^{d81}$, $C(O)OR^{a81}$, $OC(O)R^{b81}$, $OC(O)NR^{c81}R^{d81}$, $NR^{c81}R^{d81}$, $NR^{c81}C(O)R^{b81}$, $NR^{c81}C(O)OR^{a81}$, $NR^{c81}C(O)NR^{c81}R^{d81}$, $NR^{c81}S(O)_2R^{b81}$, $NR^{c81}S(O)_2NR^{c81}R^{d81}$, $S(O)_2R^{b81}$, and $S(O)_2NR^{c81}R^{d81}$, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{a81}$, $R^{c81}$, and $R^{d81}$ is independently selected from H, $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, wherein said $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl are each optionally substituted with 1, 2, 3, or 4 independently selected $R^{8B}$ substituents;

each $R^{b81}$ is independently selected from $C_{1-6}$ alkyl, $C_{1-6}$ haloalkyl, $C_{3-7}$ cycloalkyl, phenyl, 4-7 membered heterocycloalkyl, 5-6 membered heteroaryl, $C_{3-7}$ cycloalkyl-$C_{1-4}$ alkyl, phenyl-$C_{1-4}$ alkyl, 4-7 membered heterocycloalkyl-$C_{1-4}$ alkyl, and 5-6 membered heteroaryl-$C_{1-4}$ alkyl, which are each optionally substituted with 1, 2, 3, or 4 independently selected $R^{8B}$ substituents;

each $R^{8B}$ is independently selected from halo, CN, $C_{1-6}$ alkyl, $C_{1-6}$ haloalkyl, $C_{3-4}$ cycloalkyl, $OR^{a82}$, $SR^{a82}$, $C(O)R^{b82}$, $C(O)NR^{c82}R^{d82}$, $C(O)OR^{a82}$, $OC(O)R^{b82}$, $OC(O)NR^{c82}R^{d82}$, $NR^{c82}R^{d82}$, $NR^{c82}C(O)R^{b82}$, $NR^{c82}C(O)OR^{a82}$, $NR^{c82}C(O)NR^{c82}R^{d82}$, $NR^{c82}S(O)_2R^{b82}$, $NR^{c82}S(O)_2NR^{c82}R^{d82}$, $S(O)_2R^{b82}$, and $S(O)_2NR^{c82}R^{d82}$;

each $R^{a82}$, $R^{c82}$, and $R^{d82}$ is independently selected from H, $C_{1-6}$ alkyl, and $C_{1-6}$ haloalkyl; and each $R^{b82}$ is independently selected from $C_{1-6}$ alkyl and $C_{1-6}$ haloalkyl.

24. The compound of claim 1, or a pharmaceutically acceptable salt thereof, wherein:

n is 1 or 2;

$Z^1$ is $CR^4R^5$; and $Z^2$ is O; or $Z^1$ is $CR^4R^5$; and $Z^2$ is $CH_2$;
$R^4$ and $R^5$ are each independently selected from H and methyl;
$R^{4z}$ and $R^{5z}$ are each H;
Y is N;
$X^1$ is $NR^{1x}$ or $CR^1$;
$X^2$ is $NR^{2x}$ or $CR^2$;
$X^3$ is C;
wherein Ring

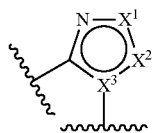

is an aromatic ring selected from:

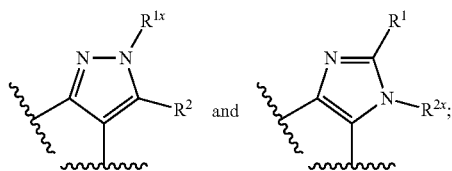

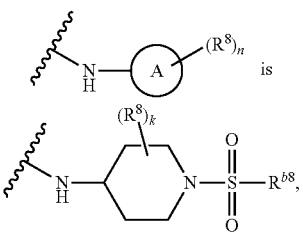 is $R^1$ is selected from H, halo, $C_{1-6}$ alkyl, phenyl, and 5-6 membered heteroaryl, wherein said $C_{1-6}$ alkyl, phenyl and 5-6 membered heteroaryl are each optionally substituted by 1 or 2 independently selected $R^{14}$ substituents;
$R^{1x}$ is selected from H, $C_{1-6}$ alkyl, $C_{3-7}$ cycloalkyl, phenyl, and 4-7 membered heterocycloalkyl, wherein said $C_{1-6}$ alkyl, $C_{3-7}$ cycloalkyl, phenyl, and 4-7 membered heterocycloalkyl are each optionally substituted by 1 or 2 independently selected $R^{14}$ substituents;
each $R^{14}$ is independently selected from halo, CN, $C_{1-6}$ alkyl, $C_{1-6}$ haloalkyl, $C_{3-4}$ cycloalkyl, $OR^{a11}$, and $NR^{c11}R^{d11}$;
each $R^{a11}$, $R^{c11}$, and $R^{d11}$ is independently selected from H and $C_{1-6}$ alkyl;
$R^2$ is selected from H, halo, CN, $C_{1-6}$ alkyl, $C_{1-6}$ haloalkyl, $C_{3-7}$ cycloalkyl, phenyl, 4-7 membered heterocycloalkyl, and 5-6 membered heteroaryl;
$R^{2x}$ is selected from H, $C_{1-6}$ alkyl, $C_{3-7}$ cycloalkyl, and phenyl-$C_{1-3}$ alkyl;
$R^8$ is $C_{1-3}$ alkyl;
each $R^{b8}$ is independently selected from $C_{1-6}$ alkyl, $C_{3-7}$ cycloalkyl, phenyl, 4-7 membered heterocycloalkyl, and 5-6 membered heteroaryl, which are each optionally substituted with 1 or 2 independently selected $R^{8A}$ substituents;

each $R^{8A}$ is independently selected from halo, CN, $C_{1-6}$ alkyl, $C_{1-6}$ haloalkyl, and 4-7 membered heterocycloalkyl; wherein said $C_{1-6}$ alkyl, $C_{1-6}$ haloalkyl, and 4-7 membered heterocycloalkyl are each optionally substituted by 1 or 2 independently selected $R^{8B}$ substituents;
each $R^{8B}$ is selected from $C_{1-6}$ alkyl and $OR^{a82}$; and
each $R^{a82}$ is independently selected from H and $C_{1-6}$ alkyl.

25. The compound of claim 1, having Formula (IVa):

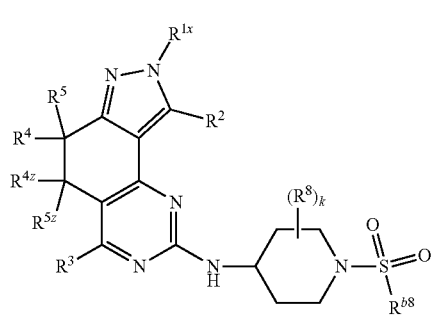

or a pharmaceutically acceptable salt thereof, wherein k is n−1.

26. The compound of claim 1, having Formula (IVb):

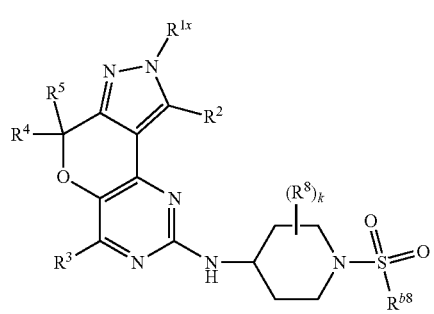

or a pharmaceutically acceptable salt thereof, wherein k is n−1.

27. The compound of claim 1, having Formula (IVc):

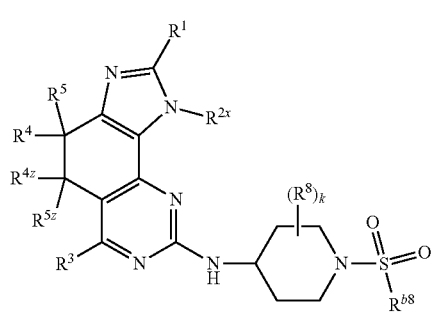

or a pharmaceutically acceptable salt thereof, wherein k is n−1.

28. The compound of claim 1, having Formula (IVd):

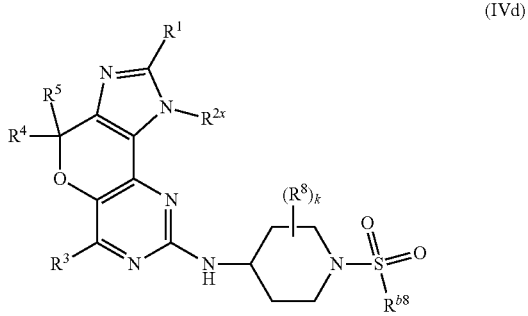

or a pharmaceutically acceptable salt thereof, wherein k is n−1.

29. The compound of claim 1, selected from:
N-(1-(Ethylsulfonyl)piperidin-4-yl)-1,2-dimethyl-4,5-dihydro-1H-imidazo[4,5-h]quinazolin-8-amine;
N-(1-(Cyclopropylsulfonyl)piperidin-4-yl)-1,2-dimethyl-4,5-dihydro-1H-imidazo[4,5-h]quinazolin-8-amine;
1,2-Dimethyl-N-(1-((1-methyl-1H-pyrazol-4-yl)sulfonyl)piperidin-4-yl)-4,5-dihydro-1H-imidazo[4,5-h]quinazolin-8-amine;
N-(1-((1H-Pyrazol-4-yl)sulfonyl)piperidin-4-yl)-1,2-dimethyl-4,5-dihydro-1H-imidazo[4,5-h]quinazolin-8-amine;
3-((4-((1,2-Dimethyl-4,5-dihydro-1H-imidazo[4,5-h]quinazolin-8-yl)amino)piperidin-1-yl)sulfonyl)benzonitrile;
N-(1-((1,2-Dimethyl-1H-imidazol-4-yl)sulfonyl)piperidin-4-yl)-1,2-dimethyl-4,5-dihydro-1H-imidazo[4,5-h]quinazolin-8-amine;
2-Methyl-N-(1-(methylsulfonyl)piperidin-4-yl)-4,5-dihydro-1H-imidazo[4,5-h]quinazolin-8-amine;
1-Benzyl-2-methyl-N-(1-(methylsulfonyl)piperidin-4-yl)-4,5-dihydro-1H-imidazo[4,5-h]quinazolin-8-amine;
8-Methyl-N-(1-(methylsulfonyl)piperidin-4-yl)-6,8-dihydro-5H-pyrazolo[3,4-h]quinazolin-2-amine;
8-Methyl-N-(1-(methylsulfonyl)piperidin-4-yl)-6,8-dihydropyrazolo[4',3':4,5]pyrano[3,2-d]pyrimidin-2-amine;
8-(2,6-Difluorophenyl)-9-methyl-N-(1-(methylsulfonyl)piperidin-4-yl)-6,8-dihydro-5H-pyrazolo[3,4-h]quinazolin-2-amine;
9-Cyclopropyl-8-methyl-N-(1-(methylsulfonyl)piperidin-4-yl)-6,8-dihydro-5H-pyrazolo[3,4-h]quinazolin-2-amine;
9-Isopropyl-8-methyl-N-(1-(methylsulfonyl)piperidin-4-yl)-6,8-dihydro-5H-pyrazolo[3,4-h]quinazolin-2-amine;
9-Cyclopropyl-N-(1-(methylsulfonyl)piperidin-4-yl)-8-(tetrahydrofuran-3-yl)-6,8-dihydro-5H-pyrazolo[3,4-h]quinazolin-2-amine;
2-(9-Cyclopropyl-2-((1-(methylsulfonyl)piperidin-4-yl)amino)-5,6-dihydro-8H-pyrazolo[3,4-h]quinazolin-8-yl)ethan-1-ol;
8,9-Dicyclopropyl-N-(1-(methylsulfonyl)piperidin-4-yl)-6,8-dihydro-5H-pyrazolo[3,4-h]quinazolin-2-amine;
1,2-Dimethyl-N-(1-(methylsulfonyl)piperidin-4-yl)-4,5-dihydro-1H-imidazo[4,5-h]quinazolin-8-amine;
2-Isopropyl-1-methyl-N-(1-(methylsulfonyl)piperidin-4-yl)-4,5-dihydro-1H-imidazo[4,5-h]quinazolin-8-amine;
1-Cyclopropyl-2-methyl-N-(1-(methylsulfonyl)piperidin-4-yl)-4,5-dihydro-1H-imidazo[4,5-h]quinazolin-8-amine;
1-Cyclopropyl-N-(1-(methylsulfonyl)piperidin-4-yl)-4,5-dihydro-1H-imidazo[4,5-h]quinazolin-8-amine;
2-Bromo-1-cyclopropyl-N-(1-(methylsulfonyl)piperidin-4-yl)-4,5-dihydro-1H-imidazo[4,5-h]quinazolin-8-amine;
1-Cyclopropyl-N-(1-(methylsulfonyl)piperidin-4-yl)-2-phenyl-4,5-dihydro-1H-imidazo[4,5-h]quinazolin-8-amine;
1-Cyclopropyl-2-(2-fluorophenyl)-N-(1-(methylsulfonyl)piperidin-4-yl)-4,5-dihydro-1H-imidazo[4,5-h]quinazolin-8-amine;
1-Cyclopropyl-2-(1,3-dimethyl-1H-pyrazol-4-yl)-N-(1-(methylsulfonyl)piperidin-4-yl)-4,5-dihydro-1H-imidazo[4,5-h]quinazolin-8-amine;
1-Cyclopropyl-2,4,4-trimethyl-N-(1-(methylsulfonyl)piperidin-4-yl)-4,5-dihydro-1H-imidazo[4,5-h]quinazolin-8-amine; and
1-Cyclopropyl-N-(1-(methylsulfonyl)piperidin-4-yl)-1,4-dihydroimidazo[4',5':4,5]pyrano[3,2-d]pyrimidin-8-amine,
or a pharmaceutically acceptable salt thereof.

30. The compound of claim 1, selected from:
1-Isopropyl-2-methyl-N-(1-(methylsulfonyl)piperidin-4-yl)-4,5-dihydro-1H-imidazo[4,5-h]quinazolin-8-amine;
1,2-Dimethyl-N-((3R,4S)-3-methyl-1-((1-methyl-1H-imidazol-4-yl)sulfonyl)piperidin-4-yl)-4,5-dihydro-1H-imidazo[4,5-h]quinazolin-8-amine;
1,2-Dimethyl-N-((3R,4S)-3-methyl-1-((6-(4-methylpiperazin-1-yl)pyridin-2-yl)sulfonyl)piperidin-4-yl)-4,5-dihydro-1H-imidazo[4,5-h]quinazolin-8-amine;
(R)-1-(5-(((3R,4S)-4-((1,2-Dimethyl-4,5-dihydro-1H-imidazo[4,5-h]quinazolin-8-yl)amino)-3-methylpiperidin-1-yl)sulfonyl)pyridin-2-yl)pyrrolidin-3-ol;
1-Cyclopropyl-2-methyl-N-((3R,4S)-3-methyl-1-((1-methyl-1H-imidazol-4-yl)sulfonyl)piperidin-4-yl)-4,5-dihydro-1H-imidazo[4,5-h]quinazolin-8-amine; and
1-Cyclopropyl-2-methyl-N-((3R,4S)-3-methyl-1-((1-methyl-1H-pyrazol-4-yl)sulfonyl)piperidin-4-yl)-4,5-dihydro-1H-imidazo[4,5-h]quinazolin-8-amine,
or a pharmaceutically acceptable salt thereof.

31. A pharmaceutical composition comprising a compound of claim 1, or a pharmaceutically acceptable salt thereof, and a pharmaceutically acceptable carrier.

32. A method of treating a cancer associated with CDK2 in a patient, comprising administering to the patient a therapeutically effective amount of the compound of claim 1, or pharmaceutically acceptable salt thereof, wherein the cancer is selected from the group consisting of ovarian, endometrial, esophagus, adenocarcinoma, adenocarcinoma of the esophagus, urothelial, gynecological, ovarian serous cystadenocarcinoma, uterine carcinoma, cervical carcinoma, endocervical adenocarcinoma, stomach (gastric), esophageal, breast, triple negative breast cancer, lung, non-small cell lung cancer, lung squamous cell carcinoma, bile duct, and bone.

33. The method of claim 32, wherein the cancer is associated with an amplification of the cyclin E1 (CCNE1) gene and/or overexpression of CCNE1.

34. The method of claim 32, wherein the human subject has been previously determined to:
(i)
(a) have a nucleotide sequence encoding a p16 protein comprising the amino acid sequence of SEQ ID NO:1; and/or
(b) have a cyclin dependent kinase inhibitor 2A (CDKN2A) gene lacking one or more inactivating nucleic acid substitutions and/or deletions;
(ii)
(a) have an amplification of the cyclin E1 (CCNE1) gene; and/or
(b) have an expression level of CCNE1 in a biological sample obtained from the human subject that is higher than a control expression level of CCNE1.

35. The method of claim 32, comprising:
(i) identifying, in a biological sample obtained from the human subject:
(a) a nucleotide sequence encoding a p16 protein comprising the amino acid sequence of SEQ ID NO:1; and/or
(b) a cyclin dependent kinase inhibitor 2A (CDKN2A) gene lacking one or more inactivating nucleic acid substitutions;
(ii) identifying, in a biological sample obtained from the human subject:
(a) an amplification of the cyclin E1 (CCNE1) gene; and/or
(b) an expression level of CCNE1 that is higher than a control expression level of CCNE1; and
(iii) administering the compound of claim 1, or a pharmaceutically acceptable salt thereof, to the human subject.

36. The method of claim 35, comprising:
(i) identifying, in a biological sample obtained from the human subject:
(a) a nucleotide sequence encoding a p16 protein comprising the amino acid sequence of SEQ ID NO:1; and/or
(b) a CDKN2A gene lacking one or more inactivating nucleic acid substitutions and/or deletions;
(ii) identifying, in a biological sample obtained from the human subject:
(a) an amplification of the CCNE1 gene; and
(iii) administering the compound or the salt to the human subject.

37. A method of evaluating the response of a human subject having a cancer associated with cyclin-dependent kinase 2 (CDK2) to a compound of claim 1, or a pharmaceutically acceptable salt thereof, comprising:
(a) administering the compound or the salt, to the human subject, wherein the human subject has been previously determined to have an amplification of the cyclin E1 (CCNE1) gene and/or an expression level of CCNE1 that is higher than a control expression level of CCNE1;
(b) measuring, in a biological sample of obtained from the subject subsequent to the administering of step (a), the level of retinoblastoma (Rb) protein phosphorylation at the serine corresponding to amino acid position 780 of SEQ ID NO:3,
wherein a reduced level of Rb phosphorylation at the serine corresponding to amino acid position 780 of SEQ ID NO:3, as compared to a control level of Rb phosphorylation at the serine corresponding to amino acid position 780 of SEQ ID NO:3, is indicative that the human subject responds to the compound or the salt,
wherein the cancer is selected from the group consisting of ovarian, endometrial, esophagus, adenocarcinoma, adenocarcinoma of the esophagus, urothelial, gynecological, ovarian serous cystadenocarcinoma, uterine carcinoma, cervical carcinoma, endocervical adenocarcinoma, stomach (gastric), esophageal, breast, triple negative breast cancer, lung, non-small cell lung cancer, lung squamous cell carcinoma, bile duct, and bone.

* * * * *

UNITED STATES PATENT AND TRADEMARK OFFICE
CERTIFICATE OF CORRECTION

PATENT NO. : 11,440,914 B2
APPLICATION NO. : 16/863770
DATED : September 13, 2022
INVENTOR(S) : Qinda Ye et al.

Page 1 of 1

It is certified that error appears in the above-identified patent and that said Letters Patent is hereby corrected as shown below:

In the Claims

Column 142, Line 61, Claim 1, delete "(OR$^{i11}$)" and insert -- (OR$^{i11}$), --;

Column 159, Line 38, Claim 22, delete "C$_{14}$ alkyl," and insert -- C$_{1-4}$ alkyl, --;

Column 161, Line 12, Claim 22, delete "azetinidin-3-yl," and insert -- azetidin-3-yl, --; and Column 168, Line 29, Claim 37, delete "salt," and insert -- salt; --.

Signed and Sealed this
Twenty-second Day of November, 2022

Katherine Kelly Vidal
*Director of the United States Patent and Trademark Office*